US012751663B2

(12) United States Patent
Nichols et al.

(10) Patent No.: US 12,751,663 B2
(45) Date of Patent: Oct. 6, 2026

(54) WEARABLE MEDICAL MODULE FOR WOUND TREATMENT, IMAGING, MONITORING AND ANALYSIS BASED ON IMAGES OF WOUND

(71) Applicant: PREH HOLDINGS, LLC, Laguna Niguel, CA (US)

(72) Inventors: Thomas Nichols, Laguna Niguel, CA (US); Samir Shreim, Irvine, CA (US)

(73) Assignee: PREH HOLDINGS, LLC, Laguna Niguel, CA (US)

( * ) Notice: Subject to any disclaimer, the term of this patent is extended or adjusted under 35 U.S.C. 154(b) by 0 days.

(21) Appl. No.: 19/009,838

(22) Filed: Jan. 3, 2025

(65) Prior Publication Data

US 2025/0221659 A1 Jul. 10, 2025

Related U.S. Application Data

(60) Provisional application No. 63/734,291, filed on Dec. 16, 2024, provisional application No. 63/734,169, (Continued)

(51) Int. Cl.
*A61B 5/00* (2006.01)

(52) U.S. Cl.
CPC ............ *A61B 5/445* (2013.01); *A61B 5/0036* (2018.08); *A61B 5/0077* (2013.01); *A61B 2562/185* (2013.01)

(58) Field of Classification Search
CPC ..... A61B 5/445; A61B 5/0036; A61B 5/0077; A61B 2562/185; A61B 5/6833
See application file for complete search history.

(56) References Cited

U.S. PATENT DOCUMENTS

D445,817 S 7/2001 Okuley
6,283,938 B1 9/2001 McConnell
(Continued)

FOREIGN PATENT DOCUMENTS

CN 109350362 A 2/2019
CN 110522419 A 12/2019
(Continued)

OTHER PUBLICATIONS

International Search Report and Written Opinion dated Nov. 1, 2022, in PCT Application No. PCT/US2022/033392 in 18 pages.
(Continued)

*Primary Examiner* — Serkan Akar
(74) *Attorney, Agent, or Firm* — Knobbe, Martens, Olson & Bear, LLP

(57) ABSTRACT

A wearable treatment and analysis system is provided. A wearable treatment and analysis system may include a module configured to be mounted to a wearable medical article, wherein the module comprises: one or more optical sensors configured to generate image data of a body surface region of a wearer of the wearable medical article, a wireless network interface configured to transmit the sensor data. A wearable treatment and analysis system may include a computing system comprising one or more computer processors and executable instructions, wherein the computing system is configured to: receive the image data from the plurality of optical sensors, receive contextual data associated with the wearer; and evaluate the image data and contextual data using a machine learning model to generate a score representing a current state of the body surface region.

19 Claims, 43 Drawing Sheets

Related U.S. Application Data filed on Dec. 15, 2024, provisional application No. 63/618,811, filed on Jan. 8, 2024.

(56) References Cited

U.S. PATENT DOCUMENTS

| | | | |
|---|---|---|---|
| 6,340,677 | B1 | 1/2002 | Nishimori et al. |
| 6,607,387 | B2 | 8/2003 | Mault |
| 6,638,231 | B2 | 10/2003 | Govari et al. |
| 6,734,858 | B2 | 5/2004 | Attar et al. |
| 6,761,697 | B2 | 7/2004 | Rubinstenn et al. |
| 6,766,184 | B2 | 7/2004 | Utzinger et al. |
| 6,889,165 | B2 | 5/2005 | Lind et al. |
| 6,907,193 | B2 | 6/2005 | Kollias et al. |
| 6,937,885 | B1 | 8/2005 | Lewis et al. |
| 6,959,119 | B2 | 10/2005 | Hawkins et al. |
| 7,006,657 | B2 | 2/2006 | Bazin |
| 7,104,800 | B2 | 9/2006 | Ortiz-Valero et al. |
| 7,151,956 | B2 | 12/2006 | Satoh et al. |
| 7,193,219 | B2 | 3/2007 | Schick et al. |
| D540,838 | S | 4/2007 | Aronsson et al. |
| 7,220,254 | B2 | 5/2007 | Altshuler et al. |
| 7,233,693 | B2 | 6/2007 | Momma |
| 7,258,675 | B2 | 8/2007 | Nichols |
| D552,809 | S | 10/2007 | Linsbichler |
| 7,309,335 | B2 | 12/2007 | Altshuler et al. |
| 7,317,818 | B2 | 1/2008 | Lefebvre |
| 7,324,668 | B2 | 1/2008 | Rubinstenn et al. |
| 7,454,046 | B2 | 11/2008 | Chhibber et al. |
| 7,477,767 | B2 | 1/2009 | Chhibber et al. |
| D589,650 | S | 3/2009 | Adriaenssen |
| 7,564,990 | B2 | 7/2009 | Kern et al. |
| 7,738,032 | B2 | 6/2010 | Kollias et al. |
| 7,764,303 | B2 | 7/2010 | Pote et al. |
| 7,828,721 | B2 | 11/2010 | Kumei et al. |
| 7,844,079 | B2 | 11/2010 | Hassebrook et al. |
| 7,856,118 | B2 | 12/2010 | Kalla et al. |
| 7,894,651 | B2 | 2/2011 | Gutkowicz-Krusin et al. |
| 7,953,613 | B2 | 5/2011 | Gizewski |
| 7,986,987 | B2 | 7/2011 | Bazin et al. |
| 8,026,942 | B2 | 9/2011 | Payonk et al. |
| 8,027,505 | B2 | 9/2011 | Edgar et al. |
| D649,636 | S | 11/2011 | Bean et al. |
| 8,062,220 | B2 | 11/2011 | Kurtz et al. |
| 8,073,223 | B2 | 12/2011 | Wilson et al. |
| 8,094,009 | B2 | 1/2012 | Allen et al. |
| 8,094,186 | B2 | 1/2012 | Fukuoka et al. |
| 8,109,875 | B2 | 2/2012 | Gizewski |
| 8,150,501 | B2 | 4/2012 | Stamatas |
| 8,155,413 | B2 | 4/2012 | Chhibber et al. |
| 8,157,753 | B2 | 4/2012 | Nichols |
| 8,238,623 | B2 | 8/2012 | Stephan et al. |
| 8,260,010 | B2 | 9/2012 | Chhibber et al. |
| 8,360,973 | B2 | 1/2013 | Bazin et al. |
| D675,829 | S | 2/2013 | Jakubow |
| 8,372,128 | B2 | 2/2013 | Reuben |
| 8,373,859 | B2 | 2/2013 | Chhibber et al. |
| 8,391,639 | B2 | 3/2013 | Hillebrand et al. |
| 8,401,300 | B2 | 3/2013 | Jiang et al. |
| 8,428,382 | B2 | 4/2013 | Sato |
| 8,437,540 | B2 | 5/2013 | Stephan et al. |
| 8,463,006 | B2 | 6/2013 | Prokoski |
| 8,463,366 | B2 | 6/2013 | Freeman et al. |
| 8,484,155 | B2 | 7/2013 | Yamaguchi et al. |
| 8,532,736 | B1 | 9/2013 | Malzbender et al. |
| D693,932 | S | 11/2013 | Nichols |
| 8,591,414 | B2 | 11/2013 | Kitamura et al. |
| 8,597,187 | B2 | 12/2013 | Nuccitelli et al. |
| 8,611,588 | B2 | 12/2013 | Kang |
| 8,620,421 | B2 | 12/2013 | Yeo |
| 8,634,648 | B2 | 1/2014 | Hyde et al. |
| D700,316 | S | 2/2014 | Nichols |
| 8,644,615 | B2 | 2/2014 | Hyde et al. |
| 8,652,042 | B2 | 2/2014 | Mattoli et al. |
| 8,696,605 | B2 | 4/2014 | Nichols |
| D713,971 | S | 9/2014 | Nichols |
| 8,823,934 | B2 | 9/2014 | Chhibber et al. |
| 8,837,796 | B1 | 9/2014 | Zalutskaya |
| 8,855,751 | B2 | 10/2014 | Kruglick |
| 8,861,863 | B2 | 10/2014 | Chhibber et al. |
| 8,884,242 | B2 | 11/2014 | Chhibber et al. |
| 8,891,087 | B2 | 11/2014 | Zuzak et al. |
| 8,915,562 | B2 | 12/2014 | Edgar et al. |
| 8,915,866 | B2 | 12/2014 | Nycz |
| 8,941,727 | B2 | 1/2015 | Rassman et al. |
| 8,965,081 | B2 | 2/2015 | Nagase et al. |
| 9,028,405 | B2 | 5/2015 | Tran |
| 9,042,967 | B2 | 5/2015 | Dacosta et al. |
| 9,075,003 | B2 | 7/2015 | Oe et al. |
| 9,076,238 | B2 | 7/2015 | Wu et al. |
| D736,399 | S | 8/2015 | Nichols |
| 9,101,320 | B2 | 8/2015 | Cummins et al. |
| D738,508 | S | 9/2015 | Nichols |
| 9,122,906 | B2 | 9/2015 | Nakamura et al. |
| 9,138,257 | B2 | 9/2015 | Revivo |
| D742,003 | S | 10/2015 | Tasar |
| 9,189,679 | B2 | 11/2015 | Yamazaki et al. |
| 9,204,830 | B2 | 12/2015 | Zand |
| D747,800 | S | 1/2016 | Dunleavy et al. |
| 9,247,802 | B2 | 2/2016 | Edgar et al. |
| 9,256,963 | B2 | 2/2016 | Cummins et al. |
| 9,259,163 | B2 | 2/2016 | Rajan |
| 9,272,141 | B2 | 3/2016 | Nichols |
| D753,400 | S | 4/2016 | Khoun et al. |
| 9,326,685 | B2 | 5/2016 | Krishnan et al. |
| 9,339,194 | B2 | 5/2016 | Adams |
| 9,351,683 | B2 | 5/2016 | Yoshida |
| 9,369,170 | B2 | 6/2016 | Sorrentino |
| 9,384,543 | B2 | 7/2016 | Stephan et al. |
| D764,173 | S | 8/2016 | Nichols |
| 9,402,546 | B2 | 8/2016 | Segman |
| 9,414,780 | B2 | 8/2016 | Rhoads |
| 9,427,187 | B2 | 8/2016 | Gilbert |
| D765,982 | S | 9/2016 | Nichols |
| 9,445,713 | B2 | 9/2016 | Douglas et al. |
| 9,492,078 | B2 | 11/2016 | Ko et al. |
| D774,774 | S | 12/2016 | Nichols |
| D780,245 | S | 2/2017 | Ruback et al. |
| 9,572,494 | B2 | 2/2017 | Dhawan |
| 9,579,250 | B2 | 2/2017 | Nichols |
| 9,603,524 | B2 | 3/2017 | Park et al. |
| 9,629,561 | B2 | 4/2017 | Weinstein et al. |
| 9,706,929 | B2 | 7/2017 | Kantor et al. |
| D795,423 | S | 8/2017 | Chen et al. |
| 9,730,758 | B2 | 8/2017 | Carlucci |
| D799,711 | S | 10/2017 | Sedic |
| D803,572 | S | 11/2017 | Nichols |
| 9,818,193 | B2 | 11/2017 | Smart |
| D805,571 | S | 12/2017 | Hogstedt et al. |
| D805,572 | S | 12/2017 | Hogstedt et al. |
| 9,854,975 | B2 | 1/2018 | Van Pieterson et al. |
| D813,203 | S | 3/2018 | Hardi |
| 9,918,640 | B2 | 3/2018 | Ntziachristos et al. |
| 9,990,472 | B2 | 6/2018 | Gurcan et al. |
| D822,843 | S | 7/2018 | Lenke |
| 10,016,164 | B2 | 7/2018 | Evans et al. |
| D825,188 | S | 8/2018 | Luo |
| 10,080,484 | B2 | 9/2018 | Yang et al. |
| 10,080,524 | B1 | 9/2018 | Xi |
| D830,700 | S | 10/2018 | Xue |
| 10,085,643 | B2 | 10/2018 | Bandic et al. |
| 10,117,617 | B2 | 11/2018 | Cantu et al. |
| 10,119,208 | B2 | 11/2018 | McMaster |
| 10,178,946 | B2 | 1/2019 | Weiss et al. |
| 10,206,604 | B2 | 2/2019 | Bergelin et al. |
| 10,226,552 | B2 | 3/2019 | Slepian |
| 10,240,265 | B2 | 3/2019 | McMaster |
| 10,252,051 | B2 | 4/2019 | Nichols |
| 10,265,219 | B2 | 4/2019 | Duesterhoft et al. |
| D848,013 | S | 5/2019 | Fuhner et al. |
| 10,285,617 | B2 | 5/2019 | Toth et al. |
| 10,285,624 | B2 | 5/2019 | Taylor et al. |
| 10,292,263 | B2 | 5/2019 | Rogers et al. |
| 10,307,098 | B2 | 6/2019 | Gareau |
| 10,314,537 | B2 | 6/2019 | Zegarelli |

(56) References Cited

U.S. PATENT DOCUMENTS

| | | | |
|---|---|---|---|
| 10,334,227 B2 | 6/2019 | Panescu et al. | |
| 10,357,201 B2 | 7/2019 | Rogers et al. | |
| 10,453,197 B1 | 10/2019 | Cholakkal | |
| 10,463,293 B2 | 11/2019 | Maharbiz et al. | |
| 10,511,777 B2 | 12/2019 | Nichols | |
| 10,542,929 B2 | 1/2020 | Kimmel | |
| 10,563,795 B2 | 2/2020 | Staton et al. | |
| 10,588,723 B2 | 3/2020 | Falkel | |
| 10,617,300 B2 | 4/2020 | Rogers et al. | |
| 10,631,626 B2 | 4/2020 | Lee et al. | |
| 10,674,957 B2 | 6/2020 | Suri et al. | |
| 10,702,153 B2 | 7/2020 | Shamim et al. | |
| 10,702,205 B2 | 7/2020 | Sharman et al. | |
| 10,722,174 B2 | 7/2020 | Pang et al. | |
| 10,736,551 B2 | 8/2020 | Rogers | |
| 10,736,805 B2 | 8/2020 | Johnson et al. | |
| 10,740,884 B2 | 8/2020 | McCall et al. | |
| 10,743,973 B2 | 8/2020 | Adams et al. | |
| 10,779,773 B2 | 9/2020 | Freeman et al. | |
| 10,786,395 B1 | 9/2020 | Temkin et al. | |
| 10,791,984 B2 | 10/2020 | Kantrowitz et al. | |
| 10,799,183 B2 | 10/2020 | Cao et al. | |
| 11,013,456 B2 | 5/2021 | Barnes et al. | |
| 11,096,602 B2 | 8/2021 | Gurevich et al. | |
| 11,122,206 B2 | 9/2021 | Nichols | |
| 11,134,848 B2 | 10/2021 | Bala et al. | |
| 11,160,491 B2 | 11/2021 | Aung et al. | |
| 11,202,572 B2 | 12/2021 | Mak et al. | |
| 11,266,345 B2 | 3/2022 | Saiko et al. | |
| 11,334,965 B2 | 5/2022 | Ben-Haim et al. | |
| 11,516,388 B2 | 11/2022 | Talbert et al. | |
| 11,583,449 B2 | 2/2023 | Ribble et al. | |
| 11,617,492 B2 | 4/2023 | Refai et al. | |
| 11,633,533 B2 | 4/2023 | Gregory et al. | |
| 11,647,922 B2 | 5/2023 | Scherer | |
| 11,660,012 B2 | 5/2023 | Nowroozi et al. | |
| 11,686,618 B2 | 6/2023 | Darty et al. | |
| 11,690,570 B2 | 7/2023 | Grubb et al. | |
| 11,712,372 B2 | 8/2023 | Levy et al. | |
| 11,717,447 B2 | 8/2023 | Brownhill et al. | |
| 11,723,809 B2 | 8/2023 | Askem et al. | |
| 11,727,560 B2 | 8/2023 | Dacosta et al. | |
| 11,744,667 B2 | 9/2023 | Shelton, IV et al. | |
| 11,783,943 B2 | 10/2023 | Armstrong et al. | |
| 11,785,330 B2 | 10/2023 | Nichols | |
| 11,805,970 B2 | 11/2023 | Faarbaek et al. | |
| 11,854,702 B2 | 12/2023 | Nichols | |
| 11,869,176 B2 | 1/2024 | Shi et al. | |
| 11,878,104 B2 | 1/2024 | Kodavanti et al. | |
| 11,963,721 B2 | 4/2024 | Hadoux et al. | |
| 11,986,296 B2 | 5/2024 | Martinez et al. | |
| 11,986,376 B2 | 5/2024 | Chen et al. | |
| 12,005,181 B2 | 6/2024 | Hartwell et al. | |
| 12,014,500 B2 | 6/2024 | Connor | |
| 12,083,262 B2 | 9/2024 | Gregory et al. | |
| 12,102,444 B2 | 10/2024 | Kennedy | |
| 12,102,447 B2 | 10/2024 | Brownhill et al. | |
| 12,114,994 B2 | 10/2024 | Hunt et al. | |
| 12,115,302 B2 | 10/2024 | Fink et al. | |
| 12,127,848 B2 | 10/2024 | Speiermann et al. | |
| 12,141,964 B2 | 11/2024 | Dacosta et al. | |
| 12,161,533 B2 | 12/2024 | Elder et al. | |
| 12,213,802 B2 | 2/2025 | Hunter | |
| 12,254,989 B2 | 3/2025 | Nichols | |
| 12,257,066 B2 | 3/2025 | Elliott et al. | |
| 12,260,555 B2 | 3/2025 | Jordan | |
| 12,262,153 B2 | 3/2025 | Katra et al. | |
| 12,272,969 B2 | 4/2025 | Kovacs et al. | |
| 12,299,772 B2 | 5/2025 | Urwin et al. | |
| 12,300,379 B2 | 5/2025 | Ahmad | |
| 12,322,109 B2 | 6/2025 | Releford | |
| 12,327,633 B2 | 6/2025 | Phillips et al. | |
| 12,329,493 B2 | 6/2025 | Lin et al. | |
| 12,357,228 B2 | 7/2025 | Gellman et al. | |
| 12,364,626 B2 | 7/2025 | Locke et al. | |
| 12,370,300 B2 | 7/2025 | Askem et al. | |
| 12,376,786 B2 | 8/2025 | Uthoff et al. | |
| 12,414,881 B2 | 9/2025 | Schoess et al. | |
| 12,416,798 B2 | 9/2025 | Dehghani et al. | |
| 12,420,006 B2 | 9/2025 | Gregory et al. | |
| 12,424,307 B2 | 9/2025 | Hunt et al. | |
| 12,430,751 B2 | 9/2025 | Kayser et al. | |
| 12,444,050 B2 | 10/2025 | Fan et al. | |
| 12,446,804 B2 | 10/2025 | Roxbury et al. | |
| 12,447,059 B2 | 10/2025 | Brar et al. | |
| 12,458,278 B2 | 11/2025 | Schoess et al. | |
| 12,458,286 B2 | 11/2025 | Quintanar | |
| 12,465,218 B2 | 11/2025 | Subhash et al. | |
| 12,482,570 B2 | 11/2025 | Nichols | |
| 12,563,279 B2 | 2/2026 | Yu et al. | |
| 2003/0012461 A1 | 1/2003 | Satoh et al. | |
| 2004/0100376 A1 | 5/2004 | Lye et al. | |
| 2004/0186359 A1 | 9/2004 | Beaudoin et al. | |
| 2004/0236254 A1 | 11/2004 | Nichols | |
| 2005/0186245 A1 | 8/2005 | Hunter et al. | |
| 2006/0015058 A1 | 1/2006 | Kellogg | |
| 2006/0047218 A1 | 3/2006 | Bloom et al. | |
| 2006/0058593 A1 | 3/2006 | Drinan et al. | |
| 2006/0241543 A1 | 10/2006 | Gura | |
| 2007/0233208 A1 | 10/2007 | Kurtz et al. | |
| 2008/0118886 A1 | 5/2008 | Liang et al. | |
| 2008/0184128 A1 | 7/2008 | Swenson et al. | |
| 2009/0204100 A1 | 8/2009 | Van Pieterson et al. | |
| 2009/0227924 A1 | 9/2009 | Conrad et al. | |
| 2009/0245603 A1 | 10/2009 | Koruga et al. | |
| 2010/0004506 A1 | 1/2010 | Saadat | |
| 2010/0139682 A1 | 6/2010 | Edgar et al. | |
| 2010/0185064 A1 | 7/2010 | Bandic et al. | |
| 2011/0178375 A1 | 7/2011 | Forster | |
| 2012/0008838 A1 | 1/2012 | Guyon et al. | |
| 2012/0041282 A1 | 2/2012 | Nichol et al. | |
| 2012/0041283 A1 | 2/2012 | Krishnan et al. | |
| 2012/0041284 A1 | 2/2012 | Krishnan et al. | |
| 2012/0061590 A1 | 3/2012 | Khojasteh et al. | |
| 2012/0116485 A1 | 5/2012 | Burgmann | |
| 2012/0209088 A1 | 8/2012 | Romem | |
| 2012/0307032 A1 | 12/2012 | Gomi et al. | |
| 2013/0046212 A1 | 2/2013 | Nichols | |
| 2013/0060176 A1 | 3/2013 | Nichols | |
| 2013/0197397 A1 | 8/2013 | Waugh et al. | |
| 2013/0200268 A1 | 8/2013 | Rafferty et al. | |
| 2013/0216971 A1 | 8/2013 | Friddell | |
| 2013/0245546 A1 | 9/2013 | Hayn | |
| 2013/0261409 A1 | 10/2013 | Pathak et al. | |
| 2014/0194790 A1 | 7/2014 | Crunick et al. | |
| 2014/0303452 A1* | 10/2014 | Ghaffari | A61B 18/20 601/3 |
| 2014/0314315 A1 | 10/2014 | Chhibber et al. | |
| 2014/0316235 A1 | 10/2014 | Davis et al. | |
| 2014/0350409 A1 | 11/2014 | Chhibber et al. | |
| 2015/0005643 A1 | 1/2015 | Whitman et al. | |
| 2015/0086104 A1 | 3/2015 | Miyamoto et al. | |
| 2015/0099947 A1 | 4/2015 | Qu et al. | |
| 2015/0105635 A1 | 4/2015 | Yoshida et al. | |
| 2015/0164372 A1 | 6/2015 | Navab et al. | |
| 2015/0173842 A1 | 6/2015 | Carlucci | |
| 2015/0182757 A1 | 7/2015 | Levine et al. | |
| 2015/0223749 A1 | 8/2015 | Park et al. | |
| 2015/0250393 A1 | 9/2015 | Tran | |
| 2015/0254847 A1 | 9/2015 | Nakamura et al. | |
| 2015/0265182 A1 | 9/2015 | Jain et al. | |
| 2015/0287190 A1 | 10/2015 | Kim et al. | |
| 2015/0287191 A1 | 10/2015 | Koruga et al. | |
| 2015/0313445 A1 | 11/2015 | Davidson et al. | |
| 2015/0342515 A1 | 12/2015 | Hutchings et al. | |
| 2015/0346936 A1 | 12/2015 | Rodan et al. | |
| 2015/0371420 A1 | 12/2015 | Yerushalmy et al. | |
| 2016/0002223 A1 | 1/2016 | Chekal et al. | |
| 2016/0007908 A1 | 1/2016 | Guo | |
| 2016/0015962 A1 | 1/2016 | Maragheh et al. | |
| 2016/0022008 A1 | 1/2016 | Rabe et al. | |
| 2016/0022009 A1 | 1/2016 | Rabe et al. | |
| 2016/0022010 A1 | 1/2016 | Rabe et al. | |
| 2016/0022011 A1 | 1/2016 | Rabe et al. | |

(56) References Cited

U.S. PATENT DOCUMENTS

2016/0076298 A1 3/2016 Header et al.
2016/0081553 A1 3/2016 Weber et al.
2016/0113495 A1 4/2016 Nanjundappa et al.
2016/0135925 A1 5/2016 Mason et al.
2016/0154992 A1 6/2016 Shinoda et al.
2016/0182224 A1 6/2016 Theis
2016/0192842 A1 7/2016 Inagaki
2016/0206242 A1 7/2016 Esposito et al.
2016/0213126 A1 7/2016 Chang
2016/0228049 A1 8/2016 Nackaerts et al.
2016/0262624 A1 9/2016 Nakajima et al.
2016/0367188 A1 12/2016 Malik et al.
2017/0000407 A1 1/2017 Saxby et al.
2017/0020402 A1 1/2017 Rogers et al.
2017/0076446 A1 3/2017 Pedersen et al.
2017/0115726 A1 4/2017 Fung
2017/0136180 A1 5/2017 Zhao et al.
2017/0150851 A1 6/2017 Sueyoshi et al.
2017/0181659 A1 6/2017 Rafferty et al.
2017/0181825 A1 6/2017 Hunter et al.
2017/0188864 A1 7/2017 Drury
2017/0202711 A1* 7/2017 Cernasov .......... A61F 13/00055
2017/0202732 A1 7/2017 Nichols
2017/0216617 A1 8/2017 Kariguddaiah
2017/0224251 A1 8/2017 Ahmad et al.
2017/0224280 A1 8/2017 Bozkurt et al.
2017/0246473 A1 8/2017 Marinkovich et al.
2017/0270593 A1 9/2017 Sherman et al.
2017/0281073 A1 10/2017 Drennan et al.
2017/0340221 A1 11/2017 Cronin et al.
2017/0340254 A1 11/2017 Davis et al.
2017/0347940 A1 12/2017 Carr et al.
2017/0367543 A1 12/2017 Straka et al.
2018/0021178 A1 1/2018 Locke et al.
2018/0028079 A1 2/2018 Gurevich
2018/0036177 A1 2/2018 Anderson et al.
2018/0125201 A1 5/2018 Nichols
2018/0160953 A1 6/2018 Valsan et al.
2018/0161211 A1 6/2018 Beckey
2018/0228436 A1 8/2018 Sonkusale et al.
2018/0242894 A1 8/2018 Brauker et al.
2018/0267012 A1 9/2018 Scherer
2018/0279762 A1 10/2018 Park et al.
2018/0317794 A1 11/2018 Mackellar et al.
2018/0333107 A1 11/2018 Sada et al.
2018/0359850 A1 12/2018 Rogers et al.
2018/0360665 A1 12/2018 Melone
2019/0008694 A1 1/2019 Piotrowski et al.
2019/0021911 A1 1/2019 Askem et al.
2019/0029572 A1 1/2019 Wisniewski et al.
2019/0029650 A1 1/2019 Parker et al.
2019/0038214 A1 2/2019 Mikhail et al.
2019/0060126 A1 2/2019 Ribble et al.
2019/0076298 A1 3/2019 Quintanar et al.
2019/0076669 A1 3/2019 Alvarez et al.
2019/0082242 A1 3/2019 Duesterhoft et al.
2019/0137436 A1 5/2019 Lillehoj et al.
2019/0139632 A1 5/2019 Adams et al.
2019/0166285 A1 5/2019 Mistry et al.
2019/0167115 A1 6/2019 Dorodvand et al.
2019/0175104 A1 6/2019 Malik
2019/0216350 A1 7/2019 Sullivan et al.
2019/0221311 A1 7/2019 Takeuchi
2019/0223728 A1 7/2019 Heidari
2019/0223751 A1 7/2019 Weinstein et al.
2019/0264049 A1 8/2019 Atashbar et al.
2019/0290496 A1 9/2019 Brownhill et al.
2019/0298263 A1 10/2019 Clasbrummel
2019/0328234 A1 10/2019 Seibel et al.
2019/0328315 A1 10/2019 LaBelle et al.
2019/0333627 A1 10/2019 Johnson
2019/0336077 A1 11/2019 Kuhn et al.
2019/0343397 A1 11/2019 Meisal
2019/0361917 A1 11/2019 Tran et al.
2019/0365571 A1 12/2019 O'Mahony et al.
2019/0374163 A1 12/2019 Faarbaek et al.
2019/0388667 A1 12/2019 Xu
2020/0008299 A1 1/2020 Tran et al.
2020/0020165 A1 1/2020 Tran et al.
2020/0054218 A1 2/2020 Xi
2020/0061379 A1 2/2020 Bogie et al.
2020/0069242 A1 3/2020 Burns et al.
2020/0069280 A1 3/2020 Behzadi et al.
2020/0069409 A1 3/2020 Klueh et al.
2020/0093571 A1 3/2020 Shanjani et al.
2020/0100019 A1 3/2020 Wagner et al.
2020/0100711 A1 4/2020 Choudhury et al.
2020/0105422 A1 4/2020 Ribble et al.
2020/0107772 A1 4/2020 Hu
2020/0121428 A1 4/2020 Pai et al.
2020/0129085 A1 4/2020 Reuel et al.
2020/0138361 A1 5/2020 Amiot et al.
2020/0169722 A1 5/2020 Fisker et al.
2020/0179089 A1 6/2020 Serval et al.
2020/0188180 A1 6/2020 Akbari et al.
2020/0214566 A1 7/2020 Allen et al.
2020/0214637 A1 7/2020 Brownhill et al.
2020/0214817 A1 7/2020 Shanjani et al.
2020/0222597 A1 7/2020 Askem et al.
2020/0237218 A1 7/2020 Irazoqui et al.
2020/0253786 A1 8/2020 Harrison et al.
2020/0253787 A1 8/2020 Hoglund et al.
2020/0260066 A1 8/2020 Liu
2020/0261629 A1 8/2020 Hunt et al.
2020/0280680 A1 9/2020 Nichols
2020/0281480 A1 9/2020 Tran
2020/0281512 A1 9/2020 Grubb et al.
2020/0281529 A1 9/2020 Grubb et al.
2020/0289329 A1 9/2020 Cole et al.
2020/0289347 A1 9/2020 Gowans et al.
2020/0294228 A1 9/2020 Hu et al.
2020/0297244 A1 9/2020 Brownhill et al.
2020/0297255 A1 9/2020 Martinez et al.
2020/0312453 A1 10/2020 Räisänen et al.
2020/0315488 A1 10/2020 Rogers et al.
2020/0334813 A1 10/2020 Salah et al.
2020/0337642 A1* 10/2020 Garai ................ A61B 5/14532
2020/0372647 A1 11/2020 Moore
2021/0027897 A1 1/2021 Rasochova
2021/0073990 A1 3/2021 Jeong et al.
2021/0142888 A1 5/2021 Adiri et al.
2021/0145359 A1 5/2021 Hunt
2021/0169417 A1 6/2021 Burton
2021/0192295 A1 6/2021 Stewart et al.
2022/0061671 A1* 3/2022 Dacosta ............... A61B 5/0013
2022/0142484 A1 5/2022 DiMaio et al.
2022/0210332 A1 6/2022 Nichols
2022/0215545 A1 7/2022 Adiri et al.
2022/0269064 A1 8/2022 Duckett, III
2022/0346650 A1 11/2022 Novak et al.
2022/0369932 A1 11/2022 Askem et al.
2022/0399123 A1* 12/2022 Nichols .................. A61F 13/05
2023/0158283 A1 5/2023 Gao et al.
2023/0172758 A1 6/2023 O'Keeffe
2023/0181042 A1 6/2023 Fan et al.
2023/0215582 A1 7/2023 Nichols
2023/0215583 A1 7/2023 Nichols
2024/0005501 A1 1/2024 Wang et al.
2024/0046419 A1 2/2024 Rutenberg et al.
2024/0050280 A1 2/2024 Hartwell et al.
2024/0087116 A1 3/2024 Jayaraman et al.
2024/0096468 A1 3/2024 Clark
2024/0108290 A1 4/2024 Jeon
2024/0115794 A1 4/2024 Quintanar
2024/0164704 A1 5/2024 Burnam et al.
2024/0180751 A1 6/2024 Meyer et al.
2024/0189500 A1 6/2024 Brearley et al.
2024/0215905 A1 7/2024 Freeman et al.
2024/0233415 A1 7/2024 Hoffman
2024/0268751 A1 8/2024 Meguid et al.
2024/0268935 A1 8/2024 Pesach et al.
2024/0277210 A1 8/2024 Wade
2024/0340625 A1 10/2024 Moore et al.
2024/0341675 A1 10/2024 Ho et al.

(56) References Cited

U.S. PATENT DOCUMENTS

| | | | |
|---|---|---|---|
| 2024/0341711 | A1 | 10/2024 | Jeraj et al. |
| 2024/0350797 | A1 | 10/2024 | Jiang et al. |
| 2024/0354935 | A1 | 10/2024 | Tokisue et al. |
| 2024/0366146 | A1 | 11/2024 | Bandodkar et al. |
| 2024/0366930 | A1 | 11/2024 | Rolandi et al. |
| 2024/0371098 | A1 | 11/2024 | Lipkewich Provoledo et al. |
| 2024/0395413 | A1 | 11/2024 | Nichols |
| 2024/0398630 | A1 | 12/2024 | Xu et al. |
| 2025/0049323 | A1 | 2/2025 | Perrone et al. |
| 2025/0049383 | A1 | 2/2025 | Wissel et al. |
| 2025/0054599 | A1 | 2/2025 | Janicak |
| 2025/0057470 | A1 | 2/2025 | Guido-Sanz et al. |
| 2025/0063245 | A1 | 2/2025 | Talbert et al. |
| 2025/0064645 | A1 | 2/2025 | LeVeen et al. |
| 2025/0073084 | A1 | 3/2025 | Lutz et al. |
| 2025/0082261 | A1 | 3/2025 | Williams et al. |
| 2025/0135093 | A1 | 5/2025 | Liu et al. |
| 2025/0166837 | A1 | 5/2025 | Agu et al. |
| 2025/0186762 | A1 | 6/2025 | Asefifeyzabadi et al. |
| 2025/0204779 | A1 | 6/2025 | Marois et al. |
| 2025/0204785 | A1 | 6/2025 | DaCosta et al. |
| 2025/0221659 | A1 | 7/2025 | Nichols et al. |
| 2025/0239343 | A1 | 7/2025 | Pesala et al. |
| 2025/0360261 | A1 | 11/2025 | Pratt et al. |

FOREIGN PATENT DOCUMENTS

| | | | |
|---|---|---|---|
| JP | 2017-99428 | A | 6/2017 |
| WO | WO 2014/147532 | A1 | 9/2014 |
| WO | WO 2020/264423 | | 12/2020 |
| WO | WO 2022/266070 | A1 | 12/2022 |
| WO | WO 2025/151342 | A1 | 7/2025 |

OTHER PUBLICATIONS

Kristiansen 2018 report in Media.com, https://medium@sorenlind/a-deep-convolutional-denoising-autoencoder-for-image-classification-26c77d3b88e; 2018.

Wang et al., "A Unified Framework for Automatic Wound Segmentation and Analysis with Deep Convolutional Neural Networks," 2015 37th Annual International Conference of the IEEE Engineering in Medicine and Biology Society, 2015, pp. 2415-2418.

Wounds UK 2021, https://wounds-uk.com/wp-content/uploads/sites/2/2023/02/191ac9b79f47de2896cf1a30f39037f5, 2021.

Canfield Scientific, Reveal Imager, website accessed dated Sep. 2, 2016.

Canfield Scientific, VISIA, website accessed dated Sep. 2, 2016.

Salzano, Megan. "Philips Develops Connected Home Health Care System." Homeworld Business. Dated Sep. 12, 2016. 111-112.

Stella, Rick, "Onvi's Smart Toothbrush Features a Live Video Feed of Your Mouth While You Brush." Digital Trends, Dated May 19, 2016 (accessed Aug. 28, 2019 using the internet archive way back machine).

International Search Report and Written Opinion for Application No. PCT/US2020/031717 dated Jul. 30, 2020 in 6 pages.

International Search Report and Written Opinion for Application No. PCT/2025/010295, dated Mar. 3, 2025 in 10 pages.

Invitation to Pay Additional Search Fees issued for PCT Application No. PCT/US2022/033392, dated Aug. 22, 2022, in 3 pages.

International Preliminary Report on Patentability and Written Opinion for PCT Application No. PCT/US2022/033392, dated Dec. 28, 2023, in 10 pages.

* cited by examiner

WEARABLE MEDICAL MODULE FOR WOUND TREATMENT, IMAGING, MONITORING AND ANALYSIS BASED ON IMAGES OF WOUND

CROSS-REFERENCE TO RELATED APPLICATIONS

The present application claims priority to U.S. Provisional Patent Application No. 63/618,811, filed on Jan. 8, 2024 and titled "CONNECTED BODY SURFACE MONITORING MODULE WITH CAMERA ARRAY," U.S. Provisional Patent Application No. 63/734,169, filed on Dec. 15, 2024 and titled "SYSTEM FOR MONITORING A WOUND COMPRISING A WEARABLE MEDICAL MODULE," and U.S. Provisional Patent Application No. 63/734,291, filed on Dec. 16, 2024 and titled "SYSTEM FOR MONITORING A WOUND COMPRISING A WEARABLE MEDICAL MODULE." Any and all applications listed or referenced in this paragraph are hereby incorporated by reference and made part of this specification under 37 C.F.R. § 1.57. Additionally, any and all applications for which a foreign or domestic priority claim is identified in the Application Data Sheet, or any correction thereto, are hereby incorporated by reference and made part of this specification under 37 C.F.R. § 1.57.

BACKGROUND

Field

This application relates, in general, to a body care device with a sensor device, and in one arrangement, to a wearable body surface monitoring device with a plurality of cameras.

Description of the Related Art

There exist various body surface care devices. For example, some devices are used for analysis of skin, such as devices that provide monitoring through imaging and volume measurements.

SUMMARY

This disclosure is related to methods, devices, and systems for wearable body surface devices or modules that can be used for treatment and/or analysis of a body surface region of a patient. The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices, and methods for wearable body surface devices.

The following disclosure describes non-limiting examples of some embodiments of connected body surface monitoring modules. For instance, other embodiments of the disclosed systems and methods may or may not include the features described herein. Any of the features of the disclosed systems and methods may be combined, in whole or in part. The disclosed systems and methods may include additional or fewer features than described herein or be combined with different features than the examples described. Moreover, disclosed advantages and benefits can apply only to certain embodiments and should not be used to limit the disclosure.

In some aspects, the techniques described herein relate to a system including: a wearable medical article configured to be placed over a wound on a body surface of a patient; and a module configured to be embedded within the wearable medical article, wherein the module includes: one or more optical sensors configured to generate image data of a body surface region of a wearer of the wearable medical article; and a wireless network interface configured to transmit the image data. In some aspects, the techniques described herein relate to a system including: a wearable medical article configured to be placed over a body surface region of a patient; and a module configured to be mounted to the wearable medical article, wherein the module includes: at least one outer portion including at least one external sidewall and at least one distal surface, the at least one external sidewall including a plurality of notches configured to allow the at least one outer portion to at least partially follow a contour of the body surface region of the patient; a proximal portion including a first transparent area, the first transparent area configured to allow visible light to pass through the first transparent area towards the body surface region of the patient; an array of one or more optical sensors configured to image a sub-region of a body surface region of a patient, each optical sensor configured to operate in conjunction with one or more light sources; a light shield configured to prevent light shunts between one or more light sources operating in conjunction with each optical sensor; a diffuser configured to diffuse light from the one or more light sources towards the body surface region of the patient; at least one polarizer configured to reduce glare from light reflected towards each optical sensor; and a wireless network interface configured to transmit data.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawing, can be arranged, substituted, combined, and designed in a wide variety of different configurations, all of which are explicitly contemplated and make part of this disclosure.

FIG. 18 shows several images: (i) a hypothetical color image (e.g., RGB image) of a body surface region and a wound that produces a rendering consistent with how the wound would appear to a physician examining the body surface region with their own eyes in an in-person visual inspection (ii) a hypothetical near infrared (NIR) image of the body surface region and wound and (iii) a hypothetical long-wave infrared thermal image of the body surface region and wound.

FIG. 19 shows a pair of images: (i) a hypothetical color image (e.g., RGB image) of a body surface region and a wound that produces a rendering consistent with how the wound would appear to a physician examining the body surface region with their own eyes in an in-person visual inspection and (ii) a hypothetical multispectral image of the body surface region and wound produced using multiple infrared bands.

DETAILED DESCRIPTION

Figure 1:
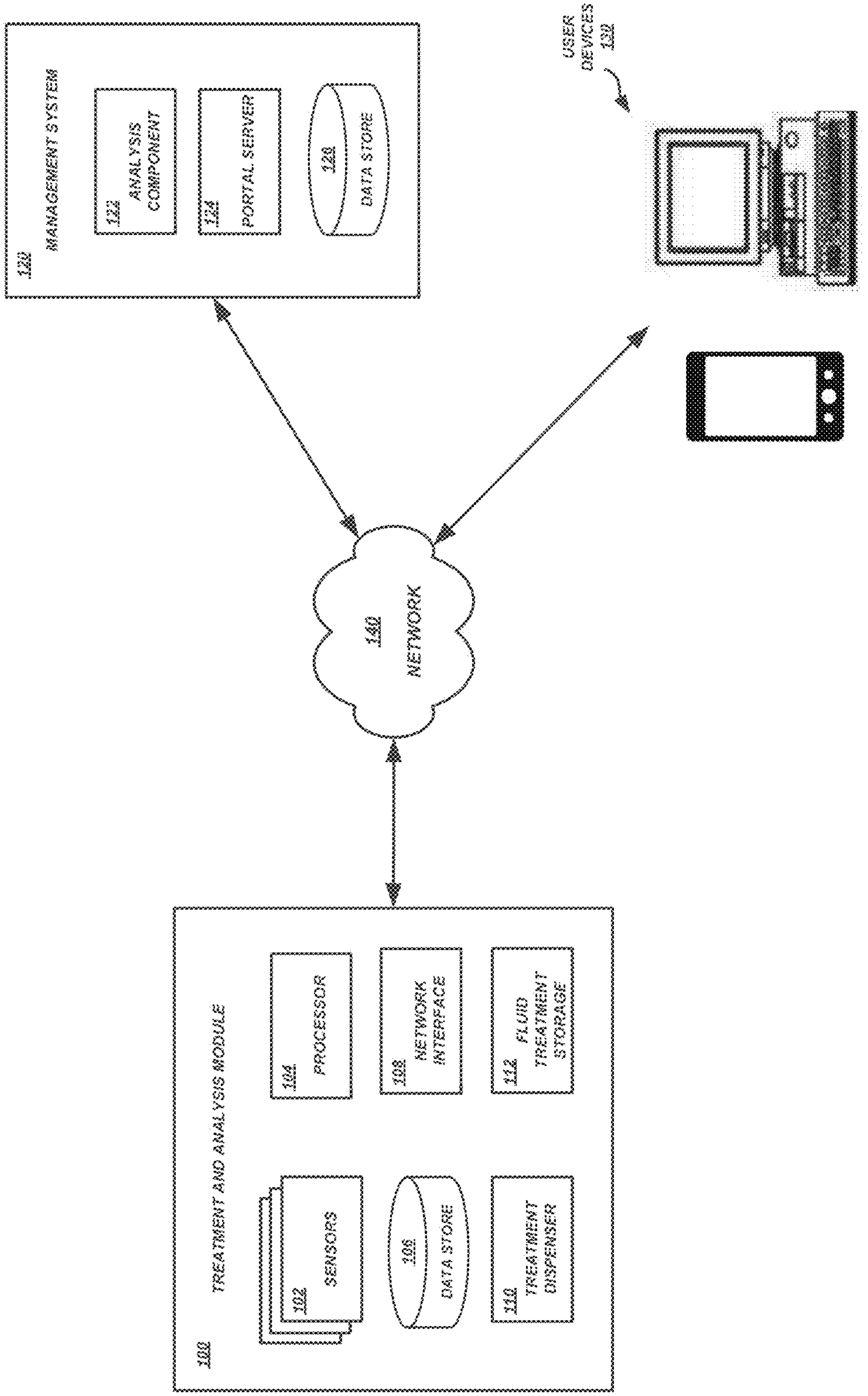
FIG. 1 is a diagram of a network environment including a treatment and analysis system, a management system, and one or more user devices according to some embodiments.

The present disclosure is directed to a wearable treatment and analysis system that is positioned on or near a body surface region of interest. The module provides remote access to sensor data, treatment administration, and/or other health care regimens via a network connection with a user device and/or management system.

Some conventional systems use sensors to measure aspects of body surface regions. Other conventional systems facilitate administration of treatment to body surfaces. However, such systems may not be remotely accessible and/or controllable. Moreover, use of wearable medical articles such as bandages, casts, and the like may inhibit use of such sensor systems and treatment systems.

Some aspects of the present disclosure address one or more of the issues noted above, among others, by providing a treatment and analysis system configured to be mounted to a bandage, wrap, cast, or other wearable medical article and positioned in proximity to a body surface region of interest, such as a wound (e.g., from an injury, disease, or surgery). The treatment and analysis system is remotely accessible to facilitate access to sensor data, treatment instructions, and the like. Thus, the treatment and analysis system aids health care professionals in monitoring and managing the treatment for post-surgical patients or patients with wounds or other skin conditions without removing the bandage, wrap, or cast. The remote monitoring and treatment management provided by the treatment and analysis system also allows for accelerated patient discharge from medical facilities.

Additional aspects of the present disclosure provide an improved imaging system of a wearable treatment and analysis system. The imaging system may include a plurality of optical sensors configured to image the body surface region. Each optical sensor may be configured to operate in conjunction with an associated illumination system, such as one or more light sources arranged adjacent the optical sensor. Each of the plurality of optical sensors and associated illumination systems may be configured to illuminate and image a sub-region of the body surface region of interest. Advantageously, the plurality of optical sensors and associated illumination systems may be configured to operate separately and/or in sequence so as to reduce power consumption requirements of the module. The output of the optical sensors may be combined into a single image for analysis. Advantageously, using a plurality of optical sensors can facilitate greater resolution and image quality of the body surface region of interest over the use of a single optical sensor, in particular at the edges of the body surface region or at the edges of the field of view of individual optical sensors.

Additional aspects of the present disclosure provide arrangement of the plurality of optical sensors on a rigid-flex circuit assembly having rigid components coupled by flexible components. In some implementations, each of the plurality of optical sensors may be arranged on a separate rigid component of the rigid-flex circuit assembly such that each optical sensor and/or rigid component can move with respect to other optical sensors, facilitating flexibility and movement of the module overall.

Additional aspects of the present disclosure provide a light shield configured to be arranged with respect to the plurality of optical sensors and/or associated illumination systems. The light shield may include a grid configured to run between optical sensor and/or illumination system arrangements and act as a shunt, providing a low-resistance path for electrical current so as to divert current away from other components arranged on the circuit board and prevent damage to other electronics.

Additional aspects of the present disclosure provide one or more optical components configured to improve illumination and/or image quality received from the plurality of optical sensors. For example, one or more optical components may include, but are not limited to a diffuser, such as a transmissive diffuser, configured to diffuse light transmitted from each illumination system towards the body surface region of the patient. In another example, one or more optical components may include, but are not limited to a polarizer configured to reduce glare in the image data obtained by the one or more optical sensors.

Additional aspects of the present disclosure provide a module having a plurality of layered components, wherein the module is configured to at partially flex to conform to a contour of the body surface region of interest when applied to the wearer or patient. In some examples, the plurality of layered components may include outer components such as a top preform and/or foam structure composed of a material having a degree of flexibility. The outer components may additionally or alternatively include a plurality of notches or cutouts configured to improve flexibility of the module, improving wear time and comfort of the module for the wearer.

Additional aspects of present disclosure provide one or more magnetized components of the module. The one or more magnetized components may be configured to help secure the wearable treatment and analysis system with a wound dressing.

Additional aspects of the present disclosure provide automated analysis of sensor data to detect body surface conditions. In some embodiments, machine learning models may be trained and used to detect body surface conditions (e.g., wounds, diseases, etc.), to determine the severity of the conditions, and/or to evaluate the change in the body surface conditions over time. For example, image analysis models may be used to classify images as depicting various body surface conditions. As another example, scoring models may be used to grade the degree and/or severity of the body surface conditions. In some embodiments, different machine learning models may be trained and targeted for use in classifying or otherwise evaluating different types of wounds, such as wounds from different types of injuries and/or surgeries. For example, sensor data from a particular treatment and analysis system regarding a particular type of wound may be evaluated using one machine learning model or set of models, while sensor data from a different treatment and analysis system regarding a different type of wound may be evaluated using a different machine learning model or set of models.

Further aspects of the present disclosure provide wearable medical articles and/or treatment and analysis system configured for particular types of wounds or other applications. In some embodiments, a treatment and analysis system configured for a particular type of wound may include a particular set of one or more sensors that provide data that is advantageous in monitoring and/or treating the particular type of wound. A treatment and analysis system configured for a different type of wound may include a different set of sensors that provide data advantageous in monitoring and/or treating the different type of wound. The sets of sensors may be different such that one set of sensors may include additional, fewer, and/or alterative sensors or sensor configurations than the other set of sensors. Differences between different wearable medical articles and/or treatment and analysis systems are not necessarily limited to different sensor configurations. In some embodiments, a wearable medical article and/or treatment and analysis system may be sized and/or shaped to target or be suitable for a particular type of wound. In some embodiments, a wearable medical article and/or treatment and analysis system may be sized, shaped, or otherwise configured for robotic placement. For example, a treatment and analysis system may include features such as structural registration points, alignment aids, or the like to facilitate being held, manipulated, and placed by a medical robot onto or near a wound.

Various aspects of the disclosure will now be described with regard to certain examples and embodiments, which are intended to illustrate but not limit the disclosure. Although the examples and embodiments described herein will focus, for the purpose of illustration, on specific devices, data, treatments, and algorithms, one of skill in the art will appreciate the examples are illustrative only, and are not intended to be limiting, essential, or exhaustive. In addition, any feature, process, device, or component of any embodiment described and/or illustrated in this specification can be used by itself, or with or instead of any other feature, process, device, or component of any other embodiment described and/or illustrated in this specification.

Example Network Environment for Remote Access to Treatment and Analysis System

FIG. 1 shows a network environment including a treatment and analysis system 100, a management system 120, and one or more user devices 130. The individual devices may communicate via one or more communication networks 140.

A communication network 140—also referred to simply as a "network"—may be a publicly accessible network of linked networks, possibly operated by various distinct parties, such as the internet. In other embodiments, a network 140 may include a private network, personal area network, local area network, wide area network, cable network, satellite network, cellular telephone network, etc. or a combination thereof, some or all of which may or may not have access to and/or from the internet.

The treatment and analysis system 100 may be, or be part of, a personal care system. The treatment and analysis system 100 may include various modules, components, and data stores to implement monitoring of characteristics of a user tissue or other body surface region (e.g., epidermis, oral mucosa, dental enamel, etc.), application of treatments (e.g., topical fluids, ozone, ultraviolet light, negative pressure wound therapy, etc.), and communication of monitoring and treatment information to and/or from other devices and systems, such as the management system 120 and/or user devices 130.

The treatment and analysis system 100 may include one or more sensors 102 to monitor and generate data regarding user skin characteristics. In some embodiments, the one or more sensors 102 may include a visualization element, such as a camera sensor, to capture images and/or generate other visualization data regarding the skin of a user. Such visualization data may be used to monitor a wound or other skin aspect over time, to diagnose a skin condition, to determine a treatment for a skin condition, and/or to monitor the treatment of a skin condition over time. In some embodiments, the one or more sensors 102 may also or alternatively include a temperature sensor to determine the temperature of the user's body surface region and/or the ambient temperature. In some embodiments, the one or more sensors 102 may also or alternatively include an accelerometer to assess movements and activities of the patient. In some embodiments, the one or more sensors 102 may also or alternatively include a pH sensor to determine the pH level of the user's body surface region. In some embodiments, the one or more sensors 102 may also or alternatively include a moisture sensor to determine the moisture content of the user's body surface region and/or the ambient moisture around a location of the user's body surface region. In some embodiments, the one or more sensors 102 may also or alternatively include a pressure sensor to determine the pressure, such as pressure within a cast, bandage, or other enclosure to which the treatment and analysis system 100 is mounted. The example sensors 102 described herein are illustrative only, and are not intended to be limiting, required, or exhaustive of the sensors 102 that may be included in a treatment and analysis system 100. In some embodiments, one treatment and analysis system 100 may be configured for use with a particular type of suture site or other wound, and may include a particular set of one or more sensors 102 that provide data that is advantageous in monitoring and/or treating the particular type of wound. Another treatment and analysis system configured for a different type of suture site or other wound may include a different set of sensors (e.g., additional, fewer, and/or alterative sensors or sensor configurations).

The treatment and analysis system 100 may include a processor 104, such as a system on a chip ("SOC") or other microprocessor to process data and commands. In some embodiments, the processor 104 may process data from one or more sensors 102 and/or the data store 106, execute one or more analysis or detection algorithms, receive and execute commands from other devices via a network interface 108, or the like. In some embodiments, the data store 106 may be a substantially persistent data store, such as flash memory, hard disk, or the like. The network interface 108 may be a wired or wireless network interface, such as a network adapter card and/or a wireless antenna (e.g., a Wi-Fi antenna, a Bluetooth® antenna, etc.).

The treatment and analysis system 100 may include components to store and administer treatment to the body surface region of a user. The treatment components may be part of the same module as an analysis system or a separate module. For example, treatment may be a topical fluid, such as a spray, lotion, ointment, or gas. The fluid treatment may be stored in a fluid treatment storage 112, and dispensation of the fluid treatment may be performed using a treatment dispenser 110. In some embodiments, the fluid treatment storage 112 may be a fluid-tight container in fluid communication with the treatment dispenser 110. The treatment dispenser 110 may include an aperture through which fluid from the fluid treatment storage 112 can be dispensed onto a body surface region of a user. In some embodiments, the treatment dispenser 110 may include or be controlled by a mechanical actuator to actively expel fluid treatment (e.g., to urge fluid from a nozzle) or to permit the release of pressurized fluid treatment (e.g., to open a valve to allow fluid to pass). As another example, treatment may include waveform-based treatments, such as ultraviolet light or ultrasound. The treatment dispenser 110 for such treatments may include corresponding emission devices, such as ultraviolet light emitting diodes ("LEDs") and/or ultrasonic transducers.

In some embodiments, the treatment and analysis system 100 may be a removable component or a plurality of components of a home-use hand-held personal care device such as, for example, a facial beauty device or hair apparatus. With reference to an illustrative embodiment of such a home-use hand-held personal care device (disclosed in U.S. Patent Application Publication No. 2020/0280680, now U.S. Pat. No. 11,122,206, which is incorporated by reference herein and forms part of this disclosure), the personal care device may include a platform that allows for application of a various modules. The platform may be adapted to incorporate aspects of the present disclosure, such as permitting application of the treatment and analysis system 100 instead of, or in addition to, a separate camera, and/or a second treatment dispenser for other treatments (e.g., a brush, an energy-delivery applicator, etc.). A user can attach a module to the personal care device at the platform, analyze and/or treat skin or other body surface region with the personal care device using the attached module, remove the module from the platform, attach a second module at the platform, etc. In some embodiments, the treatment and analysis system 100 may be configured for permanent or semi-permanent incorporation within an exterior housing of personal care devices. For example, the sensor(s) 102, processor 104, data store 106, and/or network interface 108 may be integrated into or coupled to a circuit board. In this configuration, the circuit board assembly and other components of the system 100 may be installed within the housing of a personal care device, such as a negative pressure wound therapy device, optical coherence tomography device, or micro-elastography device.

In some embodiments, the treatment and analysis system 100 may be a removable component of a personal wound care device, such as a bandage or cast. The treatment and analysis system 100 may be removably integrated with, mounted to, or otherwise attached to the personal wound care device and positioned on or near a region of interest, such as a suture site or other wound. The position may be selected to facilitate visualization of the region of interest (e.g., via a camera sensor), monitor other aspects of the region of interest (e.g., via other sensors such as a temperature and/or moisture sensor), and/or apply fluid treatment to the region of interest. Examples of personal wound care devices are described below.

In some embodiments, treatment and analysis system 100 (or a wearable medical article to which the treatment and analysis system 100 is coupled) may be sized and/or shaped to target a particular type of wound. For example, one or more dimensions (e.g., length, width, height) of the treatment and analysis system 100 may be configured based on one or more dimensions of, or the severity or type of wound present on, the body surface region on which the treatment and analysis system 100 is to be placed. In some embodiments, a treatment and analysis system 100 may be sized, shaped, or otherwise configured for robotic placement. For example, a treatment and analysis system 100 may include features such as structural registration points, alignment aids, or the like to facilitate being held, manipulated, and placed by a robotic surgical system onto a body surface region.

Figure 2:
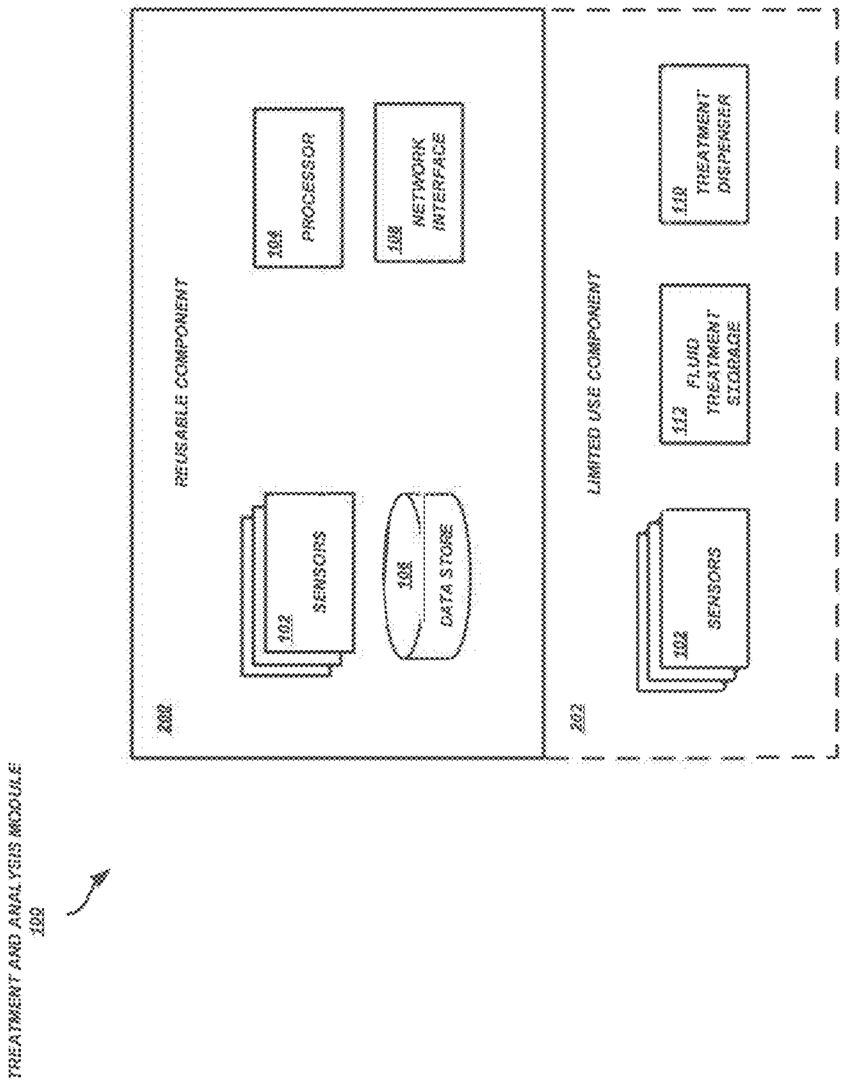
FIG. 2 is a diagram of a treatment and analysis system with a reusable component and a limited use component according to some embodiments.

In some embodiments, the treatment and analysis system 100 or components thereof may be designed for a single use or otherwise for a limited quantity or duration of use. For example, if portions of the treatment and analysis system 100 come into physical contact with a region of a user's body surface (e.g., a wound, dental enamel, or oral mucosa), the treatment and analysis system 100 as a whole may be limited use. As another example, components of the portions of the treatment and analysis system 100 that contact the body surface region may be limited use, while other portions of the treatment and analysis system may be reusable. As a further example, portions of the treatment and analysis system 100, such as the fluid treatment storage 112, may include exhaustible resources. Such portions may be refillable or replaceable. Examples and details of limited-use treatment and analysis system s 100 or components thereof are shown in FIG. 2 and described in greater detail below.

The management system 120 may include various components for providing the features described herein. Illustratively, the management system 120 may include an analysis component 122 to process data received from the treatment and analysis system 100 (e.g., sensor data, treatment data, etc.), determine treatment instructions, and the like. The management system 120 may also include a portal server 124 that may be configured to provide access to results generated by the analysis component 122, receive instructions or other input regarding the analysis or treatments, and the like. In some embodiments, the portal server 124 may be, include, or communicate with an electronic medical record ("EMR") system or electronic health record ("EHR") system. Each individual treatment and analysis system 100 (or a component thereof, such as a limited use component or a reusable component) may be associated with a different unique identifier, such as a numeric or alphanumeric serial number. The identifier may be associated with a particular patient through an entry or corresponding identifier in the patient's EMR or EHR, thereby allowing sensor data or other data from the treatment and analysis system 100—and instructions to the treatment and analysis system 100—to be handled on a patient-by-patient basis. The management system 120 may also include a data store 126 that maintains data regarding treatments, results, users, and the like. The example components and data stores of the management system 120 shown in FIG. 1 are illustrative only, and are not intended to be limiting, required, or exhaustive. In some embodiments, a management system 120 may have fewer, additional, and/or alternative components and data stores.

The management system 120 may be implemented on one or more physical server computing devices that provide computing services and resources to treatment and analysis systems 100 and user devices 130. In some embodiments, the management system 120 (or individual components thereof, such as the analysis component 122, portal server 124, data store 126, etc.) may be implemented on one or more host devices, such as blade servers, midrange computing devices, mainframe computers, desktop computers, or any other computing device configured to provide computing services and resources. For example, a single host device may execute one or more analysis components 122, one or more portal servers 124, one or more data stores 126, some combination thereof, etc. The management system 120 may include any number of such hosts.

In some embodiments, the features and services provided by the management system 120 may be implemented as web services consumable via communication network 140. In further embodiments, the management system 120 (or individual components thereof) is provided by one or more virtual machines implemented in a hosted computing environment. The hosted computing environment may include one or more rapidly provisioned and released computing resources, such as computing devices, networking devices, and/or storage devices. A hosted computing environment may also be referred to as a "cloud" computing environment.

The individual user devices 130 may be any of a wide variety of computing devices, including personal computing devices, terminal computing devices, laptop computing devices, tablet computing devices, electronic reader devices, wearable computing devices, mobile devices (e.g., smart phones, media players, handheld gaming devices, etc.), and various other electronic devices and appliances. A user device 130 may be used to access data generated by a treatment and analysis system 100 or management system 120, to provide data and/or instructions to a treatment and analysis system 100 or management system 120, etc.

The treatment and analysis system 100, also referred to herein as one or more "wearable module(s)" or "module(s)," can be controlled or monitored by application software executing on a user device 130. In some embodiments, an individual who is wearing or operating a treatment and analysis system 100 (e.g., as part of a hand-held personal care device or a personal wound care device) may use a user device 130 to interact with the treatment and analysis system 100. In some embodiments, an individual who is remotely managing or operating a treatment and analysis system 100 (e.g., a health care professional monitoring and managing the care of a patient wearing a personal wound care device or operating a hand-held personal care device) may use a user device 130 to interact with the treatment and analysis system 100 and/or the management system 120 instead of, or in addition to, a patient interacting with the treatment and analysis system 100. In some embodiments, application software to interact with the treatment and analysis system 100 and/or management system 120 may be provided to the user device 130 over a network connection. For example, a user may enter a code or scan an encoded image (e.g., a barcode, quick response or "QR" code, or the like) and be directed to a network resource (e.g., a server on the internet or an intranet) from which the application software may be downloaded. As another example, a user may manually access a network resource and download the application software.

With reference to an illustrative embodiment, the treatment and analysis system 100 may include an application programming interface ("API"). The API can be implemented within or called by the user device 130 using the software application. It will be appreciated that the module 100, user device 130, and/or management system 120 may communicate with each other via the network 140 using specialized API calls that enable one of the modules, devices, or systems to request that another module, device, or system generate responsive data to be returned via an API response. It will be further appreciated that particular aspects or functionality of the API described herein may be implemented at different modules, devices, or systems illustrated in FIG. 1. For example, the user device 130 may implement aspects of the API related to generating user interfaces that display images captured by the module 100, while a management system 120 may implement aspects of the API that employ one or more machine learning models to analyze images provided to the management system 120 by the system 100 or user device 130. The particular module, device, or system that implements particular functionality described herein, such as functionality or features described herein as being provided by the API, may depend on the processing capabilities of the given device in the given embodiment. For example, a user device 130 may be configured to execute image analysis locally or to request that such image analysis be performed remotely at the management system 120, depending on the configuration of the management system 120, or on the processing capabilities of a particular user device 130 (e.g., desktop computer, mobile phone) on which the application is operating.

In some embodiments, an API and/or application software executing on one or more of the module 100, management system 120, or user device 130 can provide any or all of following functionalities: power on or off the module 100; take before and after images via a camera sensor of the module 100; instruct the user through the user device 130 on how to perform functions of the system 100 (e.g., take images, store or access image files, schedule treatment regimens); display images on the user device 130, singularly or side-by-side, captured by a camera sensor of the module 100; calculate and monitor measurements of aspects of a region of a user's body surface (e.g., wound area, wound volume, wound depth, wound coloration, lesion area, lesion volume, wrinkle depth, fine line frequency, epidermal layer exfoliation, skin hydration) based on data provided by one or more sensors of the module 100; and/or provide detailed images to the management system 120 or another user device 130 for evaluation. For example, the module 100 may enter a low-power or "sleep mode" until a programmed data collection frequency or time is triggered, at which the module 100 is activated to a higher-power operating mode (e.g., for image capture or generation of other sensor data). As another example, a clinician device may remotely activate the module 100 from the low-power or "sleep mode" to the higher-power operating mode (e.g., while a clinician is interacting with the patient's EMR/EHR) to review the wound's healing status on-demand in substantially real time.

The management system 120 and/or user device 130 can process images from a camera of the module 100. In some arrangements, an API can be used for capturing an image with a camera sensor 102. The camera sensor 102 can use the API to provide image data via Wi-Fi or Bluetooth to the management system 120, a user device 130, other devices, or some combination thereof. For example, application software executing on a user device 130 can allow a user to program or control the operation of the system 100 via an API. The system 100 can provide for acquisition of a digital image of a region of a user's body surface at an increased magnification, such as at a magnification of about: 2×, 10×, 50×, 400×, and various intermediate values. In some embodiments, as described in greater detail below with respect to FIG. 3, the system 100 includes a camera sensor with zoom-in functionality that increases the magnification of the camera.

In some embodiments, the system 100 includes a holographic high-resolution camera sensor configured to provide non-line-of-sight ("NLoS") imaging. For example, the camera sensor may use synthetic wavelength holography in which light is indirectly scattered onto objects, including objects that may not be imaged using a conventional camera sensor due to being partially or completely obstructed by tissue (e.g., skin, bone, muscle) or other objects. Scattered light captured by a holographic camera sensor may be used to construct an image that exposes partially or completely obscured regions of interest.

In some embodiments, the system 100 includes a three-dimensional wound assessment monitor ("3D-WAM") camera sensor system. The camera sensor system may include a single optical or camera sensor or a plurality of optical or camera sensors configured to operate in conjunction with one another to capture image data of a body surface region. Advantageously, in some instances, a camera sensor system is able to measure wound size in three dimensions. A laser, such as a vertical-cavity surface-emitting laser ("VCSEL"), works in the near-infrared spectroscopy ("NIR") range (e.g., 940 nm) to generate 2D and 3D data in one shot with a multipart image, incorporating range, intensity and confidence maps.

The system 100 may generate digital photographs that one or more user devices 130 or the management system 120 can analyze to determine information relating to a condition of the skin, such as, for example, wound size, wound shape, wound depth, wound color, debris in the wound, etc. In the case of a camera sensor system comprising a plurality of optical sensors, the digital photographs captured by each optical sensor of, for example, a sub-region of a body surface region of interest, may be combined to generate a larger image of a total body surface region of interest. Storage of images (e.g., in a data store 106 of the system 100 or a data store 126 of the management system 120) can enable presentation of "before-and-after" visual results via a user interface displayed by a user device 130. For example, a user such as a wearer of the system 100 or a health care professional can cause the system 100 to take a "before" image before treating a body surface region, then cause dispensation of treatment to the body surface region via the treatment dispenser 110, and then cause the module to take an "after" image of the body surface region. In this way, the system 100 and remote access to images captured by the system 100 can be used to provide a recovery tracker that allows a user to evaluate a treatment administered to a body surface region. For example, a user can use the system 100 to take a series of images of the body surface region over the course of time (e.g., over days, weeks, months) and compare the images to one another to evaluate whether a treatment regimen applied to the body surface region is effective at improving a condition (e.g., wound healing). In some embodiments, the system 100 can allow a user to watch live digital image and/or video feed on a user device 130.

Example Treatment and Analysis System

With reference to FIG. 2, illustrative embodiments of an example treatment and analysis system 100 will be described. In some embodiments, as shown, a portion of the treatment and analysis system 100 can be implemented as a limited use component 202. For example, the limited use component 202 may be configured to contact or otherwise be exposed to an oral surface of a user (e.g., dental enamel, dentin, oral mucosa), a wound of a user, or some other body surface region. Such exposure may be advantageous for the operation of certain components of the treatment and analysis system 100, such as one or more of the sensors 102 or a treatment dispenser 110. By implementing such components as (or as a part of) a limited use component 202, contamination via exposure to a region of a user's body surface can be minimized through limited use of the content(s). As another example, the limited use component 202 may be or include a reservoir for an exhaustible resource, such as a fluid treatment storage 112. By implementing such components as (or as a part of) a limited use component 202, mechanisms to replenish the exhaustible resource do not need to be incorporated. Rather, the limited use component 202 can be replaced with a new component 202 that has a fresh supply of the exhaustible resource.

The limited use component 202 may be removably attached to a reusable substrate for use. In some embodiments, the treatment and analysis system 100 may include a reusable component 200 to which the limited use component 202 may be removably attached. The reusable component may include additional components of the treatment and analysis system 100 that are not included in the limited use component 202 or that may be alternatives to components of the limited use component 202. For example, the reusable component may include more durable and/or expensive components of the treatment and analysis system 100, such as the processor 104, data store 106, and network interface 108. One or more sensors 102 may also be included, such as those that do not need direct contact or exposure to the body surface region of the user (e.g., a motion sensor, an ambient moisture sensor, an ambient temperature sensor). In some embodiments, one or more sensors 102 that do require exposure to the body surface region of the user may be included in the reusable component 202. For example, a camera sensor may be included the reusable component 202 due to the expense, complexity, and/or other characteristics of the camera for which limited use and replacement may not be desirable. In these arrangements, the limited use component 202 may include a protected exposure portion, such as a sealed window or filtered aperture, through which the sensor of the reusable component 200 may gain exposure to a body surface region of the user.

In certain arrangements, the reusable component 200 or the treatment and analysis system 100 as a whole can be waterproof or water-resistant, allowing the reusable component 200 or system 100 to be submerged or brought into contact with water without damage. For example, the system 100 can be adapted to allow a user to use the system 100 in a shower or a bathtub. The housing of the system 100 can form a water-tight seal that prevents water from entering the internal space of the module 100, thereby protecting the internal electronics of the system 100 from being contacted by water. The housing of the system 100 can form a water-tight seal with the personal care device to which the module is attached.

Figure 3:
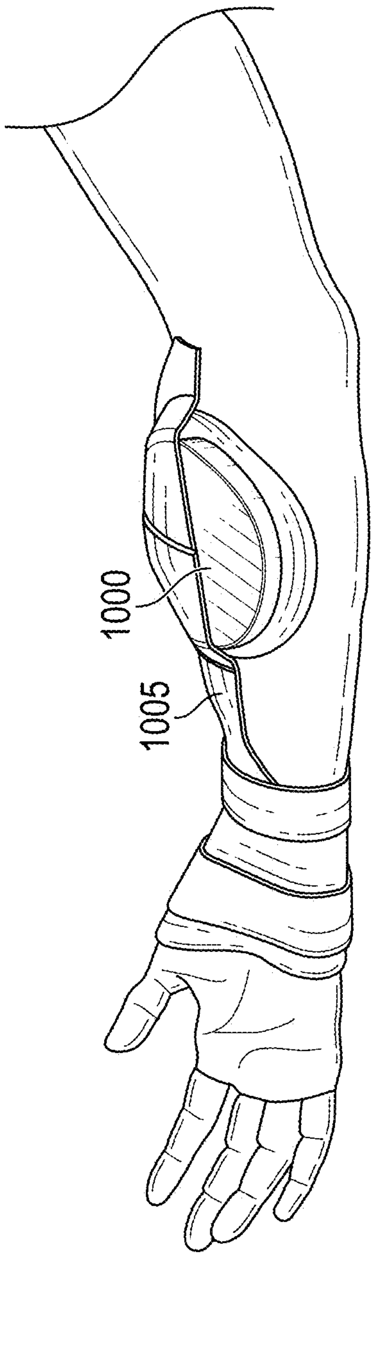
FIG. 3 is a perspective view of a module embodiment described herein, shown fully assembled and attached to a patient with a conventional wrap.

FIG. 3 illustrates an example module 1000 attached to a patient using standard adhesive bandaging 1005, such as an adhesive covering or wrap. The module 1000 may be placed on a patient, either directly on the skin, or on a dressing-based platform such as surgical foam, and then encased in a wrap, cast or other protective shell. In other embodiments, the module can be sutured to the skin, although this is less preferred.

In some embodiments, a housing of a module 1000 may be a hard, protective shell, or a flexible material. In some embodiments, the housing and internal components of the module 1000 may be formed, in whole or substantially in whole, from a material that has no or substantially no magnetic pull so that the module 100 may be permitted to remain affixed to a patient during a magnetic resonance imaging (MRI) scan, X-ray imaging, a computerized tomography (CT) scan, or the like. In some embodiments, the housing 902 of the module 100 may be formed. The housing of the module 1000 may, in whole or in part, be composed from a material configured to permit wireless communication from a network interface 108 within the housing. If the network interface 108 is or includes a high-speed wireless antenna, such as a 5G antenna, the housing may be formed of material that does not interface, or does not substantially interfere, with communications to and/or from the network interface 108. For example, the housing may be formed of or include any of the following materials from DuPont®: Crastin polybutylene terephthalate (PBT); Zytel HTN range of high-temperature polyamides; or Hytrel thermoplastic polyester elastomer.

Example Process for Use and Management of Operation of Module

Figure 4:
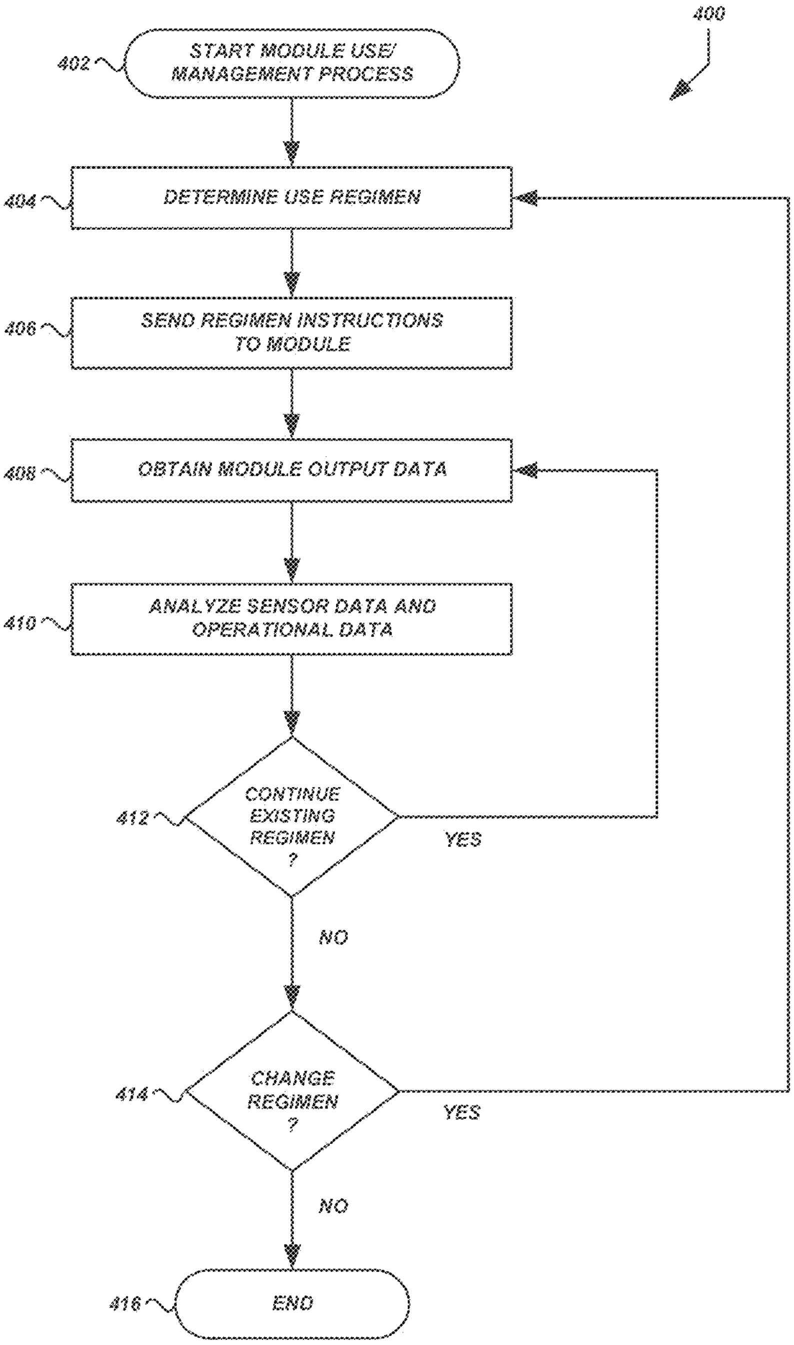
FIG. 4 is a flow diagram of an illustrative process for analyzing treatment and sensor data and implementing regimens according to some embodiments.

FIG. 4 is a flow diagram of an illustrative process 400 that may be executed to use and/or manage the operation of a treatment and analysis system or system 100. The process 400 or portions thereof may be executed by a user device 130 and/or management system 120, individually or in combination. Advantageously, execution of the process 400 allows for remote access to data generated by a treatment and analysis system 100, and remote control of operations of the treatment and analysis system 100. For example, the process 400 allows for implementation and analysis of a monitoring regimen in which sensor data is generated for analysis. As another example, the process 400 allows for implementation of a treatment regimen in which a treatment is administered to a wearer of the module 100. The wearer of the system 100 may also be referred to as a "subject" of the sensor data generated by and/or treatment administered by the module 100.

Portions of the process 400 will be described with further reference to the illustrative data flows and interactions between the treatment and analysis system 100, management system 120, clinician user device 130A, and patient user device 130B shown in FIG. 5.

The process 400 begins at block 402. The process 400 may begin in response to an event, such as when a clinician device 130A connects to the management system 120 to initiate a regimen for use of the treatment and analysis system or system 100. In some embodiments, process 400 or portions thereof may be performed on a predetermined or dynamically-determined schedule. For example, output data from the system 100 (images and/or other sensor data) may be obtained periodically, such as hourly, daily, or weekly. The system 100 may be programmed to initiate the capture and/or transfer of the output data, or another system such as the management system 120 or a user device 130 may request the output data from the module 100. In some embodiments, process 400 or portions thereof may be performed on-demand, such as when a user interacts with the module 100, a clinician device 130A, or a patient device 130B. For example, a clinician device may activate the module 100 from a low-power or "sleep mode" to a higher-power operational mode (e.g., while a clinician is interacting with the patient's EMR/EHR) to review a wound's healing status on-demand in substantially real time. In this way, process 400 may produce real time or substantially real time implementation and analysis. When the process 400 is initiated, a set of executable program instructions stored on one or more non-transitory computer-readable media (e.g., hard drive, flash memory, removable media, etc.) may be loaded into memory (e.g., random access memory or "RAM") of a computing device, such as a computing device of management system 120. In some embodiments, the process 400 or portions thereof may be implemented on multiple processors, serially or in parallel.

At block 404, the system executing the process 400 may determine a regimen for use of the module 100. In one embodiment, a regimen may specify a treatment to be administered by the module 100. For example, the system 100 may be configured to administer a topical fluid, such as a spray, lotion, or ointment. Administration of the treatment may be a one-time on-demand administration, or it may be scheduled for one or more future times according to a predetermined or dynamically determined schedule. In another embodiment, a regimen may specify sensor data to be generated, stored, and/or transmitted to a separate system such as the management system 120 or user device 130. For example, the regimen may specify a set of one or more sensor data items to be generated and transmitted. Generation and transmission of the set of sensor data items may be specified as a one-time on-demand process, or may be scheduled for one or more future times according to a predetermined or dynamically determined schedule.

Determination of the regimen may be based on a selection or other input from a user, such as a wearer of the system 100 or a health care professional. For example, a user device 130 (e.g., a clinician device 130A or a patient device 130B) may present regimen options that can be selected and implemented. A user may activate an option, and the activation may indicate determination of the particular regimen to be implemented.

In some embodiments, the regimen may be automatically generated or suggested using a recommendation algorithm. The recommendation algorithm may take input, such as information regarding the subject (e.g., demographic information, information regarding the current state of the user's body surface region being monitored and/or treated, etc.) and/or information regarding treatments used by the subject. For example, the recommendation algorithm may be a collaborative filtering algorithm, a content-based filtering algorithm, or a combination of algorithms.

In a collaborative filtering implementation, a model may be trained to generate recommendations of treatments or other regimens that were effective for similar subjects. The model may be used to evaluate information about the subject, such as features derived from the subject's demographic information and/or information regarding the current state of the user's body surface region being treated. The model may then output a recommendation of a treatment or other regimen that was effective for other subjects with same or similar features.

In a content-based filtering implementation, a model may be trained to generate recommendations of treatments or other regimens that are similar to treatments or other regimens used by the subject. The model may be used to evaluate information about the subject, such as features derived from the subject's prior treatment history (e.g., treatments that were effective) or the subject's stated treatment preferences. The model may then output a recommendation of a treatment or other regimen with the same or similar features.

At block 406, the system executing the process 400 may send regimen instructions to the module 100. In some embodiments, regimen instructions may be sent in the form of an executable function call and/or data identifying the regimen. For example, the data may represent a treatment identifier, treatment quantity, scheduled treatment time(s), sensor identifier, scheduled sensor data recording/transmission time(s), etc.

Figure 5:
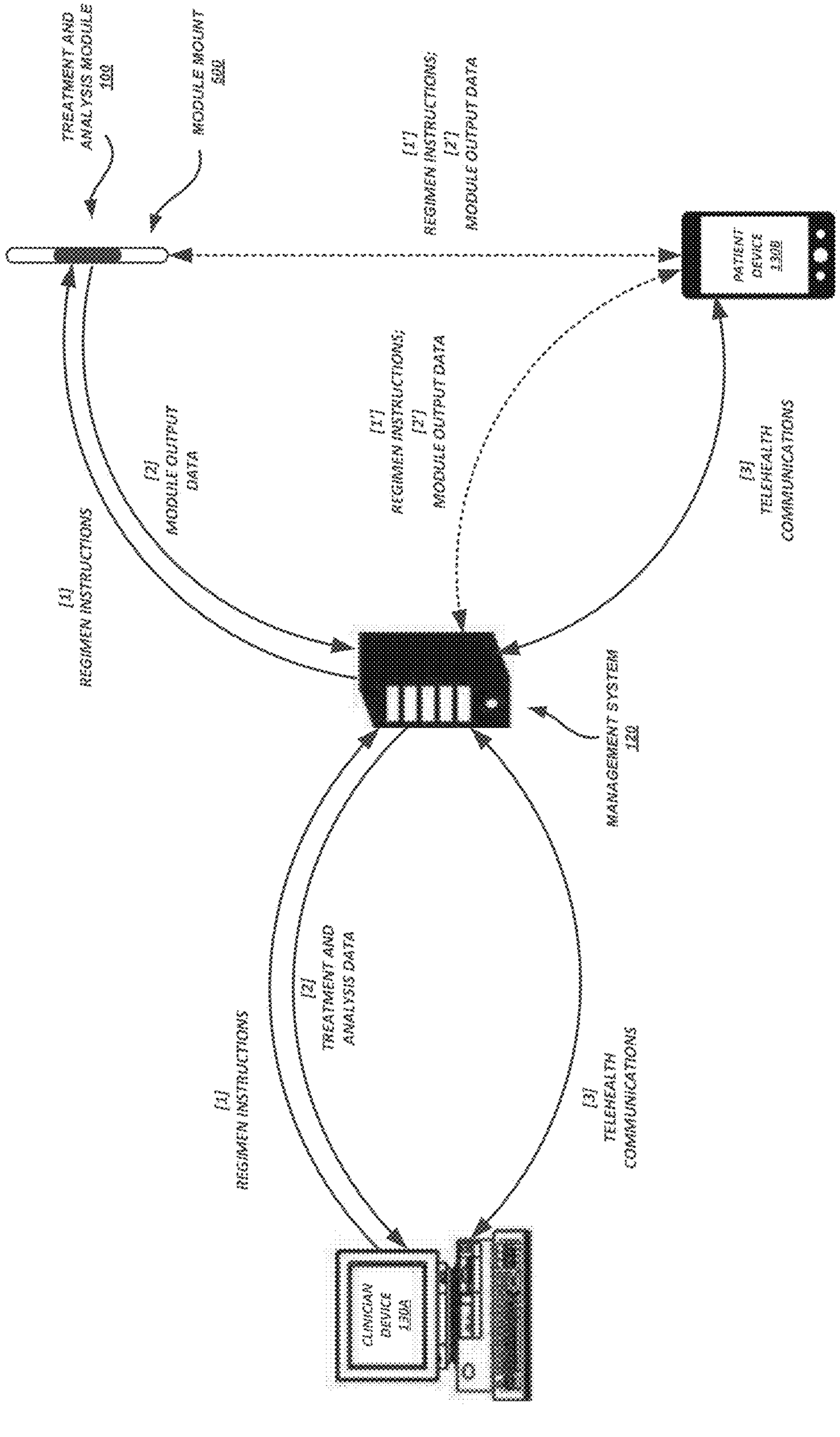
FIG. 5 is a diagram of illustrative data flows and interactions between user devices, a management system, and a treatment and analysis system according to some embodiments.

FIG. 5 illustrates an example in which a clinician device 130A generates and transmits regimen instructions to the management system 120 at [1]. The management system 120 then provides the regimen instructions to the treatment and analysis system 100. As shown, the treatment and analysis system 100 may be positioned on a subject via a module mount 500, such as a bandage, cast, strap, or other wearable medical article to which the system 100 is coupled. For example, the mount 500 may be worn such that the module 100, or individual sensors thereof (e.g., a camera sensor), is positioned over a particular body surface region of interest, such as a wound.

In some embodiments, the regimen instructions generated by the clinician device 130 may reference, include, or otherwise be associated with an identifier of a destination for the regimen instructions. For example, a unique account identifier of a user account of the wearer of the system 100 (e.g., a user account of a patient under the care of a clinician operating the clinician device 130A), or a unique identifier of the system 100 itself, may be selected or otherwise specified by the operator of the clinician device 130A. In some embodiments, the unique identifier may be numeric, or alpha-numeric. The management system 120 may maintain communication data that specifies where or how communications are to be sent to the system 100 identified in connection with the regimen instructions. For example, communication data associated with the identifier of the destination for the regimen instructions may be an internet protocol ("IP") address of a recipient, such as the system 100 or patient device 130B. Using this communication data, the management system 120 may transmit the regimen instructions. Instructions may be transmitted directly to the system 100 if the module is configured with network communication capabilities and is accessible to the management system 120. In some implementations, instructions may be transmitted to an intermediary device that is in communication with the module 100, such as the patient device 130B, indicated as [1']. A communication path between the patient device 130B and system 100 can be established to provide the regimen instructions, or data derived therefrom, to the module 100.

Returning to FIG. 4, at block 408 the system executing the process 400 may obtain data from the module 100. The data may include sensor data, data regarding a treatment administered by the module 100, other data, or some combination thereof. In some embodiments, sensor data may be or include an image of a body surface region of the wearer of the module 100, a temperature of the body surface region, an ambient temperature, a measurement of moisture of the body surface region, a measurement of ambient moisture, a measurement of pH of the body surface region, other measurements, or some combination thereof. In some embodiments, treatment data may represent a confirmation of application of the treatment, a quantity of treatment administered, or the like.

The system executing the process 400 (e.g., management system 120 or a user device 130) may obtain the data automatically, on demand, or in response to an event. For example, a clinician device 130A may request output data from the module 100. The request may be sent to the management system 120, which may provide the request to the system 100 directly or via an intermediary such as the patient device 130B, in a manner similar to that described with respect to providing regimen instructions. The module 100 may generate, access, or otherwise obtain the requested data and provide it to the requesting device. For example, as shown in FIG. 5, the module 100 may generate and provide output data (e.g., an image and/or other sensor data) at [2] to a clinician device 130A, directly or via the management system 120. As another example, the output data may be sent to the management system 120 or a different system (e.g., a dedicated EMR or EHR system) for storage with or association with an EMR or EHR of the patient. As another example, the module may generate and provide output data at [2'] to a patient device 130B, which may or may not send the output data to the clinician device 130A, directly or via the management system 120.

At block 410, the system executing the process 400 may analyze the module output data. Analysis of the module output data may be performed (e.g., at the management system or a user device 130) using one or more models to determine one or more metrics, conditions, states, and/or recommendations. In some embodiments, an image analysis model system may be used to determine a current state of a body surface region or a change over time of the body surface region, as described in greater detail below. Data regarding the current state and/or change over time of the body surface region may in some embodiments be used to generate a recommendation such as a recommendation regarding a treatment to be administered.

In some embodiments, different machine learning models may be trained and targeted for use in classifying or otherwise evaluating different types of wounds, such as wounds from different types of injuries and/or surgeries. For example, a clinician may access the management system 120 via clinician device 130A and specify a type of surgery that was performed and/or a type of wound being analyzed. The clinician may do so at various times, such as when the treatment and analysis system 100 is first configured for the patient, or when data is received for analysis. The management system 120 may select, based on the specified surgery or wound type, a model or set of models to use to analyze sensor data from the treatment and analysis system 100. Other surgeries and/or wounds may result in selection of different models, and in some cases may result in evaluation of different sensor data. To facilitate automated and consistent use of models targeted for particular surgeries or wounds, the management system 120 may maintain data that maps surgery/wound types to models, sensor data, and the like.

At decision block 412, the management system 120 or a user device 130 may determine whether to continue an existing regimen. If so, the process 400 may return to block 408 for acquisition and analysis of further module output data, such as after administration of another treatment, after passage of a period of time, etc. Otherwise, if the existing regimen is not to continue, the process 400 may proceed to decision block 414.

In some embodiments, a decision of whether to continue an existing regimen may be based on a recommendation for a treatment or other aspect of the regimen, such as a recommendation (e.g., generated as described in greater detail above with respect to block 404). If the recommended treatment and/or other aspect of the regimen is the same, the existing regimen may continue. In some embodiments, a decision of whether to continue an existing regimen may be based on a classification and/or a score representing the current state of the subject's body surface region, such as a classification and/or score generated as described in greater detail below. In some embodiments, the decision may be based on a change in classification and/or score representing the current state of the subject surface region over time. An example process for determining such a change is described in greater detail below.

The decision of whether to continue an existing regimen may be interactive. For example, classification data, scoring data, and/or treatment recommendations may be generated and displayed on an interface of a clinician device 130A or patient device 130B. A user of the device displaying the information may determine whether to continue the existing regimen, and activate a user interface control representing the decision (e.g., a button to continue or a button to stop the current regimen). Depending upon the selected option, the current regimen may be continued or stopped.

In some embodiments, as shown in FIG. 5, the clinician device 130A may communicate with the patient device 130B at [3]. The communications may include text, video, and/or audio interactions between users of the devices 130A and 130B. For example, a user of a clinician device 130A may communicate with the subject using the patient device 130B to discuss an analysis of module output data, treatment regimens, or the like. Based on these communications, the user of the clinician device 130A and/or the subject using patient device 130B may determine whether or not to continue an existing regimen, and may indicate the determination on a user interface of the respective device 130A or 130B. In some embodiments, the clinician device 130A and/or patient device 130B may prompt for or otherwise receive input regarding post-operative pain (e.g., a pain score), range of motion, swelling, total blood loss, pre- and post-operative hematocrit level differences, or the like. Such input may be stored at the clinician device 130A, patient device 130B, and/or management system 120 for use in determining and monitoring a treatment regimen.

At decision block 414, the management system 120 or a user device 130 may determine whether to change the regimen that is to be performed by the module 100. If so, the process 400 may return to block 404, where the new regimen or change to existing regimen is determined. Otherwise, if treatment is not to continue, the process 400 may terminate at block 416.

In some embodiments, a decision of whether to change an existing regimen may be based on a classification and/or a score representing the current state of the subject's body surface region, or on a change in such classification and/or score, as described above. In some embodiments, the decision of whether to continue an existing regimen may be interactive, as described above. For example, the determination may be made based on classification, scoring, or other analysis results generated and displayed on an interface of a clinician device 130A or patient device 130B, communications between a clinician device 130A and patient device 130B, etc. Based on the displayed data and/or communications, the user of the clinician device 130A and/or the patient device 130B may determine whether or not to change the existing regimen or stop the regimen.

Example Process for Image Analysis and Scoring

Figure 6:
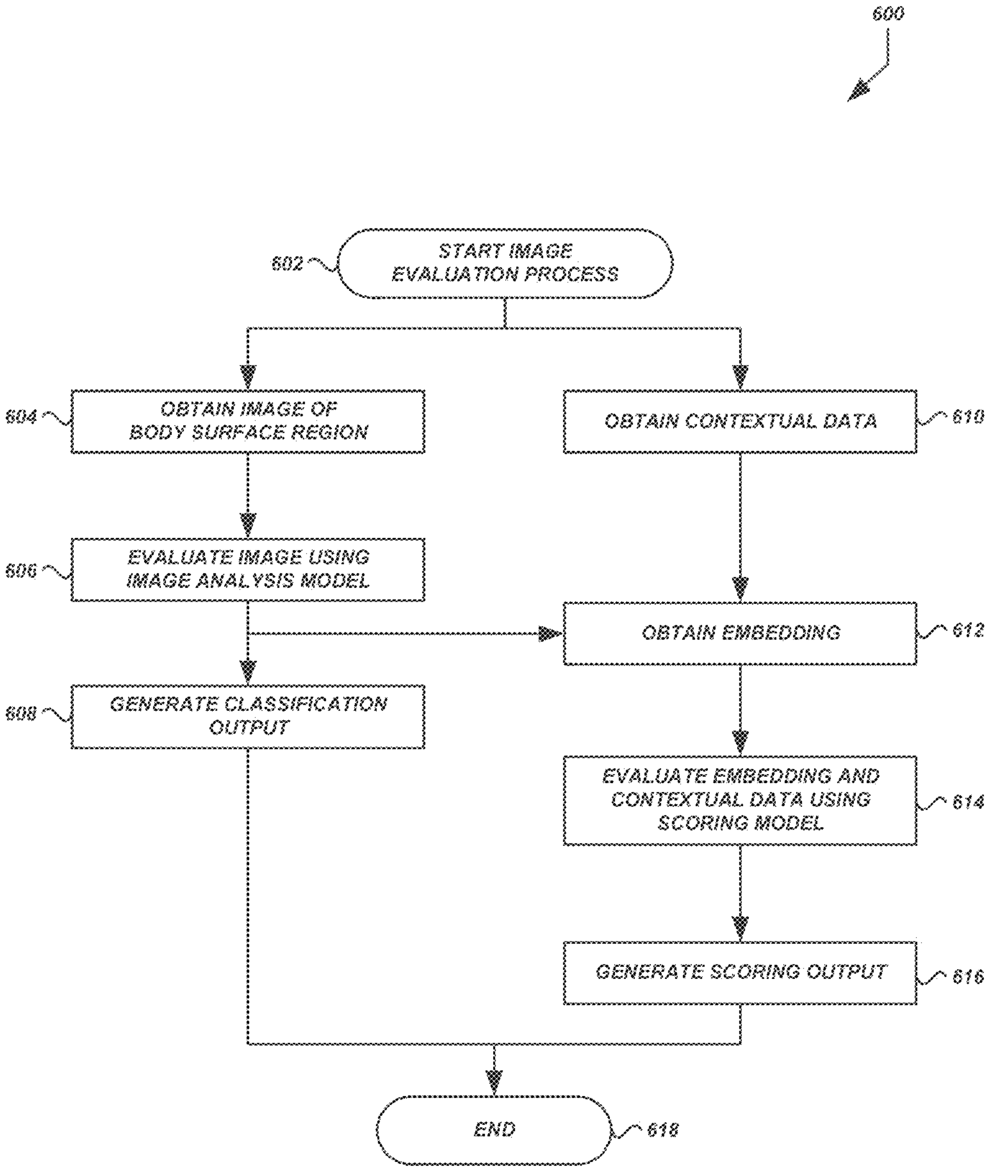
FIG. 6 is a flow diagram of an illustrative process for analyzing sensor data and contextual data according to some embodiments.

FIG. 6 is a flow diagram of an illustrative process 600 that may be executed to analyze image(s) obtained from the module 100. Analysis of an image of a patient body surface may include a comparison of the image to a database of images of "normal" results and "concerning" results, and/or use of a model trained based on such images. In some embodiments, a concerning result may cause generation of a message to the patient to submit images and analytics to a clinician (e.g., a doctor or other medical practitioner). In some embodiments, a concerning result may cause generation of a message to a clinician (e.g., rather than instructing the patient to do so).

In some embodiments, different machine learning models may be trained and targeted for use in classifying or otherwise evaluating different types of wounds, such as wounds from different types of injuries and/or surgeries. For example, a clinician may access the management system 120 via clinician device 130A and specify a type of surgery that was performed and/or a type of wound being analyzed. The clinician may do so at various times, such as when the treatment and analysis system 100 is first configured for the patient, or when data is received for analysis. The management system 120 may select, based on the specified surgery or wound type, a model or set of models to use to analyze images (and, in some cases, other sensor data) from the treatment and analysis system 100. Other surgeries and/or wounds may result in selection of different models. To facilitate automated and consistent use of models targeted for particular surgeries or wounds, the management system 120 may maintain data that maps surgery/wound types to models.

The process 600 or portions thereof may be executed by a user device 130 and/or management system 120, individually or in combination. For example, process 600 may be performed to analyze module output data from the module 100, such as during block 410 of process 400. Portions of the process 600 will be described with further reference to the illustrative image analysis model system 700 shown in FIG. 7.

The process 600 begins at block 602. The process 600 may begin in response to an event, such as when the management system 120 obtains an image captured by the module 100, when a user device 130 connects to the management system 120 to initiate analysis of an image (or set of images) captured by the module 100, or on a predetermined or dynamically-determined schedule. In some embodiments, process 600 or portions thereof may be performed on a predetermined or dynamically-determined schedule. For example, output data from the system 100 (images and/or other sensor data) may be obtained periodically, such as hourly, daily, or weekly. The system 100 may be programmed to initiate the capture and/or transfer of the output data, or another system such as the management system 120 or a user device 130 may request the output data from the module 100. In some embodiments, process 600 or portions thereof may be performed on-demand, such as when a user interacts with the module 100, a clinician device 130A, or a patient device 130B. For example, a clinician device may activate the module 100 from a low-power or "sleep mode" to a higher-power operational mode (e.g., while a clinician is interacting with the patient's EMR/EHR) to review a wound's healing status on-demand in substantially real time. In this way, process 600 may produce real time or substantially real time analysis. When the process 600 is initiated, a set of executable program instructions stored on one or more non-transitory computer-readable media (e.g., hard drive, flash memory, removable media, etc.) may be loaded into memory (e.g., random access memory or "RAM") of a computing device, such as a computing device of management system 120. In some embodiments, the process 600 or portions thereof may be implemented on multiple processors, serially or in parallel.

At block 604, the system executing the process 600 may obtain one or more images of a body surface region. The image may be captured by the system 100 and provided to a user device 130 and/or the management system 120. For example, an image of a region of a patient's skin may be captured, such as an image of a wound or skin condition. As another example, an image of a region of a patient's mouth may be captured, such as an image of an enamel surface or oral mucosa. In some embodiments, the images may be captured on demand, such as in response to a request from a clinician device 130A or patient device 130B, or in response to a direct user interaction with the module 100. The images may be obtained in the form of digital image files, such as bitmap images, tag image file format ("TIFF") images, Joint Photographic Experts Group ("JPEG") images, or the like.

Figure 7:
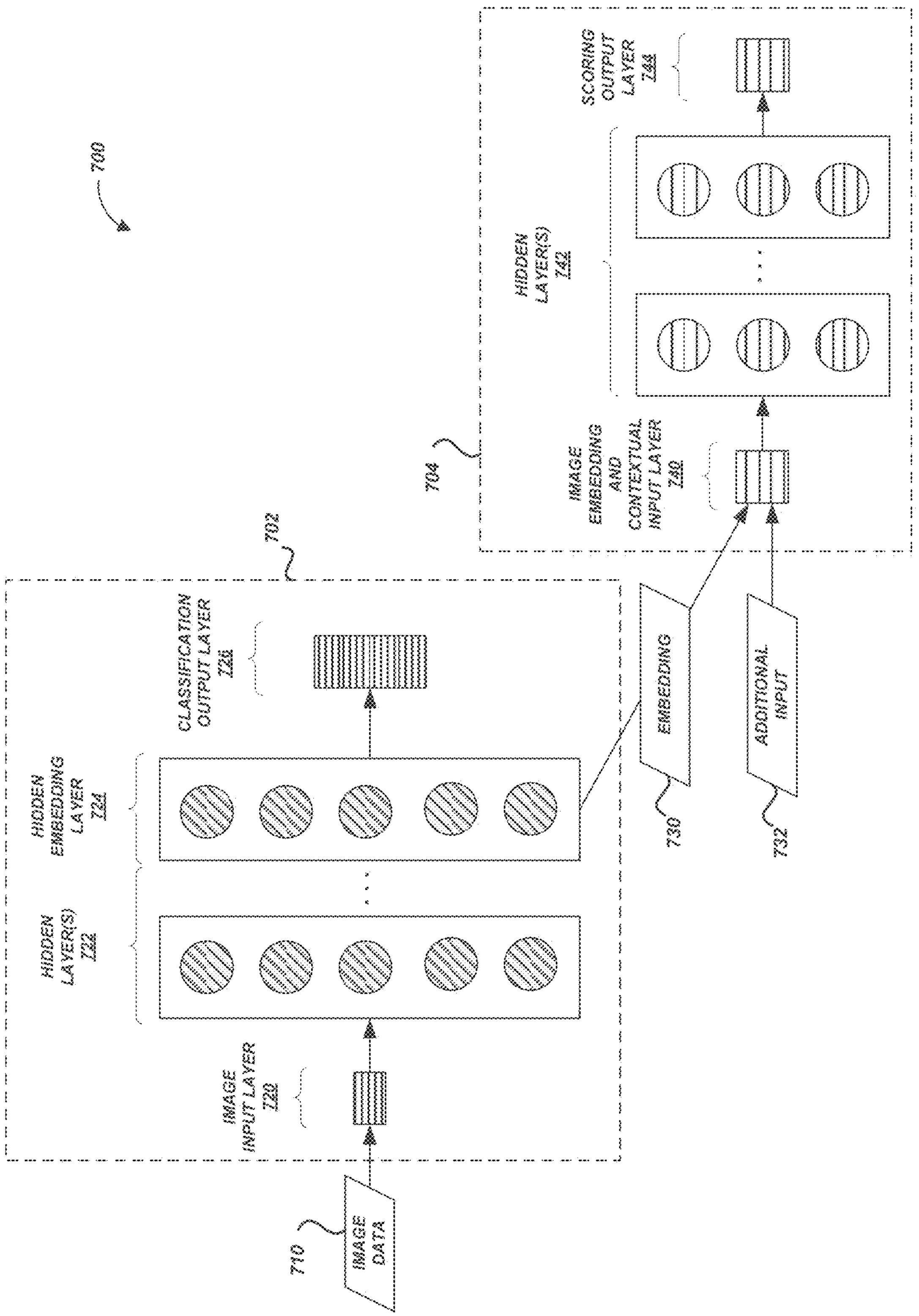
FIG. 7 is a diagram of an illustrative model system for analyzing sensor data and contextual data according to some embodiments.

At block 606, the system executing the process 600 may evaluate an image using an image analysis model or system of models, such as a machine learning model or system of such models trained to perform particular evaluations using images. FIG. 7 illustrates an example model system 700 that may be used to evaluate an image. In some embodiments, as shown, the model system 700 includes a classification model 702 and a regression model 704. The models 702 and 704 may be implemented as artificial neural networks. For example, the classification model 702 may be implemented as a convolutional neural network ("CNN") trained to classify images in any number of classes, and the regression model 704 may be implemented as a deep neural network ("DNN") trained to generate scores.

The classification model 702 may be trained to classify an image as depicting one of a set of conditions or condition severities. For example, the classification model 702 may be trained to classify an image as depicting a wound infection, a wound of a particular volume, a lesion that is a candidate for debridement, a skin abnormality, or the like. As another example, the classification model 702 may be trained to classify an image into one of a set of severity classes, such as wound severity, degree of acne, or other body surface condition severities. The set of severity classes may include a "normal" class, a "moderate" class, and a "severe" class. The training of the model may be performed using supervised or unsupervised methods. In one specific, non-limiting embodiment, the classification model 702 may be a ResNet-152 model.

The management system 120 or an external computing system may obtain training data input including a set of labeled training images (e.g., hundreds, thousands, or more individual labeled images). Various subsets of the set of labeled training images may depict body surface regions with the various conditions and/or condition severities that the model is to be trained to detect. Additional subsets of the set of labeled training images may depict body surface regions with no such conditions. The management system 120 may train the classification model 702 using the training data input, and the resulting trained classification model 702 may be deployed for use in analyzing and classifying images. In some embodiments, the set of labeled training images may be separated into two or more subsets, including one subset used to train the model, and another subset of images not used to train the model, but rather used to test the ability of the model to accurately classify. Segmenting the training data in this way can help to avoid overfitting the model to the training data. In some embodiments, the training data may be separated into k segments, or "folds" (where k is an integer greater than two) and a cross-validation procedure such as k-fold cross-validation, may be used to train and test the model.

In the embodiment illustrated in FIG. 7, the classification model 702 includes an image input layer 720 at which image data 710 is accepted (e.g., an image file, a vector derived from the image file, or some other representation of an image to be evaluated), one or more hidden layers 722 (e.g., convolutional layers, max pooling layers, fully connected layers, etc.), an embedding layer 724 (e.g., a last fully-connected layer before an output layer), and a classification output layer 726 (e.g., a layer of nodes at which sigmoid functions are evaluated to produce classification scores). The data generated at the embedding layer 724 may be structured as a vector representation of the features generated by the model 702 from the image input data. This vector representation may serve as an image embedding 730 that may be input to other models of the model system 700 for evaluation and production of output other than the classification output that the classification model 702 is trained to generate. For example, the image embedding 730 may be one input to the regression model 704.

In some embodiments, evaluation of an image of a patient body surface may include a comparison of the image to a database of images of "normal" results, a database of images of specific skin/wound conditions or otherwise "concerning" results, or to individual images that have been previously classified as "normal," indicative of specific skin or wound conditions, or otherwise "concerning." Similarity scores or other indicia of similarity may be generated as a result of comparing an image (or set of images) of a patient body surface region to previously classified images.

Returning to FIG. 6, at block 608 the system executing the process 600 may generate classification output based on evaluation of the image. In some embodiments, output produced by the output layer 726 of the classification model 702 may include one or more classification determinations, such as data indicating the particular class, of the classes for which the model 702 is trained to make classifications, in which the current image input data is most likely properly classified. For example, a classification determination may indicate the presence or absence of a body surface condition (e.g., a wound, a disease, etc.), or the severity of the body surface condition. As another example, the classification determination may indicate the volume or severity of a wound. As yet another example, the classification determination may indicate whether a body surface region is a candidate for debridement.

At block 610, the system executing the process 600 may obtain contextual data associated with the image being analyzed. The contextual data may represent one or more contextual data items regarding the subject whose body surface region is depicted in the image being analyzed, the location of the subject, and/or various other data that can be used to evaluate the confidence of the image classification. In some embodiments, the contextual data may include, but is not limited to: sensor data from one or more sensors 102 of the module 100, demographic data regarding the subject whose body surface region is depicted in an image (e.g., age, gender), skin tone data regarding the skin tone of the subject, location data representing the geographic location of the subject, weather data regarding the weather (e.g., temperature, humidity, UV index, wind conditions, etc.) at the geographic location of the subject, treatment data representing any treatment that the subject is using on the body surface region, subject-provided data (e.g., information provided by the subject regarding their activities, subjective evaluations, etc.), other contextual data, or some combination thereof. The example contextual data items described herein are illustrative only, and are not intended to be limiting, required, or exhaustive.

At block 612, the system executing the process 600 may obtain embedding data representing the image being analyzed. For example, the embedding data may be generated during evaluation of the image by the classification model 702, as described in greater detail above.

At block 614, the system executing the process 600 may evaluate the embedding data and contextual data using a scoring model or system of models, such as a machine learning model or system of such models trained to perform particular evaluations using images.

In one specific, non-limiting embodiment, the regression model 704 of the model system 700 shown in FIG. 7 may be trained to generate a score representative of a state of a body surface region, such as a state of health. Such a score may be referred to as a "state score" to distinguish it from other scores (e.g., scores representative of a confidence in a classification generated by the classification model 702). The training of the model may be performed using supervised or unsupervised methods. For example, the management system 120 or an external computing system may obtain labeled training data input including a set of image embeddings to user in a supervised training method. Each image embedding may be associated with a set of contextual data, such as the contextual data described above. Labels applied to the training data input items represent the scores to be generated for labeled training data input items by the trained model 704. The management system 120 may train the regression model 704 using the training data input, and the resulting trained regression model 704 may be deployed for use in analyzing images and additional data to generate state scores.

In the embodiment illustrated in FIG. 7, the regression model 704 includes an image embedding and contextual data input layer 740 at which an image embedding 730 and contextual input data 732 are accepted, one or more hidden layers 742, and a scoring output layer 744. The scoring output layer 744 may generate one or more scores, such a score in a range between a minimum and maximum value (e.g., 0-100). For example, the score may represent current state of health of a body surface region, where a higher score indicates a higher state of health. As another example, the score may represent current degree of severity of a health condition of a body surface region, where a higher score indicates a higher degree of severity.

Returning to FIG. 6, at block 616 the system executing the process 600 may generate scoring output based on evaluation of the image embedding and contextual data using the scoring model. For example, output produced by the output layer 744 of the regression model 704 may include one or more scores, as described above.

Example Process for State Change Analysis

Figure 8:
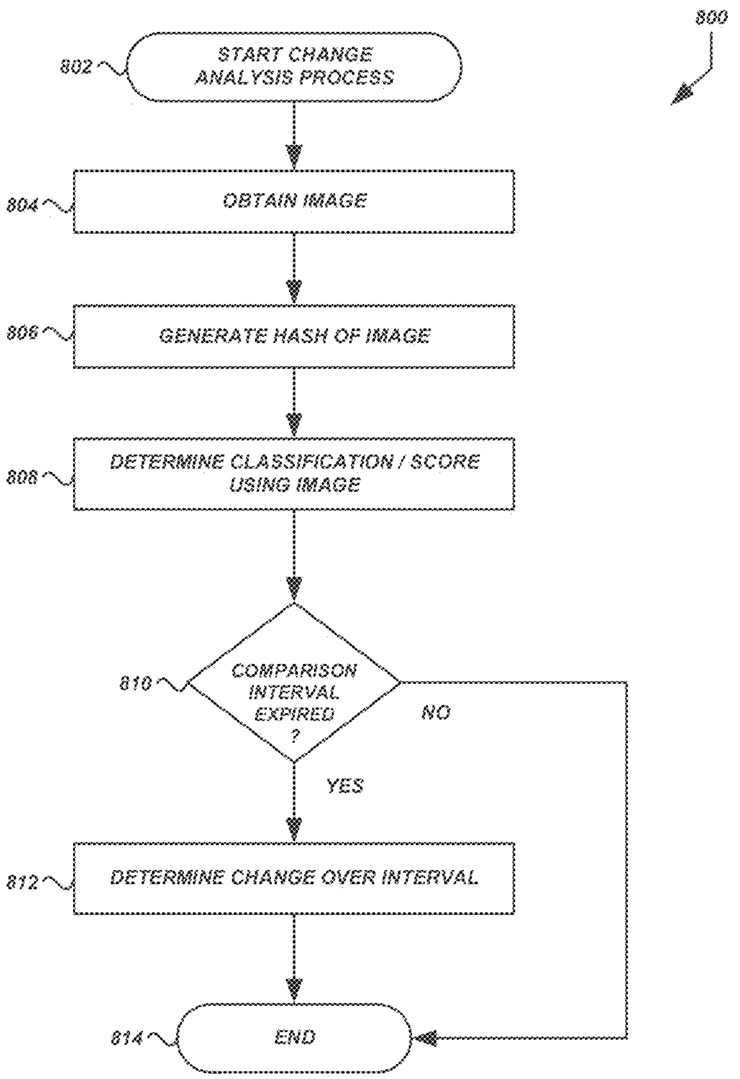
FIG. 8 is a flow diagram of an illustrative process for analyzing changes in sensor data and contextual data according to some embodiments.

FIG. 8 is a flow diagram of an illustrative process 800 that may be executed to analyze image(s) obtained from the system 100 and determine a change in state of a body surface region over time. The process 800 or portions thereof may be executed by a user device 130 and/or management system 120, individually or in combination. For example, process 800 may be performed to analyze module output data from the module 100, such as during block 410 of process 400.

The process 800 begins at block 802. The process 800 may begin in response to an event, such as when the management system 120 obtains an image captured by the module 100, when a user device 130 connects to the management system 120 to initiate analysis of an image (or set of images) captured by the module 100, or on a predetermined or dynamically-determined schedule. In some embodiments, process 800 or portions thereof may be performed on a predetermined or dynamically-determined schedule. For example, output data from the system 100 (images and/or other sensor data) may be obtained periodically, such as hourly, daily, or weekly. The system 100 may be programmed to initiate the capture and/or transfer of the output data, or another system such as the management system 120 or a user device 130 may request the output data from the module 100. In some embodiments, process 800 or portions thereof may be performed on-demand, such as when a user interacts with the module 100, a clinician device 130A, or a patient device 130B. In this way, process 800 may produce real time or substantially real time analysis. For example, a clinician device may activate the module 100 from a low-power or "sleep mode" to a higher-power operational mode (e.g., while a clinician is interacting with the patient's EMR/EHR) to review a wound's healing status on-demand in substantially real time. When the process 800 is initiated, a set of executable program instructions stored on one or more non-transitory computer-readable media (e.g., hard drive, flash memory, removable media, etc.) may be loaded into memory (e.g., random access memory or "RAM") of a computing device, such as a computing device of management system 120. In some embodiments, the process 800 or portions thereof may be implemented on multiple processors, serially or in parallel.

At block 804, the system executing the process 800 may obtain an image of a body surface region. The image may be captured by the system 100 and provided to a user device 130 and/or the management system 120. For example, an image of a region of a patient's skin may be captured, such as an image of a wound or skin condition. As another example, an image of a region of a patient's mouth may be captured, such as an image of an enamel surface or oral mucosa. In some embodiments, the images may be captured on demand, such as in response to a request from a clinician device 130A or patient device 130B, or in response to a direct user interaction with the module 100. The images may be obtained in the form of digital image files.

At block 806, the system executing the process 800 may generate an encoded version of the image, such as a hash. The encoded version may be stored for later use in comparison operations with prior or subsequent images of the same body surface region to determine whether there has been a change in the condition of the body surface region.

In some embodiments, the encoded version may be an average hash. For example, the image may be converted to grayscale and scaled to a standard size, such as an image that is 255×255 pixels. An average of pixel values may be calculated, and individual pixels or subsets thereof may be compared to the average. If the pixels are darker than average, a particular value (e.g., 1) may be added to the hash for the pixel location, and if the pixels are lighter than average, a different value (e.g., 0) may be added to the hash for the pixel location.

In some embodiments, the encoded version may be a distance hash. For example, the image may be converted to grayscale and scaled to a standard size. For each row, each pixel value may be compared to the value of an adjacent pixel, such as the pixel to the immediate right. If the current pixel value is darker than the value of the adjacent pixel, a particular value (e.g., 1) may be added to the hash for the pixel location, and if lighter than the adjacent pixel, a different value (e.g., 0) may be added to the hash for the pixel location.

In some embodiments, the encoded version may be an embedding. For example, an embedding generated during the classification and scoring process and illustrated in FIG. 7 may be stored for use in subsequent comparisons and other analyses.

The example image encoding methods and formats described herein are illustrative only, and are not intended to be limiting, required, or exhaustive.

At block 808, the system executing the process 800 may determine a classification and/or a score for the image. In some embodiments, the classification and/or score may be generated as described in greater detail above and illustrated in FIG. 7.

At decision block 810, the system executing the process 800 may determine whether a time interval for comparison has expired. If so, the process 800 may proceed to block 812. Otherwise, if the time interval for comparison has not expired, the process 800 may terminate at block 814. The time interval for comparison may be predetermined or dynamically determined. For example, the time interval may be set such that the process 800 proceeds to block 812 on a daily, weekly, or monthly basis.

At block 812, the system executing the process 800 may determine the change in the subject's body surface region over the time interval. The change may be determined using the encoded representations of images for the current image and an image preceding the time interval, classification data generated for the respective images, scoring data generated for the respective images, other data, or some combination thereof.

In some embodiments, encoded representations of the current image and a prior image may be compared to determine the difference between the encoded representations. For example, a Manhattan distance or a Euclidian distance between two encoded representations may be determined. Output may be generated indicating the degree to which the encoded representations differ based on the determined distances.

In some embodiments, the scores of the current image and a prior image may be compared to determine the difference between the encoded representations. For example, the score for the current image may be subtracted from the score for a prior image, or vice versa. The difference may represent the degree to which the condition of the body surface region has changed. Illustratively, the degree may correspond to a degree of healing of a wound, a degree of improvement or deterioration of a condition, or the like.

In some embodiments, the classifications of the current image and a prior image may be compared to determine the difference between the encoded representations. For example, each classification may be assigned a numerical value in increasing or decreasing degree of severity. The numerical value for the classification of the current image may be subtracted from the numerical value for the classification of the prior image, or vice versa. The difference may represent the degree to which the condition of the body surface region has changed. Illustratively, the degree may correspond to a degree of healing of a wound, a degree of improvement or deterioration of a condition, or the like.

The change(s) determined at block 812 may be presented to a user (e.g., via a user interface of a user device 130) and/or stored for future analysis, reporting, or the like (e.g., stored on a user device 130 or at the management system 120).

Figure 9:
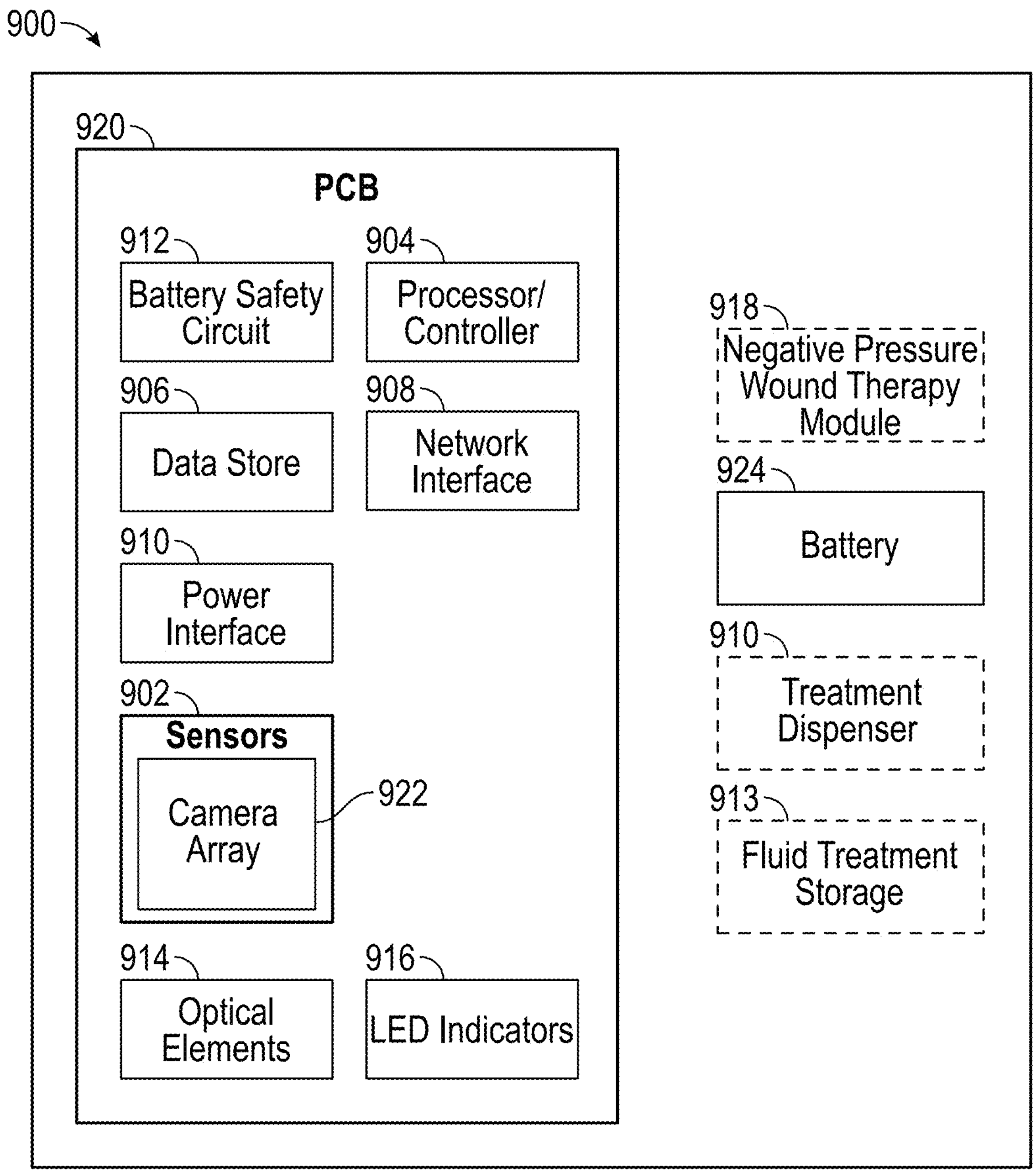
FIG. 9 is a schematic view of a module embodiment described herein.

Example of Wearable Treatment and Analysis System for Wounds and Other Skin Conditions FIG. 9 is a schematic view of an example wearable treatment and analysis system, such as described herein. The treatment and analysis system 900 may include one or more sensors 902 to monitor and generate data regarding user skin characteristics. In certain embodiments, the one or more sensors 902 may include a visualization element, such as one or more camera or optical sensors 922, to capture images and/or generate other visualization data regarding the skin of the user. Such visualization data may be used to monitor a wound or other skin aspect over time, to diagnose a skin condition, to determine a treatment for a skin condition, and/or to monitor the treatment of a skin condition over time. In certain embodiments, the one or more sensors 902 may also or alternatively include a temperature sensor to determine the temperature of the user's body surface region and/or the ambient temperature. In certain embodiments, the one or more sensors 902 may also or alternatively include an accelerometer to assess movements and activities of the patient. In certain embodiments, the one or more sensors 902 may also or alternatively include a pH sensor to determine the pH level of the user's body surface region. In some embodiments, the one or more sensors 902 may also or alternatively include a moisture sensor to determine the moisture content of the user's body surface region and/or the ambient moisture around a location of the user's body surface region. The example sensors 102 described herein are illustrative only, and are not intended to be limiting, required, or exhaustive of the sensors 102 that may be included in a treatment and analysis system 900.

The treatment and analysis system 900 may include the processor/controller 904, such as a system on a chip ("SOC") or other microprocessor to process data and commands. In some embodiments, the processor 904 may process data from the one or more sensors 902 and/or a data store 906, execute one or more analysis or detection algorithms, receive and execute commands from other devices via the network interface 908, or the like. In some embodiments, the data store 906 may be a substantially persistent data store, such as flash memory, hard disk, or the like.

The network interface 908 may be a wired or wireless network interface, such as a network adapter card and/or a wireless antenna (e.g., a Wi-Fi antenna, a Bluetooth® antenna, etc.). For example, the network interface 108 can utilize RF, infrared or other wireless circuitry (receiver or transmitter, or transceiver) to communicate with a remote device. In certain embodiments, the network interface 108 is implemented as a Wi-Fi module and/or a cellular module. In certain embodiments, the network interface 908 comprises an antenna.

In the illustrated embodiment, the network interface 908 is on the same PCB 920 as other electronics and located within a housing of the system or module. In certain embodiments, the Wi-Fi module connects the components of the PCB 920 to a LAN via a Wi-Fi connection. In certain embodiments, multiple modules 100 with multiple network interfaces 108 connect to a single LAN.

In certain embodiments, the network interface 908 comprises a cellular module. In certain embodiments, the cellular module communicates to the Internet via a mobile carrier's network. Depending on the location and carrier, various standards, such as GPRS, GSM, and CDMA, and the like may apply.

In certain embodiments, a lower surface of the system 900 supports a series of optical elements 914, for example, LEDs and lasers. The optical elements 914 can be used to illuminate the skin or wound to enhance imaging, for light therapy to help improve or heal the skin condition or wound, or both. In certain embodiments, the optical elements 914 provide waveform-based treatments, such as ultraviolet light or ultrasound. In some embodiments, optical elements 1314 may be or include: broad spectrum light emitters, visible molecular light emitters, infrared light emitters, laser diffusers, high-intensity laser therapy (HILT) emitters, low-level laser therapy (LLLT) emitters, diode lasers, near infrared laser light emitters, other emitters, or a combination thereof. In certain embodiments, the optical elements 914 emit UV light (e.g., UVA (315-400 nm), UVB (280-315 nm), and/or UVC (200-280 nm)). Exemplary indications of use for light therapy include using ultraviolet light to treat disorders of the skin (e.g., psoriasis, acne vulgaris, eczema and neonatal jaundice, etc.). For example, the optical elements 914 can emit UVC to kill pathogens without unacceptable damage to host tissue of the patient. UVB can stimulate wound healing. UV sources can include light-emitting diodes, lasers, and microwave-generated UV plasma. In certain embodiments, the optical elements 914 emit low level laser therapy for treatment of the wound. In certain embodiments, microwave-generated ultraviolet plasma may be used therapeutically.

In certain embodiments, the optical elements 914 are configured for fluorescence imaging (e.g., near-infrared fluorescence imaging). In certain embodiments, data obtained from fluorescence imaging visualizes bacteria to assist wound treatment by the healthcare provider. For example, the optical elements 914 can detect bacterial loads and location with respect to the wound. The bacterial loads can be used by the physician to assess or reassess clinical treatment of the wound.

In certain embodiments, the processor/controller 104 on the PCB 904 can control the optical elements 914 while the battery 924 powers the optical elements 914. Alternatively, the PCB 920 can support the optical elements 914 with the optical elements 914 aligned for each camera in a camera array 922.

In certain embodiments, the battery 924 supplies power to the one or more sensors/components of the module 900. In certain embodiments, the battery 924 attaches to the components by one or more detachable leads. The battery 924 can be rechargeable either by an external port on the housing 902 or by inductive charging (i.e., wireless) as explained above. In certain embodiments, the battery 924 is a rechargeable lithium ion battery with a voltage of 3.7. Of course, the type and capacity of the battery 924 are not limited to the listed type and value and instead can be any other type of battery 924 having any other capacity or value. In certain embodiments, the battery 924 is about 4.5 mm thick, 52.5 mm long, and 20.7 mm wide. The dimensions of the battery 924 can be selected to be similar to the dimensions of the PCB 904 (e.g., PCB 904—4.87 mm thick, 52.33 mm long, and 21.05 mm wide) for the exemplary battery 924 dimensions provided above. The size of the battery 924 can be selected to allow the system 100 to operate for at least one day before requiring charging. In certain embodiments, the battery 924 can be recharged while the system 900 is attached to the patient wirelessly or via a wired connection.

In certain embodiments, the system 900 includes a battery safety circuit 912. For example, in certain embodiments, the battery safety circuit 912 is configured so that the system 900 complies with International Electrotechnical Commission ("IEC") 62133 (Safety requirements for portable sealed secondary lithium cells, and for batteries made from them, for use in portable applications). In this way, the dimensions of the battery 924 and its re-chargeable characteristics comply with the standard. In certain embodiments, the battery safety circuit 912 allows safe inductive charging of the battery 924. In certain embodiments, the battery safety circuit 912 is incorporated on the PCB 920.

In certain embodiments, the system 900 includes the optical sensor system or camera array 922 described herein. In certain embodiments, the camera array 922 can include one or more optical sensors configured to be auto-focusing, rotatable or otherwise movable, and/or able to zoom in or out. In certain embodiments the controller 904 may be configured to independently operate each camera of the camera array 922. Each optical sensor in the camera array 922 may be configured to capture different sub-regions of a body surface region of interest. The images of these sub-regions may then be combined to generate an image of the total body surface region of interest or a sub-portion thereof. Advantageously, the controller 904 may be configured to operate each optical sensor in the camera array at different times in order to reduce the power consumption required to capture the image data, allowing for a smaller and more efficient battery system 924. These features allow the user (or controller 104 if automated) to capture images of all or substantially all of the affected area (e.g., the wound) or targeted skin area, as well as to image segments of the affected or targeted area (e.g., the wound's margins and healed boundaries). For these purposes, the processor/controller 104 can control the optical sensor 1202 with the battery 924 supplying power thereto. Additional filters (either physical or software) can be used to enhance the images.

In certain embodiments, the system 900 optionally includes the treatment dispenser 910 and/or the fluid treatment storage 913. For example, in some embodiments, the treatment dispenser 910 can include a dispensing medicant pump or the like that draws fluid from the fluid treatment storage 913 when operated by the processor 904. A lower surface of the system 900 can include one or more apertures. Such apertures can form part of the treatment dispenser 910 to apply a treatment agent (e.g., a therapeutic, topical fluids, ozone, etc.) to the patient's skin/wound.

In certain embodiments, the aperture(s) can also form part of a negative pressure wound therapy module 918. For example, in certain embodiments, the negative pressure wound therapy module 918 can draw fluids from within a space between the wound and the lower surface of the system 900 to reduce the pressure within that space. In certain embodiments, the negative pressure wound therapy module 918 comprises the space (e.g., a fluid collection container) and a vacuum pump. One or more tubes can channel fluid between the wound dressing, the fluid collection container, and the vacuum pump.

Example Embodiment of a Wearable Module

Figure 10A:
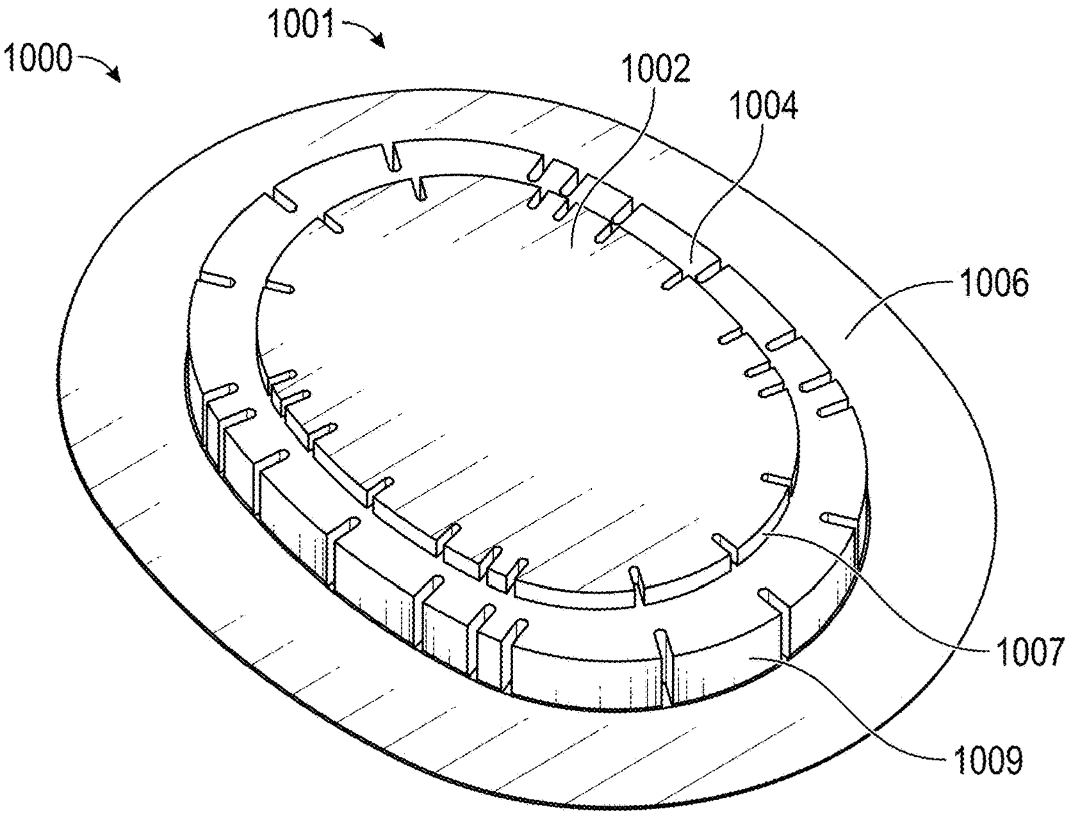
FIGS. 10A and 10B show top and bottom perspective views of an embodiment of a module.
Figure 10B:
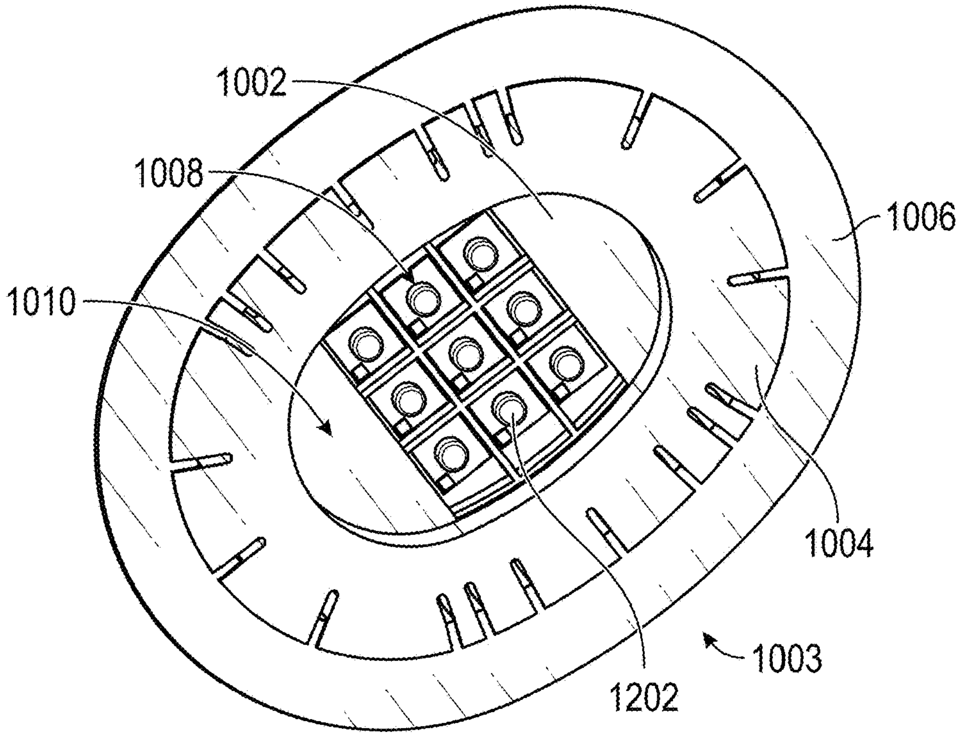
Figure 10C:
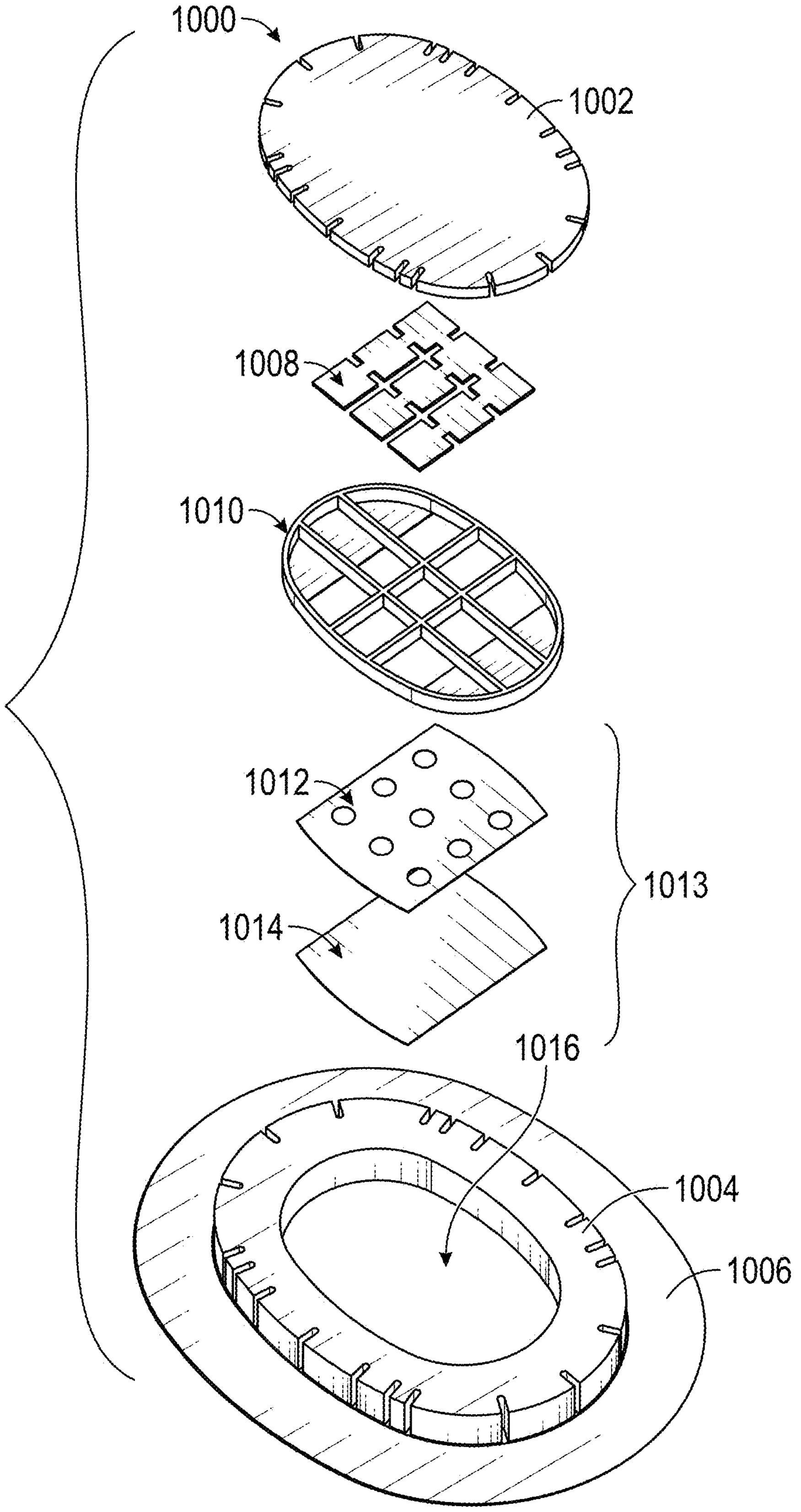
FIGS. 10C-10D show perspective and lateral exploded views of an embodiment of a module.
Figure 10D:
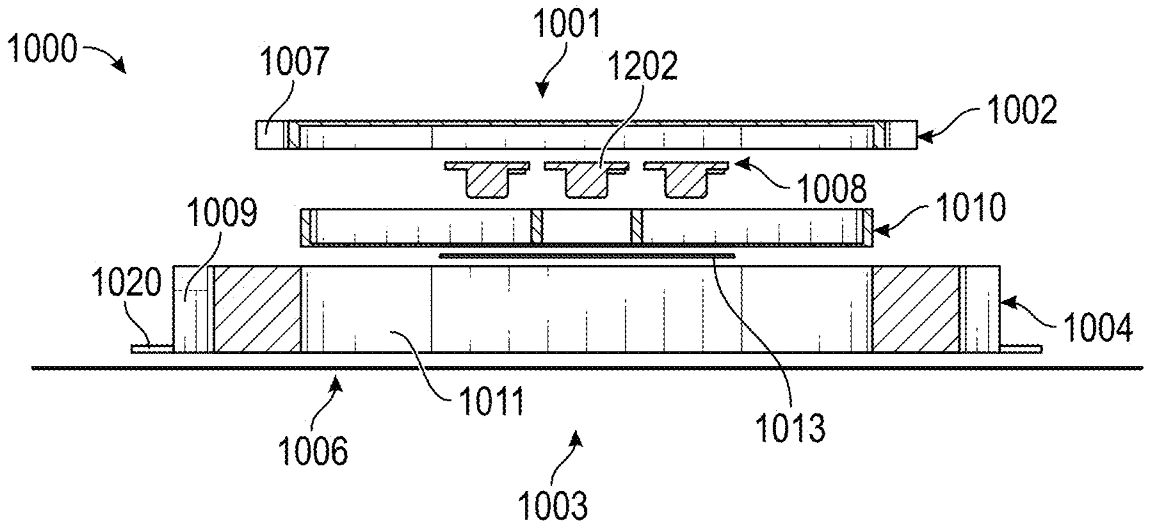
Figure 10E:
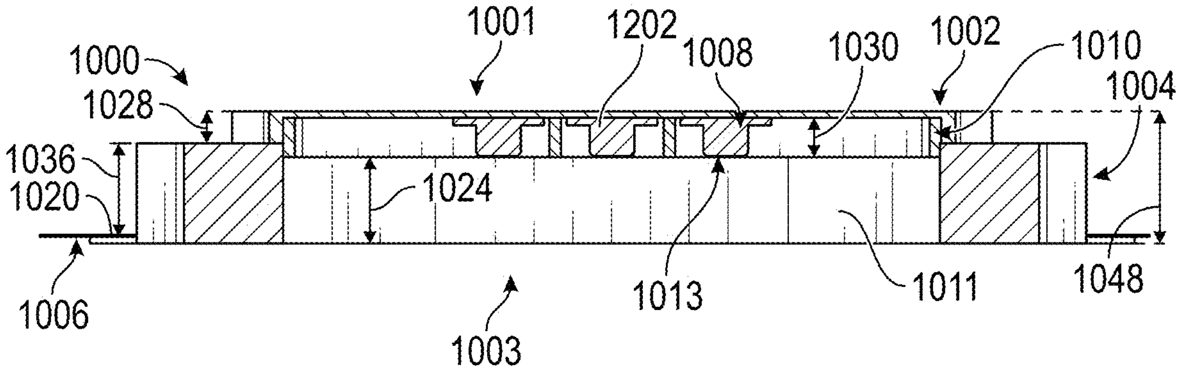
FIG. 10E shows a cross-sectional view of an example embodiment of a module.

FIGS. 10A-10E illustrate views of an example embodiment of a wearable module 1000. FIGS. 10A and 10B show top and bottom perspective views of an embodiment of the module 1000. FIGS. 10C-10D show perspective and lateral exploded views of the module 1000. FIG. 10E shows a cross-sectional view of an example module 1000. The module 1000 may be an embodiment of the treatment and analysis system 100 described herein. The module 1000 may be adaptive to a variety of wound dressing methods, such as by being affixed to or embedded within a dressing, wrap, cast, brace, or the like.

As illustrated in FIGS. 10A and 10B, a module 1000 may include a top or distal side 1001, bottom or proximal side 1003, one or more exterior sidewalls 1007, 1009, one or more interior cavities 1011, an overtape support 1006, and a transparent dressing 1016.

As illustrated in FIG. 10C, a module 1000 may include a plurality of layered components. The plurality of layered components may include, but are not limited to some combination of a top preform 1002, standoff 1004, overtape support 1006, PCBA 1008, light shield 1010, diffuser 1012, polarizer 1014, and transparent dressing 1016. While certain components are discussed herein with reference to an embodiment of a wearable treatment and analysis system 1000, they are illustrative and meant to be non-limiting. For example, greater, fewer, or different components than described may be included as described with reference to for example, FIGS. 10A-10E and further layered components, within the described layered components, as part of a separate module, or a combination thereof. Further details of the plurality of layered components illustrated in FIGS. 10A-10E are described herein with reference to FIGS. 11A-17B.

As illustrated in FIGS. 10D and 10E, the one or more interior cavities 1011 of the module 1000 may be configured to contain at least some of a plurality of layered components of the module 1000, including but not limited to one or more optical components and/or sensors configured to measure physiological data from the tissue of the patient, as will be described herein. In some implementations, the one or more interior cavities 1011 may be formed by a combination of components, such as a top preform 1002, standoff 1004, and/or transparent dressing 1016. In the illustrated example, the one or more interior cavities 1011 show a single interior cavity having an oblong cylindrical shape, forming an approximately oblong shape in a major cross section of the module 1000 (in a major plane approximately parallel to the tissue site) and an approximately rectangular shape in a minor cross section of the module 1000 (in a minor plane approximately perpendicular to the tissue site). However, other shapes and/or cavities are also possible. In some examples, an interior cavity 1011 shape may parallel an overall shape of the module 1000, such that an approximately circular module 1000 may include an approximately circular interior cavity 1001. In some examples, an interior cavity 1011 shape may be informed by the shape of plurality of layered components within the module 1000.

The top side 1001 of the module 1000 may be distal to the tissue of the patient. The top side 1001 may be comprised of one or more distal components configured to at least partially enclose one or more components held within the one or more interior cavities 1011. These one or more distal components may be configured to at least partially protect interior contents of the module 1000 from external sources of damage. In some examples, the one or more distal components may include the top preform 1002. The top preform 1002 may include a major surface larger than the major cross section of the interior cavity 1011 so as to enclose the cavity 1011. The top side 1001 may or may not be planar in whole or in part. For example, the top side 1001 may be contoured, stepped and/or composed of a plurality components. In the illustrated example, the top side 1001 comprises at least the top preform 1002 and at least a portion of the standoff 1004. As illustrated in FIGS. 10C, 10D, and 10E, the top preform 1002 may have a smaller outer dimension than the outer dimension of the standoff 1004 such that an outer edge of the top preform 1002 is stepped back from the outer wall 1009 of the standoff 1004.

While in some implementations, the module 1000 can have a housing composed of a single component (such as a combination of the top preform 1002 and standoff 1004), having a housing with multiple layers, such as the top preform 1002 and standoff 1004 as separate components, can, advantageously, better enable the overall device to conform to curved geometry by allowing the components (such as the top preform 1002 and standoff 1004) to slide and/or otherwise move with respect to one another. In contrast, a single housing component may be more structurally rigid because of resistance to shear, which may not be beneficial based on the context of application of the module. Further, having separable outer housing components can help facilitate ease of manufacture and reusability of the module. For example, a top preform 1002 and/or one or more other components of the module 1000, such as the PCBA 1008 and associated sensors, light shield 1010, one or more optical components 1013 and/or other interior components, may be reusable and/or refurbishable while one or more other components of the module 1000, such as the standoff 1004, overtape support 1006, transparent dressing 1016 and/or other components that come into direct contact with patient tissue or are incorporated into or interact with a wound dressing may be disposable or single use.

The bottom side 1003 of the module 1000 may be proximal to the tissue of the patient and/or be configured to at least partially contact with the patient's skin and/or tissue. The bottom side 1003 may include one or more proximal components configured to at least partially enclose interior contents of the module 1000, such as one or more components held within the one or more interior cavities 1011 at a proximal side of the module 1000. In some examples, the bottom side 1003 may be comprised of some combination of components and/or portions of components, including, but not limited to the transparent dressing 1016, overtape support 1006, and/or standoff 1004. The bottom side 1003 may be at least partially transparent and/or open to facilitate measurement of physiological data from the body surface region of interest. For example, the bottom side 1003 may be transparent at the transparent dressing 1016.

The one or more exterior sidewalls 1007, 1009 may be configured to at least partially enclose one or more components held within the one or more interior cavities 1011. An overall height 1048 of the module 1000 may preferably be between approximately 0.25 and 2 inches, or a value greater or less than bounded by that range. The dimensions, such as the height, of the one or more exterior sidewalls 1007, 1009 may be informed by requirements of one or more sensors 1202 and/or other components within the one or more interior cavities 1011. For example, the one or more interior cavities 1011 may include one or more PCBA boards 1008 containing one or more cameras 1202 and/or other sensors. The desired field of view of the one or more cameras 1202 and/or other sensors may be impacted by the distance that the one or more cameras sit from the tissue site. In some implementations, the height 1036 of the sidewall 1009 of the standoff 1004 is selected so that the distance 1024 between the bottom side 1003 of the module 1000 and the bottom of the camera sensor 1202 on the PCBA 1008 is fixed for the desired field of view of the cameras. For example, the height 1036 can be preferably between approximately 0.25 and 0.75 inches, or a value greater or less than bounded by that range and the height 1024 can be preferably between approximately 0.25 and 0.75 inches, or a value greater or less than bounded by that range.

The module 1000 in whole or in part may be configured to flex so as to at least partially conform to the contour of a patient's tissue when applied to a patient. The module 1000 may be configured to at least partially flex with the patient during movement and/or maintain at least partial contact with the patient's tissue during movement. Thus, the module 1000 may be applied to larger portions of tissue and/or at areas of the body subject to greater flexion or movement, such as at or near the knee or elbow. Additionally, increased flexibility of the module 1000 may facilitate improved length of wear of the module 1000 by reducing strain on the adhesive coupling the module 1000 to the tissue of the patient. Thus, the plurality of layered components may be arranged, configured, and/or composed of materials to provide at least some flexibility to one or more portions of the module 1000. For example, the top preform 1002 may be composed of silicone or other flexible material and/or contain one or more cutouts 1114 and/or tabs 1112 to facilitate movement, as will be described herein. Similarly, the standoff 1004 may be composed of a foam or other flexible material and/or contain one or more cutouts 1512 and/or tabs 1510 to facilitate movement, as will be described herein. Further, the overtape support 1006 may be composed of a material, such as a fabric and/or tape, configured to conform with the tissue of the patient.

One or more of the plurality of layered components may be configured to couple to one or more other components of the module 1000. The components may be coupled using one or more permanent or semi-permanent coupling methods, such as a glue or adhesive. In other examples, components may be press-fit or removably coupled together. For example, the top preform 1002 may be configured to couple to one or more other components, including but not necessarily limited to the standoff 1004. The standoff 1004 may be configured to couple to one or more other components, including, but not limited to the overtape support 1006.

The plurality of layered components may or may not be incorporated within a separate housing, such as a waterproof or water-resistant housing. In some examples, one or more of the plurality of layered components may themselves serve as a protective layer and/or housing for other of the plurality of layered components. For example, the top preform 1002 may be configured to protect and cover one or more other of the plurality of layered components from damaging forces coming from the top side 1001 of the module 1000. For example, the top preform 1002 may be configured to encase the PCBA 1008, light shield 1010, and one or more optical components such as the diffuser 1012 and polarizer 1014 from a top side of the module 1000. Additionally, the standoff 1004 may be configured to encase the PCBA 1008, light shield 1010, and one or more optical components, such as the diffuser 1012 and polarizer 1014 from lateral sides of the module 1000.

Example Top Preform of an Embodiment of a Module

Figure 11A:
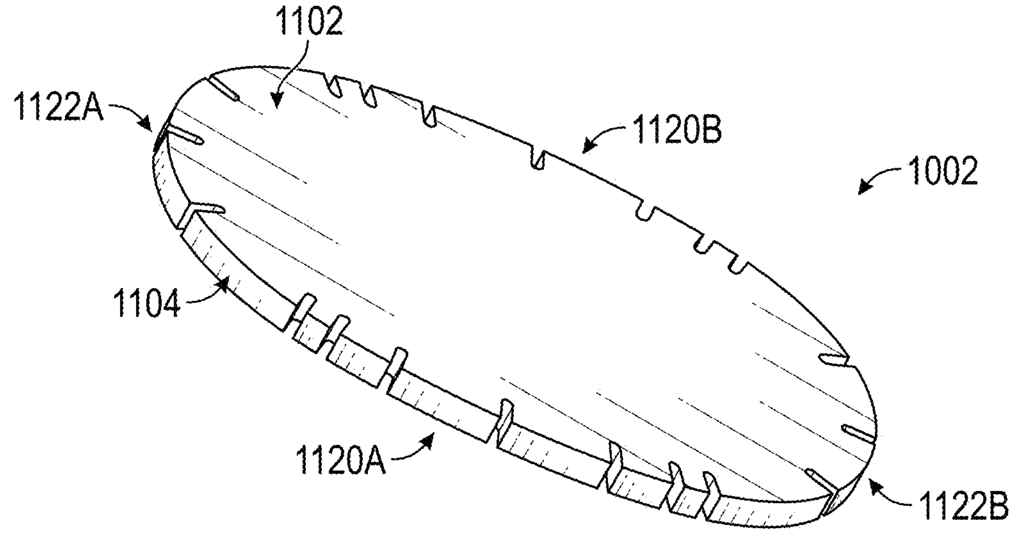
FIGS. 11A and 11B show top and bottom perspective views of a top preform of an embodiment of a module.
Figure 11B:
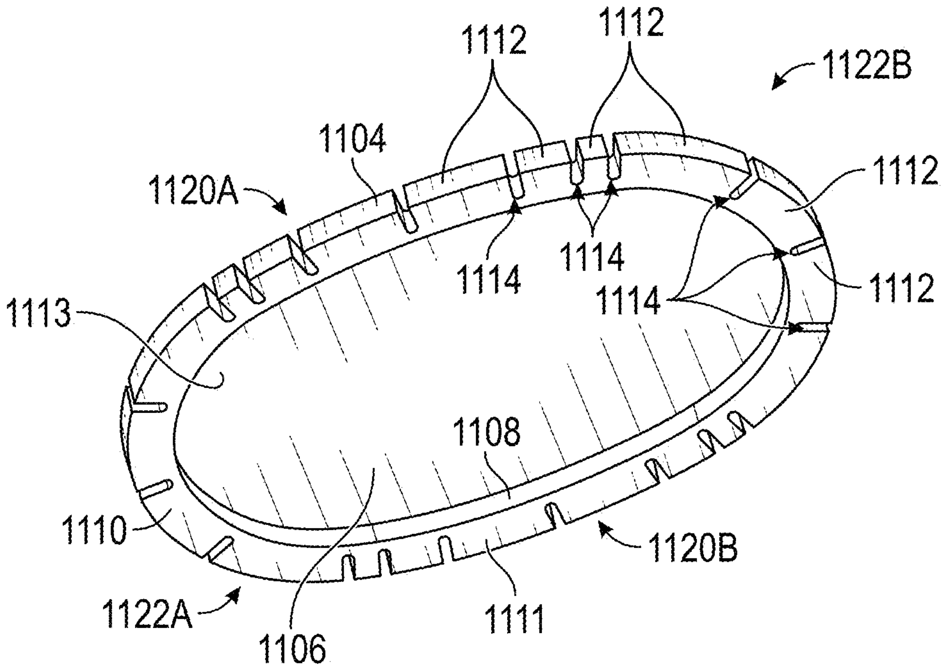
Figure 11C:
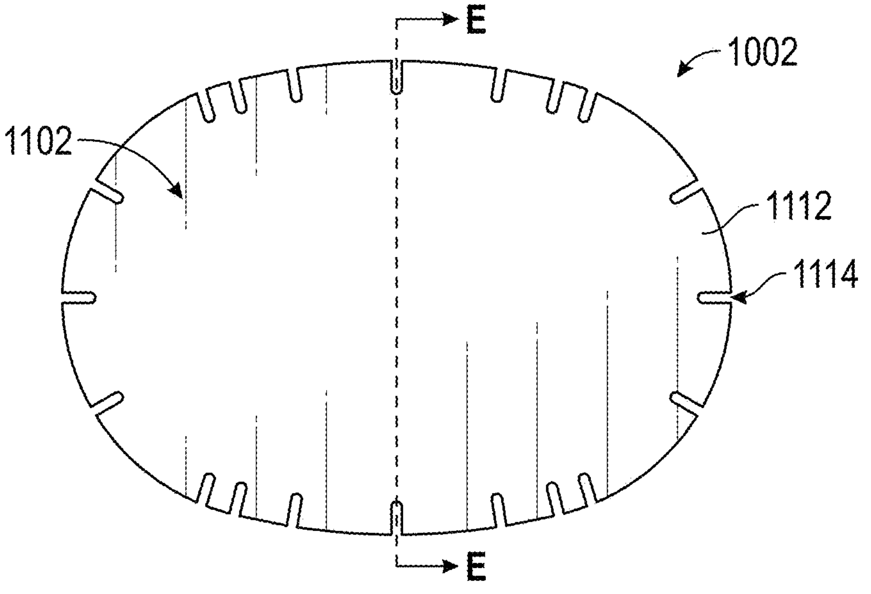
FIGS. 11C, 11D, and 11E show top, bottom, and lateral cross-sectional views of a top preform embodiment illustrated in FIGS. 11A-11B.
Figure 11D:
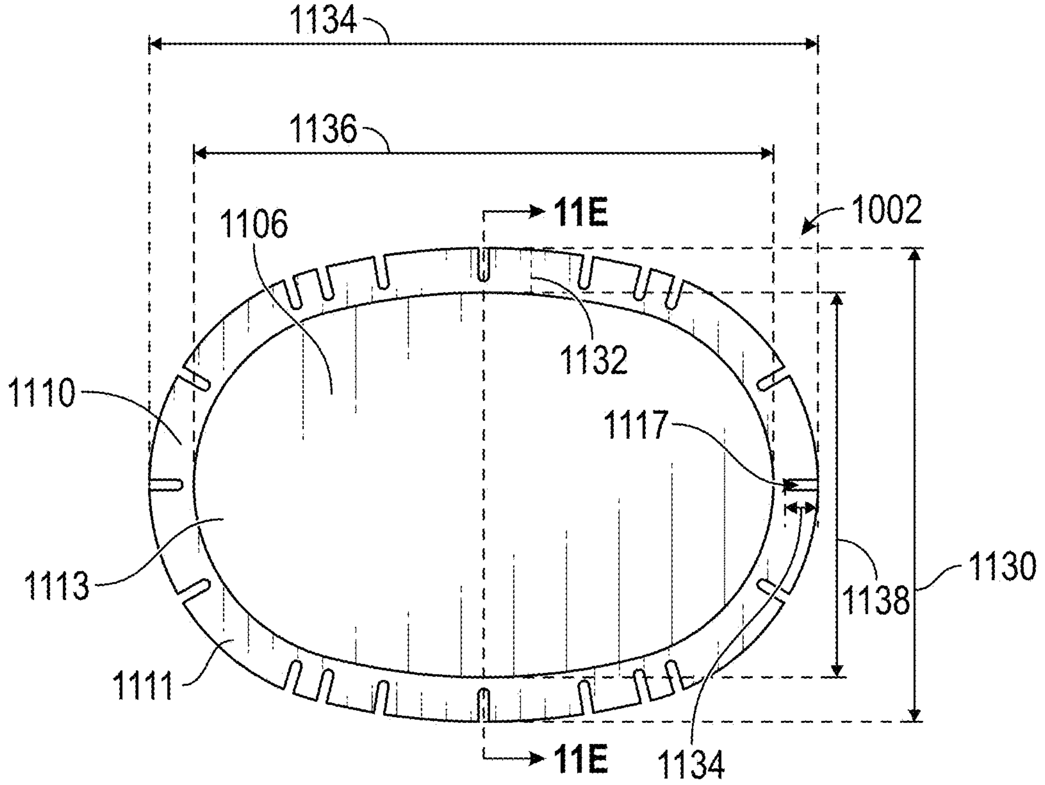
Figure 11E:
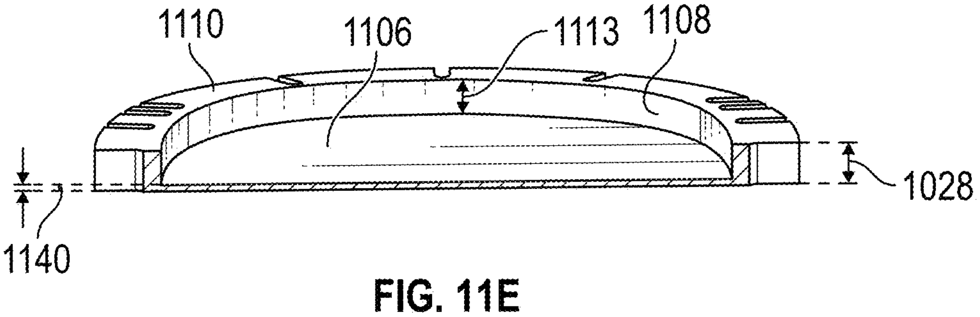

Details of an example top preform 1002 of an embodiment of a module 1000 are discussed herein. FIGS. 11A and 11B show top and bottom perspective views of a top preform 1002. FIGS. 11C-11E show top, bottom, and lateral cross-sectional views of a top preform 1002.

The top preform 1002 may include one or more portions, such as a top side 1102, an interior bottom side 1106, one or more external sidewalls 1104, one or more internal sidewalls 1108, a lip 1110, one or more cutouts or notches 1114, and/or one or more tabs 1112.

The top preform 1002 may be composed of a single material or component and/or a combination of materials or components. In some examples, the top preform 1002 may be a single molded or cut shape comprising a medical grade silicone or another flexible material. The top preform 1002 may be composed of a material configured to provide at least partial protection to other components of the module 1000 that may be covered by the top preform 1002. The top preform 1002 may serve as the outermost layer of the module 1000. However, in some examples, the top preform 1002 may be contained within another external housing. The top preform 1002 may be coupled to other components of the module 1000, including but not limited to a standoff 1004.

The top side 1102 of the top preform 1002 may be configured to face distally away from the tissue site of the patient and/or other components of the module 1000. The top side 1102 may be an approximately flat and/or planar surface and/or have a contour or other shape. The area of the top side 1102 may be approximately oblong in shape. However, other shapes are also possible.

The bottom section of the top preform 1002 may include an interior bottom side 1106 and/or a lip 1110. The interior bottom side 1106 may be configured to face proximally towards the tissue site of the patient. The lip 1110 may include one or more internal sidewalls 1108, one or more external sidewalls 1104, and/or a bottom surface 1111. The bottom surface 1111 of the lip 1110 may be configured to face proximally towards the tissue of the patient. The lip 1110 may include a structure configured to extend from the top side 1102 and form a raised structure around an edge of the interior bottom side 1106. The lip 1110 may include one or more external sidewalls 1104 extending from the top side 1102 to a bottom surface 1111 of the lip 1110. The lip 1110 may include one or more internal sidewalls 1108 configured to extend proximally from the interior bottom side 1106 towards the bottom surface 1111 of the lip 1110. The bottom surface 1111 of the lip 1110 and/or one or more internal sidewalls 1108 may be configured to be approximately flat and/or have surfaces approximately parallel to the plane of the top side 1102. However, other shapes of the lip 1110 and/or interior bottom side 1106 are also possible.

The combination of the lip 1110 and interior bottom side 1106 may be configured to form a space and/or cavity 1113 on the proximal side of the top preform 1002. The cavity 113 may be of an approximate size and shape to receive one or more components of the module, such as the PCBA 1008, light shield 1010, the like or a combination thereof. In some examples, the one or more components of the module may be configured to be coupled to the top preform 1002 within the cavity 1113. For example, the one or more components may be coupled to the interior bottom side 1106 and/or one or more internal sidewalls 1108 of the top preform 1002. In some examples, the one or more components may be glued, press-fit, or otherwise attached to the top preform 1002. In other examples, the one or more components may be received into the cavity 1113 without being coupled to the top preform 1002.

The top preform 1002 may include a plurality of tabs 1112 and/or cutouts or notches 1114 around the exterior surface(s) (such as at the one or more external sidewalls 1104) of the top preform 1002. The plurality of tabs 1112 may be formed by the placement of two adjacent notches 1114. The size, shape, and/or placement of the plurality of tabs 1112 may provide a measure of flexibility at the exterior surface(s) and/or edge(s) (such as at the one or more external sidewalls 1104) of the top preform 1002. The flexibility may be such so as to allow the top preform 1002 and/or portions of the module 1000 to conform at least partially to the contour of the tissue of the patient. The size and/or shape of the tabs 1112 may be different or the same at various locations around the exterior surface(s) of the top preform 1002 to facilitate the desired flexibility and/or conformity of the top preform 1002. For example, where the lateral cross-sectional shape of the top preform 1002 is an oblong shape, such as illustrated, the top preform 1002 may include two or more tabs of similar size and/or shape at each of the short sides 1122A, 1122B and a combination of larger and smaller tabs at each of the long sides 1120A, 1120B, where a larger tab is defined as a tab 1112 formed by two adjacent notches 1114 spread further apart along the edge of the top preform 1002 and a smaller tab is defined as a tab 1112 formed by two adjacent notches 1114 spread closer together along the edge of the top preform 1002. In some examples, the top preform 1002 may have smaller tabs at areas of higher curvature along the one or more external sidewalls 1104/and larger tabs at areas of lower curvature along the one or more sidewalls. However, other configurations are also possible. The notches 1114 may be formed by a cut or indentation along the one or more external sidewalls 1104 that runs at least a portion of the way into the lip 1110 without cutting into or otherwise engaging the interior bottom side 1106 such that the notches 1114 have a depth 1117. The notches 1114 may run a full height 1028 of the top preform 1002 such that the notches cut through both the top side 1102 and the bottom surface 1111 of the lip 1110. In some instances, the notches 1114 may be of the same depth and/or height. However, in other instances, the notches 1114 may have varying depths and/or heights. The width of the notches 1114 may be varying or the same. In some examples. The width of each of the notches 1114 may be different based on their location along the one or more external sidewalls 1104 and/or geometry of the top preform 1002. The width of each of the one or more notches 1114 may be smaller than a width of one or more of the tabs 1112.

With reference to FIGS. 11C and 11D and the cross section shown in FIG. 11E, an external major width 1134 of the top preform 1002 may preferably be between approximately 1 and 10 inches. or a value greater or less than bounded by that range. An external minor width 1130 of the top preform 1002 may preferably be between approximately 1 and 10 inches, or a value greater or less than bounded by that range. A width 1132 of the lip 1110 may be consistent around the edge of the top preform 1002 and preferably be between approximately 0.5 and 0.75 inches, or a value greater or less than bounded by that range. The interior space or cavity 1113 may have a major width 1136 and a minor width 1138 sized to accommodate optical and electronic components, including an un-encumbered antenna for wireless communications and inset from the outside dimensions by, for example, approximately 0.03 to 0.75 inches. A height 1028 of the top preform 1002 may preferably be between approximately 0.02 and 0.125 inches, or a value greater or less than bounded by that range. A height or distance 1140 between the interior bottom side 1106 and top side 1102 may preferably be between approximately 0.02 and 0.125 inches, or a value greater or less than bounded by that range and a height or depth 1142 of the cavity 1113 may be sized to accommodate electronics, optics, films, air gaps, and/or other considerations related to operation of the module 1000 and its components, such as between approximately 0.093 and 1.5 inches, or a value greater or less than bounded by that range. While certain ranges, numbers, and shapes are listed here, they are for illustrative purposes only and any of the dimensions of the top preform 1002 may be within or outside this range.

Example PCBA and Optical Sensors of an Embodiment of a Module

Figure 12A:
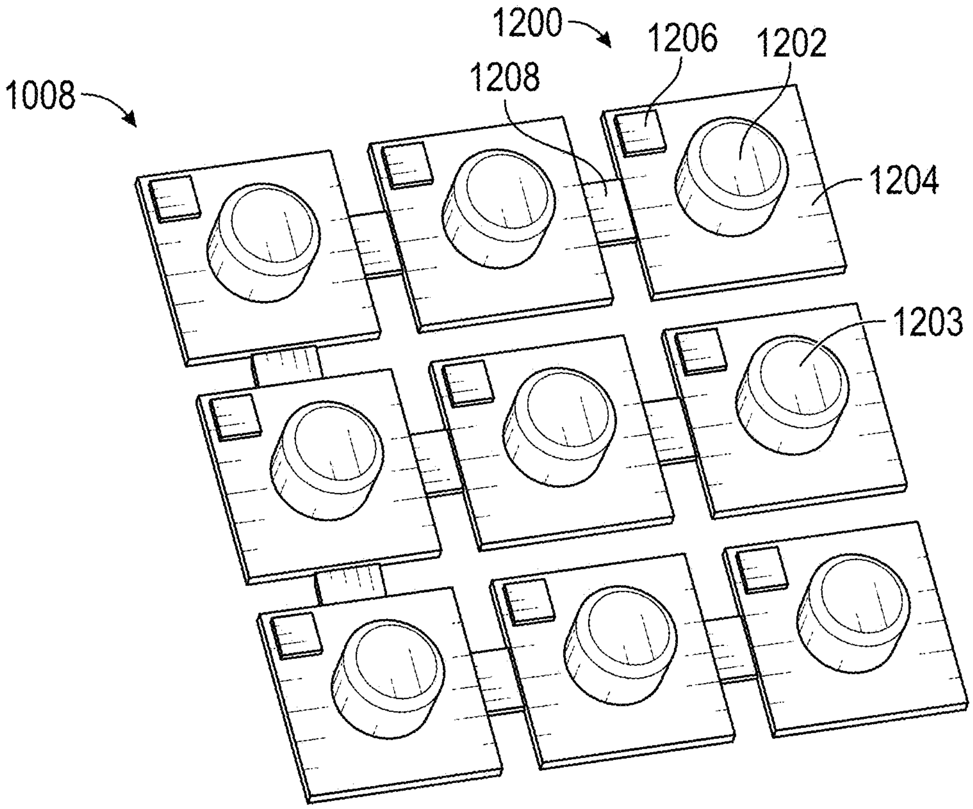
FIGS. 12A-12B illustrate top and bottom perspective views of an example PCBA of an embodiment of a module with one or more optical sensors.
Figure 12B:
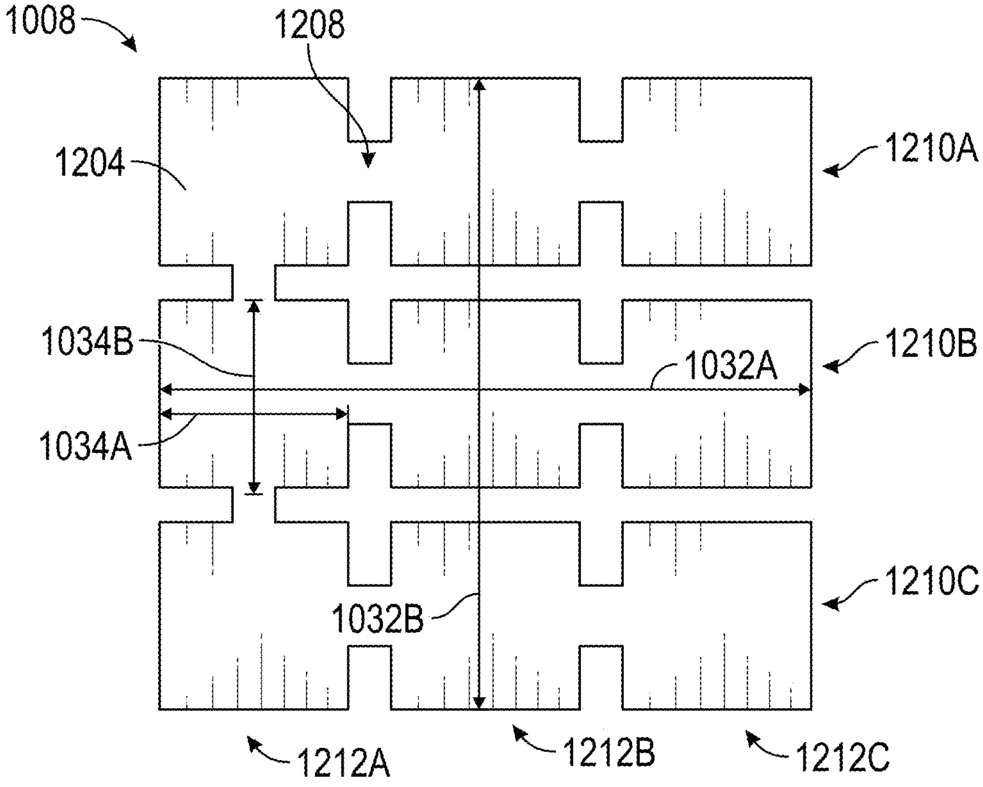
Figure 12C:
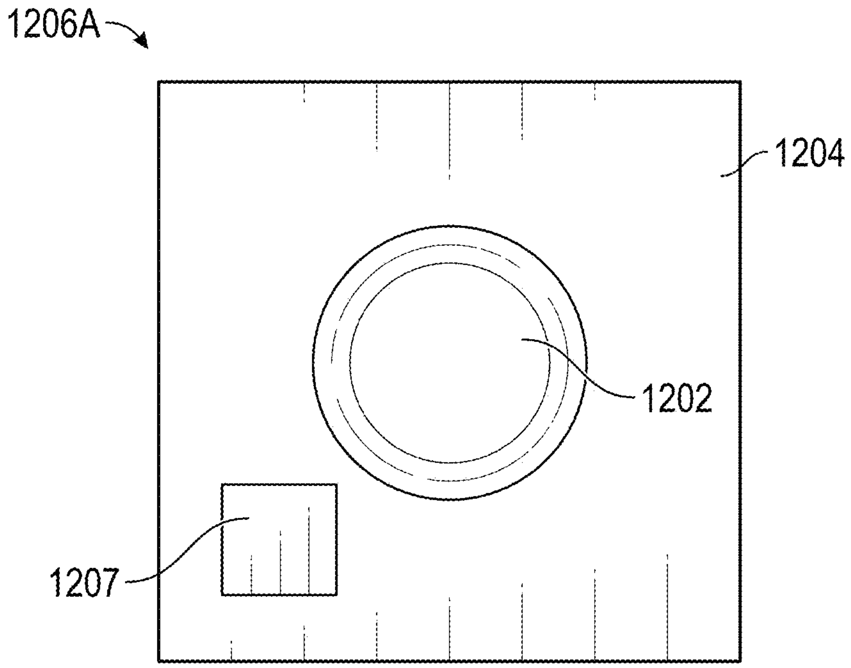
FIGS. 12C-12D illustrate example embodiments or different orientations of a camera and illumination system that may be part of a PCBA illustrated in FIGS. 12A-12B.
Figure 12D:
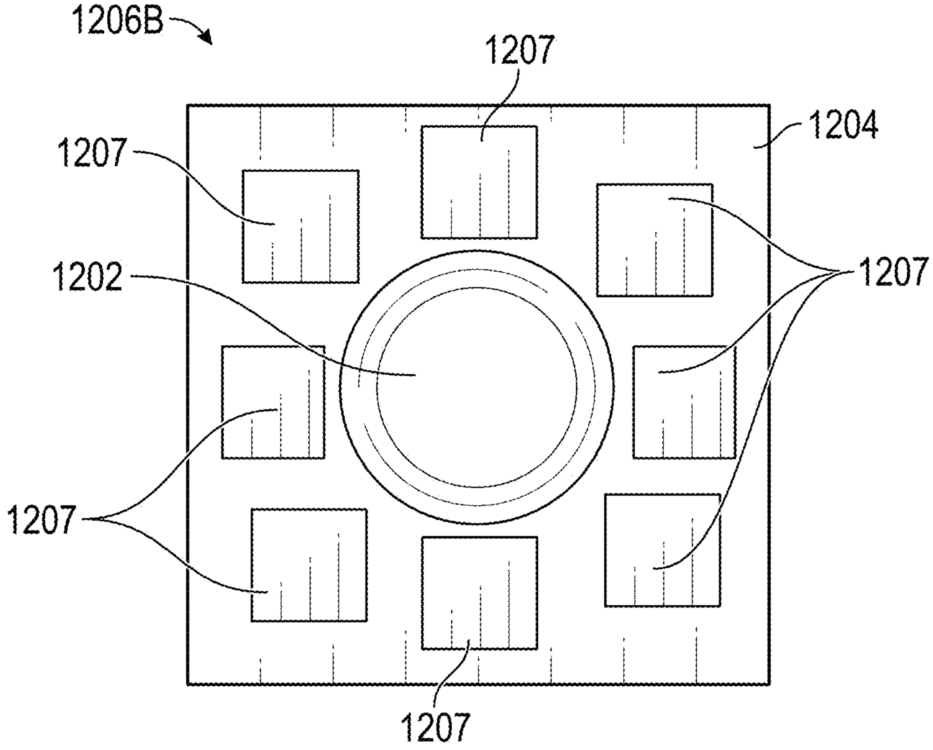
Figure 12E:
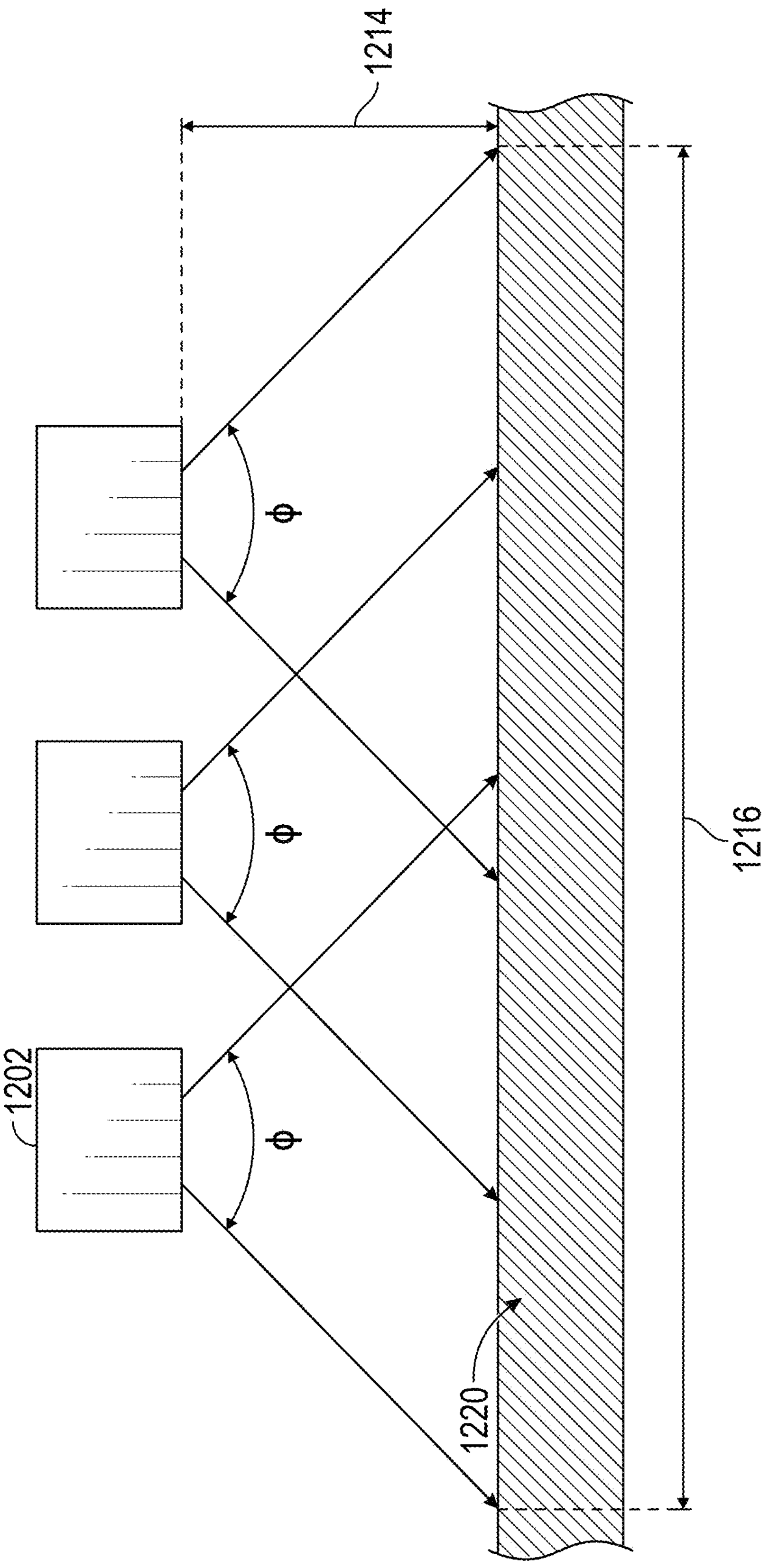
FIG. 12E illustrates an example illumination environment of an embodiment of a tissue site by an embodiment of an illumination system such as described herein.

Details of an example printed circuit board assembly (PCBA) 1008 and/or associated sensors are described herein. FIGS. 12A-12B illustrate top and bottom perspective views of an example PCBA with one or more optical sensors 1202. FIGS. 12C-12D illustrate example embodiments or different orientations of a camera and illumination system that may be part of a PCBA. FIG. 12E illustrates an example illumination environment of an embodiment of a tissue site by an embodiment of an illumination system such as described herein.

With reference to FIG. 12A, a PCBA 1008 may be a rigid-flex PCB having one or more rigid components 1204, one or more flexible components 1208, one or more optical sensors 1202, one or more illumination systems 1206, and/or other sensor systems and or electronic components, such as a battery, temperature sensor, controller, or other.

The PCBA 1008 may be configured to at least partially move or flex in order to at least partially follow the contour of a patient's tissue or move in response to tissue movement. For example, the one or more flexible components 1208 are configured to flex to allow the one or more rigid components 1204 to move in relation to each other. The one or more flexible components 1208 may be configured to include one or more flexible circuits or other constructions in order to facilitate communication and/or functioning of electronics on the PCBA. In some examples, the one or more rigid components 1204 may include one or more circuits, sensors 1202, and/or other constructions configured to support the one or more sensors 1202 mounted to the one or more rigid components 1204. In other examples, the PCBA 1008 may be entirely flexible or entirely rigid.

In some examples, the PCBA 1008 may contain one or more rigid components 1204 connected to one or more other rigid components 1204 by at least one flexible component 1208. The plurality of rigid components 1204 may be arranged in a grid or array layout. However, other arrangements, such as a staggered grid, circular arrangement, or other layout are also possible. An advantage of a layout in the form of an array is that it can facilitate an even arrangement of sensors 1202 that may be associated with each of the rigid components 1204, facilitating a more even coverage of the sensor system of the module 1000 in imaging a body surface region of interest on the patient.

In the illustrated example, the PCBA 1008 contains a grid of one or more rigid components 1204 having a set of rows 1210A, 1210B, 1210C, and columns 1212A, 1212B, 1212C. Each of the one or more rigid components 1204 in each row 1210A, 1210B, 1210C may be connected by a flexible component 1208. However, each of the one or more rigid components 1204 may or may not be connected across rows. For example, a single rigid component 1204 for each row 1210A, 1210B, 12010C may be connected to a rigid component 1204 in a different row at a single column 1212A such that only one connection from row to row is made. Thus, the PCBA 1008 may reduce the number of connections and/or flexible components 1208 needed in the PCBA 1008 while still maintaining connectivity. This arrangement has an additional advantage of improving flexibility of the PCBA 1008 by reducing connection points between rigid components 1204.

While a certain arrangement of the one or more rigid components 1204 and one or more flexible components 1208 are shown and described herein, other arrangements and connections or connection points are also possible. Additionally, while the illustrated example shows a grid of 9 rigid components 1204 and 8 flexible components 1208 or connections, other numbers and arrangements of rigid components 1204 and flexible components 1208 are also contemplated, such as 4, 10, 12, or 16 rigid components 1204. It is also of note that the grid may or may not contain an even number of rigid components 1204 and may or may not have a square or rectangular configuration.

The PCBA 1008 may be approximately square and/or rectangular in shape when laid flat on a planar surface. However, other shapes are also possible. With reference to FIG. 12B, the dimensions of the PCBA 1008 are described with reference to the PCBA 1008 in a flat plane. A total depth 1032A of the PCBA 1008 may preferably be between approximately 0.1 and 1.5 inches, or a value greater or less than bounded by that range. A total width 1032B of the PCBA 1008 may preferably be between approximately 0.5 and 10 inches, or a value greater or less than bounded by that range. An individual width 1034A of each of the one or more rigid components 1204 may preferably be between approximately 0.1 and 2 inches, or a value greater or less than bounded by that range. An individual depth 1034B of each of the one or more rigid components 1204 may preferably be between approximately 0.1 and 1.5 inches, or a value greater or less than bounded by that range. While certain ranges, numbers, and shapes are listed here, they are for illustrative purposes only and any of the dimensions of the PCBA 1008 may be within or outside this range. While each of the one or more rigid components 1204 are shown as being of the same size and shape, one or more of the one or more rigid components 1204 may be of a different size and/or shape from one or more other rigid components 1204.

The one or more rigid components 1204 may be configured to include at least one optical sensor 1202, such as a camera, and/or other sensing systems, such as a temperature sensor or other. Each optical sensor 1202 may include at least one image sensor, at least one lens, at least one aperture and/or other optical components. In some examples, the optical sensor 1202 may include a digital camera mounted to the rigid component 1204 of the PCBA 1008. For example, the optical sensor 1202 may include a CCD, CID, or CMOS sensor system. However, other types of optical sensors 1202 are also possible.

The at least one optical sensor 1202 on each of the one or more rigid components 1204 may be paired with an illumination system 1206. The illumination system 1206 may be configured to provide illumination within the field of view each of the at least one optical sensors 1202. An illumination system 1206 may include one or more light sources 1207, such as one or more LEDs configured to emit light in one or more wavelengths or wavelength ranges. Each light source 1207 of an illumination system 1206 may be configured to emit a different wavelength range or the same wavelength range. In one embodiment, the illumination system 1206 may be configured to emit light in a visible wavelength range. However, other wavelength ranges are also possible. For example, an illumination system 1206 may be configured to output wavelength ranges in an infrared or ultraviolet wavelength. In some examples, an illumination system 1206 may be configured to emit different ranges of light at different times, such as infrared and/or visible light at different intervals. For example, the illumination system 1206 may be configured to emit light with wavelengths in a range of approximately 400 nm to 750 nm (or in a visible wavelength range), approximately 700 nm to 1060 nm (or in a Near Infrared or NIR wavelength range), and/or approximately 900 nm to 1700 nm (or in a short wave infrared or SWIR wavelength range). In some examples, the choice of wavelength for an optical sensor 1202 and/or illumination system 1206 may be informed by the monitoring and/or analysis goals of the module 1000. For example, an illumination system 1206 may be configured to emit light in a wavelength associated with a wavelength range of one or more chromophores being monitored by an optical sensor 1202. For example, an illumination system 1206 may be configured to emit light in a visible wavelength range, such as between 400 nm and 750 nm in order for an optical sensor 1202 to monitor visible chromophores, such as oxy- and deoxy-hemoglobin and met-hemoglobin. In another example, an illumination system 1206 may be configured to emit light in an IR or SWIR wavelength range, such as between 780 nm and 1700 nm in order to monitor chromophores that absorb light in those wavelengths, such as water.

FIGS. 12C-12D illustrate example implementations and/or arrangements of illumination systems 1206A, 1206B. As illustrated in FIG. 12C, an illumination system 1206A may include a single light source 1207 adjacent to the optical sensor 1202 on the rigid component 1204 of the PCBA 1008. As illustrated in FIG. 12D, an illumination system 1206B may include a plurality of light sources 1207 surrounding the optical sensor 1202 on each of the one or more rigid components 1204. Advantageously, the illumination system 1206B including a ring of illumination can allow for the use of light sources 1207 requiring less power than with the illumination system 1206A while still providing even and consistent lighting to the field of view of the associated optical sensor 1202.

Each of the optical sensors 1202 may be configured to generate optical data associated with a sub-region of the total sensed tissue area 1216 of the body surface region of interest 1220, such as illustrated in FIG. 12E. The optical sensors 1202 may be configured to image the body surface region 1220 in the same or similar wavelength ranges or different wavelength ranges. In some examples, the optical sensors 1202 may be configured to capture image data in a visible light wavelength range. Additionally, or alternatively, one or more optical sensors 1202 may be configured to capture image data in non-visible light wavelength ranges, such as infrared or ultraviolet light. In some examples, different optical sensors 1202 may be configured to capture data in different wavelength ranges than other optical sensors 1202 of the PCBA 1008. In some examples, each optical sensor 1202 may be configured to capture a plurality of wavelengths or wavelength ranges that may or may not overlap.

In some examples, one or more optical sensors 1202 may be configured to capture overlapping sub-regions of the total sensed tissue area 1216. A controller 904 may then be configured to combine image data from the optical sensors 1202 to generate image data for the total sensed tissue area 1216. For example, an optical sensor 1202 may include a lens system and/or other optics that facilitate a field of view greater than 90 degrees, such as 170 degrees, or greater than 200 degrees. For example, a lens system may include a fisheye lens or other increased field of view optical system. The field of view of the lens system may be selected based on a balance of a desire to reduce the amount of compression at the edges of the field of view and the desired field of view and/or overlapping field of view needed to combine image data from the one or more optical sensors 1202.

Each optical sensor 1202 may be configured to be controlled by a controller 904 associated with the PCBA 1008. The optical sensors 1202 may be configured to collect data associated with the body surface region of interest on the patient. The controller 904 may be configured to control each of the optical sensors 1202 separately and/or simultaneously to collect the data associated with the body surface region of interest on the patient. The optical sensors 1202 may be configured to capture snapshots or a series of point in time images of the body surface region of interest in whole or in part. In some examples, the controller 904 may be configured to operate a subset of the plurality of optical sensors 1202 at intervals so as to minimize the power consumption due to sensor operation while still producing a set of images that appear to be taken simultaneously, due to the slow rate of visual change of the wound being imaged. For example, the controller 904 may be configured to operate each optical sensor 1202 of the plurality of optical sensors 1202 individually or in batches pseudo-simultaneously or periodically after short periods. For example, the controller 904 may be configured to operate each optical sensor 1202 of the plurality of optical sensors 1202 at 3 second intervals. However, other intervals of different durations are also possible. Advantageously, by delaying the activation of individual optical sensors 1202—and activation of the corresponding illumination systems 1206—for a period of time from optical sensor 1202 to optical sensor 1202, the instantaneous power throughput required of the battery 924 is reduced in comparison with activating each optical sensor 1202 and corresponding illumination system 1206 simultaneously. Moreover, the total power drawn from the battery 924 for the entire set of optical sensors 1202 and corresponding illumination systems 1206 activated sequentially and spaced-out temporally is less than the total power drawn from the battery 924 for the same set of optical sensors 1202 and corresponding illumination system 1206 if activated simultaneously. As a result, a smaller, lighter, and/or less expensive battery 924 may be used.

Example light shield of an embodiment of a module

Figure 13A:
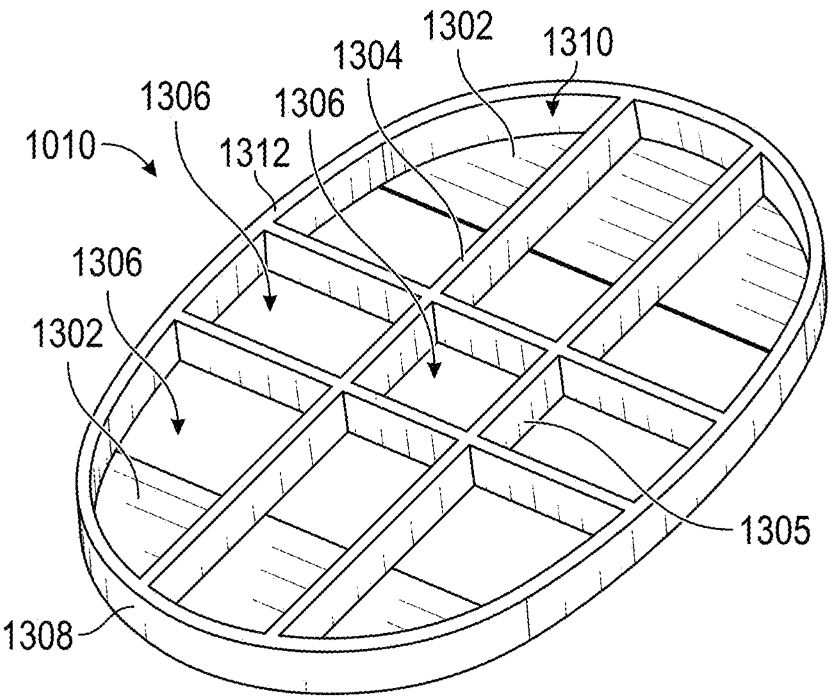
FIGS. 13A and 13B show top and bottom perspective views of an example light shield of an embodiment of a module.
Figure 13B:
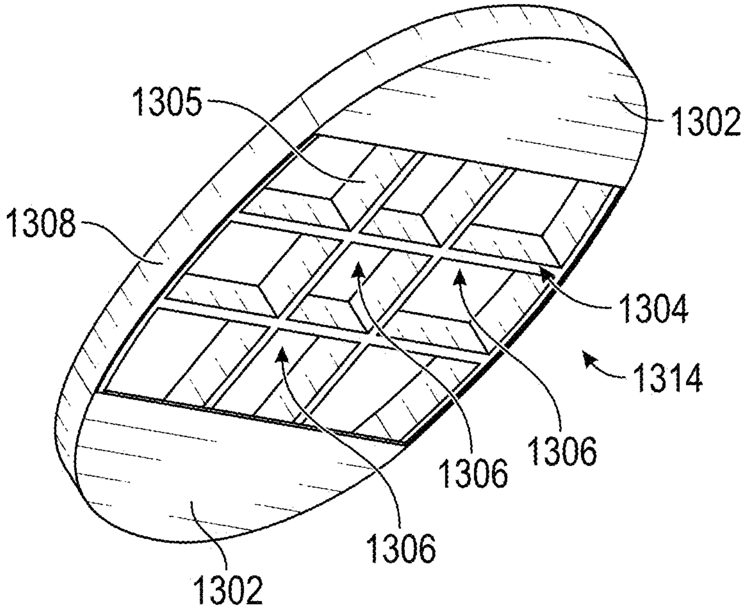
Figure 13C:
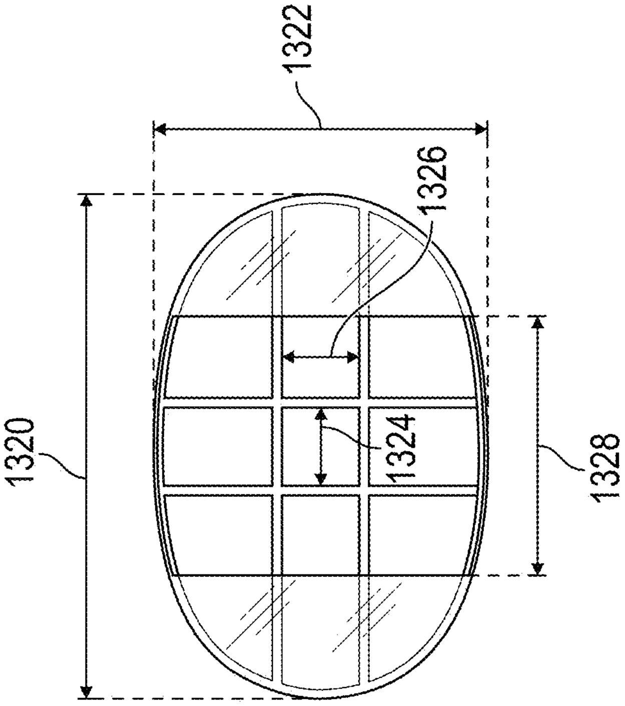
FIGS. 13C-13D show top-down and lateral cross-sectional views of a light shield illustrated in FIGS. 13A and 13B.
Figure 13D:
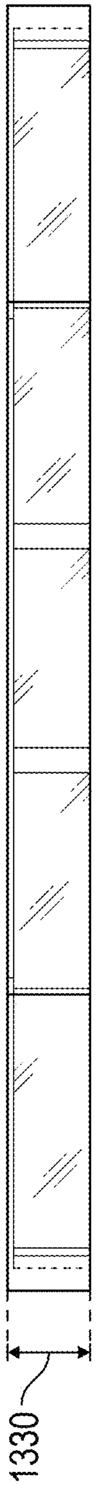
Figure 13E:
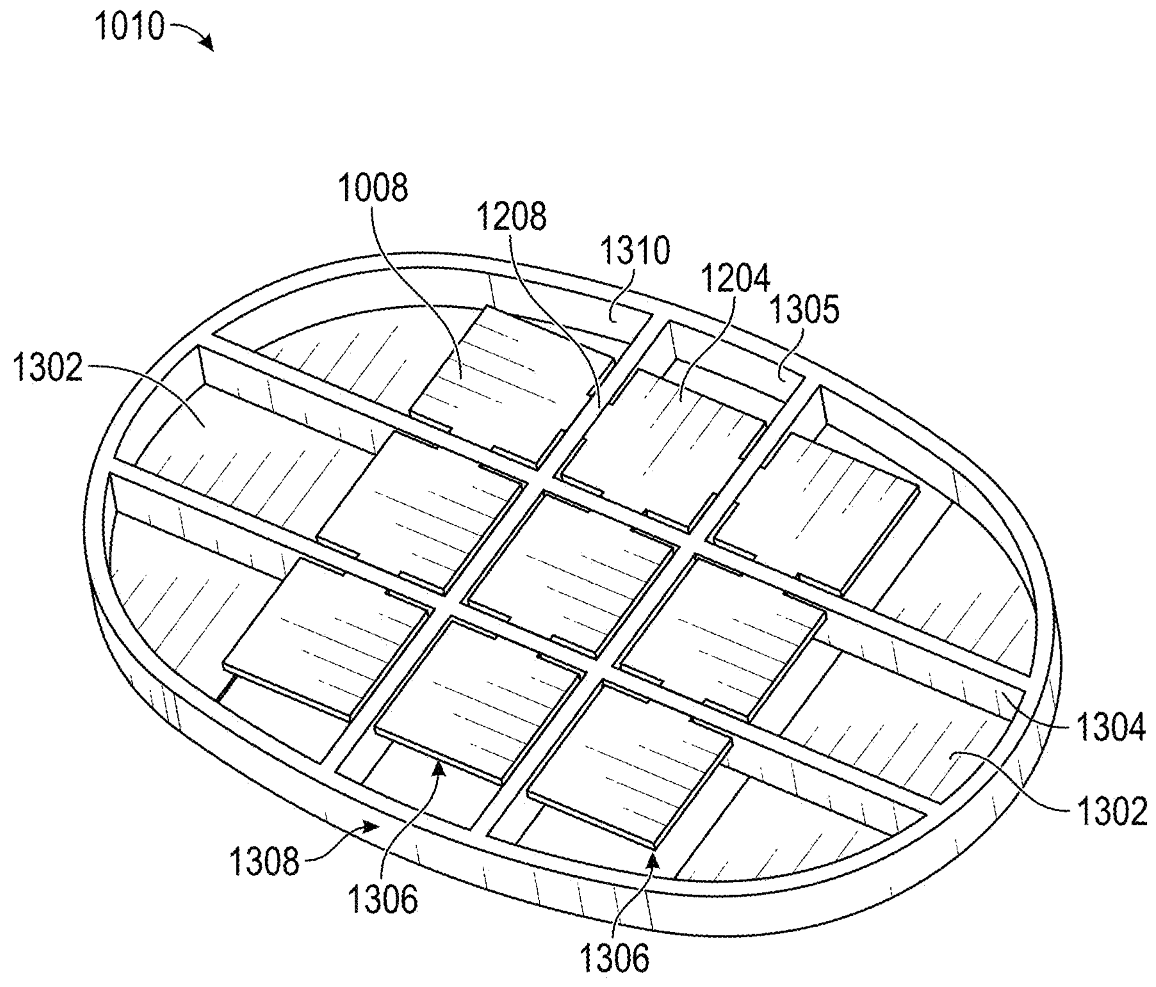
FIGS. 13E, 13F, and 13G show top, bottom, and side perspective views of an example light shield illustrated in FIGS. 13A-13D in arrangement with an embodiment of a PCBA of a module.
Figure 13F:
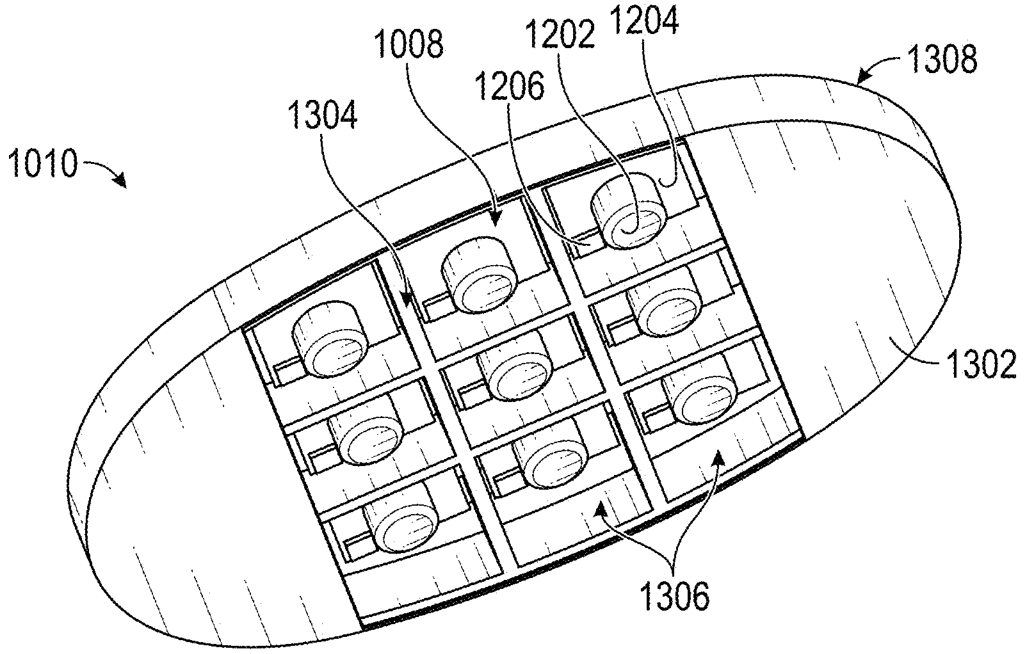

Disclosed herein are details of an example light shield 1010 of an embodiment of a module 1000. FIGS. 13A and 13B show top and bottom perspective views of an example light shield 1010. FIGS. 13C-13D show top-down and lateral cross-sectional views of a light shield 1010. FIGS. 13E-13F show top, bottom, and side perspective views of an example light shield 1010 in arrangement with a PCBA 1008.

The light shield 1010 may be configured to prevent light shunts across one or more illumination systems of the PCBA 1008. The light shield 1010 may be configured to be arranged with respect to the plurality of optical sensors 1202 and/or associated illumination systems 1206. The light shield 1010 may include a grid 1304 configured to run between optical sensor and/or illumination system arrangements and act as a shunt, providing a low-resistance path for electrical current so as to divert current away from other components arranged on the circuit board and prevent damage to other electronics.

The light shield 1010 may have a top or distal facing side 1312 and a bottom or proximal facing side 1314 and at least one external surface 1308. The top or distal facing side 1312 may be configured to receive at least a portion of the PCBA 1008 and associated sensors. The bottom or proximal facing side 1314 may be configured to face the tissue of the patient and/or receive one or more optical components, such as a diffuser 1012 and/or polarizer 1014 as described herein.

The light shield 1010 may be configured to be received in whole or in part into the top preform 1002 and/or standoff 1004. The light shield 1010 may or may not be coupled to the top preform 1002 and/or standoff 1004. For example, the light shield 1010 may be coupled at a top or distal facing side 1312 or at least one external surface 1308 to the top preform 1002 and/or standoff 1004. The light shield 1010 may be coupled by a permanent or semi-permanent method of fixation, such as glue or other adhesive. In some examples, the light shield 1010 may be press-fit into at least a portion of the top preform 1002 and/or standoff 1004.

In some examples, the light shield 1010 may be approximately oblong in shape. In some examples, the light shield 1010 may have a similar size and/or shape as the overall module 1000 itself and/or the cavity 1113 formed within the module 1000 as described above. However, other shapes are also possible. With reference to FIGS. 13C and 13D, the dimensions of the light shield 1010 are described herein. A depth 1330 of the light shield 1010 may be configured to mitigate stray light that has not interacted with the target tissue, for example preferably between approximately 0.04 and 2 inches, or a value greater or less than bounded by that range. A major width 1320 of the light shield may preferably be between approximately 1 and 10 inches, or a value greater or less than bounded by that range. A minor width 1322 of the light shield 1010 may be between preferably be between approximately 1 and 10 inches, or a value greater or less than bounded by that range. A minimum width 1324 and height 1326 of each opening 1306 may be sized to accommodate at least one illumination system 1206 and one or more optical sensor 1202 component of a rigid component of a PCBA 1008 within the opening 1306. For example, a minimum width 1324 of each opening 1306 may preferably be between approximately 0.1 and 1 inches, or a value greater or less than bounded by that range and a minimum height 1326 of each opening 1306 may preferably be between approximately 0.1 and 1 inches, or a value greater or less than bounded by that range. Additionally, a total width 1328 along the major axis of the light shield 1010 of an opening formed by the one or more surfaces 1302 on the bottom or proximal facing side 1314 may be preferably between approximately 1 and 10 inches, or a value greater or less than bounded by that range, and a total width along the minor axis of the light shield 1010 of the opening formed by the one or more surface 1302 on the bottom or proximal facing side 1314 may be the same or smaller than the minor width 1322 of the light shield 1010. While certain dimensions and shapes are referenced herein, one or more dimensions of the light shield 1010 and/or openings 1306 may be within or outside of the ranges provided.

Figure 13G:
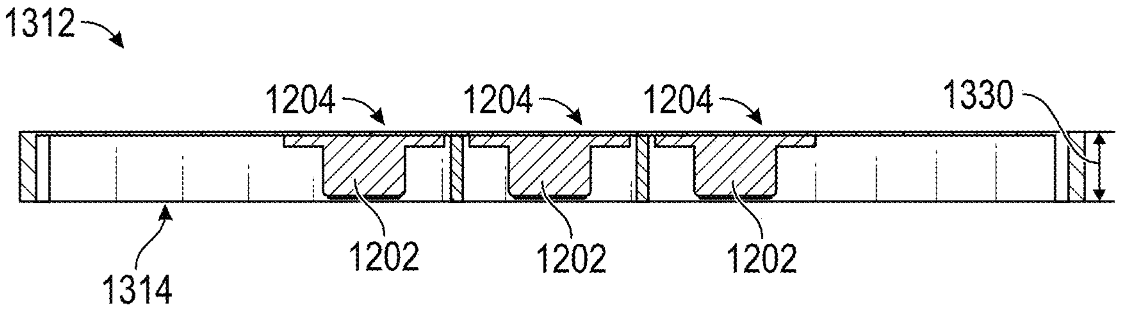

With reference to FIGS. 13E-13G, the light shield 1010 may include a plurality of internal walls 1305 forming the grid 1304 and a plurality of external walls 1310. The plurality of walls 1305, 1310 may form a plurality of openings 1306 open on both a top or distal side 1312 and bottom or proximal side 1314. The plurality of openings 1306 may be configured to receive and at least partially align with one or more sensors 1202 of a PCBA 1008 when the PCBA 1008 is placed in arrangement with the light shield 1010, such as shown in the perspective views illustrated in FIGS. 13E-13G. The one or more openings 1306 may or may not be of similar size and/or shape. In the illustrated example, the one or more openings 1306 have differing size and shape depending on their location in the light shield 1010 and/or the geometry of the light shield 1010 and/or module 1000. For example, openings 1306 closer to an external wall 1310 of the light shield 1010 may be larger than openings 1306 at a center of the light shield 1010.

As illustrated in FIGS. 13E-13G, each opening of the grid may receive a single optical sensor 1202 and/or associated illumination system 1206. Additionally, or alternatively, each opening 1306 may be configured to receive a single rigid component 1204 of the PCBA 1008 so that the flexible components 1208 are configured to travel between the plurality of openings 1306, such as over or through the walls 1305 of the grid 1304. In some implementations, the depth 1330 of the light shield 1010 may be such that the grid 1304 of the light shield 1010 is not visible in the field of view of each of the optical sensors 1202 of the PCBA 1008. For example, the bottom surface of one or more optical sensors 1202 may be aligned with the bottom or proximal facing side 1314 of the light shield 1010.

The bottom side 1314 may include one or more surfaces 1302 configured to block one or more areas adjacent an edge of the light shield 1010 and/or provide a guide or inset opening to receive and/or facilitate placement of one or more optical components, such as a diffuser 1012 and/or polarizer 1014 described herein. The shape of the opening provided by the placement of the one or more surfaces 1302 may facilitate more accurate placement of the optical components and/or alignment of the optical components with the one or more optical sensors 1202 of the PCBA 1008, as will be described herein.

Example Optical Components of an Embodiment of a Module

Figure 14A:
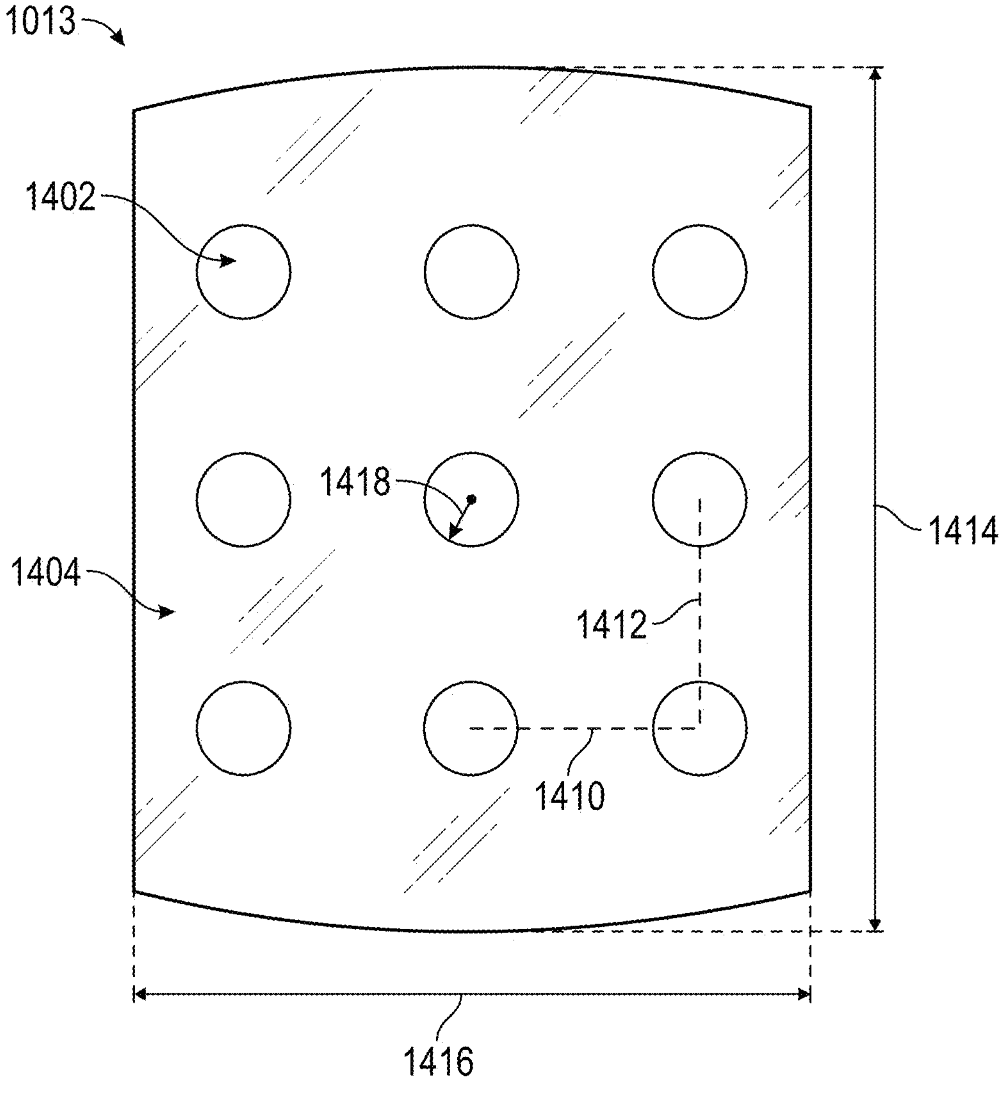
FIGS. 14A, 14B, and 14C show top and bottom perspective views of an example set of one or more optical components of a module.
Figure 14B:
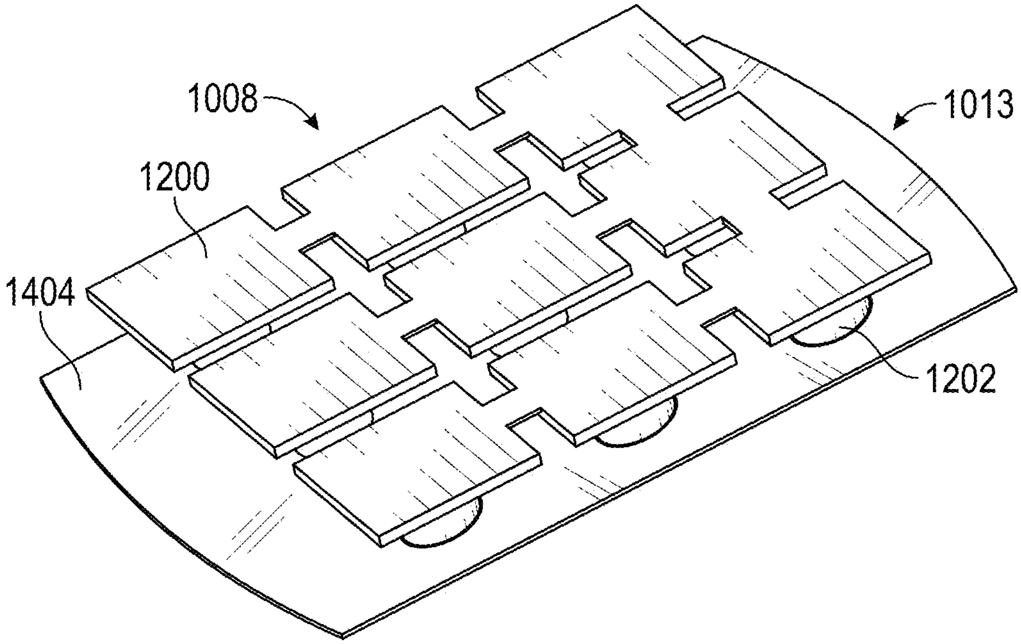
Figure 14C:
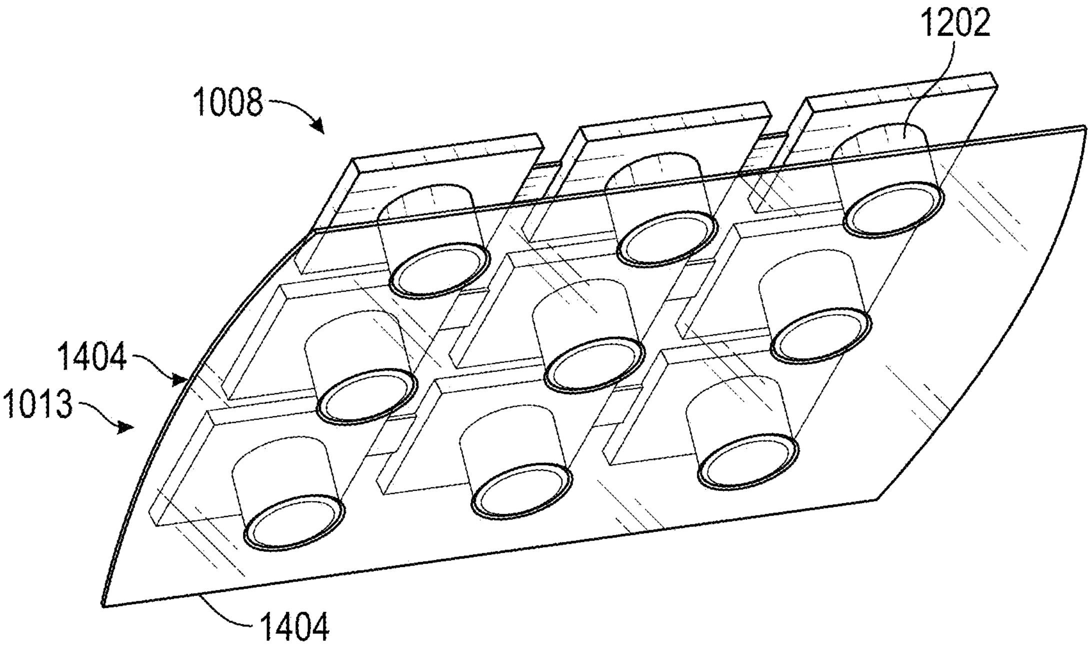
Figure 14D:
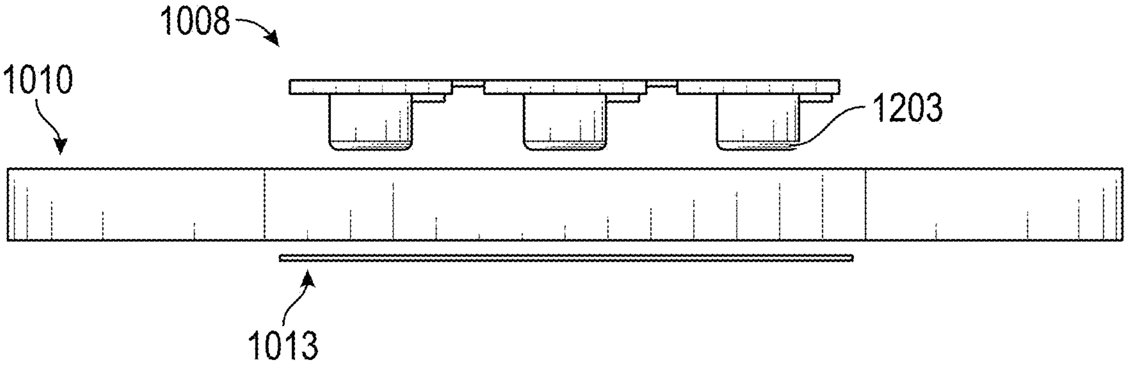
FIGS. 14D-14E show top-down and lateral cross-sectional views of an example set of one or more optical components illustrated in FIGS. 14A-14C.
Figure 14E:
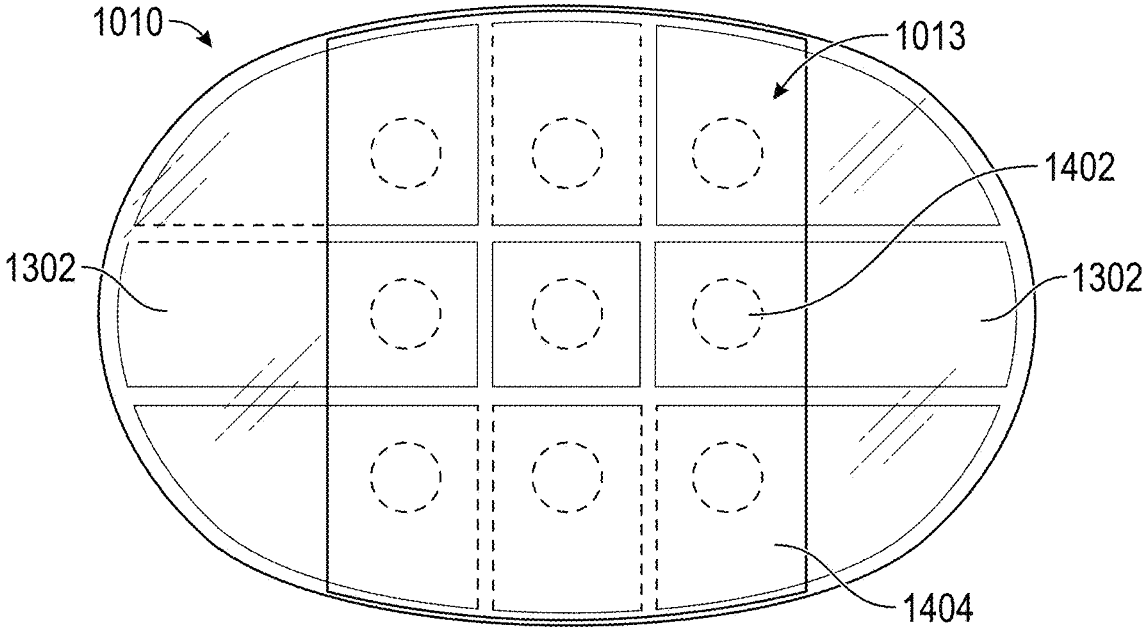

As referenced above, a module 1000 may include one or more optical components 1013, such as a diffuser 1012 and/or polarizer 1014, to provide enhanced imaging through consistent illumination across the field of view and/or reduced glare from the wound being imaged. The one or more optical components 1013 may include, but are not limited to one or more diffusers 1012 configured to diffuse or scatter light from one or more illumination system 1206 associated with one or more optical sensors 1202 of a PCBA 1008 and one or more optical filters, such as one or more polarizers 1014 configured circularly or linearly polarize light transmitted towards and/or reflected from the body surface region of interest. Other optical components may also be utilized. While certain optical components are noted in relation to a certain orientation and/or arrangement within the module 1000, different orientations and/or arrangements of components are also possible. FIGS. 14A-14C show top and bottom perspective views of an example set of one or more optical components 1013. FIGS. 14D-14E show top-down and lateral cross-sectional views of an example set of one or more optical components 1013.

One or more optical components 1013 may include a diffuser 1012. The diffuser 1012 may be a transmissive diffuser at least in part. Thus, in at least some geometric regions, the diffuser 1012 may be configured to diffuse or scatter at least a portion of the light from one or more illumination sources of one or more illumination systems 1206 of a PCBA 1008 towards the tissue site of the patient being imaged. The diffuser 1012 may be configured to diffuse light in a variety of wavelength ranges, including but not limited to visible, infrared, and ultraviolet. The diffuser 1012 may be composed of one or more materials and include one or more diffuse layers. For example, the diffuser 1012 may include an optical filter, exhibiting a wavelength dependent degree of absorption.

A diffuser 1012 may be composed of one or more material layers. For example, a diffuser may include a plurality of diffusion layers having an air gap in between. Thus, allowing for a more homogenous illumination of the body surface region being imaged than without the plurality of layers. The one or more material layers may include, but are not limited to holographic diffusers, white diffusing glass, ground glass diffusers, the like or a combination thereof.

The diffuser 1012 may be configured to diffuse light in some areas and allow light to pass through without any or without significant diffusion in other areas. For example, as illustrated in FIG. 14A, a diffuser 1012 may include a plurality of non-diffuse regions 1402 and one or more diffuse regions 1404. The one or more non-diffuse regions may be configured to allow for an optical sensor 1202 aligned with the non-diffuse region 1402 to measure optical data from at least a sub-portion of a body surface region of interest as described above without significant scattering by the diffuser 1012. The one or more non-diffuse regions 1402 may be a plurality of non-diffuse regions each corresponding to a single optical sensor 1202 of a PCBA 1008. As illustrated in FIGS. 14B-14C, the plurality of non-diffuse regions 1402 may be aligned with the optical sensors 1202 such that a center of each non-diffuse region 1402 aligns with a center of an optical sensor 1202. For example, where the one or more optical sensors 1202 are aligned in a grid having a first horizontal distance 1410 and a second horizontal distance 1412 between centers of adjacent optical sensors 1202, the corresponding non-diffuse regions will be aligned to have approximately the same first horizontal distance 1410 and a second horizontal distance 1412 between centers of the non-diffuse regions. A radial size 1418 of one or more non-diffuse regions 1402 may be informed by one or more considerations, such as the height of the cavity 1113 and/or module 1000, the individual field of view of an optical sensor 1202, camera pitch, and number of diffusers. For example, the radial size 1418 may preferably be between approximately 0.188 and 1 inches, or a value greater or less than bounded by that range. In some examples, the radial size 1418 may roughly correspond to a size and/or field of view of an associated optical sensor 1202.

In some implementations, one or more optical components 1013 may include at least one polarizer 1014 (or polarizing layer). The at least one polarizer 1014 may be configured to allow light of a specific polarization to transmit through the one or more optical components 1013 and/or be reflected back from the one or more optical components 1013. In some examples, the at least one polarizer 1014 may be a linear polarizer, circular polarizer, circular polarizer, and/or elliptical polarizer. The at least one polarizer 1014 may be configured to reduce glare from light in the image data of the body surface region of interest.

In some examples, the one or more optical components 1013 may include at least one polarizing layer or polarizer between the diffuser 1012 and the one or more optical sensors 1202. However, other locations of polarizing layer(s) and/or polarizers may also be possible. For example, the at least one polarizer 1014 may be configured to be on, at, or otherwise near a lens 1203 and/or illumination system 1206. In some examples, the at least one polarizer 1014 may be at a top or distal surface of the one or more optical components 1013. Additionally, or alternatively, the at least one polarizer 1014 may be at a bottom or proximal surface of the one or more optical components 1013 and/or at another location within the one or more optical components 1013 or other area of the module 1000.

With reference to FIGS. 14D and 14E, the positioning of the one or more optical components 1013 in relation to other components of the module 1000 may be such that the one or more optical components 1013 is arranged proximal of the PCBA 1008 and proximal of the light shield 1010. In some examples, the position of the one or more optical components 1013 may be approximately centered in relation to the light shield 1010. For example, the one or more optical components 1013 may be arranged between the one or more surfaces 1302 of the light shield 1010 on the proximal side of the light shield 1010. However, other configurations and arrangements are also possible.

Example Standoff Structure of an Embodiment of a Module

Figure 15A:
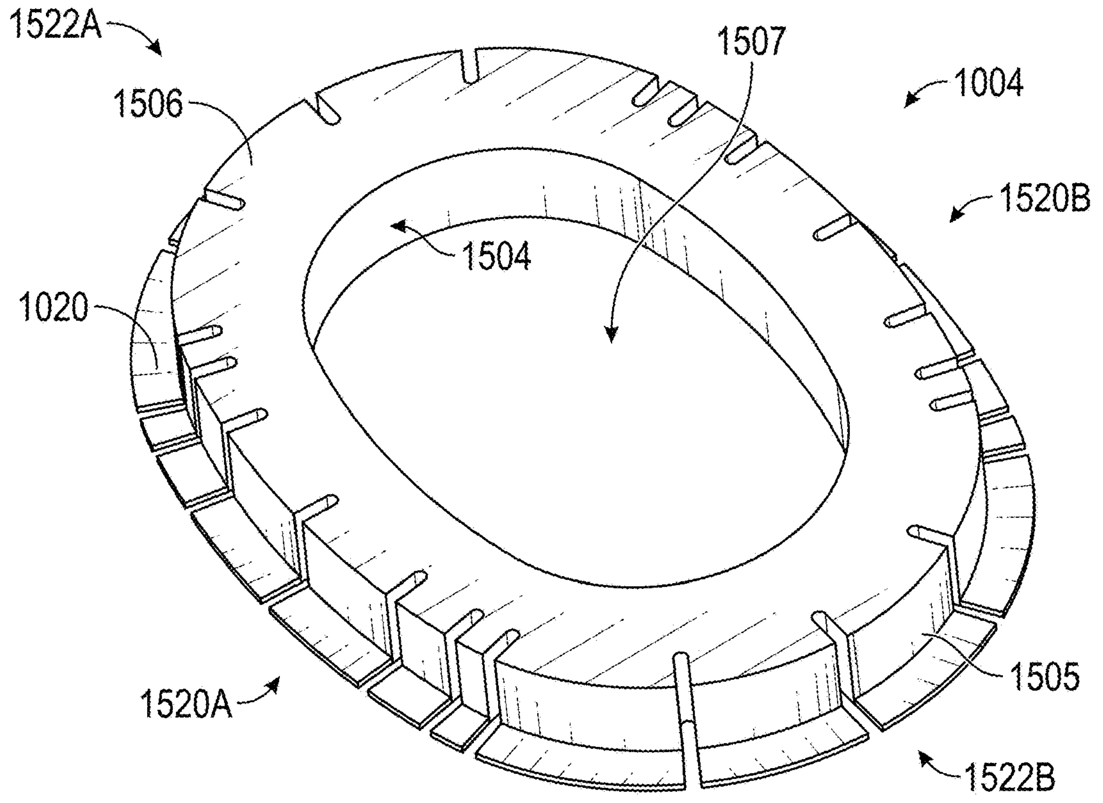
FIG. 15A shows a top perspective view of an example standoff of an embodiment of a module.
Figure 15B:
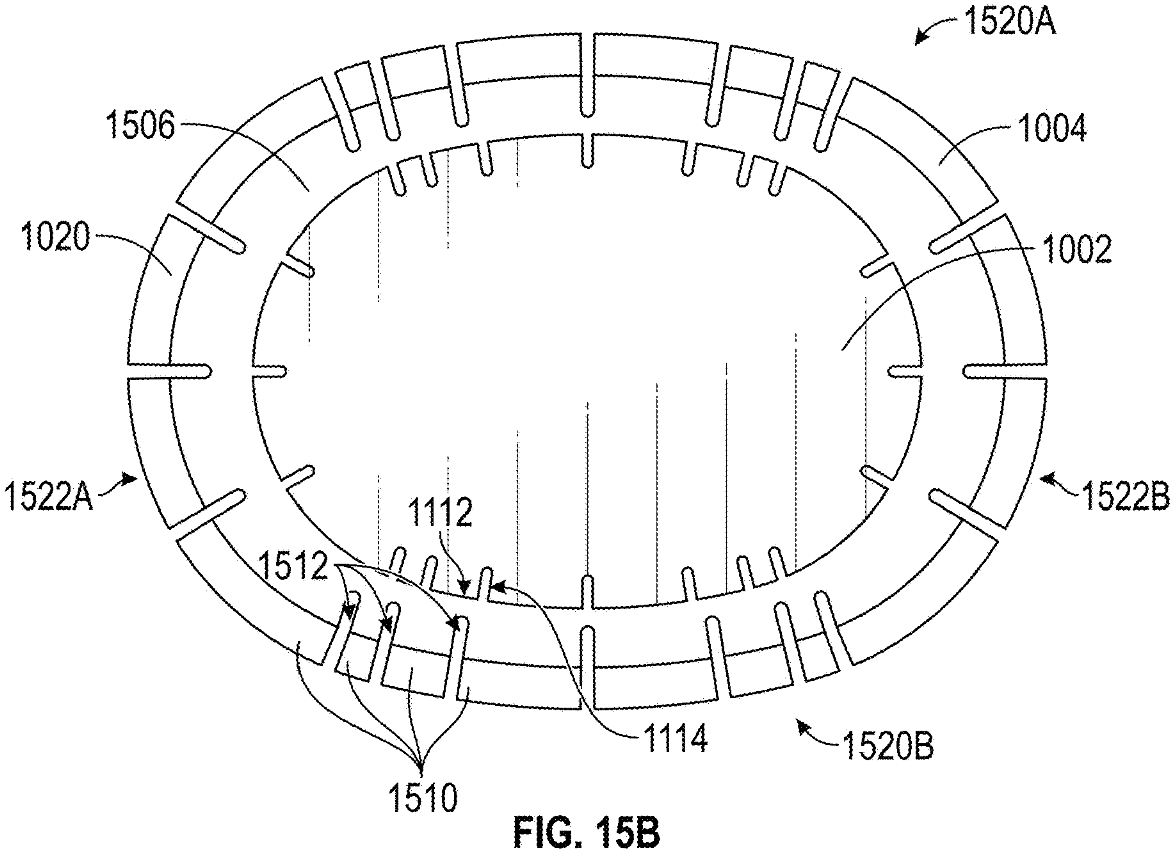
FIG. 15B shows a top-down view of an example standoff illustrated in FIG. 15A in arrangement with a top preform embodiment of an example module.
Figure 15C:
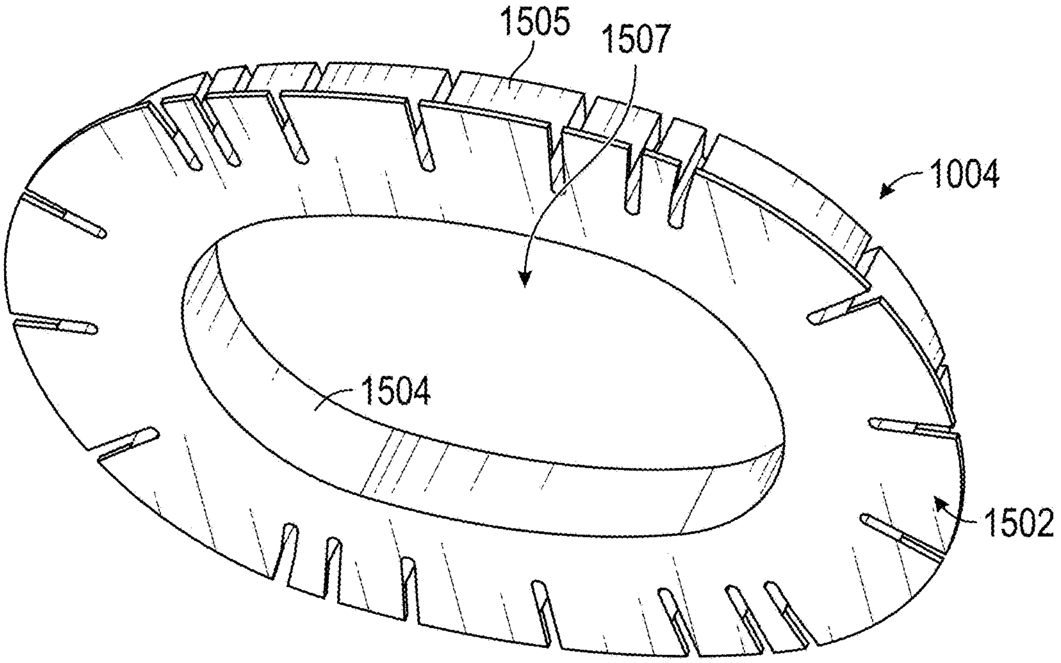
FIG. 15C shows a bottom perspective view of an example standoff illustrated in FIGS. 15A and 15B.
Figure 15D:
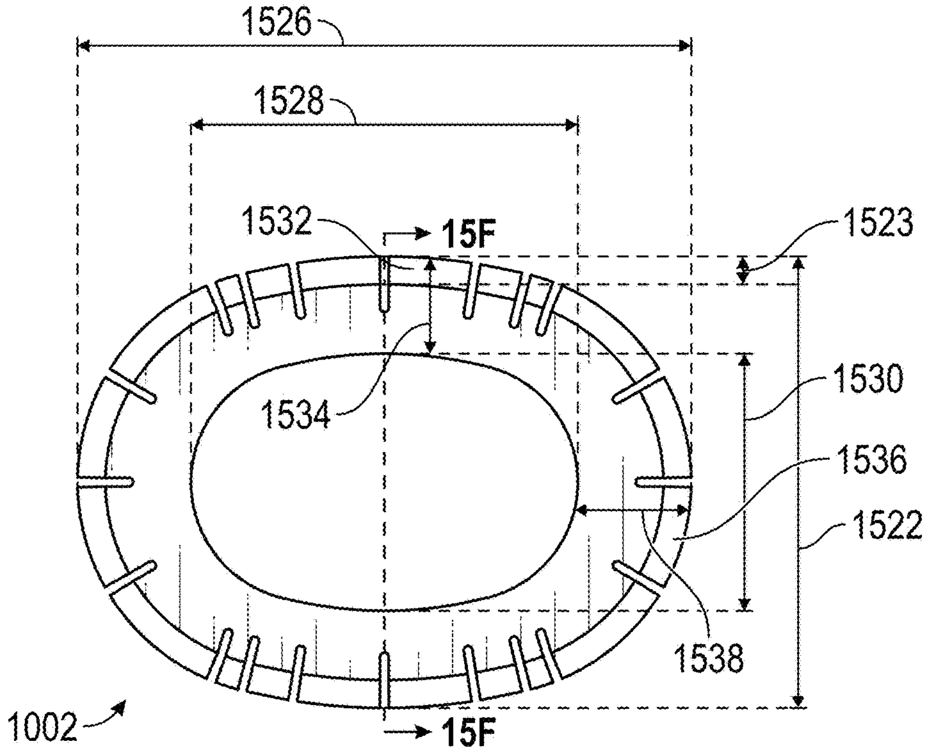
FIGS. 15D, 15E, and 15F show top-down, bottom-up, and lateral cross-sectional views of an example standoff illustrated in FIGS. 15A-15C.
Figure 15E:
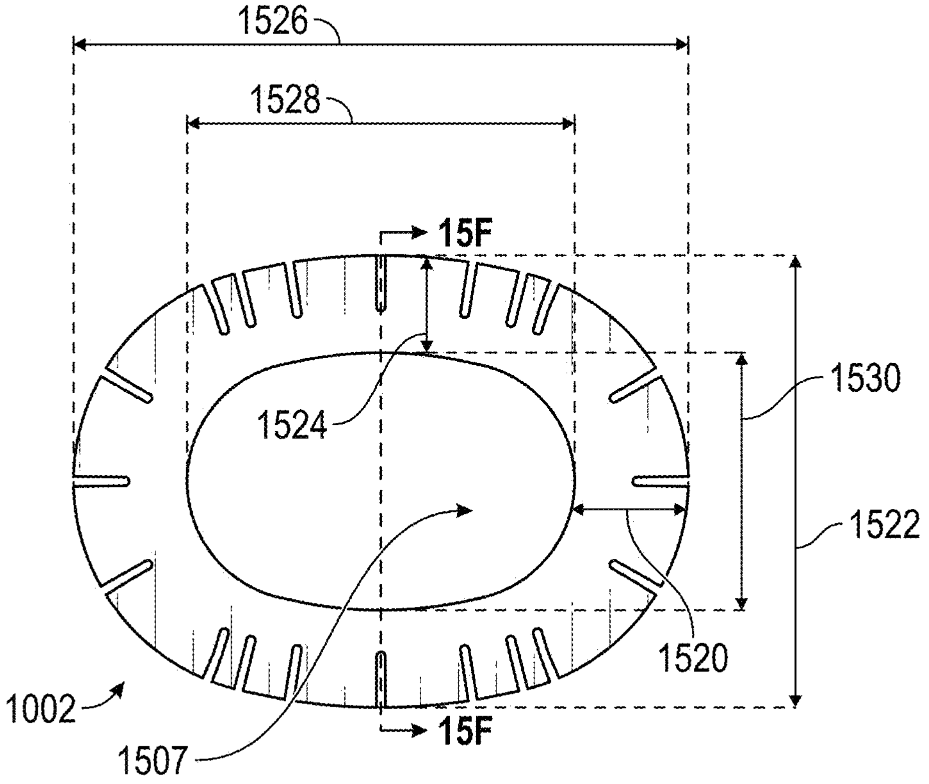
Figure 15F:
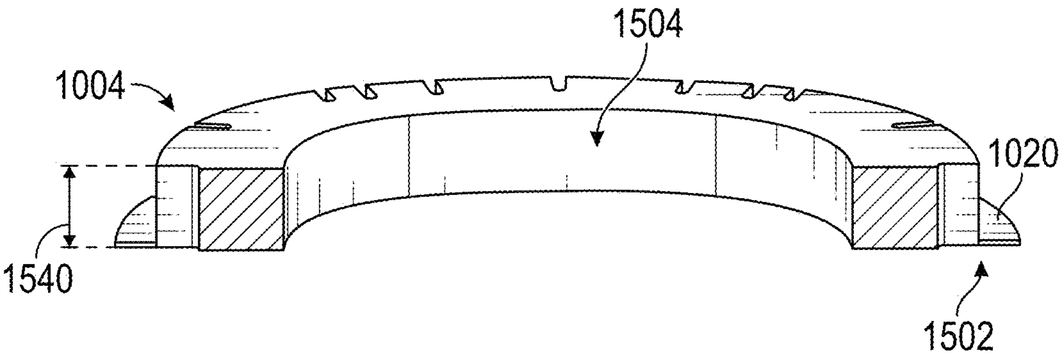
Figure 15G:
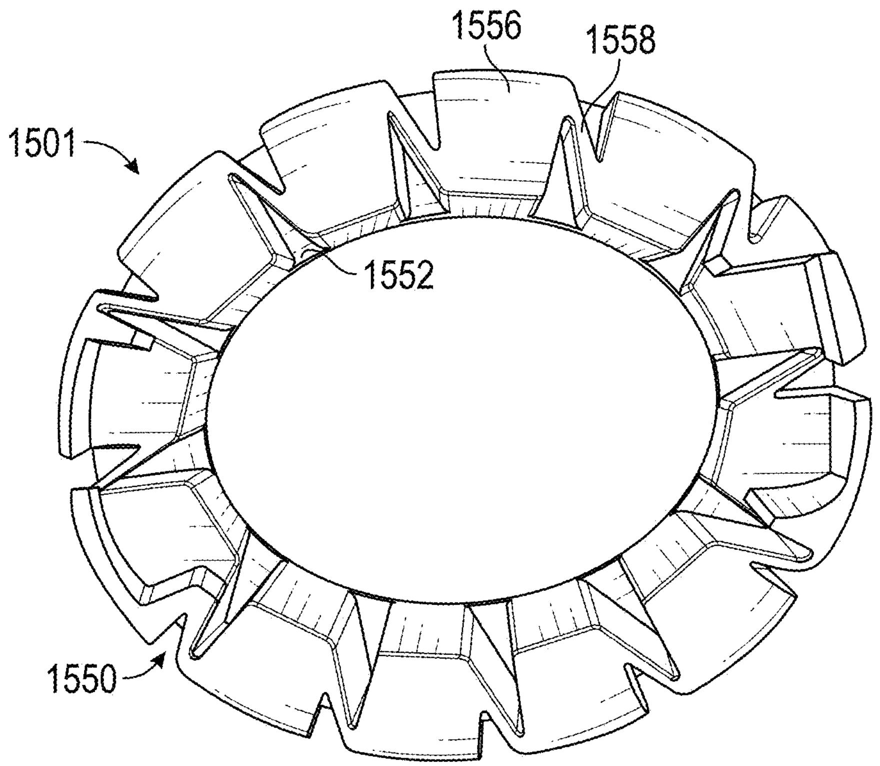
FIGS. 15G-15H show an alternative implementation of a standoff of a module.
Figure 15H:
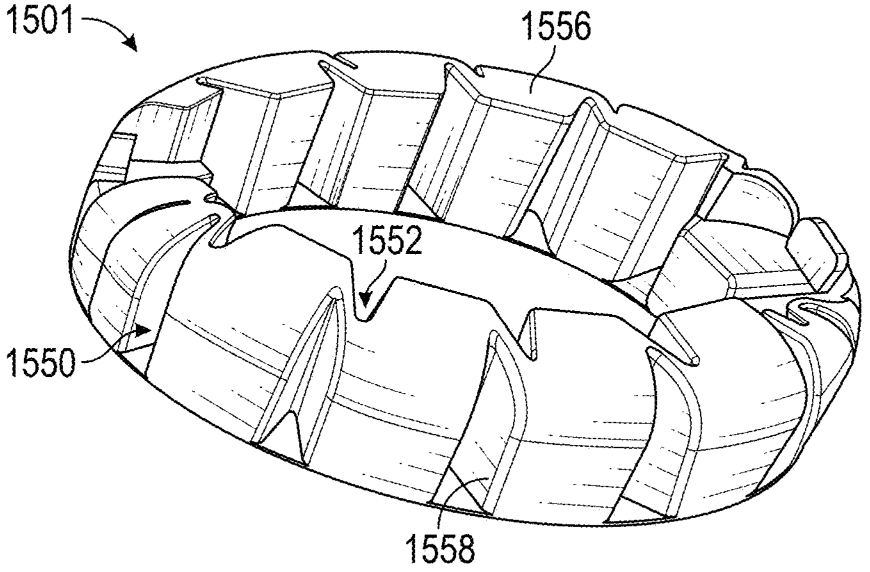

Disclosed herein are details of example standoff structures 1004, 1501 of embodiments of a module 1000. FIG. 15A shows a top perspective view of an example standoff 1004. FIG. 15B shows a top-down view of an example standoff 1004 in arrangement with a top preform 1002. FIG. 15C shows a bottom perspective view of an example standoff 1004. FIGS. 15D-15F show top-down, bottom-up, and lateral cross-sectional views of an example standoff 1004. FIGS. 15G-15H show an alternative implementation of a standoff 1004.

The standoff 1004 may be composed of a single material or component and/or a combination of materials or components. In some examples, the standoff 1004 may be a single molded or cut shape comprising surgical foam, silicone, other flexible or semi-flexible or semi-rigid material, or other material having one or more similar physical or material properties similar to surgical foam, such as thermal stability, permeability, tensile strength, density, compressive strength, or other material property.

The standoff 1004 may include one or more portions, including but not limited to a top side 1506, a lip 1020, one or more external sidewalls 1505, one or more internal sidewalls 1504, a bottom side 1502, one or more cutouts or notches 1512, and one or more tabs 1510.

The top side 1506 of the standoff 1004 may be configured to face distally away from the tissue site of the patient. The bottom side 1502 may be configured to face proximally towards the tissue site of the patient. In some configurations, the bottom side 1502 may be configured to contact the patient's skin or tissue. In some configurations, the top side 1506 may be configured to couple to the top preform 1002.

The top side 1506 of the standoff 1004 may include an opening 1507 extending to the bottom side 1502. The opening 1507 may have one or more walls 1504 extending from the top side 1506 to the bottom side 1502. The opening 1507 may have an oblong shape and/or other shape consistent or mirroring the overall shape of the module 1000. However, other shapes are also possible. In some examples, the opening 1507 may be configured to visually expose the body surface region of interest to one or more optical sensors 1202 arranged within and/or above the opening 1507, such as on a PCBA 1008.

An exterior surface of the standoff 1004 may include, but is not limited to, one or more one or more external sidewalls 1505 and/or one or more lips 1020 at a bottom side 1502 of the standoff 1004. As illustrated in FIGS. 15A and 15B, the lip 1020 may extend along plane of the bottom side or proximal surface 1502 of the standoff 1004. The lip 1020 may extend laterally away from the one or more external sidewalls 1505. The lip 1020 may include a flat, approximately flat, contoured, or other geometric surface.

The standoff 1004 may include a plurality of tabs 1510 and/or cutouts or notches 1512 around the exterior surface(s) (such as at the one or more external sidewalls 1505 and the lip 1020) of the standoff 1004. The plurality of tabs 1510 may be formed by the placement of two adjacent notches 1512. The size, shape, and/or placement of the plurality of tabs 1510 may provide a measure of flexibility at the exterior surface(s) and/or edge(s) (such as at the one or more external sidewalls 1505 and/or lip 1020) of the standoff 1004. The flexibility may be such so as to allow the standoff 1004 and/or portions of the module 1000 to conform at least partially to the contour of the tissue of the patient. The size and/or shape of the tabs 1510 may be different or the same at various locations around the exterior surface(s) of the standoff 1004 to facilitate the desired flexibility and/or conformity of the standoff 1004. As shown in FIG. 15B, the size, shape, and/or placement of the tabs 1510 may be informed and/or roughly aligned with the placement of tabs in other components of the module 1000, such as the placement of tabs 1112 of the top preform 1002. Accordingly, the entirety of the exterior of the module 1000 as formed by the standoff 1004 and top preform 1002, in the illustrated example, may be configured to flex at similar or the same locations along the exterior of the module 1000. In some examples, where the lateral cross-sectional shape of the standoff 1004 is an oblong shape, such as illustrated, the standoff 1004 may include two or more tabs of similar size and/or shape at each of the short sides 1522A, 1522B and a combination of larger and smaller tabs at each of the long sides 1520A, 1520B, where a larger tab is defined as a tab 1510 formed by two adjacent notches 1512 spread further apart along the edge of the standoff 1004 and a smaller tab is defined as a tab 1510 formed by two adjacent notches 1512 spread closer together along the edge of the standoff 1004. In some examples, the standoff 1004 may have smaller tabs at areas of higher curvature along the one or more external sidewalls 1505 and larger tabs at areas of lower curvature along the one or more sidewalls. However, other configurations are also possible. The notches 1512 may be formed by a cut or indentation along the one or more external sidewalls 1505 that runs at least a portion of the way towards the opening 1507 without cutting into or otherwise engaging the opening 1507. Thus, the notches 1512 may in some implementations cut through both the lip 1020 and the one or more external sidewalls 1505. The notches 1512 may run a full height 1028 of the standoff 1004 such that the notches cut through both the top side 1506 and the bottom surface 1502. In some instances, the notches 1512 may be of the same depth and/or height. However, in other instances, the notches 1512 may have varying depths and/or heights. The width of the notches 1512 may be varying or the same. In some examples. The width of each of the notches 1512 may be different based on their location along the one or more external sidewalls 1505 and/or geometry of the standoff 1004. The width of each of the one or more notches 1512 may be smaller than a width of one or more of the tabs 1510.

FIGS. 15G-15H illustrate an example alternative embodiment of an example standoff 1501 having a different arrangement of notches. In the illustrated example, a standoff 1501 may include a plurality of notches 1550 on an interior surface 1552 and exterior surface 1556. The plurality of notches 1550 may be staggered along the interior 1552 and exterior 1556 to form an accordion like shape, facilitating flexibility and movement of the standoff 1501 in at least two degrees of freedom when applied to a patient's tissue.

With reference to FIGS. 15D and 15E, showing a top-down and bottom-up perspective view of the standoff 1004 and the cross section shown in FIG. 15F, an external major width 1526 of the standoff 1004 including the lip 1020 may preferably be between approximately 1 and 10 inches, or a value greater or less than bounded by that range. An external minor width 1522 of the standoff 1004 including the lip 1020 may preferably be between approximately 1 and 10 inches, or a value greater or less than bounded by that range. An external major width 1526 of the standoff 1004 excluding the lip 1020 (such as the external major width of the top surface 1506) may preferably be between approximately 0.75 and 9.75 inches, or a value greater or less than bounded by that range. An external minor width 1522 of the standoff 1004 excluding the lip 1020 (such as the external minor width of the top surface 1506) may preferably be approximately 0.75 and 9.75 inches, or a value greater or less than bounded by that range. A width 1523 of the lip 1020 may be consistent around the edge of the standoff 1004 and large enough to enable placement of additional tape over adhesive of the module 1000. For example, a width 1523 may be preferably between approximately 0.25 and 1.5 inches, or a value greater or less than bounded by that range. The interior space (e.g., cavity or opening 1507) may have a major width 1528 of between approximately 0.5 and 9.5 inches, or a value greater or less than bounded by that range and a minor width 1530 of between approximately 0.5 and 9.5 inches, or a value greater or less than bounded by that range. A height 1540 of the standoff 1004 may be between approximately 0.04 and 0.75 inches, or a value greater or less than bounded by that range. While certain ranges, numbers, and shapes are listed here, they are for illustrative purposes only and any of the dimensions of the top preform 1002 may be within or outside this range.

Example Overtape Support of an Embodiment of a Module

Figure 16A:
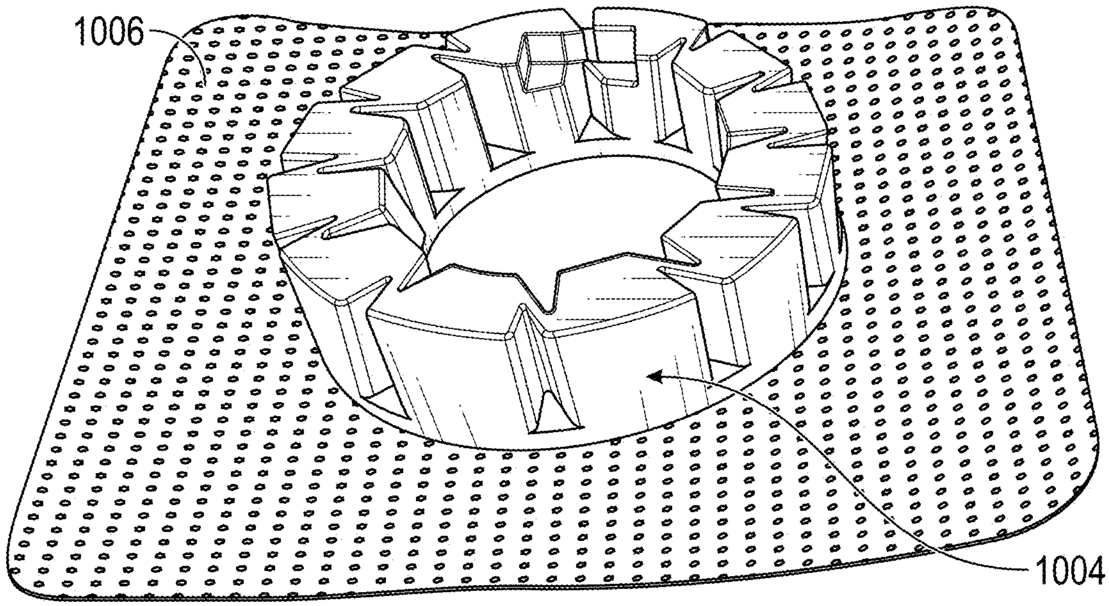
FIGS. 16A, 16B, and 16C show perspective, top down, and lateral cross-sectional views of an example overtape support of an embodiment of a module.
Figure 16B:
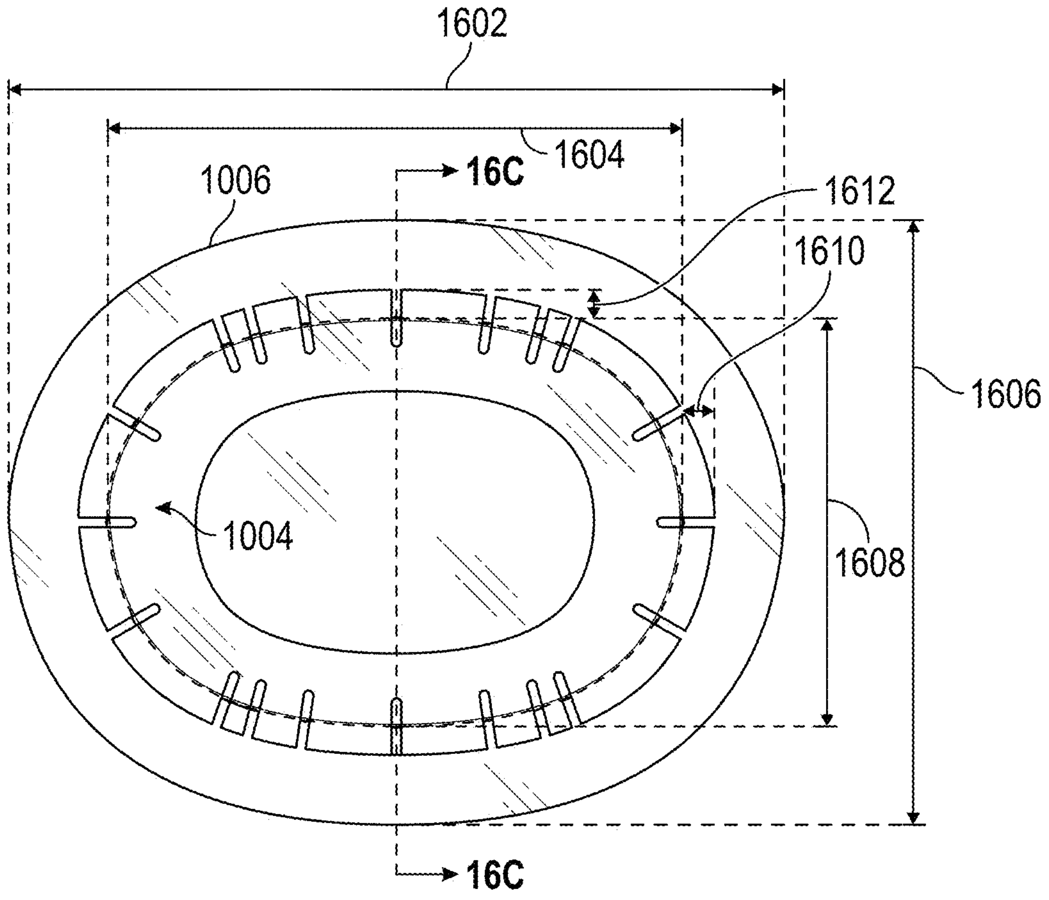
Figure 16C:
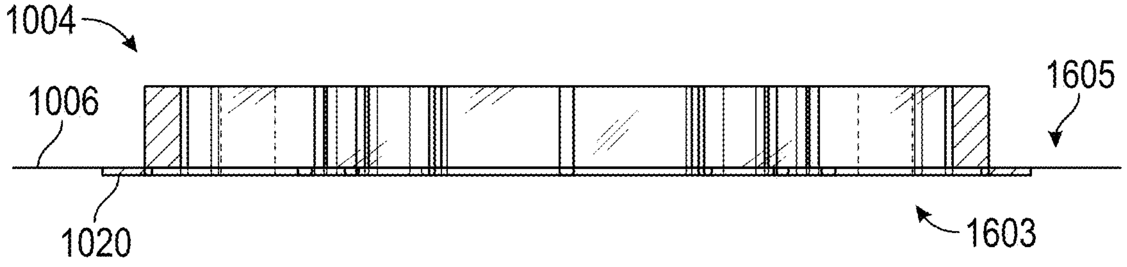

Disclosed herein are details of an example overtape support 1006 of an embodiment of a module 1000. FIGS. 16A-16C show perspective, top down, and lateral cross-sectional views of an example overtape support 1006.

In some examples, the overtape support 1006 may have an opening having dimensions 1604, 1606 of similar size and shape to at least one outer dimension of the module 1000 so as to receive at least a portion of the module 1000. The opening may be large enough to receive at least a portion of the module and small enough to allow the overtape support 1006 to overlap at least partially with one or more other portions of the module 1000, such as lip 1020 of the standoff 1004.

The overtape support 1006 may be configured to couple to one or more of the standoff 1004 and/or tissue of the patient. For example, the overtape support 1006 may include one or more adhesive areas, such as on a proximal side 1603 of the overtape support 1006 and one or more non-adhesive areas, such as on a distal side 1605 of the overtape support 1006. The one or more adhesive areas may be configured to temporarily or semi-permanently adhere to the tissue or skin of the patient and/or one or more portions of the module 1000. In some examples, the overtape support 1006 may be configured to be removed and/or replaced in some implementations. In some examples, the one or more adhesive areas may include a medical grade adhesive.

In the illustrated example of FIG. 16B. the amount of overlap of the overtape support 1006 over the standoff 1004 may be the entirety or a subportion of the lip 1020. For example, the amount of overlap 1610 may preferably be between approximately 0.25 and 1.5 inches, or a value greater or less than bounded by that range. In some examples, the major width 1602 of the overtape support 1006 may preferably be between approximately 1 and 10 inches, or a value greater or less than bounded by that range. However, the major and/or minor width of the overtape support 1006 may be smaller or larger than the described ranges and/or of a different geometry and/or dimension than described herein. For example, as shown in FIG. 16A, the overtape support 1006 may be square or rectangular. In another example, the geometry of the 1006 may be similar in shape to the shape of the module 1000. However, other shapes are also possible.

Figure 17A:
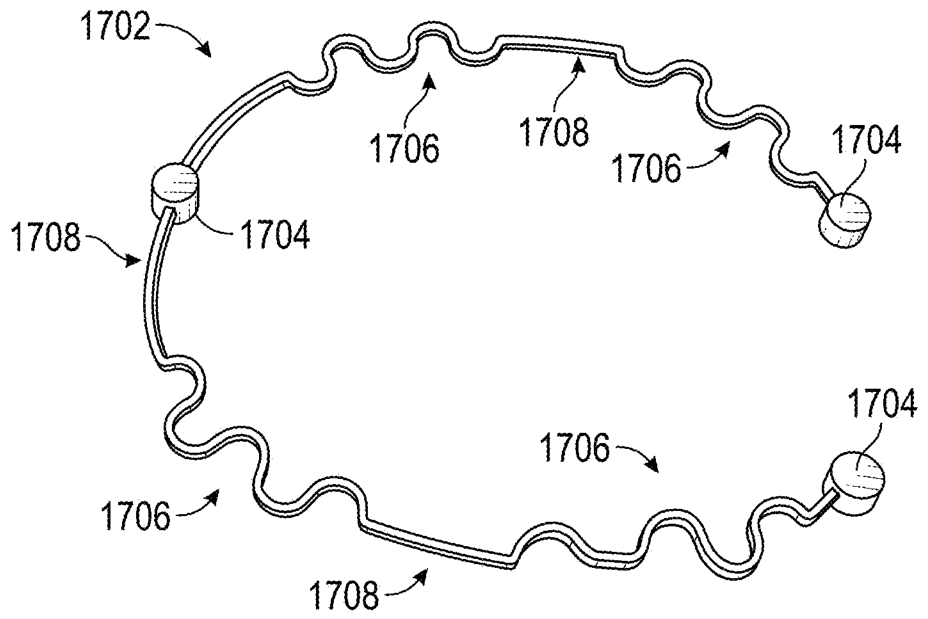
FIG. 17A illustrates an example magnetized component of an embodiment of a module.
Figure 17B:
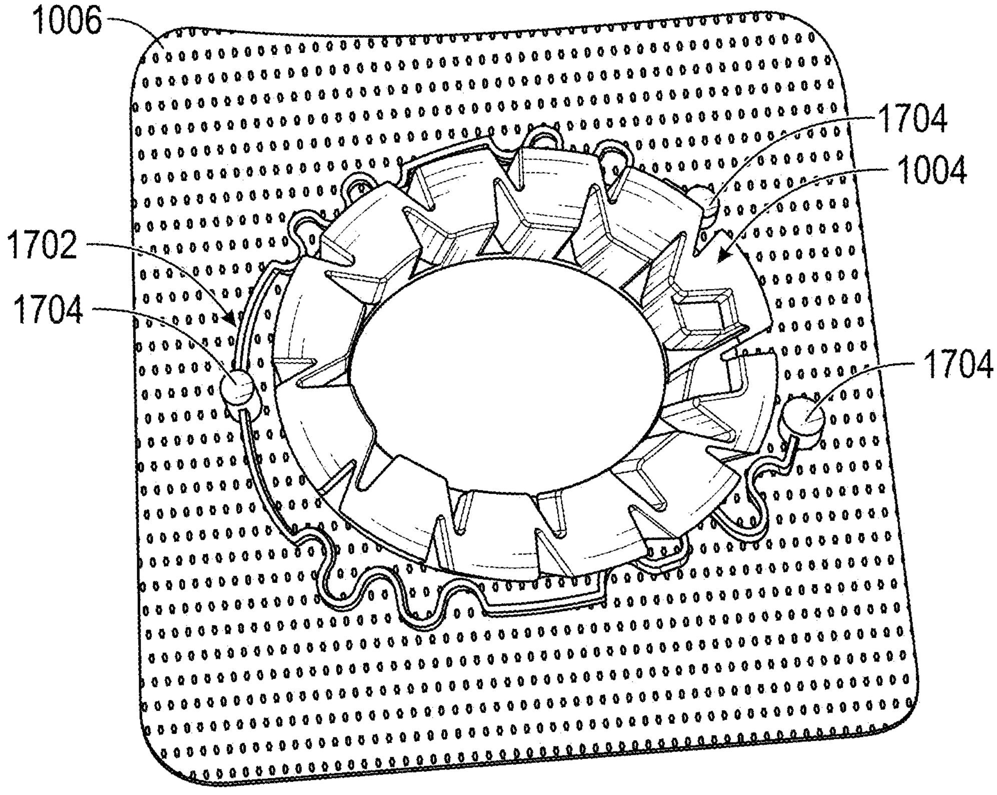
FIG. 17B illustrates an example magnetized component illustrated in FIG. 17A in arrangement with an implementation of a standoff of an example embodiment of a module.

In some examples, an overtape support 1006 may include or operate in conjunction with one or more magnetized components, such as the magnetized component 1702 illustrated in FIGS. 17A and 17B. FIG. 17A illustrates an example magnetized component 1702 alone and FIG. 17B illustrates an example magnetized component 1702 in arrangement with an implementation of a standoff 1004.

The magnetized component 1702 may be configured to include a plurality of magnets or magnetized portions 1704 and at least one connective portions 1706, 1708 between the magnetized portions 1704. In other implementations, the entire length or a subportion of the length of the magnetized portions 1704 may be magnetized. The at least one connective portion 1706, 1708 may include a plurality of contoured portions 1706 and a plurality of approximately straight or curved portions 1708. The connective portions may be arranged so as to allow a measure of flexibility in order to help conform the magnetized component 1702 to the contour of the body surface of the patient. In the illustrated example, the magnetized component 1702 includes a combination of two or more contoured portions 1706 connected with one or more straight or curved portions 1708 between adjacent magnetized portions 1704.

In some examples, the magnetized component 1702 may be arranged in a ring, partial ring (or horseshoe shape), other connected or unconnected shape, or other geometry. In some examples, the magnetized component 1702 may include a plurality of magnetized portions 1704 without connective portions such that the magnetized portions 1704 are embedded in another portion of the module 1000, such as the overtape support 1006 and/or standoff 1004.

The magnetized portions 1704 may be configured to couple to one or more metallic or other magnetized components embedded in a dressing, such as a dressing 1005 illustrated in FIG. 10A and magnetically secure the module 1000 to the dressing 1005. The magnetized component 1702 may be coupled to, embedded in, or adjacent to the overtape support 1006, standoff 1004, or other component of a module 1000. In some examples, magnets may be overmolded, mechanically confined between housing components, or adhered to the module 1000 using an adhesive. In some examples, retention points such as the magnetized component 1702 may be selectively glued to the module 1000 while the other components of the magnetized component 1702 may be allowed to move or translate with respect to the module 1000.

Multispectral and Hyperspectral Imaging

Figure 18:
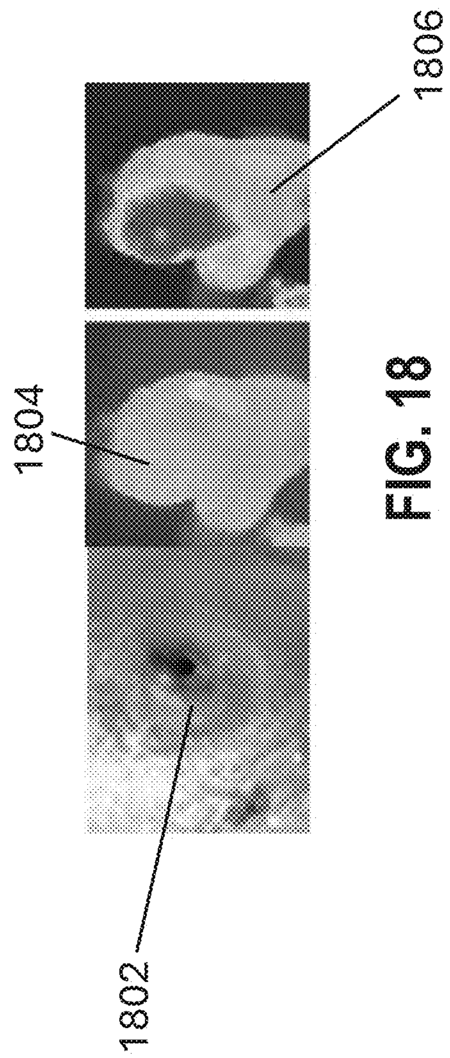
FIG. 18, by using a hypothetical example, illustrates how multispectral imaging can be employed to monitor the state of a wound.

Various implementations of the system, devices, and methods described herein including, in particular, the wearable treatment and analysis system or module or wearable module that is positioned on or near a body surface region of interest describe herein and the one or more optical sensors therein may enable capture of images and/or image data of the body surface region and thus the wound at different wavelengths and in different wavelength ranges. FIG. 18, for example, shows a plurality of images 1802, 1804, 1806 obtained at different wavelengths or wavelength ranges or bands. FIG. 18 is thus an example of multispectral imaging and, although a hypothetical example only, explains how multispectral imaging could be produced by systems, devices, and methods such as described herein and potentially used to monitor a wound and the surrounding tissue.

The first image 1802 shown in FIG. 18 may, for example, comprise a visible image obtained from an optical sensor configured to capture color images such as red green blue (RGB) images, for example, of the body surface images and/or wound and/or surrounding tissue. Such color images may be referred to herein as digital images. Similarly color optical sensors (e.g., RGB or CMY optical sensors) and/or color imaging sensors (e.g., RGB or CMY optical sensors) may be referred to as digital optical sensors, digital imaging sensor, digital sensors, and/or digital cameras. Such optical sensors are ubiquitous, for example, in our cell phones, automobiles, digital cameras, etc. Such optical sensors may capture wavelengths such as red, green and blue that mimic how our eyes see the world. Such visible, color or digital images therefore can provide physicians, nurses and other medical professionals a depiction of the body surface region and the wound therein that is akin to an in-person visual inspection. The image produced by such a camera would appear the same as or at least substantially the same as, if one were looking directly at the patient with their own eyes.

In general, optical sensors described herein, for example for use in visualization of the body surface region and/or wound and/or surrounding tissue may comprise an image sensor comprising a two-dimensional array of optical detectors, such as a CCD, CID, or CMOS array. In various implementations, such imaging sensors comprise an array of optical detectors (commonly referred to as pixels) for measuring amounts of light at different spatial locations. A lens positioned in front of the 2-D optical detector array may image objects or scenes onto the 2-D optical detector array. Light from the object or scene is mapped onto the 2-D array of optical detectors or pixels. The different pixels will output electrical signals based on the amount of light directed onto the pixel. In this manner, the light distribution across a scene or reflected from an object can be sensed and recorded electronically and/or reproduced on a display and/or such images may be processed such as describe herein.

Cameras (e.g., color cameras or digital cameras comprising, for example, color optical sensors possibly RGB or CMY optical sensors) may employ an optical detector array comprising a filter to collect color light or more particularly, a plurality of filters to collect a plurality of colors of light. Such camera may, for example, comprise an optical detector array and a plurality of optical filters to collect several different wavelength ranges of visible light that can be used to reproduce images in a color scheme that our brains are accustomed to. Without subscribing to any scientific theory, the eye contains three types of cones, which are receptive to red, green, and blue light, respectively. Accordingly, RGB imaging sensors that separately sense red, green, and blue light levels are common. The pixels in such optical sensors may comprise sub-pixels with different color filters such as red sub-pixels with red filters, green sub-pixels with green filters and blue sub-pixels with blue filters as is the case in many RGB image sensors. The red, green and blue filters may comprise bandpass filters with transmission peaks in the red, green and blue, respectively. Such a configuration enables the optical sensor to measure red, green, and blue light levels at the individual pixels to reproduce a color image of objects or scenes imaged onto the two-dimensional detector array via a lens. The recorded red, green and blue light levels can be used to generate an image that replicates human color perception. As an alternative to RGB sensors, other visible image sensors may be employed. A cyan, magenta, yellow sensor with cyan, magenta and yellow filters may also be employed to produce a color image that yields colored renditions of objects and scenes also fairly consistent with the images captured by human eyes and perceived by the brain.

In various implementations, therefore, a color optical sensor such as an RGB optical sensor may be employed to capture color images such as RGB images of the body surface region and the wound. As referenced above, the first image 1802 in FIG. 18 shows such a color image obtained by a color camera or color optical sensor such as an RGB optical sensor. Such color cameras or color optical sensors may be referred herein as digital cameras or digital optical sensors. These cameras and optical sensors may capture color images, which may be referred to herein as digital images. (Similarly, these cameras and optical sensors may capture color image data, which may be referred to herein as digital image data.)

FIG. 18 also shows two other images 1804, 1806. In theory, e.g., in this hypothetical scenario, these images 1804, 1806 could have been obtained, for example, from optical sensors configured to capture images, for example, of the body surface images and/or wound and/or surrounding tissue at different respective wavelengths or in different respective wavelength ranges or bands. The one or more wavelengths or wavelength ranges or bands need not be in the visible spectrum, but may, for example, be in the infrared or ultraviolet. As such wavelengths are invisible to the human eye, false color may be used to represent the intensity levels of such wavelengths in an image. The second image may, for example, in theory (e.g., in this hypothetical scenario), be an image captured by an optical sensor that is sensitive to one or more narrow bands of near infrared (NIR) light. The second image may use false color to depict the varying light levels of light within those narrow bands that are reflected by the body surface region. Different colors may represent different light levels. FIG. 18 also shows a third theoretical image, which may, for example, in theory have been captured by an optical sensor that is sensitive to one or more bands of long-wave infrared light, e.g., in the range of 8-14 microns (μm), that can be used to produce a thermal image. Once again, because long wave infrared (LWIR) light is also invisible, false color may be used to represent the different light levels at different spatial locations in this wavelength range. The images shown in FIG. 18 may be of the same body surface region or portion or portions thereof (or at least overlap over a substantial portion thereof), and thus in various implementations, may provide different spectral, potentially complementary, information for this body surface region or portion thereof. Although this is a hypothetical example, such an NIR image and a long-wave infrared thermal image may be used by the clinician to supplement a color or RGB image to assess the state of the wound and/or surrounding area. As such, multispectral imaging may be advantageously employed in wound monitoring systems, devices, and/or methods.

Figure 19:
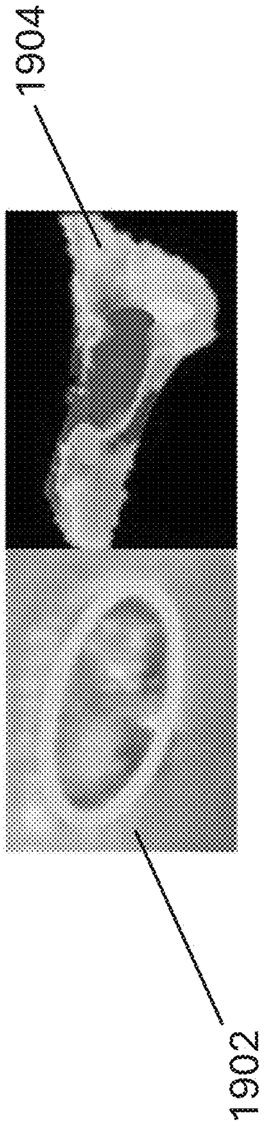
FIG. 19, by using another hypothetical example, shows how a multispectral image can be employed to monitor the state of a wound.

FIG. 19, although a hypothetical example only, shows how a multispectral image could be produced by systems, devices or methods such as described herein and potentially be used to monitor a wound and the surrounding tissue. Similar to FIG. 18, FIG. 19 shows a first image 1902 that may, for example, comprise a color image obtained from an optical sensor configured to capture color images such as an RGB optical sensor configured to capture or obtain red green blue (RGB) images. As discussed above, such optical sensors mimic how our eyes see the world. Such color images therefore can provide physicians, nurses and other medical professionals a depiction of the body surface region and wound therein that is akin to an in-person visual inspection. The color image produced by such a camera would appear the same as or at least substantially the same as if one were looking directly at the patient with their own eyes.

FIG. 19 also shows a hypothetical multispectral image 1904 formed using a plurality of infrared bands. In this hypothetical scenario, the image may, for example, have been formed using a plurality of optical sensors that capture images in different respective infrared bands. Since infrared wavelengths are invisible to the human eye, false color may be used to represent the intensity levels of such wavelengths in an image. The second image may, for example, in theory be an image captured by a first optical sensor that is sensitive to a first narrow band of infrared light, a second optical sensor that is sensitive to a second narrow band of infrared light, a third optical sensor that is sensitive to a third narrow band of infrared light, and a fourth optical sensor that is sensitive to a fourth narrow band of infrared light. In various implementations, these images captured by the first, second, third, and fourth optical sensor may be of the same body surface region or portion or portions thereof (or at least overlap over a substantial portion thereof), and thus in various implementations, may provide different spectral, potentially complementary, information for this body surface region or portion thereof. The first, second, third, and fourth optical sensors could, for example, comprise first, second, third and fourth infrared band pass filters, respectively, that selectively transmit the respective first, second, third and fourth infrared bands, for example, to the exclusion or substantially to the exclusion of other wavelengths. Accordingly, in this hypothetical example, the first, second, third, and fourth optical sensors may measure light levels of the respective first, second, third and fourth infrared bands across the pixels of the respective optical sensors. These intensity distributions may track the distribution of light in those bands reflected from the body surface region and wound. Electronics may assemble a single image from the image data captured by the four separate optical sensors. For example, the brightness or darkness and/or hue of a first color in the image 1904 may represent the light level of the first infrared band, the brightness or darkness and/or hue of a second color in the image may represent the light level of the second infrared band, the brightness or darkness and/or hue of a third color in the image may represent the light level of the third infrared band and the brightness or darkness and/or hue of a fourth color in the image may represent the light level of the fourth infrared band. This multispectral image may thus contain information regarding a plurality of different wavelength bands that are invisible to the eye such as infrared wavelengths. Nevertheless, these wavelengths may have valuable information for assessing the state of recovery of the wound.

The hypothetical examples in FIGS. 18 and 19 illustrate multispectral imaging and the use of multispectral images. In some cases, however, hyperspectral imaging may be employed. Image data from a larger number of wavelength ranges may be separately captured. The number of wavelength ranges separately captured may be in excess of 20, 25, 30, 40, 50, 75, 100, 125, 150, 175, 200, 225, 250, 275, 300, 350, 400, 500, 600, 700, 800, 900, 1000, or any range formed by any of these values or possibly larger or smaller. Such large number of wavelengths or wavelength bands may be used to produce individual optical spectrums over a range of wavelengths (e.g., 100 nm, 200 nm, 300 nm, 400 nm, 500 nm, 600 nm, 700 nm, 800 nm, 900 nm, 1000 nm, 1200 nm, 1500 nm, 1800 nm, 2000 nm, 3000 nm, 4000 nm, 5000 nm, 8000 nm, 10,000 nm, 20,000 nm, or any range formed by any of these values) for different spatial locations (e.g., different x and y locations across the body surface region and similarly different pixels across the optical sensor or imaging sensor). In some cases, this information may be represented in a three-dimensional data cube (e.g., voxels) that includes the different two-dimensional spatial distributions for a number of different wavelength ranges forming a 3D data set with first and second (e.g., X and Y) spatial dimensions and wavelength range along the third (e.g., Z) axis or the spatial position (e.g., in X and Y) and individual optical spectra in wavelength for the individual spatial positions along the third (e.g., Z direction).

Figure 20:
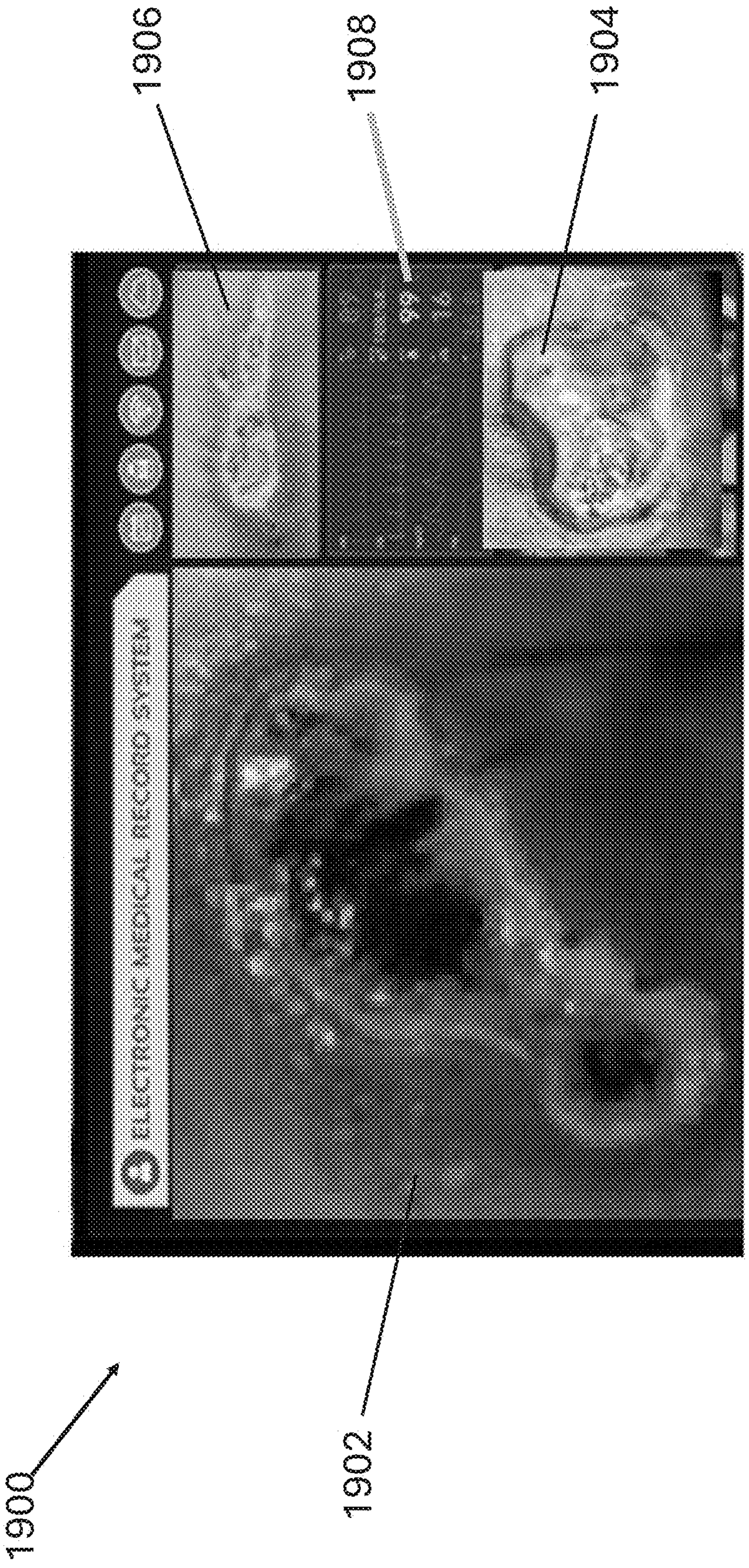
FIG. 20 shows a hypothetical electronic medical record including a plurality of images, e.g., color images, of wounds. Other data is additionally included in the medical record.

As discussed above, data collected such as different images of the body surface region and/or wound may be included in an electronic medical record or electronic health record 1900 such as for example shown in FIG. 20. In this example, three images 1902, 1904, 1906 (in this example, color or digital images) are shown together with other data 1908 in the view of the electronic medical record. Providing images of the wound and the body surface image, for example, obtained at different times may show the progress in healing. Images in different spectral bands obtained by the systems, devices, methods, such as the module configured to be embedded in a wearable medical article (e.g., dressing, wrap, cast, etc.) placed over a wound on a body surface of a wearer of the wearable medical article described herein, may be included in the electronic medical record or electronic health record 1900. Additionally multispectral and/or hyperspectral images, e.g., obtained by the systems, devices, methods, modules described herein, may be included in the record 1900. Similarly, data from multispectral imaging and/or hyperspectral imaging, e.g., obtained by the systems, devices, methods, modules described herein, may be available in the electronic medical record 1900. Although the imaging data may be processed on electronics included on the module and/or with the patient, in various implementations the imaging data may be processed elsewhere. For example, in various designs, the image data of the body surface region may be sent to a remote site, e.g., uploaded to the Cloud and/or processed at remote locations.

To obtain a number of different images in different respective wavelength bands, different sensor arrays sensitive to the respective wavelength bands may be used. To provide sensitivity to different spectral bands, different optical sensors may have different optical filters that are selectively transmissive to the different respective wavelength bands. With such an approach, increasing the number of wavelength bands may involve adding more optical sensors. In various implementations, these different optical sensors sensitive to different spectral bands are configured to image the same body surface region and/or portion or portions thereof (or at least overlap over a substantial portion thereof), and thus in various implementations, may provide different spectral, potentially complementary, information for this body surface region or portion thereof.

For example, the module configured to be embedded in a wearable medical article (e.g., dressing, wrap, cast, etc.) placed over a wound on a body surface of a wearer of the wearable medical article may comprise a first optical sensor with a first filter selectively transmissive to a first wavelength band configured to capture an image of the body surface region in the first wavelength band. The module may additionally comprise a second optical sensor with a second filter selectively transmissive to a second wavelength band configured to capture an image of the body surface region in the second wavelength band. In some implementations, the module may additionally comprise a third optical sensor with a third filter selectively transmissive to a third wavelength band configured to capture an image of the body surface region in the third wavelength band. Depending on the design, the number of optical sensors configured to capture images in different respective wavelength bands may comprise 2, 3, 4, 5, 6, 7, 8, 9, 10, 11, 12, 13, 14, 15, 16, 17, 18, 19, 20, 21, 22, 24, 25 or any range formed by any of these values such as from 2-8 or 2-16 or 2-20 or possibly more. Accordingly, such configurations may provide for multispectral image data and/or hyperspectral image data to be obtained for a body surface region. Multiple images at different wavelength bands of the same body surface region and/or portion or portions thereof (or at least overlapping over a substantial portion thereof) may be obtained. In some cases, different images respectively of different wavelength bands can be transmitted to the physician, nurse, technician or other health care provider or medical professional and/or become part of the patient's medical record, e.g., electronic medical record or electronic health record. In some implementations, multispectral images may be formed from the images captured of different wavelength bands of the same body surface region and/or portion or portions thereof (or at least overlapping over a substantial portion thereof).

In some implementations, the first optical sensor includes a first light source configured to emit light to provide illumination to the body surface region, wherein the first light source includes light within the first wavelength band. Similarly, the second optical sensor may include a second light source configured to emit light to provide illumination to the body surface region, wherein the second light source includes light within the second wavelength band. In some implementations, the first and second light sources emit light that includes both the first and second wavelength bands. In fact, in some designs, the first and second light sources may have the same emission spectrum that is sufficiently broad to include both the first and second wavelength bands. Similarly, the module may include a third optical sensor and a third light source configured to emit light to provide illumination to the body surface region, wherein the third light source includes light within the third wavelength band. In some implementations, the first, second, and third light sources each emit light that includes first, second, and third wavelength bands. The first, second and third light sources may, in fact, have the same emission spectrum that is sufficiently broad to include each of the first, second, and third wavelength bands. In other designs, possibly with additional optical sensors configured for different respective wavelength bands, the optical sensors can have respective light sources that provide illumination in the respective band. In some cases, a broad band light source may be used for the different optical sensors that includes the different bands. Such a broadband light source may include for example a full spectrum light source such as a full spectrum LED. The broadband light source may in some implementations include (any one or more colors) and infrared wavelengths (e.g., NWIR, MWIR, SWIR) and/or ultraviolet wavelengths or any combination of these.

In some designs, more than one light source may be included for the optical sensor such as shown in FIG. 12D. In some such implementations, the plurality of optical sensors may have the same emission spectra and thus may be duplicates. Having a plurality of light sources that emit wavelengths in the same band(s) may, however, provide for more uniform illumination of the body surface region. Other configurations are possible. One or more of the plurality of optical sensors, for example, any combination of the first, second, and/or third optical sensors, may share one or more light sources. Such light sources may, for example, have sufficiently broad emission spectrum to provide light for the different optical sensors sharing the light source.

In some implementations, however, the light sources have different emission spectra. A first light source for the first optical sensor may emit more light in the first wavelength band than in the second wavelength band (or in the third wavelength band). Similarly, a second light source for the second optical sensor may emit more light in the second wavelength band than in the first wavelength band (or in the third wavelength band). Likewise, in the case where the module includes the third optical sensor, a third light source for the third optical sensor may emit more light in the third wavelength band than in the first or second wavelength bands. In such designs, the first light source may be closer to the first optical sensor than to the second optical sensor (or the third optical sensor). (See, e.g., FIGS. 10B, 12A, and/or 13F.) Similarly, the second light source may be closer to the second optical sensor than to the first optical sensor (or the third optical sensor). Likewise, in the case where the module includes a third optical sensor, the third light source may be closer to the third optical sensor than to the first optical sensor or the second optical sensor. Still other designs are possible. An alternative approach can be used to capture different images at different wavelengths. For example, a single optical sensor and a plurality of light sources may be employed. The light sources may emit light in different wavelength bands. For example, a first light source may emit light in a respective first wavelength band, a second light source may emit light of in a second respective wavelength band, a third light source may emit light of in a third respective wavelength band, and so on. A single optical sensor that is sensitive to wavelengths in the different (e.g., first, second, third wavelength bands, etc.) may be used to capture images, for example, of the same body surface region and/or portion thereof. Different light sources can be turned on at different times to capture images at different wavelength bands with a single optical sensor. A larger number of wavelength bands may be used in such a configuration as, in general, light sources (e.g., solid state light sources such as LEDs) may be smaller than 2D detector arrays.

Figure 21:
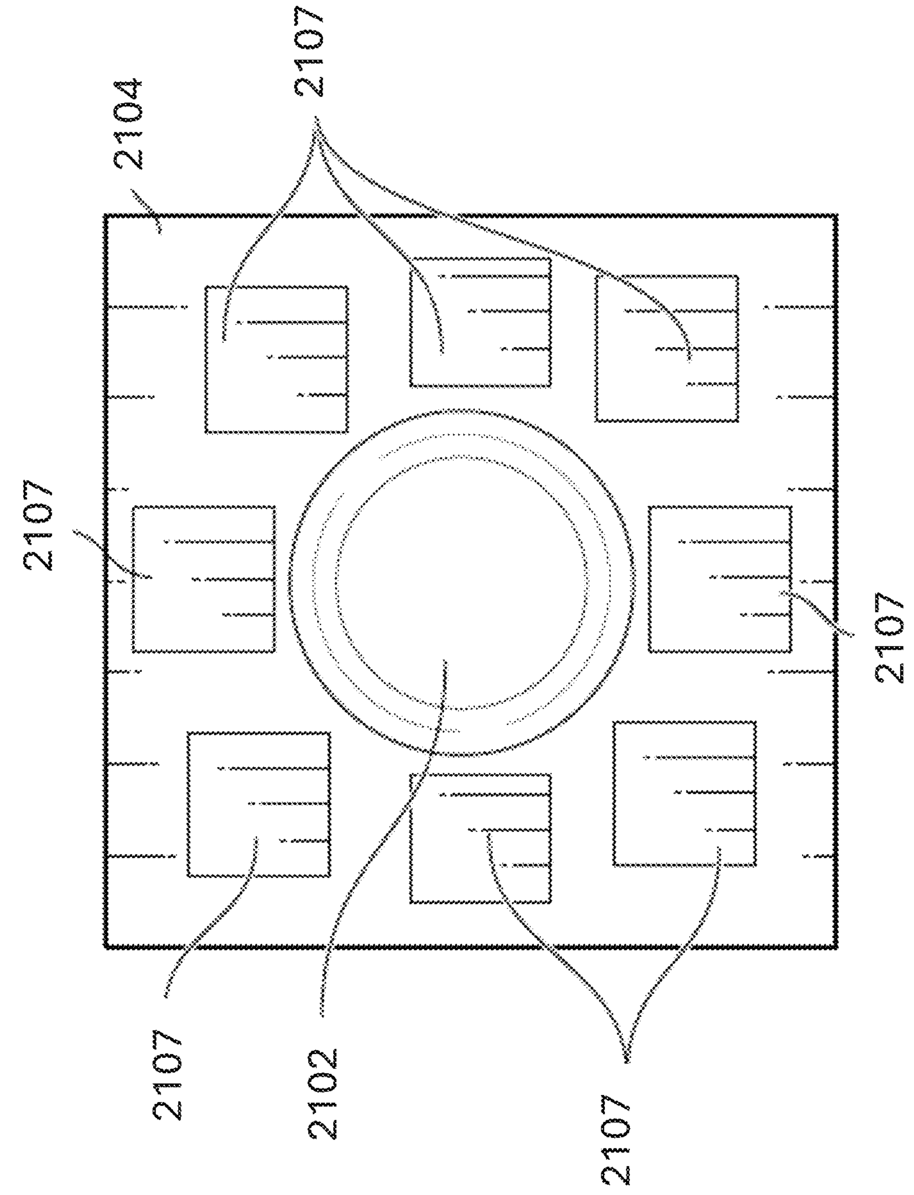
FIG. 21 is a schematic drawing showing an optical sensor with a plurality of light sources wherein the light sources are configured to have different spectral outputs such that the different light sources can be caused to illuminate the body surface region with different spectral bands at different times.

FIGS. 21 and 22 show different configurations that may be employed. In FIG. 21, a single optical sensor 2102 comprising an imaging sensor comprising a 2D array of optical detectors may be employed to capture images. FIG. 21 also shows eight different light sources 2107, which may, for example, output or emit eight respective non-overlapping (and/or overlapping but different) wavelength or spectral bands in this example. The imaging sensor 2102 and the light sources 2107 are shown on a rigid component 2104. The optical sensor 2102 may comprise a lens disposed in front of an imaging sensor (e.g., 2D optical detector array) to form images of the body surface region and wound on the imaging sensor. In this example, the eight different light sources may be caused to illuminate the body surface region and wound at different times. For example, the optical sensor 2102 may capture an image in the first wavelength band when the first light source 2107 that primarily or solely emits light in the first band is illuminated and the rest of the light sources are not emitting light. Similarly, the optical sensor 2102 may capture an image in the second wavelength band when the second light source 2107 that emits light primarily or solely of the second wavelength band is illuminated and the rest of the light sources are not emitting light, and so on. In this manner, multiple images of the same body surface region and/or portion may be obtained for different wavelength bands.

Figure 22A:
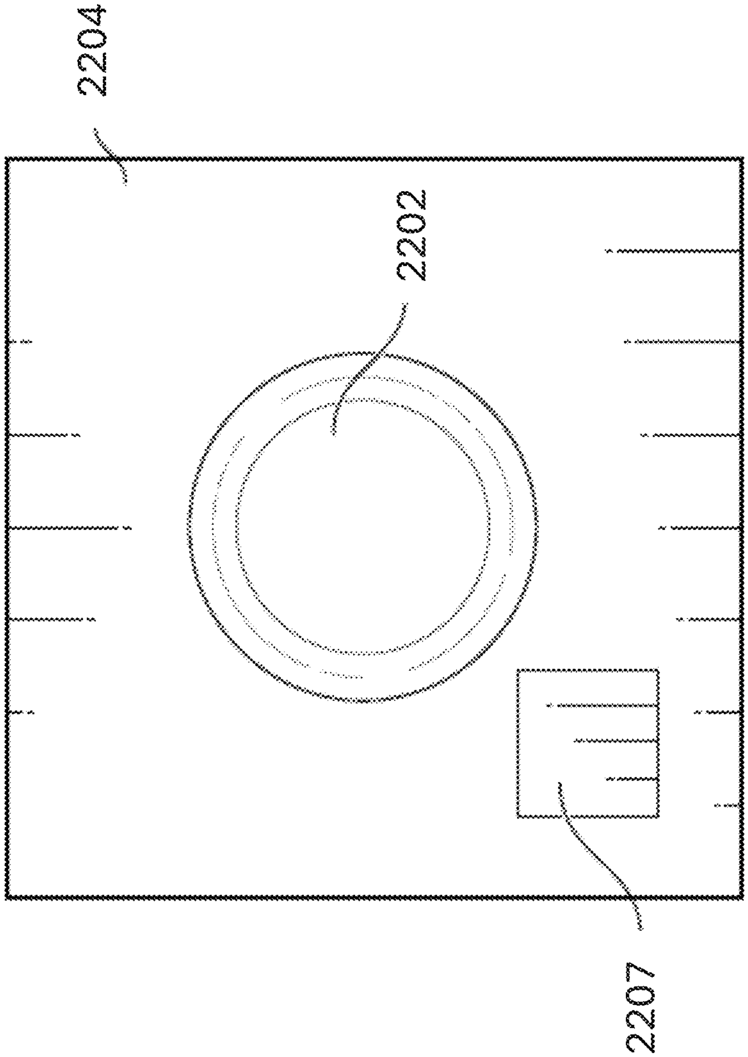
FIG. 22A is a schematic drawing showing an optical sensor with a plurality of light sources (for example in a miniature array) wherein the light sources are configured to have different spectral outputs such the different light sources can be caused to illuminate the body surface region with different spectral bands at different times.
Figure 22B:
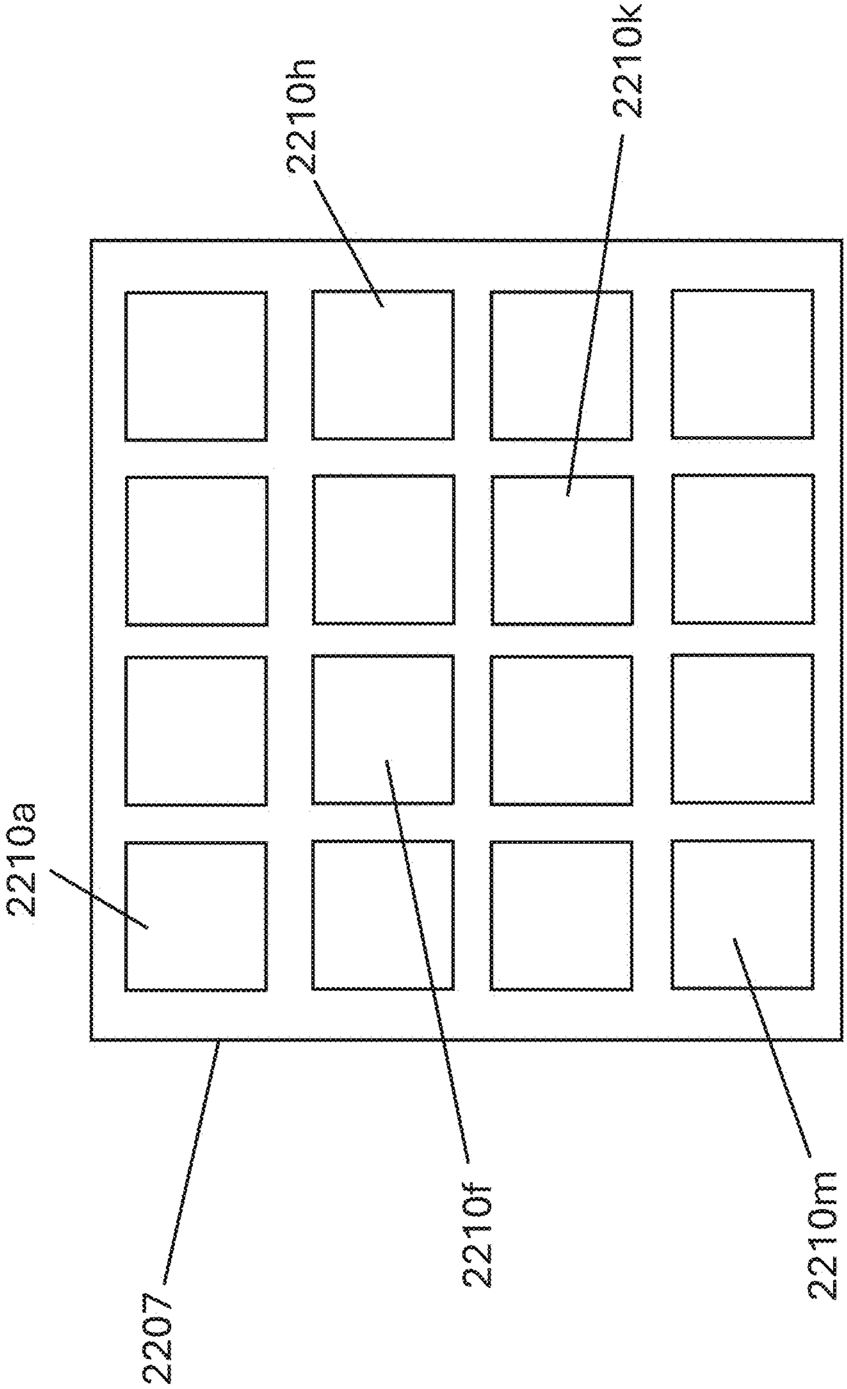
FIG. 22B is a schematic drawing showing a plurality of light sources (e.g., solid state emitters such as LEDs) in an array such as shown in FIG. 22A.

As shown in FIG. 21, the light sources 2107 are arranged around the optical sensor 2102. In FIG. 22A, the light sources comprise a small array of emitters (e.g., 20 emitters) such as LEDs with different emitters outputting light in different respective wavelength ranges. An example of such an array of emitters is shown in FIG. 22B. The light source 2107 includes a plurality of emitters 2210, such as solid-state emitters such as LEDs. Different of these emitters 2210 may emit light of different respective wavelengths or wavelength bands. For example, one emitter 2210*a* may emit light having a spectral distribution different than other emitters in the array. Another emitter 2210*f* may similarly emit light having a spectral distribution different than other emitters in the array. Other emitters 2210*h*, 2210*k*, 2210*m* may also have different respective emission spectra. All or some of the emitters 2210 may have different (e.g., unique) emission spectra. Therefore, by activating different such emitters 2210 (e.g., some of the emitters identifies 2210*a*, 2210*f*, 2210*h*, 2210*k*, 2210*m*) at different times, the body surface region or portion thereof may be illuminated by different wavelength of light at different times so, for example, different images of the body surface region or portion thereof can be obtained for different wavelength bands. Multispectral and/or hyperspectral image data may thus be collected.

The example emitter array shown includes 16 emitters. The emitters may emit in different bands. The different bands may extend across a broader spectrum, such as for example, 250 nm to 2000 nm. However, different wavelength bands and spectrums are possible. The emitters may be turned on and off or modulated rapidly. For example, the 16 emitters may be turned on and off to cycle through the different wavelength bands in 300 msec. Accordingly, emitters may be turned on an off or modulated at a frequency of 1 Hz, 2 Hz, 3 Hz, 4 Hz, 5 Hz, 6 Hz, 8 Hz, 10 Hz, 20 Hz, 30 Hz, 40 Hz, 50 Hz, 60 Hz, 80 Hz, 100 Hz, 200 Hz, 300 Hz, 500 Hz or any range formed by any of these values, such as between 10 Hz and 100 Hz or 20 Hz and 200 Hz or 30 Hz and 70 Hz or possibly at higher or lower frequencies. Because all the emitters are not on at the same time, the peak current and/or peak power is reduced and may in some cases be a 100 mA or less or 200 mA or 300 mA or less or 400 mA or less, or 500 mA or less, or 600 mA or less, or 800 mA or less, or 1000 mA or less, or 50 mA or less, or 40 mA or less, or 30 mA or less or 20 mA or less or 10 mA or less or any range formed by any of these values, e.g., 20 to 200 mA or 50 to 500 mA, or possibly larger or smaller.

As discussed above with regard to FIG. 21, the optical sensor 2202 may capture an image in the first wavelength band when the first light emitter that primarily or solely emits light in the first band is illuminated and the rest of the light emitters are not emitting light. Similarly, the optical sensor 2102 may capture an image in the second wavelength band when the second light emitter that primarily or solely emits light in the second wavelength band is illuminated and the rest of the light emitters are not emitting light, and so on. A large number of emitters or light sources having different respective wavelength bands may be used to capture image data for a large number of wavelength bands. In this manner, multiple images of the same body surface region and/or portion may be obtained for different wavelength bands. Multispectral and/or hyperspectral imaging data may be collected.

With a configuration such as shown in FIGS. 21 and 22A/22B, the optical sensor 2202 may comprise an imaging sensor (e.g., a 2-D optical detector array) that does not include sub-pixels with different filters as does an RGB imaging sensor. Instead, a monochrome optical sensor comprising a monochrome imaging sensor or 2D optical detector array (e.g., CCD, CID, CMOS array) may be employed. A red-light source, green light source, and blue-light source can be illuminated at different times to collect image data for red light, image data for green light, and image data for blue light, respectively. By removing the different filters (e.g., red, green and blue filters from the three-subpixels per pixel), the spatial resolution of the imaging sensor (e.g., 2D optical detector array) can be increased, for example, by three in this case.

In various designs, the optical sensor comprises detector array sensitive to a range of wavelength over which the light sources emit. In some cases, the optical sensor comprises a silicon detector array, which may be sensitive to light in the wavelength range of 400 to 970 nm. In some designs, UV enhanced silicon detector arrays that may detect ultraviolet may be employed for some applications. Similarly, III-V material detector array may be employed. An InGaS detector array may be employed, which may be sensitive to infrared light such as in the wavelength range of 800-2000 nm. Accordingly, detector arrays that detect light in the visible, infrared (short wave infrared, mid wave infrared, long wave infrared), or ultraviolet, or any combination of these may be used. Other types of detector arrays and optical sensors may be employed.

For different applications, different fields of view, e.g., different size field of views, may be desired. For example, different field of view may be useful for different size wounds. For smaller wounds, a smaller field of view may provide larger magnification. For larger wounds, a larger field of view may be desired to include the entire wound and possibly surrounding tissue in the images. The size of the wound may vary with the ailment, injury and/or surgical procedure. This field of view may, for example, comprise at least 0.5 cm, 1 cm, 2 cm, 3 cm, 4 cm, 5 cm, 6 cm, 7 cm, 8 cm, 9 cm, 10 cm, 11 cm, 12 cm, 13 cm, 14 cm, 15 cm or any range formed by any of these values such as from 1 cm to 9 cm, e.g., 7.22 cm or 8 cm, or possibly larger or smaller.

As discussed above, the optical sensors may comprise an imaging sensor (e.g., a 2-D optical detector array such as a CCD, CID, or CMOS detector array) with a lens in front thereof to form images of objects or scenes such as the body surface region and/or wound on the imaging sensor. This lens may affect the field of view. In some implementations, for example, this lens may comprise a wide field of view lens such as fish eye lens. In some designs, the lens may comprise multiple lens elements to improve the quality of imaging and/or provide a particular field of view, especially given the short working distance. This working distance, for example, the distance from the optical sensor to the body surface region and/or wound or portion thereof such as the working distance from the lens on the imaging sensor to the body surface region and/or wound or portion thereof may be, for example, at least or smaller than 0.1 cm, 0.2 cm, 0.3 cm, 0.4 cm, 0.5 cm, 0.6 cm, 0.8 cm, 0.9 cm, 1 cm, 1.2 cm, 1.4 cm, 1.5 cm, 1.6 cm, 1.8 cm, 2.0 cm, 2.1 cm, 2.2 cm, 2.4 cm, 2.5 cm, 2.6 cm, 2.7 cm, 2.8 cm, 2.9 cm, 3.0 cm, 3.2 cm, 3.5 cm, 3.6 cm, 4.0 cm, 4.2 cm, 4.5 cm, 4.8 cm, 5.0 cm, 5.5 cm, 6.0 cm, 7 cm, 8 cm, 9 cm, 10 cm, or any range formed by any of these values, e.g., 1 cm to 3 cm or 0.5 cm to 2.5 cm, or possibly larger or smaller.

Figure 23:
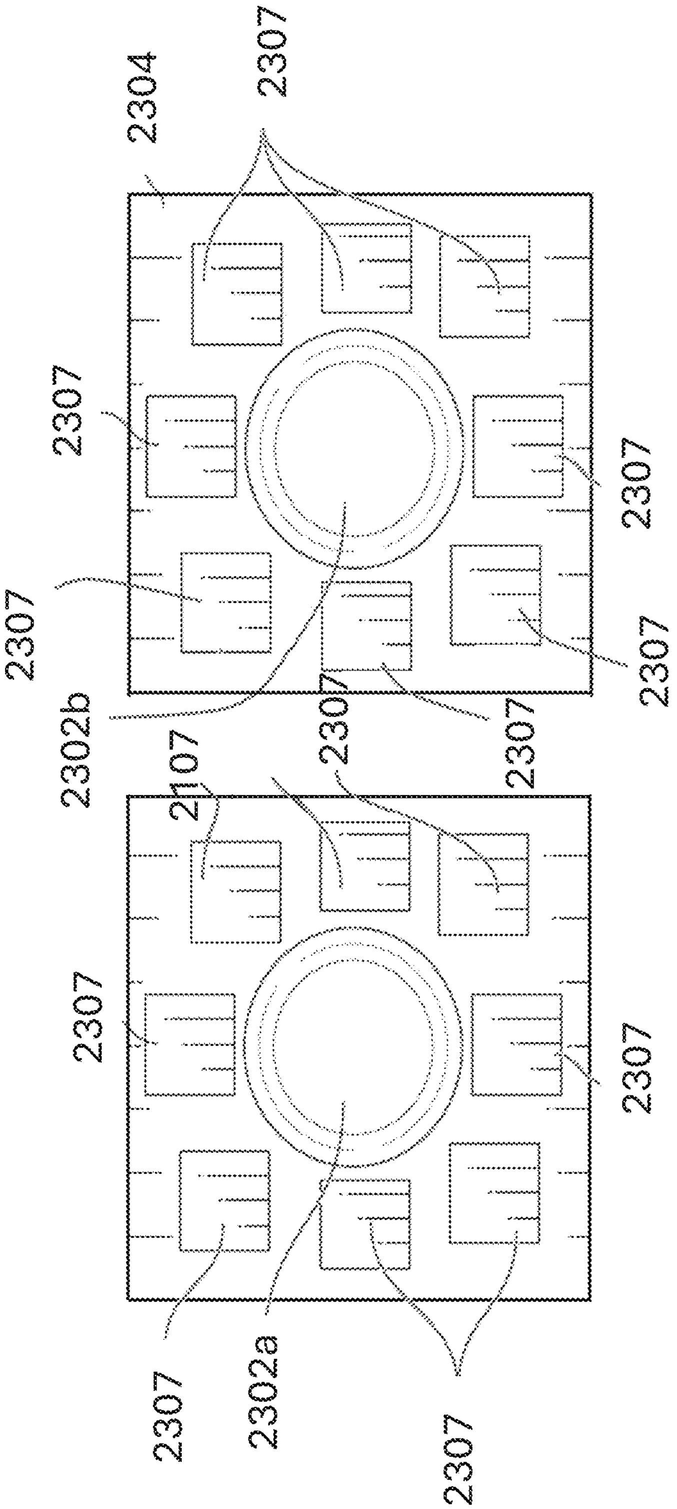
FIG. 23 is a schematic drawing showing a pair of optical sensors each with a plurality of light sources. The optical sensors can be configured (e.g., pointed differently) so as to image different portions of the body surface region. Images from the two sensors can be stitched together to provide an aggregate image that extends over a larger field of view and portion of the body surface region than provided by the individual optical sensors alone.

Another approach to increasing the field of view is to employ multiple optical sensors for different portions of the body surface region and/or wound. FIG. 23, for example, shows first and second optical sensors 2302*a*, 2302*b*. These first and second optical sensors 2302*a*, 2302*b* may be configured to image different first and second portions of the body surface region and/or wound. The less overlap of the first and second portion, the more area of the body surface region and/or wound is covered by the first and second optical sensors 2302*a*, 2302*b*.

In various designs, these optical sensors 2302*a*, 2302*ab* are of the same type and/or have the same (or substantially the same) spectral responsivity in various implementations. For example, both the first and second optical sensors may comprise silicon detector arrays (e.g., with a spectral range between 400 to 970 nm although other spectral ranges are possible.) Or both sensors may comprise InGaS detector arrays, which may be sensitive to infrared light (e.g., in the wavelength range of 800-2000 nm. The first and second optical sensors 2302*a*, 2302*b*, however may have the same spectral responsivity (or substantially the same spectral responsivity).

In the example shown, the first optical sensor 2302*a* has a plurality of light sources 2307 and the second optical sensor 2302*b* has a plurality of light sources 2307. In various implementations, the plurality of light sources 2307 used to provide light to the first portion to be imaged by the first optical sensor 2302*a* may be configured to emit light into different wavelength bands at different times so that the first optical sensor can capture separate images of the first portion in different wavelength ranges. Similarly, the plurality light sources used to provide light to the second portion to be imaged by the second optical sensor 2302*b* may be configured to emit light into different wavelength bands at different times so that the second optical sensor can capture separate images of the second portion in different wavelength ranges.

In some implementations, images from the first and second optical sensors 2302*a*, 2302*b* can be combined, e.g., stitched together, to provide a larger field of view. The combination of the first portion and the second portion imaged by the first and second optical sensors 2302*a*, 2302*b*, respectively, is larger than the first portion alone or the second portion alone. For example, a 4K image may be achieved by combining two 2K images obtained by each of the first and second optical sensors 2302*a*, 2302*b*.

Figure 24:
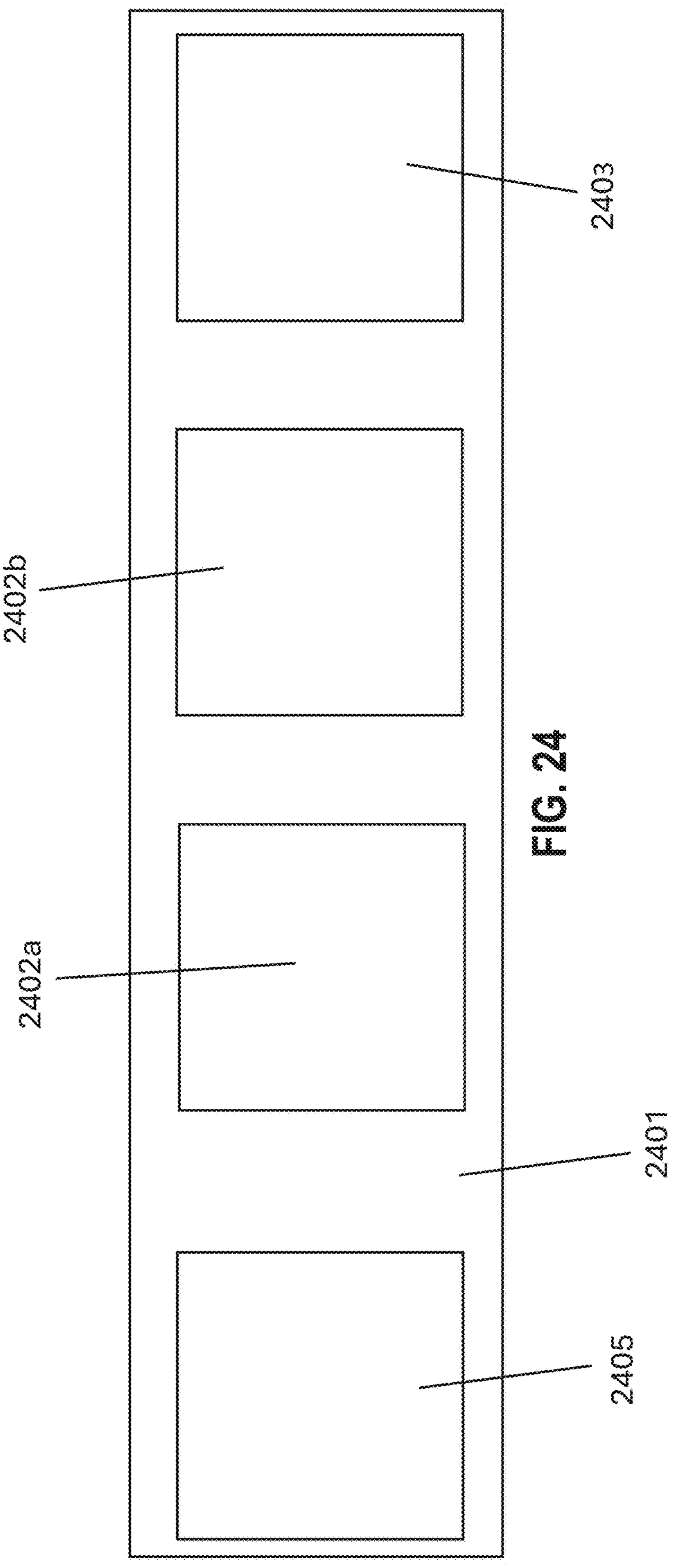
FIG. 24 is a schematic drawing showing a pair of optical sensors on a flexible ribbon cable together with a battery and microcontroller.

FIG. 24 shows first and second optical sensors 2402*a*, 2402*b* on a or attached to flexible cable 2401 such as flexible flat ribbon cable. The first and second optical sensors 2402*a*, 2402*b* may comprise optical sensors 2302*a*, 2302*b* similar to those discussed above with regard to FIG. 23. The first and second optical sensors 2402*a*, 2402*b* may be configured, e.g., pointed or located, to image first and second portions of the body surface region and/or wound. The first and second optical sensors 2402*a*, 2402*b* may have first and second groups of light sources to illuminate the first and second portions of the body surface region and/or wound, respectively. Images of the first and second portions of the body surface region and/or wound captured by the first and second optical sensors 2402*a*, 2402*b*, respectively, with illumination from the same wavelength bands, can be stitched together to provide a larger field of view. As discussed above, the plurality light sources 2307 used to provide light to the first portion to be imaged by the first optical sensor 2402*b* may be configured to emit light into different wavelength bands at different times so that the first optical sensor can capture separate images of the first portion in different wavelength ranges. Similarly, the plurality light sources used to provide light to the second portion to be imaged by the second optical sensor 2402*b* may be configured to emit light into different wavelength bands at different times so that the second optical sensor can capture separate images of the second portion in different wavelength ranges.

As discussed above, in this example, optical sensors 2402*a*, 2402*b* having the same spectral responsivity are employed. In other designs, however, the first and second optical sensors 2402*a*, 2402*b* may have different spectral responsivities. Such different spectral responses may result from different detector array types (and/or different filters). Different detector arrays may be sensitive to different wavelength bands of the optical spectrum. Some detector arrays are sensitive to visible light or visible light and infrared light such as near infrared (NIR). Other detectors arrays may be sensitive to infrared, for example, any one or more of NWIR, MWIR or LWIR wavelengths. Some detector arrays are sensitive to LWIR wavelengths and can provide thermal imaging. Some detector arrays are sensitive to ultraviolet (UV) light. Examples of some detector arrays that may be employed for the optical sensors include silicon detector arrays, e.g., which may be sensitive to light in the wavelength range of 400 to 970 nm, UV enhanced silicon detector arrays, e.g., which may detect ultraviolet light, and III-V material detector arrays such as InGaS detector arrays which may be sensitive to infrared light such as in the wavelength range of 800-2000 nm. Any combination of these and/or other types of detector arrays can be used for the first and second optical sensors 2402*a*, 2402*b*. Likewise, the first and second optical sensors 2402*a*, 2402*b* may have different spectral responsivities. Any combination of optical sensors 2402*a*, 2402*b* with different spectral responsivities are possible. For example, the first optical sensors 2402*a* may have a spectral responsivity in the visible (or more in the visible) and the second optical sensor 2402*b* may have a spectral responsivity in the infrared (or more in the infrared), such as in the NIR, or in the MWIR, or in the SWIR or any combination of these. Similarly, the first optical sensors 2402*a* may have a spectral responsivity in the visible (or more in the visible) and the second optical sensor 2402*b* may have a spectral responsivity in the ultraviolet (or more in the ultraviolet). Or the first optical sensor 2402*a* may have a spectral responsivity in the NIR and the second optical sensor may have a spectral responsivity in the LWIR. Other combinations and variations are possible and other types of detector arrays having different spectral responsivities may be employed.

As discussed above, the different light sources having different wavelengths may be turned on and off at different times to obtain images at different wavelength bands. In this example design, since the first optical sensor may have a different responsivity than the second optical sensor, the light sources for the first optical sensor may have different emission spectra than the light sources for the second optical sensor. For example, in a design where the first optical sensor comprises a visible wavelength sensor and the second optical sensor comprises an infrared optical sensor, the light sources for the first optical sensor may emit at different respective visible wavelength bands at different times while the light sources for the second optical sensor may emit at different respective infrared wavelength bands at different times. Similarly, for a design where the first optical sensor comprises a near infrared (NIR) optical sensor and the second optical sensor comprises a long wave infrared (e.g., LWIR) optical sensor, the light sources for the first optical sensor may emit at different respective NIR bands at different times while the light sources for the second optical sensor may emit at different respective LWIR wavelength bands at different times. Other detectors with other spectral responsivities (as well as other light sources with other emission spectra) may be employed to obtain image and/or image data at other wavelength bands.

In various implementations, the first and second optical sensors may be pointed or oriented (and/or located) to image the same portion or mostly the same of the body surface region and/or wound and/or surrounding tissue. Accordingly, images of the same body surface region or portion thereof may be obtained but in different spectral bands. Accordingly, detector arrays that detect light in the visible, infrared (short wave infrared, mid wave infrared, long wave infrared), or ultraviolet, or any combination of these may be used to obtain different spectral images. Other types of detector arrays and optical sensors may be employed. A wide range of multispectral images or image data may be obtained.

Although two optical sensors are shown in the example depicted in FIGS. 23 and 24, more than two optical sensors may be employed. The different optical sensors may have different spectral responsivities, for example, to obtain images and image data for different spectral regions. Alternatively, some of the optical sensors may have the same spectral responsivity. For example, the plurality of optical sensors may be oriented or located so as to obtain images of different portions of the body surface region and these images may be combined or stitched together. In some designs, the module includes optical sensors having different spectral responsivities and optical sensors having the same spectral responsivities. For example, the module may include a first pair of optical sensors primarily sensitive to a first region of the spectrum (e.g., the visible wavelengths) and a second pair of optical sensors primarily sensitive a second region of the spectrum such as infrared wavelengths (e.g., NIR, SWIR, and/or LWIR). (Or the module may include a first pair of optical sensors with a spectral response primarily in the visible and a second pair of optical sensors with a spectral response primarily in the infrared wavelengths and a third pair of optical sensors with a optical response primarily in the ultraviolet.) The optical sensors in a given pair may be configured to image different portions of the body surface region and/or wound and/or surrounding tissue that can be stitched together. Any number of optical sensors with same or different spectral responses that are directed to the same or different portions of the body surface image may be used.

FIG. 24 also shows a battery, e.g., a lithium battery 2403, on the flexible ribbon cable 2401 as well as electronics 2405, e.g., a microcontroller, on the flexible ribbon cable 2401. Such lithium batteries may be rechargeable and may (e.g., on average) maintain a charge for weeks, e.g., 6, 7, 8, 9, 10, 11, 12, 13, 14, 15, 16, 17, 18, 19, 20, 22, 24, 25, 27, 28, 30 weeks or in any range formed by any of these values, for example from 12 to 16 weeks, e.g., 14 weeks or possibly larger or smaller. In contrast, the average weeks to heal between acute and chronic wound may be 11 weeks. In some implementation the electronics 2405, e.g., microcontroller, comprises one or more chips mounted on the flexible ribbon cable 2401. However, in various implementations, the electronics 2405 may comprise a plurality of smaller electrical components formed directly on or in or otherwise integrated with the flexible ribbon cable.

Using one or more flexible ribbon cables 2401 may be conducive to bending about the body of the subject. The human body includes many locations that are not flat. The ability to bend may, therefore, be advantageous in many circumstances for wounds on different locations of the body. Using a flex ribbon cable 2401 to connect parts, e.g., the first optical the battery 2403, the optical sensor or optical sensors 2402*a*, 2402*b*, the electronics (e.g., microcontroller) 2405 or any combination of these may be useful. Although a flexible cable (e.g., flexible ribbon cable, flat flexible ribbon cable, flex cable, etc.) 2401 is shown in FIG. 24, more than one flexible cable may be employed. Also, flexible circuits or circuitry may be employed as well. Further discussion regarding such flexible cable, flexible ribbon cable, flex circuits, and rigid-flexible technology, etc., is provided below in connection with FIG. 26 as well as elsewhere herein.

Figure 25:
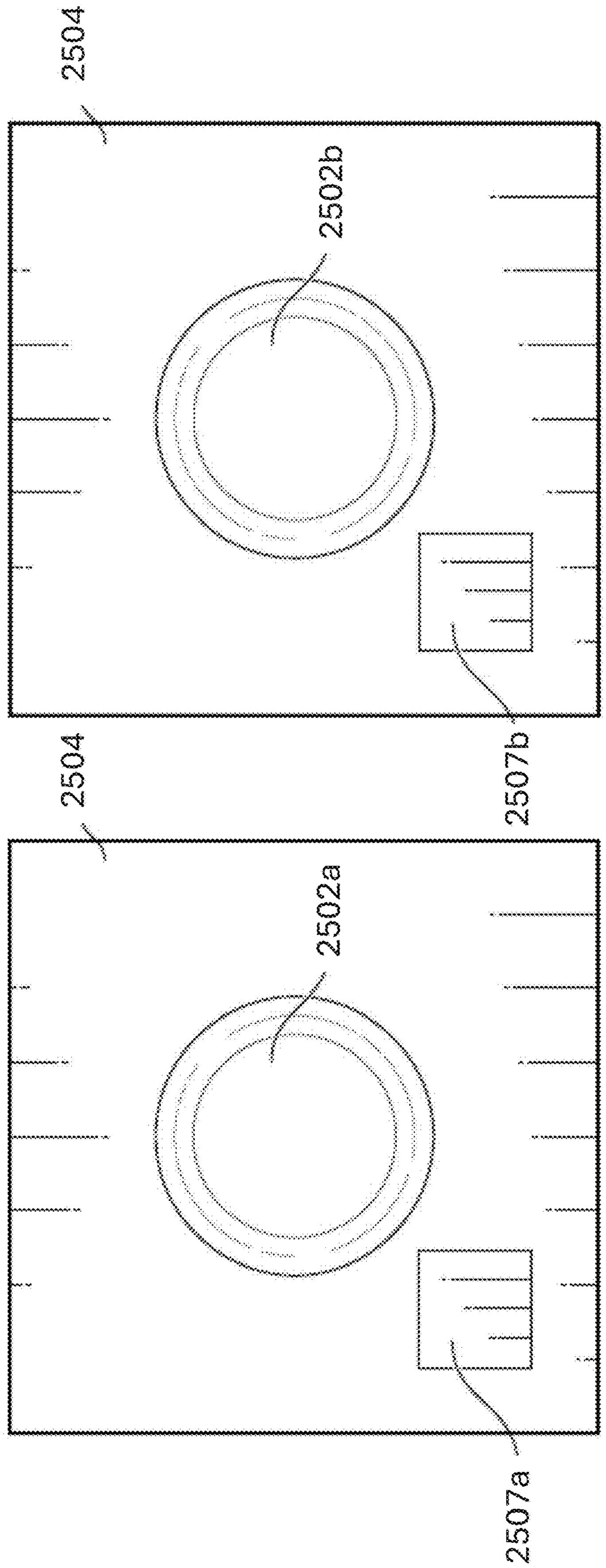
FIG. 25 is a schematic drawing showing a pair of optical sensors each with an associated emitter array.

FIG. 25 shows another pair of optical sensors 2502*a*, 2502*b* that can be used (for example, in the systems, methods, devices, and modules discussed above in connection with FIGS. 23 and 24). FIG. 25, for example, shows first and second optical sensors 2502*a*, 2502*b*, which may, for example, be configured to image different first and second portions of the body surface region and/or wound in some implementations. The less overlap of the first and second portions, the more area of the body surface region and/or wound is covered by the first and second optical sensors 2502*a*, 2502*b*. In the example shown, the first optical sensor 2502*a* has a plurality of light sources. The plurality of light sources are included in the emitter array 2507*a*, which is similar to the array shown in FIG. 22B. The emitter array 2507*a* includes a plurality of emitters 2210 such as for example 16 emitters 2210 such as shown in FIG. 22B. The emitters 2210 may emit light in different respective bands. The emitters 2210 may be turned on and off or modulated rapidly to provide illumination in different wavelength bands at different times and capture different images of the body surface region or portion thereof in the different respective wavelength band.

The second optical sensor 2502*b* also has a plurality of light sources associated therewith. The plurality of light sources are included in the emitter array 2507*b*, which is similar to the array shown in FIG. 22B. The emitter array 2507*b* includes a plurality of emitters 2210 such as for example 16 emitters 2210 such as shown in FIG. 22B. The emitters 2210 may emit light in different respective bands. The emitters 2210 may be turned on and off or modulated rapidly to provide illumination in different wavelength bands at different times and capture different images of the body surface region or portion thereof in the different respective wavelength band.

Likewise, in various implementations, the plurality of light sources used to provide light to the first portion to be imaged by the first optical sensor 2502*a* may be configured to emit light into different wavelength bands at different times so that the first optical sensor can capture separate images of the first portion in different wavelength ranges. Similarly, the plurality light sources used to provide light to the second portion to be imaged by the second optical sensor 2502*b* may be configured to emit light into different wavelength bands at different times so that the second optical sensor can capture separate images of the second portion in different wavelength ranges. As discussed above, images of the first and second portions obtained for the same wavelength band(s) can be combined, e.g., stitched together.

As discussed above, however, in other configurations, the optical sensors 2502*a*, 2502*b* may be used differently. For example, as discussed above in connection with FIGS. 23 and/or 24, the optical sensors 2502*a*, 2502*b* may be pointed so as to image substantially the same body surface region or portion thereof. The optical sensors 2502*a*, 2502*b*, however, may have different spectral responsivities. Similarly, the light sources associated with the first optical sensor 2502*a* may have different emission spectrums than the light sources associated with the second optical sensor 2502*b*.

Other variations, however, are possible. For example, any number of optical sensors with same or different spectral responses that are directed to the same or different portions of the body surface image may be used. Accordingly, the discussions above with respect to FIGS. 23 and/or 24 and the different variations in configurations are applicable regardless of whether a plurality of light sources are arranged about the optical sensor such as shown in FIG. 23 or the plurality of light sources are included in an array such as shown in FIGS. 22A, 22B and/or 25.

Multiple arrays of light sources (e.g., multiple chips) may also be used for a given optical sensor, for example, to increase uniformity of illumination, or to provide different wavelengths if the light source arrays have different emission spectra. Accordingly, although one array is shown in FIGS. 22A and 25, multiple such arrays could used, for example, for a given optical sensor and may be disposed about the optical sensor. Likewise, the light sources 2107 shown in FIGS. 21 and 23 may in some designs comprise light emitter arrays such as for example shown in FIG. 22B. Of course, the array need not be an ordered array of emitters having 16 emitters as shown in FIG. 22B. The array may have more or less emitters and may be arranged in other than straight rows and columns of the same number and/or size. Still other variations are possible.

As discussed above, the module may include one or more diffusers and/or polarizers. Such diffusers may, for example, be positioned to receive and diffuse light output by the light sources. Such polarizers may be positioned to polarize light directed to the optical sensor. The polarizer may, for example, be positioned between the body surface region (e.g., the wound) and the optical sensor(s). In some implementations, the polarizer is configured to reduce glare. In some designs, the polarizer comprises an optical film such as an anti-glare film configured to reduce glare. The polarizer may, for example, reduce scattered light. The polarizer, however, may additionally or alternatively highlight features in the image, e.g., in the body surface region in some cases. The polarizer may comprise, for example, a linear polarizer. In some implementation, the linear polarizer is oriented vertically, however, the polarizer can be oriented horizontally, or in other orientations. In some cases, the polarizer comprises a circular polarizer such as, for example, a B+W polarizer. In some cases, for example, the polarizer comprises a B+ polarizer. The polarizer may, for example, reduce or eliminate the potential for glare created by the LED lights when illuminating the wound area. Additionally, the polarizer may increase the capture of the more of the margin (possibly allowing for complete capture) of the field of view when imaging device is placed over an area of curvature.

Due to the module's compact nature, the illumination sources (e.g., LEDs) are close to the target, e.g., the body surface region, which can lead to glare in the image, thereby reducing image quality. Glare may be in the form of specular reflection. Moreover, this glare may be s-polarized.

In some implementations, the illumination provided by the module, for example, the light source(s), is unpolarized. Glare, however, will primarily be s-polarized. Accordingly, these reflections can be blocked with a linear polarizer aligned to transmit p-polarization and attenuator, reflect, or have reduced transmission for s-polarization. This linear polarizer oriented to selectively transmit p-polarization light can therefore reduce or eliminate glare. A linear polarizer such as one or more linear polarization films, for example, can be positioned in the path of the glare producing reflective surface and the optical sensor. A linear polarizer, for example, can be placed in front of or on the optical sensor. This linear polarizer may be oriented to transmit more p-polarization light than s-polarization light and reflect or attenuate more s-polarized light than p-polarized light.

In some implementations, the illumination provided by the module or light source(s) is linearly polarized and aligned to reduce the s-polarization component. Specular reflections are more efficient for s-polarized light. Accordingly, reducing s-polarized illumination may potentially reduce glare. Thus, in various designs, the polarization of the illumination provided by the module or the light sources is the average p polarization direction for the target. The light source may for example be provided with a linear polarizer and this linear polarizer may be oriented in this p-direction. A polarizer can also be provided for the detector or camera. This polarizer may be oriented in the p direction, for example, this polarizer may be oriented to transmit more p-polarization light than s-polarization light and/or reflect or attenuate more s-polarized light than p-polarized light. In some designs the same linear (p-polarized) polarizer is positioned in front of both the light source and the optical sensor. Other configurations, however, are possible. For example, separate linear (p-polarized) polarization films may be use on the light source(s) and/or detectors.

In some implementations, both illumination and detection involve circularly polarized with the same handedness. The illumination provided by the module or light source(s) may be circular polarized for example using a circular polarizer. A circular polarizer, for example, can be positioned to receive light from the light source (e.g., LED) to provide illumination having circular polarization. This circular polarizer may be positioned, for example, in front of the light source. Another circular polarizer of the same handedness may be included in the path (e.g., from the body surface region) to the detector, for example, this circular polarizer may be positioned, for example, at or in front of the optical sensor or detector or camera. Glare, which comprises specular reflection, produces an inversion (change in handedness of the circular polarized light, for example, from right-handed polarized to left-handed polarized or vice versa) such that the electric field vector rotates in the opposite direction. The second circular polarizer such as one or more circular polarizing films can be positioned in the optical path to the imaging sensor or camera (e.g., in front of the imaging sensor or detector array) and much of the glare with the changed handedness is rejected or not transmitted to the camera, which reduces or potentially eliminates glare. In some designs, the same circular polarizer is positioned in front of both the light source and the optical sensor. Other configurations, however, are possible. For example, separate circular polarization films may be used on the light source(s) and/or detectors.

Systems, devices, and methods described herein can provide wound monitoring including, for example, real time monitoring as well monitoring on a pre-programmed frequency. Such wound monitoring may include capturing image data and/or images of the body surface region including the wound and surrounding tissue. Such images and/or image data may be obtained even of body surface region (e.g., wound and surrounding tissue) in the presence of a biologic dressing. In some cases, such biologics and biologic dressings may be more transmissive to light of certain wavelengths or wavelengths bands than others. Accordingly, by capturing images at certain wavelengths, images of the wound and/or surrounding tissue may be obtained even if the wound and/or surrounding tissue are covered by a biologic or biologic dressing. The optical sensors and/or light sources may be configured to capture images or images data of the body surface region using wavelengths that are more transmissive to the biologic(s) and/or biologic dressing despite the biologic and/or biologic dressing being physically between the optical sensor and the body surface region (e.g., wound). In some cases, therefore, multispectral imaging and/or hyperspectral imaging may be used for biologic dressings, for example, for imaging the body surface regions (e.g., wound and/or surrounding tissue) in the presence of a biologic dressing. In some situations, a color image (e.g., a digital image, for example, acquired by a digital camera or digital imaging sensor such as a color imaging sensor like an RGB imaging sensor) of a suture and/or open wound, for example, that is not covered by a biologic dressing or biologic between the body surface region and the optical sensor may also be captured. Such digital camera or color imaging sensor (e.g., RGB imaging sensor) may be able to image the body surface region in other situations where the body surface region is not covered by a biologic and/or a biologic dressing. Color images (e.g., a digital image, for example, acquired by a digital camera or digital imaging sensor such as a color imaging sensor like an RGB imaging sensor) may be able to capture images of a wound covered by a biologic or a biologic dressing or where a biologic is between the body surface region and the optical sensor as well.

As disclosed herein, image data and/or images may be obtained at different wavelengths or wavelength bands. For example, image data and/or images may be captured at any wavelength, wavelengths, wavelength band or wavelength bands of light in any range formed by any of the following wavelengths: 200 nm, 220 nm, 230 nm, 240 nm, 250 nm, 260 nm, 270 nm, 280 nm, 300 nm, 310 nm, 320 nm, 330 nm, 350 nm, 360 nm, 370 nm, 380 nm, 390 nm, 400 nm, 410 nm, 420 nm, 430 nm, 450 nm, 460 nm, 470 nm, 480 nm, 490 nm, 500 nm, 510 nm, 520 nm, 530 nm, 550 nm, 560 nm, 570 nm, 580 nm, 590 nm, 600 nm, 610 nm, 620 nm, 630 nm, 650 nm, 660 nm, 670 nm, 680 nm, 690 nm, 700 nm, 710 nm, 720 nm, 730 nm, 750 nm, 760 nm, 770 nm, 780 nm, 790 nm, 800 nm, 810 nm, 820 nm, 830 nm, 850 nm, 860 nm, 870 nm, 880 nm, 890 nm, 900 nm, 910 nm, 920 nm, 930 nm, 950 nm, 960 nm, 970 nm, 980 nm, 990 nm, 1000 nm, 1010 nm, 1020 nm, 1030 nm, 1050 nm, 1060 nm, 1070 nm, 1080 nm, 1090 nm, 1100 nm, 1110 nm, 1120 nm, 1130 nm, 1150 nm, 1160 nm, 1170 nm, 1180 nm, 1190 nm, 1200 nm, 1210 nm, 1220 nm, 1230 nm, 1250 nm, 1260 nm, 1270 nm, 1280 nm, 1290 nm, 1300 nm, 1310 nm, 1320 nm, 1330 nm, 1350 nm, 1360 nm, 1370 nm, 1380 nm, 1390 nm, 1400 nm, 1410 nm, 1420 nm, 1430 nm, 1450 nm, 1460 nm, 1470 nm, 1480 nm, 1490 nm, 1500 nm, 1510 nm, 1520 nm, 1530 nm, 1550 nm, 1560 nm, 1570 nm, 1580 nm, 1590 nm, 1600 nm, 1650 nm, 1700 nm, 1750 nm, 1800 nm, 1850 nm, 1900 m, 1950 nm, 2000 nm, 2100 nm, 2200 nm, 2300 nm, 2400 nm, 2500 nm, 2600 nm, 2700 nm, 2800 nm, 2900 nm, 3000 nm, 3500 nm, 4000 nm, 4500 nm, 5000 nm, 5500 nm, 6000 nm, 6500 nm, 7000 nm, 7500 nm, 8000 nm, 8500 nm, 9000 nm, 9500 nm, 10 m, 10.5 m, 11 m, 11.5 m, 12 m, 12.5 nm, 13 nm, 13.5 m, 14 am, 14.5 am, 15 am, 15.5 am, 16 am, 17 am, 18 am, 19 am, 20 nm such as from 250 nm to 900 nm, or 250 to 2000 nm or from 9 am to 14 am or possibly wavelength and bands larger or smaller. The bandwidths of the bands may be at least or less than 1 nm, 2 nm, 3 nm, 4 nm, 5 nm, 6 nm, 7 nm, 8 nm, 10 nm, 12 nm, 15 nm, 20 nm, 25 nm, 30 nm, 40 nm, 50 nm 60 nm, 70 nm, 80 nm, 100 nm, 150 nm, 200 nm, 300 nm, 400 nm, 500 nm, 600 nm, 700 nm, 800 nm, 900 nm, 1000 nm, or any range formed by these values or possibly larger or smaller. Any number of bands may be used in capturing an image including 1 band, 2 band, 3 bands, 4 bands, 5 bands 6 bands, 7 bands, 8 bands, 9 bands, 10 bands, or any range formed by any of these values or possibly larger or smaller. Moreover, any number of bands may be used in capturing multispectral or hyperspectral image data or forming a multispectral or hyperspectral image or multiple multispectral or hyperspectral images including 2 bands, 3 bands, 4 bands, 5 bands 6 bands, 7 bands, 8 bands, 9 bands, 10 bands, 11 bands, 12 band, 13 bands, 14 bands, 15 bands, 16 bands, 17 bands, 18 bands, 19 bands, 20 bands, 21 bands, 22 bands, 24 bands, 25 bands, 26 bands, 27 bands, 28 bands, 30 bands, 32 bands, 35 bands, 40 bands, 42 bands, 45 bands, 50 bands, 55 bands, 60 bands, 70 bands, 80 bands, 90 bands, 100 bands, 110 bands, 120 bands, 130 bands, 140 bands, 150 bands, 160 bands, 170 bands, 180 bands, 190 bands, 200 bands, 220 bands 240 bands, 250 bands, 260 bands, 275 bands, 280 bands, 300 bands, 350 bands, 400 bands, 450 bands, 500 bands, 600 bands, 700 bands, 800 bands, 900 bands, 1000 bands, 1200 bands or any range formed by any of these values or possibly larger or smaller. In some cases, image data and/or images are captured or obtained at a single isolated wavelength band. In some cases, image data and/or images are capture or obtained at multiple wavelength bands separated from each other. The specific of bands may depend on any combination of the absorption spectrum, reflection spectrum, transmission spectrum of chemicals of interest and/or not of interest. Such wavelengths or wavelength bands may be used in multispectral imaging and/or hyperspectral imaging of the body surface region, e.g., wound and/or surrounding tissue. Similar, such wavelengths or wavelength ranges may be employed in producing multispectral images and/or hyperspectral images of the body surface region, e.g., wound and/or surrounding tissue.

In some implementations, hyperspectral image data capture includes obtaining data for (possibly continuous) spectrums over a range of wavelength formed by many different bands for many different spatial locations, for example most or all the pixels on the optical sensor. Such range of wavelength may extend over 100 nm, 200 nm, 300 nm, 400 nm, 500 nm, 600 nm, 700 nm, 800 nm, 900 nm, 1000 nm, 1100 nm, 1200 nm, 1300 nm, 1400 nm, 1500 nm, 1600 nm, 1800 nm, 2000 nm, 2200 nm, 2500 nm, 2800 nm, 3000 nm, 3500 nm, 4000 nm, 5000 nm, 6000 nm, 7000 nm, 8000 nm, 9000 nm, 10,000 nm, 12000 nm, 14000 nm, 15,000 nm, 16,000 nm, 18,000 nm, 20,000 nm, 22000 nm or any range formed by any of these values or possibly larger or smaller. Hyperspectral data cubes can be formed which include an optical spectrum for a plurality of spatial locations. For example, the data cube may correspond to pixels in rows and columns of the imaging sensor across the x and y axes of the data cube and values for different wavelength of the spectrum across the z axis of the data cube.

As discussed herein, wounds such as acute and/or chronic wounds may be monitored with digital (e.g., color) imaging, multispectral, hyperspectral imaging technology or any combination thereof that is embedded in dressing. Such monitoring may be in real time, although period data collection (e.g., scheduled, such as daily, a couple times a day, periodically throughout a week, etc.) may also be used. Such technology can be used for early detection of complications, for example, before they become more serious. Multispectral, hyperspectral and digital or color imaging under a dressing may be employed in any combination. For example, multispectral and/or hyperspectral imaging may be employed when biologics or biologic dressing are used and potentially cover the wound potentially otherwise impairing direct visualization of the wound with a color or digital camera or imaging sensor. The monitoring device may be a single patient per episode of treatment disposable embedded in the dressing. The device and/or system may be synched with MRN.

Accordingly, remote wound monitoring may be provided without the removal of dressings. As discussed, real-time wound imaging can be provided. Multispectral (and/or hyperspectral) imaging and images can be combined with digital or color imaging and images. In some implementations, such imaging may be combined with other types of imaging such as three-dimensional or 3D imaging. Other configurations are possible.

Figure 26:
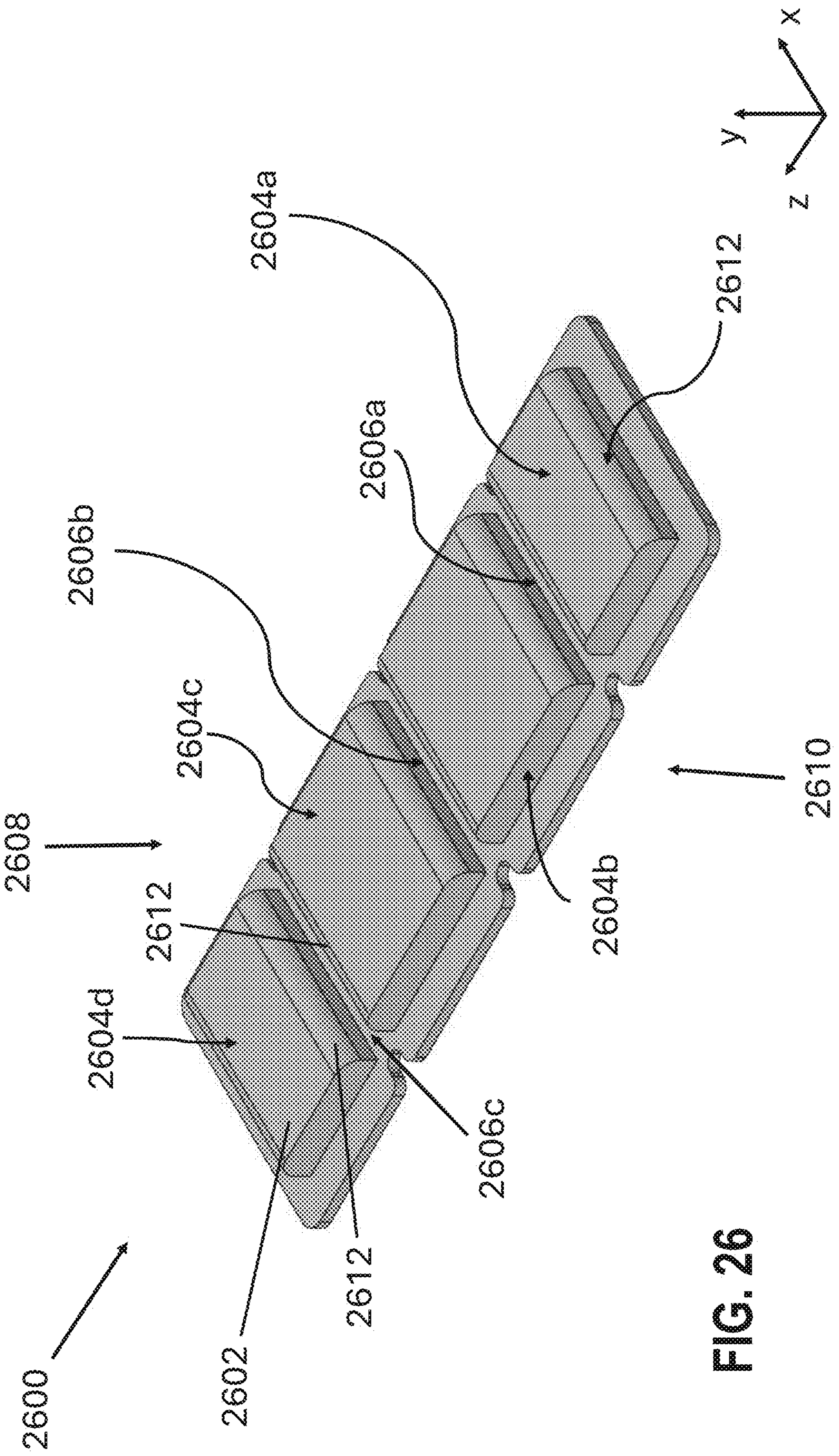
FIG. 26 is a perspective view showing a module comprising a housing with a plurality of compartments and gaps between adjacent compartments to provide for flexure of the housing.

As discussed herein, a module is configured to be embedded in a wearable medical article placed over a wound on a body surface of a wearer of the wearable medical article. This module may include at least one optical sensor configured to obtain images and/or to generate image data of a body surface region of the wearer of the wearable medical article. FIG. 26 illustrates an example module 2600 that may include a plurality of optical sensors, in this case two optical sensors or two cameras. In particular, FIG. 26 shows a housing 2602 having a plurality of compartments 2604*a*, 2604*b*, 2604*c*, 2604*d* including, in this example, two compartments 2604*b*, 2604*c* for two optical sensors. These two compartments 2604*b*, 2604*c* include areas for two optical sensors which may be referred to as camera areas. The housing 2602 shown in FIG. 26 also includes a compartment 2604*a* comprising an area for a battery and a compartment 2604*d* comprising an area for electronics such as a microcontroller. This electronics (e.g., the microcontroller) can be used to control the operation of the two optical sensors in the two camera compartments 2604*b*, 2604*c* such as the collection of imaged and/or imaging data from the two cameras.

In certain implementations such as the example shown in FIG. 26, the module 2600 and the housing 2602 are elongate. The module 2600 and/or housing 2602 has a length in one direction, the longitudinal direction (e.g., the z-direction parallel to the z-axis in FIG. 26), that is longer than a width in a transverse direction (in the orthogonal x-direction parallel to the x-axis in FIG. 26) and thickness in a transverse direction (in the orthogonal y-direction parallel to the y-axis in FIG. 26). In the example, the length, width, and thickness are in orthogonal directions. In various designs such as in the example shown, the compartments 2604*a*, 2604*b*, 2604*c*, 2604*d* extend along the length (e.g., the longitudinal or z-direction) of the module 2600 and/or housing 2602. In some such designs, such as shown, the compartments 2604 are arranged along the length of the housing such that at least one compartment is between two others. For example, the second compartment 2604*b* may be between the first compartment 2604*a* and the third compartment 2604*b* and/or the third compartment may be between the second compartment and the fourth compartment 2604*d*. Accordingly, the first, second and third compartments 2604*a*, 2604*b*, 2604*c* may be arranged along the length of the housing (and the module) and/or the second, third, and fourth compartments 2604*b*, 2604*c*, 2604*d* extend across the length of the housing (and the module). Such an arrangement may facilitate bending of the housing 2602 and module 2600 along the length thereof, e.g., bending along the longitudinal direction.

In various implementations, the housing 2602 is configured to bend about a curved or bending body surface. As the module 2600 is embedded in a wearable medical article such as a dressing placed on an anatomical body part that may have a curved surface or may bend with movement of the patient, the module may benefit from being able to bend (e.g., along the length or longitudinal direction thereof) to conform more closely to the shape of the surface of the body and/or to the movement of patient. Accordingly, in certain designs such as shown in the example in FIG. 26, adjacent compartments 2604*a*/2604*b*, 2604*b*/2604*c*, 2604*c*/2604*d* or compartments that are next to each other (as compared to compartments having another compartment therebetween), are spaced apart from each other by a gap 2606*a*, 2606*b*, 2606*c* (e.g., an air gap) in the housing 2602 to allow said adjacent compartments to tilt with respect to each other thereby providing flexure of the housing. In FIG. 26, for example, the first and second compartments 2604*a*, 2604*b* are separated by a gap 2606*a* such that the first and second compartments 2604*a*, 2604*b* can tilt with respect to each other such as along the length of the housing when the housing bends along its length (e.g., along the longitudinal or z-direction or direction parallel to the z-axis shown in FIG. 26), thereby providing flexure to the housing. Portions of the first and second compartments 2604*a*, 2604*b* may, for example, be further in the orthogonal transverse direction (e.g., y direction) than the gap 2606*a* when the housing 2602 is bent along the longitudinal direction.

Similarly, in FIG. 26, the second and third compartments 2604*b*, 2604*c* are separated by a gap 2606*b* such that the second and third compartments 2604*b*, 2604*c* can tilt with respect to each other such as along the length of the housing 2602 when the housing bends along its length (e.g., along the longitudinal or z-direction or direction parallel to the z-axis shown in FIG. 26) thereby providing flexure to the housing. Portions of the second and third compartments 2604*b*, 2604*c* may, for example, be further in the orthogonal transverse direction (e.g., y direction) than the gap 2606*b* when the housing 2602 is bent along the longitudinal direction.

Additionally, in FIG. 26, the third and fourth compartments 2604*c*, 2604*d* are separated by a gap 2606*c* such that the third and fourth compartments 2604*c*, 2604*d* can tilt with respect to each other such as along the length of the housing 2602 when the housing bends along its length (e.g., along the longitudinal or z-direction or direction parallel to the z-axis shown in FIG. 26) thereby providing flexure to the housing. Portions of the third and fourth compartments 2604*b*, 2604*c* may, for example, be further in the orthogonal transverse direction (e.g., y direction) than the gap 2606*c* when the housing 2602 is bent along the longitudinal direction.

As shown, the housing 2602 may have an upper (top or distal) side 2608 and a lower (bottom or proximal) side 2610. When the module 2600 is embedded in a dressing for example that is affixed to a person's (e.g., patient's) body, the lower (proximal) side 2610 is closer to the person/patient's body, the body surface region, and/or the wound than the upper (distal) side 2608 in many instances. The gap(s) 2606 in the housing 2604 is in the upper (distal) side 2608 of the housing. The lower (proximal) side 2610 includes a base portion 2612 that may be affixed or more affixed and/or closer to the body surface. The gap(s) 2606 in the housing 2604 may facilitate flexure or bending of the housing such that the lower (proximal) side more closely conforms to the body surface region than if the housing were ridged and did not flex or bend.

In various implementations the gap 2606 in the housing 2604 may facilitate flexure or bending of the housing such that the lower (proximal) side more closely conforms to the body surface region than if the housing were rigid and did not flex or bend. In various designs, the gap extends toward the lower (proximal) side of the housing a depth of at least 10%, 15%, 20%, 25%, 30%, 40%, 50%, 60%, 70%, 80%, 90%, 100% of the thickness of the housing and/or of the compartment, or any range therebetween. In some designs, the size of the gap such as the separation of the adjacent compartments 2604*a*/2604*b*, 2604*b*/2604*c*, 2604*c*/2604*d* (e.g., along the length of the housing 2602 or module 2600 in the longitudinal or z-direction in an example elongate housing such as shown in FIG. 26) is about 20%, 30%, 40%, 50%, 60%, 70%, 80%, 90%, 100%, 100%, 120%, 150%, 175%, 200%, 250%, 300%, 350%, 400%, 500% the depth of the gap, or any range formed by any of these values or possibly larger or smaller. Likewise, the size of the gap 2606 (e.g., in the longitudinal direction/along the length of the housing) and/or the separation be between adjacent compartments 2604*a*/2604*b*, 2604*b*/2604*c*, 2604*c*/2604*d* may be larger (or smaller) than the depth of the gap.

As in the example shown in FIG. 26, the individual compartments 2604*a*, 2604*b*, 2604*c*, 2604*d* may have a rectangular shape when as viewed from the upper (distal) side 2608 (or the lower/proximal side 2610) of the housing 2602. Accordingly, the cross-section of the individual compartments 2604*a*, 2604*b*, 2604*c*, 2604*d* along the length and width of the housing 2602 (e.g., parallel to the x-z plane) may be rectangular. Other shapes are possible.

Also, the example housing 2602 and module 2600 shown in FIG. 26 includes four compartments. More or less compartments may be included. For example, the housing 2602 may have 2, 3, 4, 5, 6, 7, 8, 9, 10, 12, 15, 18, 20, 24, 25, 30, 40, 50 compartments or any range formed by any of these values, e.g., 3-5 compartments, or possibly more. Similarly, the housing 2602 may have 1, 2, 3, 4, 5, 6, 7, 8, 9, 11, 14, 17, 19, 23, 24, 29, 39, 49, gaps 2606 or any range formed by any of these values, e.g., 2-4 gaps, or possibly more.

As illustrated in FIG. 26, the compartments may have different sizes. For example, for the housing 2602 shown in FIG. 26, the first and second compartments have the same size and the second and third housings have the same size but the first and fourth compartments have a different size than the second and third compartments. Accordingly, one or more compartments may be the same size (and/or shape) and/or one or more compartments may be different size (and/or shape). Each of the compartments may be the same size (and/or shape) or each of the compartments may be different size (and/or shape). Likewise, the sizes and/or shapes of the compartments may be the same and/or different in various designs.

In the example housing shown in FIG. 26, the housing 2602 is rounded and/or beveled along at least some edges 2612 closer to said upper side 2608 of said housing. In various designs, such as shown, the housing 2602 is rounded and/or beveled along at least some edges 2612 along the gap(s) 2606.

The housing may thus be flexible. The gaps between the compartments may provide for flexure of the housing. In some implementations, the housing may also comprise materials that are flexible such as foam(s).

As discussed above, different compartments 2604 may be for any one or more of the optical sensors or cameras, a battery, electronics or possibly other components. Which compartment and for which component may vary with the design. However, in various designs, the module includes a plurality of optical sensors and different optical sensors are in different but adjacent compartments (e.g., with no compartment therebetween that does not include an optical sensor). In some implementations, the compartments for the battery and electronics may be on opposite sides of the compartments of for the optical sensors. Other configurations, however, are possible.

In various implementations, the housing 2602 includes one or more openings on the bottom (proximal) side 2610 thereof that provides access to the compartments 2604. For example, the housing 2602 may include an opening on the bottom (proximal) side 2610 of the housing in the compartment 2604 for the at least one optical sensor for transmission of light from the body surface region. The housing 2602 may include an opening on the bottom (proximal) side 2610 of the housing in the compartment 2604 for the electronics and/or the battery for connection to electrical wiring such as electrical cables such as one or more flexible ribbon cables (e.g., flexible flat ribbon cables or flex cables).

Various components such as the optical sensors and/or electronics may be included on a printed circuit board assembly (PCBA) as discussed above. Likewise, one or more, possibly all, of the components shown the example of FIG. 27 may be included on a on a printed circuit board assembly (PCBA).

As discussed above, the module may comprise rigid-flex circuits, circuitry, technology, for example, a rigid-flex circuit board assembly comprising a plurality of rigid components and plurality of flexible components. Some of the plurality of flexible components may be configured to couple at least some of the plurality of rigid components together. In some implementations, one or more are coupled to the rigid-flex circuit board assembly.

As discussed above, the PCBA may be configured to at least partially move or flex in order to at least partially follow the contour of a patient's tissue or move in response to tissue movement. For example, the one or more flexible components are configured to flex to allow the one or more rigid components to move in relation to each other. In some examples, the PCBA may contain one or more rigid components connected to one or more other rigid components by at least one flexible component. In some designs, the one or more flexible components may be configured to include one or more flexible circuits or other constructions in order to facilitate communication and/or functioning of electronics on the PCBA. In some examples, the one or more rigid components may include one or more circuits, optical sensors, and/or other constructions configured to support the one or more optical sensors mounted to the one or more rigid components. In other examples, the PCBA may be entirely flexible or entirely rigid.

Thus, in some implementations, a rigid-flexible circuit assembly may be used with some components, e.g., optical sensors, battery, etc. being rigid, connected to others via flexible components or connections. In some implementations, electronics may be implemented via flexible circuitry (flex circuits) and/or circuitry, which possibly may or may not be integrated into flexible ribbon cable, flat flexible ribbon cable or flex cable.

In some implementations, flexible ribbon cable (e.g., flat flexible ribbon cable) connects the battery, the at least one sensor, and the electronics. As stated above, in some implementations, a rigid-flexible circuit assembly may be used with some components, e.g., optical sensors, battery, etc. being rigid, connected to others via flexible components or connections. In some implementations, electronics may be implemented via flexible circuitry or circuits (flex circuits) and/or circuitry or circuits, which possibly may or may not be integrated into flexible ribbon cable or flex cable.

Figure 27:
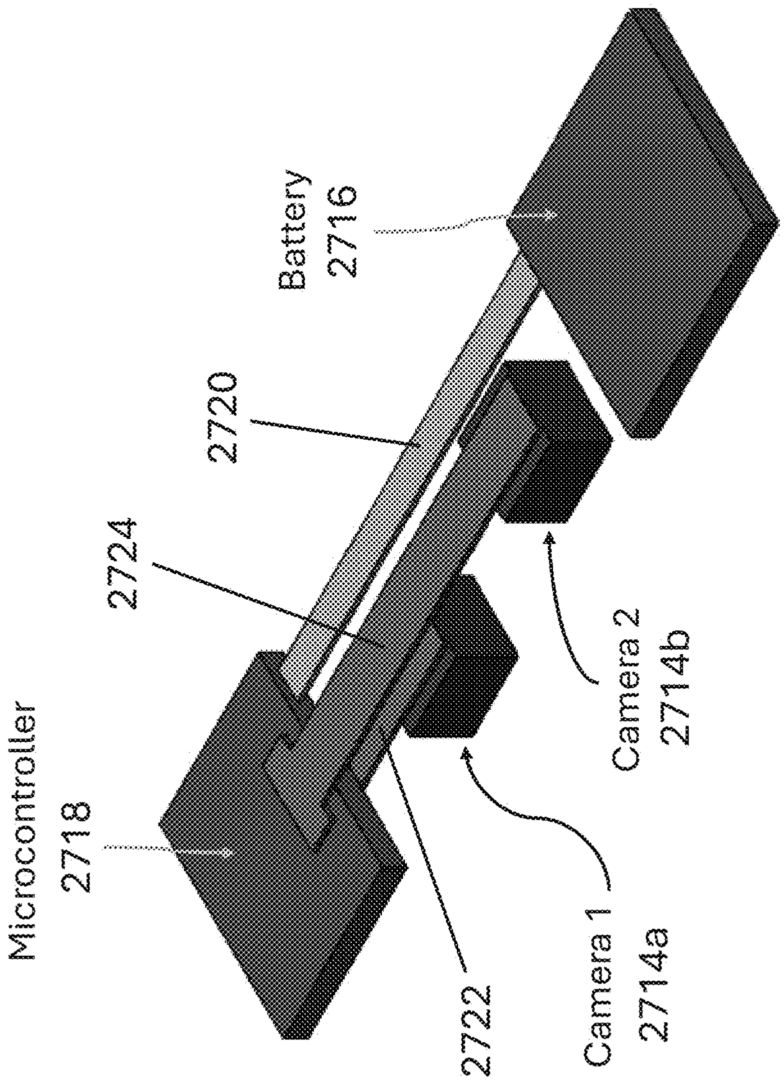
FIG. 27 is a perspective view showing a pair of optical sensors electrically connected to electronics and a battery via flexible ribbon cable (e.g. flexible flat ribbon cable).

FIG. 27 shows and example arrangement of first and second optical sensors or cameras 2714*a*, 2714*b*, a battery 2716, and electronics (e.g., a microcontroller) 2718. The battery 2716 is electrically connected to the electronics (e.g., microcontroller) 2718 with a first flexible ribbon cable (e.g., flexible flat ribbon cable or flex cable) 2720. The electronics (e.g., microcontroller) 2718 is electrically connected to the first optical sensor 2714*a* with a second (e.g., flexible flat ribbon cable or flex cable) 2722. The electronics (e.g., microcontroller) 2718 is electrically connected to the second optical sensor 2714*b* with a second flexible ribbon cable (e.g., flexible flat ribbon cable or flex cable) 2724. Other configurations and arrangements are possible.

As discussed above, in various implementations, the first and second optical sensors may be configured to image different portions of the body surface region and/or wound and may thus have fields of view that are different. In some implementations, for example, most of the field of view of the first cameras does not overlap the field of view of the second camera and vice versa. Images and/or portions of images from the first optical sensor 2714*a* may be combined with images and/or portions of images from the second optical sensor 2714*b* to provide a larger field of view. As discussed above, the images or image data from the two cameras can be stitched, for example, to provide this larger field of view of the body surface region and/or wound. In some designs, for example, a 4K image may be produced from first and second optical sensors having less than 4 k resolution. Other configurations, however, are possible.

In some implementations, for example, the first and second optical sensors 2714*a*, 2714*b* may have different spectral responsivities and obtain images (or image data) at different spectral wavelengths or spectral bands. In some cases, these first and second optical sensors 2714*a*, 2714*b* are configured capture images or image data of the same portion of the body surface image, but in different spectral bands. Accordingly, multispectral images may be obtained and/or multispectral imaging may be performed as discussed above.

The electronics (e.g., microcontroller) 2718 may in some implementations have wireless capable. Accordingly, as discussed herein, the module may be configured to communicate, for example, wirelessly, with remotely located systems, devices, resources, etc.

In various implementations, different optical sensors have their own channels. The microcontroller may be programmed to collect images from each channel. The electronics may include multiplexers to place each camera on its own channel.

Figure 28:
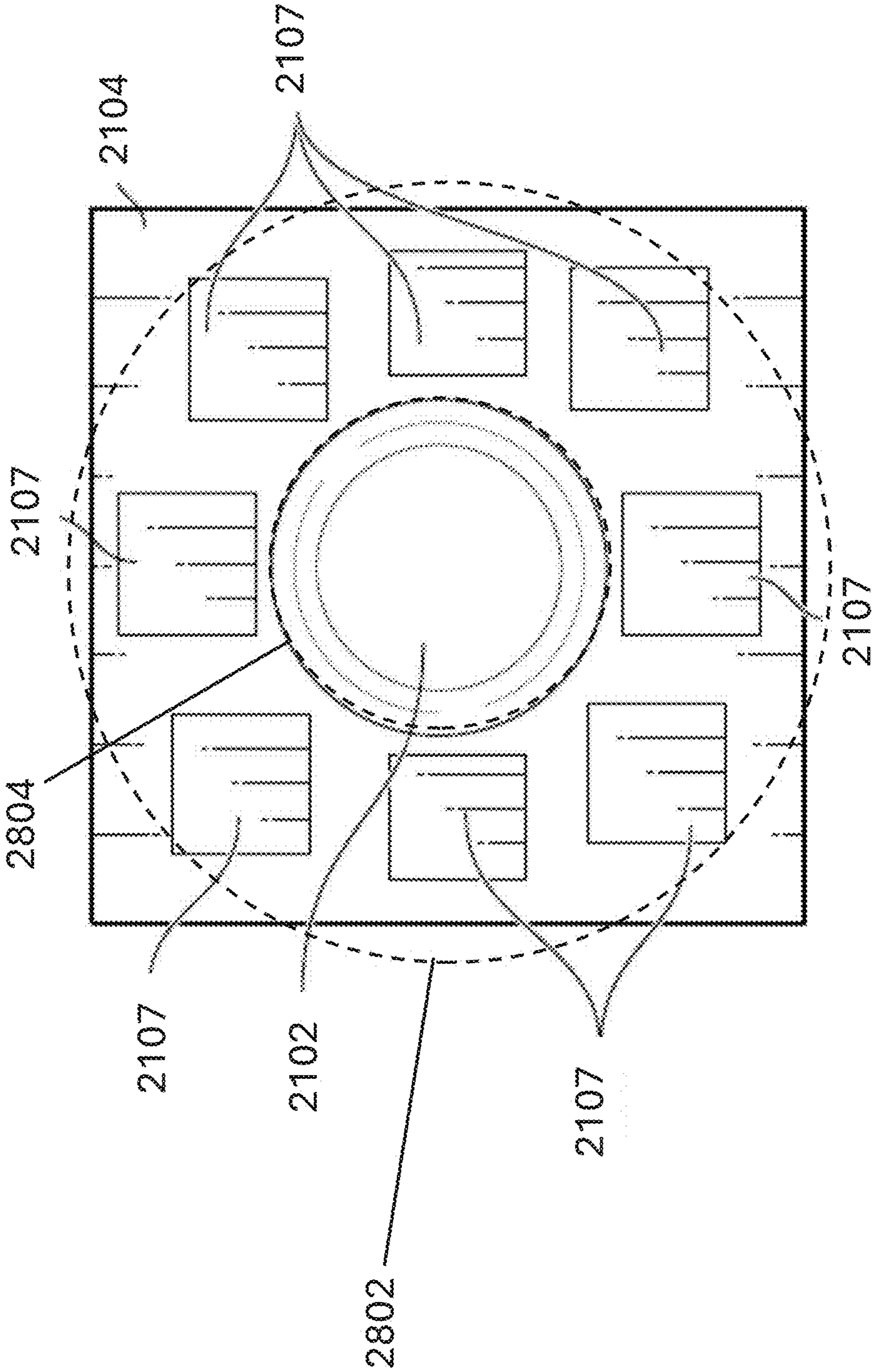
FIG. 28 is a schematic drawing showing a diffuser in front of a plurality of light sources. The diffuser is ring shaped and has a central hole for light to pass to the optical sensor.

As discussed above, a diffuser may be employed to provide more uniform illumination of the body surface region. The diffuser may be disposed in front of the light source or light sources. FIG. 28 shows an example of such a diffuser 2802. In this example, the diffuser 2802 is ring shaped, but may have other shapes. This diffuser is a transmissive diffuser, diffusing light transmitted therethrough. Light from the light source will be transmitted through the diffuser to produce diffusely distributed light onto the body surface region. In some implementations, the diffuser is a white diffuser.

The diffuser 2802 shown in FIG. 28 has a central aperture or hole 2804. This hole 2804 is in front of the optical sensor 2102 such that the light reflected from the body surface region goes through the hole to reach the optical sensor and not through the diffuser. The diffuser 2802, however, is in front of the light sources 2107 such that light from the light sources passes through the diffuser to diffuse the light incident on the body surface region. The diffuser may therefore provide more uniform illumination. The light sources may comprise one or more white light source, color light sources, infrared light sources, or possibly ultraviolet light sources. As discussed above, in some implementations, the light sources 2107 may all have the same emission spectra, for example, may each comprises a broad band or white light source such as potentially a full spectrum LED although other types of light sources are possible.

As discussed above, these light sources 2107 may comprise arrays of light emitter such as an array like that shown in FIG. 22B. The light emitters in the array may have different emission spectra. The electronics may be configured to drive emitters having the same emission spectra in the different light sources (in different arrays) to turn on at the same time. For example, a plurality, e.g., all, the emitters of a first band in the different arrays 2107 may be activated (while the others emitters of different bands are off). Then, the emitters of the first band may be deactivated and the a second group of emitters of a second band are activated. Subsequently, the emitters of the second band may be deactivated and a third group of emitters emitting at third band are activated, and so on. The light sources 2107 can thereby provide different wavelength light emission at different times. The diffuser 2802 may be disposed in front of the plurality of light source 2107, e.g. the plurality of arrays, such that regardless what emitters in the arrays are activated and what wavelength light is being emitted, the light from plurality of light source passes through the diffusers to more evenly distribute the illumination on the body surface region.

The diffuser may comprise a variety of different types and types of materials. The diffuser may be a surface diffuser or a volume diffuser. The diffuser may, for example, comprise ground glass, or the diffuser may comprise Teflon. In some cases, the diffuser comprises Spectralon, which may comprise, for example, a fluoropolymer. The diffuser may be an engineered diffuser. The diffuser may be a diffractive optical element or hologram that diffuses. A randomized microlens array may also be used in some implementations.

In some designs, at least two diffusers may be stacked one in front of the other, possibly with an air gap therebetween.

In some cases, the diffuser may be integrated with the light source. For example, the diffuser may be formed on the packaging or casing (e.g., metal packaging or casing) which houses the solid state emitter or emitters (e.g., the LED or LEDs). The LEDs may comprise semiconductor material and may be included in packaging such as a metal cylindrical shaped package or casing. The diffuser may be included above the (e.g., solid state, possibly semiconductor) emitters (possibly at the top of the metal casing) and below a lens. The diffuser may be formed in a medium such as epoxy above and/or encasing the (e.g., solid state, possibly semiconductor) emitter. This medium (e.g., epoxy) may for example have diffusing particles therein. In such designs, the diffuser has a smaller footprint.

In various designs, interior surfaces (e.g., walls or sidewall) within the module (e.g., within the cavities formed the module) from which light from the light sources may reflect may comprise diffuse reflecting surfaces to reduce glare and/or provide more uniform illumination of the body surface region. These surfaces (e.g. walls, sidewalls) may have a surface finish to provide such diffuse reflection. In some implementations, embedding particles the material forming the surface may provide for diffuse reflection. Embedding titanium dioxide in a material such as silicone is an example of such a design. A combination of embedded particulates and surface finish may be employed to provide for diffusely reflecting surfaces.

The module may also comprise other materials that provide for diffuse reflection, thereby reducing glare. Some materials include silicone, such as white silicone, e.g., white pigmented silicone, Teflon (or polytetrafluoroethylene or PTFE), or barium sulfate (or use barium sulfite). In some cases, the diffuser comprises Spectralon, which may comprise, for example, a fluoropolymer. In various implementations, however, the diffusely reflecting surface are white or whitish (or other light colors such as beige, yellow, light orange, light blue, light red, light green, light purple, etc.), which may increase reflection.

In some implementations, the module is opaque to block ambient light such that ambient light is not incident on the body surface region covered by the module and interferes with image formation having the intended spectral content. However, as described above, the module may be diffusely reflective for example to provide for increase uniformity in illumination of the body surface region by the light sources. In some designs, the module may comprise a black or dark (e.g., dark color, dark blue, dark brown, dark purple, dark green or even medium tones of such colors) outside surface (e.g., a black outer shield). In some designs, the module may have a white reflective interior or inner shell. In some implementations, the module has the black exterior and the white or light (e.g., yellow, beige) interior, In some cases, the diffuse reflectivity of the interior surfaces of the module has a flat reflectance or a reflectance within 25%, 20%, 15%, 10%, 5%, 4%, 3%, 2%, 1%, 0.1%, or any range formed by any of these percentages or possible more or less across a range of wavelengths at least 100 nm, 200 nm, 300 nm, 400 nm, 500 nm, 600 nm, 700 nm, 800 nm, 900 nm, 1000 nm, 1100 nm, 1200 nm, 1500 nm, 1600 nm, 1800 nm, 2000 nm, 3000 nm, 5000 nm, 8000 nm, 10000 nm, or any range formed by any of these values of wavelength or possible over larger or smaller wavelength ranges. In some cases, interior surfaces are Lambertian reflective surfaces, e.g., with a Cos θ distribution.

Systems, devices and methods described herein may provide for multispectral, hyperspectral, fluorescent, thermal and digital (e.g. RGB) imaging and acquisition of image data or any combination of these of wounds to monitor the healing of wound. Real time monitoring or periodic monitoring may be provided.

These different types of imaging modalities, for example, multispectral, hyperspectral, fluorescent, thermal and digital (e.g. RGB) imaging can potentially detect changes in the microenvironment of a wound. Visual observation is a powerful clinical tool for managing patients with wounds. Embedded connected wound care imaging technology described herein allows clinicians visual observation to monitor, optionally in real time, the healing process of acute and chronic wounds with a non-invasive multispectral, hyperspectral, thermal, fluorescent, digital imaging technology or any combination of these without having to see the patients or remove the dressings, bandages, wraps, or casts for the early detection of complications before they become serious.

Images and their inclusion in the documentation and patient records can provide clinicians with a powerful, informative, and non-invasive approach for examining, quantifying, and documenting wounds and for the creation of large databases for research, educational, and diagnostic purposes, particularly those with machine learning support.

Remote evaluation and assessment of the wound are also of increasing importance through the use of a telemedicine approach.

As described herein, digital imaging can produce images of the body's soft tissues and internal structures. Multispectral (MSI) and Hyperspectral (HSI) imaging utilize the ability to split light into multiple narrow bands beyond the three conventional red, green, and blue (RGB) visible spectral bands, enabling analysis of images not seen with the naked eye. Detection (e.g., imaging, collection of image data) of different wavelengths can be used to provide diagnostic capabilities different from and supplemental to RGB or a physician's visual inspection alone.

Thermal imaging, or thermography, can be used to detect problems in wound healing by identifying temperature differences in the skin. Higher local temperatures indicate inflammation. Lower local temperatures can indicate infection. Decreased oxygen in the region can indicate slow healing. Thermal imaging techniques can be used to predict the healing status of a venous leg ulcer. Comparing the skin temperature distribution of both feet can help predict ulceration. The foot with a higher temperature is at a higher risk of ulceration.

Thermal imaging can be used to assess a variety of wounds, including surgical incisions. Thermal imaging can be used to monitor the healing progress of surgical incisions. Thermal imaging can be used to predict the healing trajectory of venous leg ulcers. Thermal imaging can be used to measure the healing potential of burn wounds.

In various implementations, the module, for example, the light source(s) and/or the optical sensor(s) are configured for fluorescence imaging or fluorescence data collection. In such cases, the light source may output light having a wavelength that will induce fluorescence and the optical sensor will be sensitive to the fluorescent wavelength. The incident wavelength and the fluorescing wavelength may be different. For example, the fluorescent wavelength may be longer (or shorter) than the incident wavelength from the light source that induces the fluorescence. Fluorescence imaging can be used to detect wound bacteria and may lead to reduction in antibiotic use and antimicrobial dressing expenditure while improving healing rates. Fluorescence imaging can detect high bacterial loads in wounds, which can lead to complications and impede healing. Some fluorescence imaging methods employ illumination of fluorescently labeled proteins or other intracellular molecules with a defined wavelength of light ideally near the peak of the fluorophore excitation spectrum, and detection of light emitted at a longer wavelength. Others fluorescence methods may also be used.

Systems, devices and methods described herein any one or more of these types of imaging, for example, thermal imaging, fluorescent imaging, infrared imaging (e.g., NIR or MWIR imaging), visible light imaging, using a module that is embedded in a dressing placed over a wound. The imaging can be performed and the images and/or image data can be relayed to the physician, nurse, technician or other medical professional or analyzed without needing to remove the dressing, bandages, wraps, or casts, for example, for the early detection of complications before they become serious. Multiple types of imaging such as thermal and digital (e.g., RGB) or fluorescent and digital (e.g., RGB) or infrared (e.g., NIR or MWIR) and digital (e.g. RGB) or thermal and fluorescent or fluorescent and infrared can be performed by the module embedded in the dressing, for example, to monitor the wound. Likewise multispectral imaging may be performed by the module configured to be embedded in a wearable medical article (e.g., dressing, bandage, wrap cast, etc.) placed over a wound on a body surface of a wearer of the wearable medical article. Multispectral may be used for imaging when biologic dressing are used, while digital (e.g., RGB images) may be useful for sutures and open wounds. Dual imaging modalities or more may be employed by the module to provide information about the wound and its healing. Images may be captured at more than two wavelength ranges. Likewise, multispectral and/or hyperspectral imaging may be provided by this module. Similarly more than two modalities may be employed by the module embedded in the dressing. In some implementations, for example, multispectral, hyperspectral and digital imaging under the dressing may be performed. Or thermal, fluorescent and digital (RGB) imaging may be performed by the module configured to be embedded in a wearable medical article (e.g., dressing, bandage, wrap cast, etc.) placed over a wound on a body surface of a wearer of the wearable medical article.

The module configured to be embedded in a wearable medical article (e.g., dressing, bandage, wrap cast, etc.) placed over a wound on a body surface of a wearer of the wearable medical article may be a single use or disposable device. In some implementations, the device may thus be a single patient per episode treatment disposable that is embedded in dressing for monitoring the wound. As discussed above, the module or device may be synched with the medical record number.

Moreover, this non-invasive device or module with potential multispectral, hyperspectral, thermal, fluorescent, infrared (NIR), digital (RGB) imaging or any combination of these may be connected to the EHR or EMR. For example, in patient monitoring may be provided using a WiFi antenna within the device that sends images to the EHR patient record for clinician review and diagnosis. For remote patient monitoring—mHealth (mobile health) private wireless networks through FDA approved carriers using LTE and 5G to the cloud and EHR may be employed. An alert system and/or anomaly detection can be provided. Data analysis and interpretation of the multi-wavelength, or infrared, or thermal, or fluorescent, or hyperspectral, or multispectral or digital (e.g., RGB) images or any combination of these can be performed, for example, remotely, data being communicated to remote location, e.g., wirelessly. Alerts and/or communication back to the patient and/or to the physician, nurse, technician or other health care professional can be provided.

EXAMPLES

The following is a numbered list of example embodiments that are within the scope of this disclosure. The example embodiments that are listed should in no way be interpreted as limiting the scope of the embodiments. Various features of the example embodiments that are listed can be removed, added, or combined to form additional embodiments, which are part of this disclosure.

Part 1

1. A system comprising:
   a module configured to be embedded in a wearable medical article placed over a wound on a body surface of a wearer of the wearable medical article, wherein the module comprises:
      a plurality of optical sensors configured to generate image data of a body surface region of the wearer of the wearable medical article, said plurality of optical sensors comprising:
         a first optical sensor configured to capture a first image of said body surface region at a first wavelength range; and
         a second optical sensor configured to capture a second image of said body surface region at a second wavelength range different than the first wavelength range.

2. The system of any of the examples above, further comprising respective first and second optical filters for said first and second optical sensors, said first and second optical filters configured to transmit different first and second wavelength ranges, respectively.

3. The system of any of the examples above, wherein said plurality of optical sensors comprises at least three optical sensors configured to capture images of said body surface region at three different respective wavelength ranges.

4. The system of any of the examples above, wherein said plurality of optical sensors comprises at least four optical sensors configured to capture images of said body surface region at four different respective wavelength ranges.

5. The system of any of the examples above, wherein said plurality of optical sensors comprises at least six optical sensors configured to capture images of said body surface region at six different respective wavelength ranges.

6. The system of any of the examples above, wherein said plurality of optical sensors comprises at least eight optical sensors configured to capture images of said body surface region at eight different respective wavelength ranges.

7. The system of any of the examples above, wherein said plurality of optical sensors further comprises a red-green-blue (RGB) optical sensor configured to capture RGB images of said of said body surface region.

8. The system of any of the examples above, wherein said plurality of optical sensors further comprising a cyan yellow and magenta optical sensor configured to capture cyan yellow and magenta images of said of said body surface region.

9. The system of any of above, further comprising at least one light source to illuminate at least a portion of said of said body surface region.

10. The system of any of Examples 9, wherein said at least one light source comprises a light source configured to output light in both said first and second wavelengths.

11. The system of any of Examples 9, wherein said at least one light source comprises a first light source configured to output more in said first wavelength range than said second wavelength range and a second light source configured to output more of said second wavelength range than said first wavelength range.

12. The system of Example 11, wherein said first light source is closer to said first optical sensor than said second optical sensor, and said second light source is closer to said second optical sensor than said first optical sensor.

13. The system of any of Examples 9-12, wherein said at least one light source comprises at least one light emitting diode (LED).

14. The system of any of Examples 9-12, further comprising at least one diffuser configured to diffuse light from said at least one light source.

15. The system of any of the examples above, further comprising at least one polarizer configured to polarize light directed to at least one of said optical sensors.

16. The system of any of the examples above, wherein said first and second wavelength ranges comprise infrared wavelengths.

17. The system of any of the examples above, wherein at least one of said first and second wavelength ranges comprise a near infrared (NIR) wavelength.

18. The system of any of the examples above, wherein at least one of said optical sensors comprises a thermal imager or thermal camera configured to capture thermal images.

19. The system of any of the examples above, wherein at least said first wavelength range comprises a wavelength in the range of 9-14 micrometers (μm).

20. The system of any of the examples above, wherein at least one of said first and second wavelength ranges comprise an ultraviolet wavelength.

21. The system of any of the examples above, wherein at least one of said first and second wavelength ranges comprise a visible wavelength.

22. The system of any of the examples above, wherein at least one of said optical sensors comprises a wide angle lens.

23. The system of any of the examples above, wherein at least one of said optical sensors comprises a fish eye lens.

24. The system of any of the examples above, wherein said plurality of optical sensors comprises at least a first and second groups of optical sensors, wherein most of the portion of said body surface region that said first group of optical sensors images does not overlap most of the portion of said body surface region that said second group of optical sensors images.

25. The system of Example 24, further comprising electronics configured to stitch together images captured by optical sensors in said first group of optical sensors with images captured by optical sensors in said second group to form images of a wider field of view.

26. The system of Example 24, further comprising electronics configured to form a 4K image of a wider field of view by stitching together images captured by at least one optical sensor from first the first group of optical sensors and at least one optical sensor from the second group of optical sensor when said images captured by said at least one sensor from said first group and said at least one sensor from said second group are not 4K images.

27. The system of any of Examples 24 to 26, wherein said first optical sensor and said second optical sensor are in said first group of optical sensors.

28. The system of any of the examples above, further comprising electronics configured to assemble multispectral images from image data from said plurality of optical sensors.

29. The system of any of the examples above, further comprising electronics configured to form multispectral images from image data from said first and second optical sensors.

30. The system of any of the examples above, further comprising electronics configured to assemble hyperspectral image data from said plurality of optical sensors.

31. The system of any of the examples above, further comprising electronics configured to assemble hyperspectral images data from image data from said plurality of optical sensors.

32. The system of any of the examples above, wherein said wearable medical article together with said plurality of optical sensors are configured to be disposable or single use.

33. The system of any of the examples above, wherein said module comprises a housing.

34. The system of any of the examples above, wherein said plurality of optical sensors are positioned proximal to said body surface region of the wearer.

35. The system of any of the examples above, wherein said plurality of optical sensors are positioned within 3 cm of said body surface region of the wearer.

36. The system of any of the examples above, wherein said plurality of optical sensors further comprises a color optical sensor configured to capture color images of said of said body surface region.

37. The system of any of the examples above, configured to transmit to cloud based system that processed images or image data to detect properties of wound or wound healing.

38. The system of any of the examples above, further comprising a wireless network interface configured to transmit the image data.

39. The system of any of the examples above, further comprising a computing system comprising one or more computer processors and executable instructions, wherein the computing system is configured to:

receive the image data from the plurality of optical sensors;

receive contextual data associated with the wearer; and determine a current state of the body surface region based at least partly on the image data and the contextual data.

40. The system of examples 39, wherein to determine the current state of the body surface region, the computing system is configured to evaluate the image data and contextual data using a machine learning model to generate a score representing the current state of the body surface region.

41. The system of examples 39, wherein the image data comprises a plurality of overlapping sub-sections of the body surface region and wherein the computing system is configured to generate a combined image for analysis based on the plurality of overlapping sub-sections.

42. The method of any of the examples above, wherein module is embedded in a wearable medical article.

43. The method of any of the examples above, wherein module is embedded in a dressing, bandage, wrap or cast.

44. The method of any of the examples above, wherein the module is placed on a subject above a wound together with wearable medical article.

Part 2

1. A system comprising:

a module configured to be embedded in a wearable medical article placed over a wound on a body surface of a wearer of the wearable medical article, wherein the module comprises:

at least one optical sensor configured to generate image data of a body surface region of the wearer of the wearable medical article, a plurality of light sources configured to provide illumination to said body surface region, said plurality of light sources comprising:

a first light source configured to emit light in first wavelength range; and a second light source configured to emit light in a second wavelength different than the first wavelength range, wherein said first and second light sources are configured to emit said light in said respective first and second wavelength ranges at different times.

2. The system of any of Example 1, wherein said plurality of light sources comprises at least four light sources configured to emit light at four different respective wavelength ranges.

3. The system of any of the examples above, wherein said plurality of light sources comprises at least six light sources configured to emit light at six different respective wavelength ranges.

4. The system of any of the examples above, wherein said plurality of light sources comprises at least ten light sources configured to emit light at ten different respective wavelength ranges.

5. The system of any of the examples above, wherein said plurality of light sources comprises at least sixteen light sources configured to emit light at sixteen different respective wavelength ranges.

6. The system of any of the examples above, wherein said plurality of light sources comprises light emitting diodes (LEDs).

7. The system of any of the examples above, further comprising at least one diffuser configured to diffuse light from said plurality of light sources.

8. The system of any of the examples above, further comprising at least one polarizer configured to polarize light directed to said at least optical sensors.

9. The system of any of the examples above, wherein said first and second wavelength ranges do not overlap.

10. The system of any of the examples above, wherein said first wavelength range comprise visible wavelengths.

11. The system of any of the examples above, wherein said first wavelength range comprise red, green, and blue wavelengths.

12. The system of any of the examples above, wherein said first wavelength range comprises cyan, magenta, and yellow wavelengths.

13. The system of any of the examples above, wherein said first wavelength range comprise white light.

14. The system of any of the examples above, wherein said second wavelength range comprises infrared wavelengths.

15. The system of any of the examples above, wherein said second wavelength range comprises ultraviolet wavelengths.

16. The system of any of the examples above, wherein second wavelength ranges comprise a near infrared (NIR) wavelength.

17. The system of any of the examples above, wherein said second wavelength range comprises long wave infrared light such that said at least one optical sensor is configured to capture a thermal image.

18. The system of any of the examples above, wherein said second wavelength ranges comprises a wavelength in the range of 9-14 micrometers (μm).

19. The system of any of the examples above, wherein further comprising a third light source emitting light in a third wavelength range different from said first and second wavelength ranges, said first second and third light sources configured to emit said light in said respective first, second and third wavelength ranges at different times.

20. The system of any of the examples above, wherein said third wavelength range comprises visible wavelengths.

21. The system of any of the examples above, wherein said third wavelength range comprises infrared wavelengths.

22. The system of any of the examples above, wherein said third wavelength range comprises NIR wavelengths.

23. The system of any of the examples above, wherein said third wavelength range comprises long wave infrared light such that said at least one optical sensor is configured to capture a thermal image.

24. The system of any of the examples above, wherein said third wavelength ranges comprises a wavelength in the range of 9-14 micrometers (μm).

25. The system of any of the examples above, wherein said third wavelength range comprise ultraviolet wavelengths.

26. The system of any of the examples above, wherein said at least one optical sensor comprises a wide angle lens.

27. The system of any of the examples above, wherein said at optical sensor comprises a fish eye lens.

28. The system of any of the examples above, wherein said at least one optical sensor comprises only one optical sensor such that only one imaging sensor is included in said module.

29. The system of any of the examples above, wherein said at least one optical sensor comprises a monochrome optical sensor comprising a monochrome imaging sensor.

30. The system of any of the examples above, wherein said at least one optical sensor comprises at least first and second optical sensors, wherein most of the portion of said body surface region that said first optical sensor images does not overlap most of the portion of said body surface region that said second optical sensor images.

31. The system of Example 30, further comprising electronics configured to stitch together images captured from first optical sensors with images captured from second optical sensors to form images of a wider field of view.

32. The system of Example 30, further comprising electronics configured to form a 4K image of a wider field of view by stitching together images captured by said first optical sensor and said second optical sensor when said images captured by said first optical sensor and images captured by said second optical sensor are not 4K images.

33. The system of any of the examples above, further comprising electronics configured to assemble multispectral images from image data from said at least one optical sensor.

34. The system of any of the examples above, further comprising electronics configured to assemble hyperspectral image data from said at least one optical sensor.

35. The system of any of the examples above, further comprising electronics configured to assemble hyperspectral images data from image data from said at least one optical sensor.

36. The system of any of the examples above, wherein said wearable medical article together with said at least one optical sensor and said plurality of light sources are configured to be disposable or single use.

37. The system of any of the examples above, wherein said plurality of light sources further comprises a third light source configured to emit light in a third wavelength range and said first, second and third wavelength ranges comprise red, green, and blue wavelengths, respectively.

38. The system of any of the examples above, wherein said plurality of light sources further comprises a third light source configured to emit light in a third wavelength range and said first, second and third wavelength ranges comprise cyan, magenta, and yellow wavelengths, respectively.

39. The system of any of the examples above, wherein said at least one optical sensor is positioned proximal to said body surface region of the wearer.

40. The system of any of the examples above, wherein said at least one optical sensor is positioned within 3 cm of said body surface region of the wearer.

41. The system of any of the examples above, wherein said at least one optical sensor further comprises a color optical sensor configured to capture color images of said of said body surface region.

42. The system of any of the examples above, configured to transmit to cloud based system that processed images or image data to detect properties of wound or wound healing.

43. The system of any of the examples above, further comprising a wireless network interface configured to transmit the image data.

44. The system of any of the examples above, further comprising a computing system comprising one or more computer processors and executable instructions, wherein the computing system is configured to:

- receive the image data from the plurality of optical sensors;
- receive contextual data associated with the wearer; and
- determine a current state of the body surface region based at least partly on the image data and the contextual data.

45. The system of examples 44, wherein to determine the current state of the body surface region, the computing system is configured to evaluate the image data and contextual data using a machine learning model to generate a score representing the current state of the body surface region.

46. The system of examples 44, wherein the image data comprises a plurality of overlapping sub-sections of the body surface region and wherein the computing system is configured to generate a combined image for analysis based on the plurality of overlapping sub-sections.

47. The method of any of the examples above, wherein module is embedded in a wearable medical article.

48. The method of any of the examples above, wherein module is embedded in a dressing, bandage, wrap or cast.

49. The method of any of the examples above, wherein the module is placed on a subject above a wound together with wearable medical article.

Part 3

1. A system comprising:

- a module configured to be embedded in a wearable medical article placed over a wound on a body surface of a wearer of the wearable medical article, wherein the module comprises:
  - at least one optical sensor configured to generate image data of a body surface region of the wearer of the wearable medical article; and
  - at least one light source configured to provide illumination to said body surface region,
- wherein said at least one sensor and said at least light source are configured to capture thermal images.

2. The system of Example 1, wherein said at least one optical sensor comprises a thermal imager or thermal camera configured to capture a thermal images.

3. The system of Example 1 or 2, wherein said at least one optical sensor is configured to output light in a wavelength range that comprises long wave infrared light such that said at least one optical sensor is configured to capture a thermal image.

4. The system of any of the examples above, wherein at least one light source is configured to output light comprising a wavelength in the range of 9-14 micrometers (μm).

5. The system of any of the examples above, wherein said at least one optical sensor is positioned proximal to said body surface region of the wearer.

6. The system of any of the examples above, wherein said at least one optical sensor is positioned within 3 cm of said body surface region of the wearer.

7. The system of any of the examples above, further comprising respective first and second optical filters for first and second optical sensors, said first and second optical filters configured to transmit different first and second wavelength ranges, respectively.

8. The system of any of the examples above, wherein said at least one optical sensor comprises at least three optical sensors configured to capture images of said body surface region at three different respective wavelength ranges.

9. The system of any of the examples above, wherein said at least one optical sensor comprises at least four optical sensors configured to capture images of said body surface region at four different respective wavelength ranges.

10. The system of any of the examples above, wherein said at least one optical sensor comprises at least six optical sensors configured to capture images of said body surface region at six different respective wavelength ranges.

11. The system of any of the examples above, wherein said at least one optical sensor comprises at least eight optical sensors configured to capture images of said body surface region at eight different respective wavelength ranges.

12. The system of any of the examples above, wherein said at least one optical sensor further comprises a color optical sensor configured to capture color images of said of said body surface region.

13. The system of any of the examples above, wherein said at least one optical sensor further comprises a red-green-blue (RGB) optical sensor configured to capture RGB images of said of said body surface region.

14. The system of any of the examples above, wherein said at least one optical sensor further comprising a cyan yellow and magenta optical sensor configured to capture cyan yellow and magenta images of said of said body surface region.

15. The system of any of the examples above, wherein said at least one light source comprises at least one light emitting diode (LED).

16. The system of any of the examples above, further comprising at least one diffuser configured to diffuse light from said at least one light source.

17. The system of any of the examples above, further comprising at least one polarizer configured to polarize light directed to at least one of said optical sensors.

18. The system of any of the examples above, wherein said at least one optical sensor is configured to capture images or image data at infrared wavelengths.

19. The system of any of the examples above, wherein said at least one optical sensor is configured to capture images or image data at near infrared (NIR) wavelength.

20. The system of any of the examples above, wherein said at least one optical sensor is configured to capture images or image data at an ultraviolet wavelength.

21. The system of any of the examples above, wherein said at least one optical sensor is configured to capture images or image data at a visible wavelength.

22. The system of any of the examples above, wherein at least one of said optical sensors comprises a wide angle lens.

23. The system of any of the examples above, wherein at least one of said optical sensors comprises a fish eye lens.

24. The system of any of the examples above, wherein said at least one sensor comprises at least a first and second groups of optical sensors, wherein most of the portion of said body surface region that said first group of optical sensors images does not overlap most of the portion of said body surface region that said second group of optical sensors images.

25. The system of Example 24, further comprising electronics configured to stitch together images captured by optical sensors in said first group of optical sensors with images captured by optical sensors in said second group to form images of a wider field of view.

26. The system of Example 24, further comprising electronics configured to form a 4K image of a wider field of view by stitching together images captured by at least one optical sensor from first the first group of optical sensors and at least one optical sensor from the second group of optical sensor when said images captured by said at least one sensor from said first group and said at least one sensor from said second group are not 4K images.

27. The system of any of the examples above, further comprising electronics configured to assemble multispectral images from image data from said at least one optical sensor.

28. The system of any of the examples above, further comprising electronics configured to form multispectral images from image data from said at least one optical sensor.

29. The system of any of the examples above, further comprising electronics configured to assemble hyperspectral image data from said at least one optical sensor.

30. The system of any of the examples above, further comprising electronics configured to assemble hyperspectral images data from image data from at least one optical sensor.

31. The system of any of the examples above, wherein said wearable medical article together with said plurality of optical sensors are configured to be disposable or single use.

32. The system of any of the examples above, wherein said module comprises a housing.

33. The system of any of the examples above, configured to transmit to cloud based system that processed images or image data to detect properties of wound or wound healing.

34. The system of any of the examples above, further comprising a wireless network interface configured to transmit the image data.

35. The system of any of the examples above, further comprising a computing system comprising one or more computer processors and executable instructions, wherein the computing system is configured to:

receive the image data from the plurality of optical sensors;

receive contextual data associated with the wearer; and determine a current state of the body surface region based at least partly on the image data and the contextual data.

36. The system of examples 35, wherein to determine the current state of the body surface region, the computing system is configured to evaluate the image data and contextual data using a machine learning model to generate a score representing the current state of the body surface region.

37. The system of examples 35, wherein the image data comprises a plurality of overlapping sub-sections of the body surface region and wherein the computing system is configured to generate a combined image for analysis based on the plurality of overlapping sub-sections.

38. The method of any of the examples above, wherein module is embedded in a wearable medical article.

39. The method of any of the examples above, wherein module is embedded in a dressing, bandage, wrap or cast.

40. The method of any of the examples above, wherein the module is placed on a subject above a wound together with wearable medical article.

Part 4

1. A system comprising:
- a module configured to be embedded in a wearable medical article placed over a wound on a body surface of a wearer of the wearable medical article, wherein the module comprises:
  - at least one optical sensor configured to generate image data of a body surface region of the wearer of the wearable medical article; and
  - at least one light source configured to provide illumination to said body surface region,
- wherein said plurality of optical sensors comprises at least first and second optical sensors, and wherein most of the portion of said body surface region that said first optical sensor images does not overlap most of the portion of said body surface region that said second optical sensor images.

2. The system of Example 1, further comprising electronics configured to stitch together images captured from said first optical sensors with images captured from said second optical sensors to form images of a wider field of view.

3. The system of Example 1, further comprising electronics configured to form a 4K image of a wider field of view by stitching together images captured by said first optical sensor and said second optical sensor when said images captured by said first optical sensor and images captured by said second optical sensor are not 4K images.

4. The system of any of the examples above, wherein said at least one optical sensor is positioned proximal to said body surface region of the wearer.

5. The system of any of the examples above, wherein said at least one optical sensor is positioned within 3 cm of said body surface region of the wearer.

6. The system of any of the examples above, further comprising respective first and second optical filters for first and second optical sensors, said first and second optical filters configured to transmit different first and second wavelength ranges, respectively.

7. The system of any of the examples above, wherein said at least one optical sensor comprises at least three optical sensors configured to capture images of said body surface region at three different respective wavelength ranges.

8. The system of any of the examples above, wherein said at least one optical sensor comprises at least four optical sensors configured to capture images of said body surface region at four different respective wavelength ranges.

9. The system of any of the examples above, wherein said at least one optical sensor comprises at least six optical sensors configured to capture images of said body surface region at six different respective wavelength ranges.

10. The system of any of the examples above, wherein said at least one optical sensor comprises at least eight optical sensors configured to capture images of said body surface region at eight different respective wavelength ranges.

11. The system of any of the examples above, wherein said at least one optical sensor further comprises a color optical sensor configured to capture color images of said of said body surface region.

12. The system of any of the examples above, wherein said at least one optical sensor further comprises a red-green-blue (RGB) optical sensor configured to capture RGB images of said of said body surface region.

13. The system of any of the examples above, wherein said at least one optical sensor further comprising a cyan yellow and magenta optical sensor configured to capture cyan yellow and magenta images of said of said body surface region.

14. The system of any of the examples above, wherein said at least one light source comprises at least one light emitting diode (LED).

15. The system of any of the examples above, further comprising at least one diffuser configured to diffuse light from said at least one light source.

16. The system of any of the examples above, further comprising at least one polarizer configured to polarize light directed to at least one of said optical sensors.

17. The system of any of the examples above, wherein said at least one optical sensor is configured to capture images or image data at infrared wavelengths.

18. The system of any of the examples above, wherein said at least one optical sensor is configured to capture images or image data at near infrared (NIR) wavelength.

19. The system of any of the examples above, wherein at least one of said optical sensors comprises a thermal imager or thermal camera configured to capture thermal images.

20. The system of any of the examples above, wherein said at least one optical sensor is configured to capture images or image data at a wavelength in the range of 9-14 micrometers (μm).

21. The system of any of the examples above, wherein said at least one optical sensor is configured to capture images or image data at an ultraviolet wavelength.

22. The system of any of the examples above, wherein said at least one optical sensor is configured to capture images or image data at a visible wavelength.

23. The system of any of the examples above, wherein at least one of said optical sensors comprises a wide angle lens.

24. The system of any of the examples above, wherein at least one of said optical sensors comprises a fish eye lens.

25. The system of any of the examples above, further comprising electronics configured to assemble multispectral images from image data from said at least one optical sensor.

26. The system of any of the examples above, further comprising electronics configured to form multispectral images from image data from said at least one optical sensor.

27. The system of any of the examples above, further comprising electronics configured to assemble hyperspectral image data from said at least one optical sensor.

28. The system of any of the examples above, further comprising electronics configured to assemble hyperspectral images data from image data from at least one optical sensor.

29. The system of any of the examples above, wherein said wearable medical article together with said plurality of optical sensors are configured to be disposable or single use.

30. The system of any of the examples above, wherein said module comprises a housing.

31. The system of any of the examples above, configured to transmit to cloud based system that processed images or image data to detect properties of wound or wound healing.

32. The system of any of the examples above, further comprising a wireless network interface configured to transmit the image data.

33. The system of any of the examples above, further comprising a computing system comprising one or more computer processors and executable instructions, wherein the computing system is configured to:
- receive the image data from the plurality of optical sensors;
- receive contextual data associated with the wearer; and determine a current state of the body surface region based at least partly on the image data and the contextual data.

34. The system of examples 33, wherein to determine the current state of the body surface region, the computing system is configured to evaluate the image data and contextual data using a machine learning model to generate a score representing the current state of the body surface region.

35. The system of examples 33, wherein the image data comprises a plurality of overlapping sub-sections of the body surface region and wherein the computing system is configured to generate a combined image for analysis based on the plurality of overlapping sub-sections.

36. The method of any of the examples above, wherein module is embedded in a wearable medical article.

37. The method of any of the examples above, wherein module is embedded in a dressing, bandage, wrap or cast.

38. The method of any of the examples above, wherein the module is placed on a subject above a wound together with wearable medical article.

Part 5

1. A system comprising:

a module configured to be embedded in a wearable medical article placed over a wound on a body surface of a wearer of the wearable medical article, wherein the module comprises:

at least one optical sensor configured to generate image data of a body surface region of the wearer of the wearable medical article;

at least one light source configured to provide illumination to said body surface region; and at least one diffuser configured to diffuse light from said at least one light source.

2. The system of any of the examples above, wherein said at least one optical sensor is positioned proximal to said body surface region of the wearer.

3. The system of any of the examples above, wherein said at least one optical sensor is positioned within 3 cm of said body surface region of the wearer.

4. The system of any of the examples above, further comprising respective first and second optical filters for first and second optical sensors, said first and second optical filters configured to transmit different first and second wavelength ranges, respectively.

5. The system of any of the examples above, wherein said at least one optical sensor comprises at least three optical sensors configured to capture images of said body surface region at three different respective wavelength ranges.

6. The system of any of the examples above, wherein said at least one optical sensor comprises at least four optical sensors configured to capture images of said body surface region at four different respective wavelength ranges.

7. The system of any of the examples above, wherein said at least one optical sensor comprises at least six optical sensors configured to capture images of said body surface region at six different respective wavelength ranges.

8. The system of any of the examples above, wherein said at least one optical sensor comprises at least eight optical sensors configured to capture images of said body surface region at eight different respective wavelength ranges.

9. The system of any of the examples above, wherein said at least one optical sensor further comprises a color optical sensor configured to capture color images of said of said body surface region.

10. The system of any of the examples above, wherein said at least one optical sensor further comprises a red-green-blue (RGB) optical sensor configured to capture RGB images of said of said body surface region.

11. The system of any of the examples above, wherein said at least one optical sensor further comprising a cyan yellow and magenta optical sensor configured to capture cyan yellow and magenta images of said of said body surface region.

12. The system of any of the examples above, wherein said at least one light source comprises at least one light emitting diode (LED).

13. The system of any of the examples above, further comprising at least one polarizer configured to polarize light directed to at least one of said optical sensors.

14. The system of any of the examples above, wherein said at least one optical sensor is configured to capture images or image data at infrared wavelengths.

15. The system of any of the examples above, wherein said at least one optical sensor is configured to capture images or image data at near infrared (NIR) wavelength.

16. The system of any of the examples above, wherein at least one of said optical sensors comprises a thermal imager or thermal camera configured to capture thermal images.

17. The system of any of the examples above, wherein said at least one optical sensor is configured to capture images or image data at a wavelength in the range of 9-14 micrometers (μm).

18. The system of any of the examples above, wherein said at least one optical sensor is configured to capture images or image data at an ultraviolet wavelength.

19. The system of any of the examples above, wherein said at least one optical sensor is configured to capture images or image data at a visible wavelength.

20. The system of any of the examples above, wherein at least one of said optical sensors comprises a wide angle lens.

21. The system of any of the examples above, wherein at least one of said optical sensors comprises a fish eye lens.

22. The system of any of the examples above, wherein said at least one sensor comprises at least a first and second groups of optical sensors, wherein most of the portion of said body surface region that said first group of optical sensors images does not overlap most of the portion of said body surface region that said second group of optical sensors images.

23. The system of Example 22, further comprising electronics configured to stitch together images captured by optical sensors in said first group of optical sensors with images captured by optical sensors in said second group to form images of a wider field of view.

24. The system of Example 22, further comprising electronics configured to form a 4K image of a wider field of view by stitching together images captured by at least one optical sensor from first the first group of optical sensors and at least one optical sensor from the second group of optical sensor when said images captured by said at least one sensor from said first group and said at least one sensor from said second group are not 4K images.

25. The system of any of the examples above, further comprising electronics configured to assemble multispectral images from image data from said at least one optical sensor.

26. The system of any of the examples above, further comprising electronics configured to form multispectral images from image data from said at least one optical sensor.

27. The system of any of the examples above, further comprising electronics configured to assemble hyperspectral image data from said at least one optical sensor.

28. The system of any of the examples above, further comprising electronics configured to assemble hyperspectral images data from image data from at least one optical sensor.

29. The system of any of the examples above, wherein said wearable medical article together with said plurality of optical sensors are configured to be disposable or single use.

30. The system of any of the examples above, wherein said module comprises a housing.

31. The system of any of the examples above, configured to transmit to cloud based system that processed images or image data to detect properties of wound or wound healing.

32. The system of any of the examples above, further comprising a wireless network interface configured to transmit the image data.

33. The system of any of the examples above, further comprising a computing system comprising one or more computer processors and executable instructions, wherein the computing system is configured to:

receive the image data from the plurality of optical sensors;

receive contextual data associated with the wearer; and determine a current state of the body surface region based at least partly on the image data and the contextual data.

34. The system of Example 33, wherein to determine the current state of the body surface region, the computing system is configured to evaluate the image data and contextual data using a machine learning model to generate a score representing the current state of the body surface region.

35. The system of Example 33, wherein the image data comprises a plurality of overlapping sub-sections of the body surface region and wherein the computing system is configured to generate a combined image for analysis based on the plurality of overlapping sub-sections.

36. The method of any of the examples above, wherein module is embedded in a wearable medical article.

37. The method of any of the examples above, wherein module is embedded in a dressing, bandage, wrap or cast.

38. The method of any of the examples above, wherein the module is placed on a subject above a wound together with wearable medical article.

Part 6

1. A system comprising:

a module configured to be embedded in a wearable medical article placed over a wound on a body surface of a wearer of the wearable medical article, wherein the module comprises:

at least one optical sensor configured to generate image data of a body surface region of the wearer of the wearable medical article;

at least one light source configured to provide illumination to said body surface region; and at least one polarizer configured to polarize light directed to said at least one optical sensor.

2. The system of any of the examples above, wherein said polarizer is configure to reduce glare.

3. The system of any of the examples above, wherein said polarizer comprises a linear polarizer.

4. The system of any Example 3, wherein said polarizer is oriented to transmit more p-polarized light than s-polarized light.

5. The system of any of the examples above, further comprising a polarizer configured to polarize light from said light source that is directed toward said body surface region.

6. The system of any of Example 5, wherein said polarizer configured to polarize light directed to said at least one optical sensor and said polarizer configured to polarize light from said light source have the same polarization orientation.

7. The system of any Example 5 or 6, wherein said polarizer configured to polarize light from said light source is oriented to transmit more p-polarized light than s-polarized light.

8. The system of any of the examples above, wherein said polarizer comprises a circular polarizer.

9. The system of any of the examples above, further comprising a circular polarizer configured to polarize light from said light source that is directed toward said body surface region.

10. The system of any of Example 9, wherein said polarizer configured to polarize light directed to said at least one optical sensor and said polarizer configured to polarize light from said light source have the same circular polarization handedness.

11. The system of any of Example 9, wherein said polarizer configured to polarize light directed to said at least one optical sensor and said polarizer configured to polarize light from said light source are right hand circular polarizers that transmit more right hand circular polarized light than left hand circular polarized light.

12. The system of any of Example 9, wherein said polarizer configured to polarize light directed to said at least one optical sensor and said polarizer configured to polarize light from said light source are left hand circular polarizers that transmit more left hand circular polarized light than right hand circular polarized light.

13. The system of any of the examples above, wherein said at least one optical sensor is positioned proximal to said body surface region of the wearer.

14. The system of any of the examples above, wherein said at least one optical sensor is positioned within 3 cm of said body surface region of the wearer.

15. The system of any of the examples above, further comprising respective first and second optical filters for first and second optical sensors, said first and second optical filters configured to transmit different first and second wavelength ranges, respectively.

16. The system of any of the examples above, wherein said at least one optical sensor comprises at least three optical sensors configured to capture images of said body surface region at three different respective wavelength ranges.

17. The system of any of the examples above, wherein said at least one optical sensor comprises at least four optical sensors configured to capture images of said body surface region at four different respective wavelength ranges.

18. The system of any of the examples above, wherein said at least one optical sensor comprises at least six optical sensors configured to capture images of said body surface region at six different respective wavelength ranges.

19. The system of any of the examples above, wherein said at least one optical sensor comprises at least eight optical sensors configured to capture images of said body surface region at eight different respective wavelength ranges.

20. The system of any of the examples above, wherein said at least one optical sensor further comprises a color optical sensor configured to capture color images of said of said body surface region.

21. The system of any of the examples above, wherein said at least one optical sensor further comprises a red-green-blue (RGB) optical sensor configured to capture RGB images of said of said body surface region.

22. The system of any of the examples above, wherein said at least one optical sensor further comprising a cyan yellow and magenta optical sensor configured to capture cyan yellow and magenta images of said of said body surface region.

23. The system of any of the examples above, wherein said at least one light source comprises at least one light emitting diode (LED).

24. The system of any of the examples above, further comprising at least one diffuser configured to diffuse light from said at least one light source.

25. The system of any of the examples above, wherein said at least one optical sensor is configured to capture images or image data at infrared wavelengths.

26. The system of any of the examples above, wherein said at least one optical sensor is configured to capture images or image data at near infrared (NIR) wavelength.

27. The system of any of the examples above, wherein at least one of said optical sensors comprises a thermal imager or thermal camera configured to capture thermal images.

28. The system of any of the examples above, wherein said at least one optical sensor is configured to capture images or image data at a wavelength in the range of 9-14 micrometers (μm).

29. The system of any of the examples above, wherein said at least one optical sensor is configured to capture images or image data at an ultraviolet wavelength.

30. The system of any of the examples above, wherein said at least one optical sensor is configured to capture images or image data at a visible wavelength.

31. The system of any of the examples above, wherein at least one of said optical sensors comprises a wide angle lens.

32. The system of any of the examples above, wherein at least one of said optical sensors comprises a fish eye lens.

33. The system of any of the examples above, wherein said at least one sensor comprises at least a first and second groups of optical sensors, wherein most of the portion of said body surface region that said first group of optical sensors images does not overlap most of the portion of said body surface region that said second group of optical sensors images.

34. The system of Example 25, further comprising electronics configured to stitch together images captured by optical sensors in said first group of optical sensors with images captured by optical sensors in said second group to form images of a wider field of view.

35. The system of Example 25, further comprising electronics configured to form a 4K image of a wider field of view by stitching together images captured by at least one optical sensor from first the first group of optical sensors and at least one optical sensor from the second group of optical sensor when said images captured by said at least one sensor from said first group and said at least one sensor from said second group are not 4K images.

36. The system of any of the examples above, further comprising electronics configured to assemble multispectral images from image data from said at least one optical sensor.

37. The system of any of the examples above, further comprising electronics configured to form multispectral images from image data from said at least one optical sensor.

38. The system of any of the examples above, further comprising electronics configured to assemble hyperspectral image data from said at least one optical sensor.

39. The system of any of the examples above, further comprising electronics configured to assemble hyperspectral images data from image data from at least one optical sensor.

40. The system of any of the examples above, wherein said wearable medical article together with said plurality of optical sensors are configured to be disposable or single use.

41. The system of any of the examples above, wherein said module comprises a housing.

42. The system of any of the examples above, configured to transmit to cloud based system that processed images or image data to detect properties of wound or wound healing.

43. The system of any of the examples above, further comprising a wireless network interface configured to transmit the image data.

44. The system of any of the examples above, further comprising a computing system comprising one or more computer processors and executable instructions, wherein the computing system is configured to:

receive the image data from the plurality of optical sensors;

receive contextual data associated with the wearer; and determine a current state of the body surface region based at least partly on the image data and the contextual data.

45. The system of Example 44, wherein to determine the current state of the body surface region, the computing system is configured to evaluate the image data and contextual data using a machine learning model to generate a score representing the current state of the body surface region.

46. The system of Example 44, wherein the image data comprises a plurality of overlapping sub-sections of the body surface region and wherein the computing system is configured to generate a combined image for analysis based on the plurality of overlapping sub-sections.

47. The method of any of the examples above, wherein module is embedded in a wearable medical article.

48. The method of any of the examples above, wherein module is embedded in a dressing, bandage, wrap or cast.

49. The method of any of the examples above, wherein the module is placed on a subject above a wound together with wearable medical article.

Part 7

1. A system comprising:

a module configured to be embedded in a wearable medical article placed over a wound on a body surface of a wearer of the wearable medical article, wherein the module comprises:

at least one optical sensor configured to generate image data of a body surface region of the wearer of the wearable medical article; and at least one light source configured to provide illumination to said body surface region, wherein said at least one optical sensor and said at least one light source are configured to obtain a first image in a first wavelength ranges and a second image in a second wavelength range.

2. The system of any of the examples above, wherein said at least one optical sensor is positioned proximal to said body surface region of the wearer.

3. The system of any of the examples above, wherein said at least one optical sensor is positioned within 3 cm of said body surface region of the wearer.

4. The system of any of the examples above, further comprising respective first and second optical filters for first and second optical sensors, said first and second optical filters configured to transmit different first and second wavelength ranges, respectively.

5. The system of any of the examples above, wherein said at least one optical sensor comprises at least three optical sensors configured to capture images of said body surface region at three different respective wavelength ranges.

6. The system of any of the examples above, wherein said at least one optical sensor comprises at least four optical sensors configured to capture images of said body surface region at four different respective wavelength ranges.

7. The system of any of the examples above, wherein said at least one optical sensor comprises at least six optical sensors configured to capture images of said body surface region at six different respective wavelength ranges.

8. The system of any of the examples above, wherein said at least one optical sensor comprises at least eight optical sensors configured to capture images of said body surface region at eight different respective wavelength ranges.

9. The system of any of the examples above, wherein said at least one optical sensor further comprises a color optical sensor configured to capture color images of said of said body surface region.

10. The system of any of the examples above, wherein said at least one optical sensor further comprises a red-green-blue (RGB) optical sensor configured to capture RGB images of said of said body surface region.

11. The system of any of the examples above, wherein said at least one optical sensor further comprising a cyan yellow and magenta optical sensor configured to capture cyan yellow and magenta images of said of said body surface region.

12. The system of any of the examples above, wherein said at least one light source comprises at least one light emitting diode (LED).

13. The system of any of the examples above, further comprising at least one diffuser configured to diffuse light from said at least one light source.

14. The system of any of the examples above, further comprising at least one polarizer configured to polarize light directed to at least one of said optical sensors.

15. The system of any of the examples above, wherein said at least one optical sensor is configured to capture images or image data at infrared wavelengths.

16. The system of any of the examples above, wherein said at least one optical sensor is configured to capture images or image data at near infrared (NIR) wavelength.

17. The system of any of the examples above, wherein at least one of said optical sensors comprises a thermal imager or thermal camera configured to capture thermal images.

18. The system of any of the examples above, wherein said at least one optical sensor is configured to capture images or image data at a wavelength in the range of 9-14 micrometers (μm).

19. The system of any of the examples above, wherein said at least one optical sensor is configured to capture images or image data at an ultraviolet wavelength.

20. The system of any of the examples above, wherein said at least one optical sensor is configured to capture images or image data at a visible wavelength.

21. The system of any of the examples above, wherein at least one of said optical sensors comprises a wide angle lens.

22. The system of any of the examples above, wherein at least one of said optical sensors comprises a fish eye lens.

23. The system of any of the examples above, wherein said at least one sensor comprises at least a first and second groups of optical sensors, wherein most of the portion of said body surface region that said first group of optical sensors images does not overlap most of the portion of said body surface region that said second group of optical sensors images.

24. The system of Example 23, further comprising electronics configured to stitch together images captured by optical sensors in said first group of optical sensors with images captured by optical sensors in said second group to form images of a wider field of view.

25. The system of Example 23, further comprising electronics configured to form a 4K image of a wider field of view by stitching together images captured by at least one optical sensor from first the first group of optical sensors and at least one optical sensor from the second group of optical sensor when said images captured by said at least one sensor from said first group and said at least one sensor from said second group are not 4K images.

26. The system of any of the examples above, further comprising electronics configured to assemble multispectral images from image data from said at least one optical sensor.

27. The system of any of the examples above, further comprising electronics configured to form multispectral images from image data from said at least one optical sensor.

28. The system of any of the examples above, further comprising electronics configured to assemble hyperspectral image data from said at least one optical sensor.

29. The system of any of the examples above, further comprising electronics configured to assemble hyperspectral images data from image data from at least one optical sensor.

30. The system of any of the examples above, wherein said wearable medical article together with said plurality of optical sensors are configured to be disposable or single use.

31. The system of any of the examples above, wherein said module comprises a housing.

32. The system of any of the examples above, configured to transmit to cloud based system that processed images or image data to detect properties of wound or wound healing.

33. The system of any of the examples above, further comprising a wireless network interface configured to transmit the image data.

34. The system of any of the examples above, further comprising a computing system comprising one or more computer processors and executable instructions, wherein the computing system is configured to:

- receive the image data from the plurality of optical sensors;
- receive contextual data associated with the wearer; and
- determine a current state of the body surface region based at least partly on the image data and the contextual data.

35. The system of Example 34, wherein to determine the current state of the body surface region, the computing system is configured to evaluate the image data and contextual data using a machine learning model to generate a score representing the current state of the body surface region.

36. The system of Example 34 wherein the image data comprises a plurality of overlapping sub-sections of the body surface region and wherein the computing system is configured to generate a combined image for analysis based on the plurality of overlapping sub-sections.

37. The method of any of the examples above, wherein module is embedded in a wearable medical article.

38. The method of any of the examples above, wherein module is embedded in a dressing, bandage, wrap or cast.

39. The method of any of the examples above, wherein the module is placed on a subject above a wound together with wearable medical article.

Part 8

1. A system comprising:

a module configured to be embedded in a wearable medical article placed over a wound on a body surface of a wearer of the wearable medical article, wherein the module comprises:

at least one optical sensor configured to generate image data of a body surface region of the wearer of the wearable medical article; and at least one light source configured to provide illumination to said body surface region, wherein said at least one optical sensor and said at least one light source are configured to capture multispectral or hyperspectral image data.

2. The wound care monitoring system of any of the examples above, wherein said at least one optical sensor and said at least one light source are configured to capture multispectral image data.

3. The wound care monitoring system of any of the examples above, wherein said at least one optical sensor and said at least one light source are configured to capture hyperspectral image data.

4. The wound care monitoring system of any of the examples above, wherein said at least one optical sensor and said at least one light source are configured to perform multispectral imaging.

5. The wound care monitoring system of any of the examples above, wherein said at least one optical sensor and said at least one light source to are configured to perform hyperspectral imaging.

6. The wound care monitoring system of any of the examples above, further comprising electronics configured to assemble at least some of said multispectral image data to form a multispectral image.

7. The wound care monitoring system of any of the examples above, further comprising electronics configured to assemble at least some of said hyperspectral image data to form a hyperspectral image.

8. The wound care monitoring system of any of the examples above, wherein said at least one optical sensor is positioned proximal to said body surface region of the wearer.

9. The wound care monitoring system of any of the examples above, wherein said at least one optical sensor is positioned within 3 cm of said body surface region of the wearer.

10. The system of any of the examples above, further comprising respective first and second optical filters for first and second optical sensors, said first and second optical filters configured to transmit different first and second wavelength ranges, respectively.

11. The system of any of the examples above, wherein said at least one optical sensor comprises at least three optical sensors configured to capture images of said body surface region at three different respective wavelength ranges.

12. The system of any of the examples above, wherein said at least one optical sensor comprises at least four optical sensors configured to capture images of said body surface region at four different respective wavelength ranges.

13. The system of any of the examples above, wherein said at least one optical sensor comprises at least six optical sensors configured to capture images of said body surface region at six different respective wavelength ranges.

14. The system of any of the examples above, wherein said at least one optical sensor comprises at least eight optical sensors configured to capture images of said body surface region at eight different respective wavelength ranges.

15. The system of any of the examples above, wherein said at least one optical sensor further comprises a color optical sensor configured to capture color images of said of said body surface region.

16. The system of any of the examples above, wherein said at least one optical sensor further comprises a red-green-blue (RGB) optical sensor configured to capture RGB images of said of said body surface region.

17. The system of any of the examples above, wherein said at least one optical sensor further comprising a cyan yellow and magenta optical sensor configured to capture cyan yellow and magenta images of said of said body surface region.

18. The system of any of the examples above, wherein said at least one light source comprises at least one light emitting diode (LED).

19. The system of any of the examples above, further comprising at least one diffuser configured to diffuse light from said at least one light source.

20. The system of any of the examples above, further comprising at least one polarizer configured to polarize light directed to at least one of said optical sensors.

21. The system of any of the examples above, wherein said at least one optical sensor is configured to capture images or image data at infrared wavelengths.

22. The system of any of the examples above, wherein said at least one optical sensor is configured to capture images or image data at near infrared (NIR) wavelength.

23. The system of any of the examples above, wherein at least one of said optical sensors comprises a thermal imager or thermal camera configured to capture thermal images.

24. The system of any of the examples above, wherein said at least one optical sensor is configured to capture images or image data at a wavelength in the range of 9-14 micrometers (μm).

25. The system of any of the examples above, wherein said at least one optical sensor is configured to capture images or image data at an ultraviolet wavelength.

26. The system of any of the examples above, wherein said at least one optical sensor is configured to capture images or image data at a visible wavelength.

27. The system of any of the examples above, wherein at least one of said optical sensors comprises a wide angle lens.

28. The system of any of the examples above, wherein at least one of said optical sensors comprises a fish eye lens.

29. The system of any of the examples above, wherein said at least one sensor comprises at least a first and second groups of optical sensors, wherein most of the portion of said body surface region that said first group of optical sensors images does not overlap most of the portion of said body surface region that said second group of optical sensors images.

30. The system of Example 29, further comprising electronics configured to stitch together images captured by optical sensors in said first group of optical sensors with images captured by optical sensors in said second group to form images of a wider field of view.

31. The system of Example 29, further comprising electronics configured to form a 4K image of a wider field of view by stitching together images captured by at least one optical sensor from first the first group of optical sensors and at least one optical sensor from the second group of optical sensor when said images captured by said at least one sensor from said first group and said at least one sensor from said second group are not 4K images.

32. The system of any of the examples above, further comprising electronics configured to assemble multispectral images from image data from said at least one optical sensor.

33. The system of any of the examples above, further comprising electronics configured to form multispectral images from image data from said at least one optical sensor.

34. The system of any of the examples above, further comprising electronics configured to assemble hyperspectral image data from said at least one optical sensor.

35. The system of any of the examples above, further comprising electronics configured to assemble hyperspectral images data from image data from at least one optical sensor.

36. The system of any of the examples above, wherein said wearable medical article together with said plurality of optical sensors are configured to be disposable or single use.

37. The system of any of the examples above, wherein said module comprises a housing.

38. The system of any of the examples above, configured to transmit to cloud based system that processed images or image data to detect properties of wound or wound healing.

39. The system of any of the examples above, further comprising a wireless network interface configured to transmit the image data.

40. The system of any of the examples above, further comprising a computing system comprising one or more computer processors and executable instructions, wherein the computing system is configured to:

receive the image data from the plurality of optical sensors;

receive contextual data associated with the wearer; and determine a current state of the body surface region based at least partly on the image data and the contextual data.

41. The system of Example 40, wherein to determine the current state of the body surface region, the computing system is configured to evaluate the image data and contextual data using a machine learning model to generate a score representing the current state of the body surface region.

42. The system of Example 40 wherein the image data comprises a plurality of overlapping sub-sections of the body surface region and wherein the computing system is configured to generate a combined image for analysis based on the plurality of overlapping sub-sections.

43. The method of any of the examples above, wherein module is embedded in a wearable medical article.

44. The method of any of the example above, wherein module is embedded in a dressing, bandage, wrap or cast.

45. The method of any of the examples above, wherein the module is placed on a subject above a wound together with wearable medical article.

Part 9

1. A system comprising:

a module configured to be embedded in a wearable medical article placed over a wound on a body surface of a wearer of the wearable medical article, wherein the module comprises:

at least one optical sensor configured to generate image data of a body surface region of the wearer of the wearable medical article; and a housing configured to bend about a curved or bending body surface, said housing having a plurality of compartments including at least one compartment for said at least one optical sensor, wherein said plurality of compartments comprises at least a first compartment and a second compartment, said first and second compartments spaced apart from each other by a gap in the housing to allow said first and second compartments to tilt with respect to each other providing flexure of the housing.

2. The system of any of the examples above, wherein the plurality of compartments further comprises a third compartment, said second and third compartments being spaced apart from each other by a gap in the housing to allow said second and third compartments to tilt with respect to each other providing flexure of the housing.

3. The system of any of the examples above, wherein the plurality of compartments further comprises a four compartment, said third and fourth compartments being spaced apart from each other by a gap in the housing to allow said third and fourth compartments to tilt with respect to each other providing flexure of the housing.

4. The system of any of the examples above, wherein the housing is elongate, having a length in one direction that is longer than a width and thickness in orthogonal directions.

5. The system of any of Example 4, wherein said plurality of compartments are arranged along the length of said housing such that at least one compartment is between two others.

6. The system of any of the examples above, wherein said at least one optical sensor comprises first and second optical sensors and said at least one compartment for said at least one optical sensor comprises first and second compartments for said first and second optical sensors, respectively.

7. The system of any of the examples above, wherein said housing includes at least one compartment for electronics.

8. The system of Example 7, further comprising said electronics in said compartment for said electronics.

9. The system of Example 7 or 8, wherein said electronics comprises a microcontroller.

10. The system of any of the examples above, wherein one of said plurality of compartments is for a battery.

11. The system of Example 10, further comprising said battery in said compartment for said battery.

12. The system of any of the examples above, wherein said housing includes a top side and a bottom side, said bottom side configured to be closer to the body surface region than said top side.

13. The system of Example 12, wherein said housing includes one or more openings on the bottom side thereof that provides access to said compartments.

14. The system of Example 12, wherein said housing includes an opening in said compartment for said at least one optical sensor on said bottom side of said housing for transmission of light from said body surface region.

15. The system of any of Examples 12-14, wherein said gap in said housing is in the upper side of said housing.

16. The system of any of the Examples 12-15, wherein said gap extends toward the lower side of said housing a depth of at least a quarter of the depth of the compartment.

17. The system of any of the Examples 12-15, wherein said gap extends toward the lower side of said housing a depth of at least a third of the depth of the compartment.

18. The system of any of the Examples 12-15, wherein said gap extends toward the lower side of said housing a depth of at least half the depth of the compartment.

19. The system of any of the Examples 12-18, wherein said housing is rounded and/or beveled along at least some edges closer to said upper side of said housing.

20. The system of any of the Examples 12-18, wherein said housing is rounded and/or beveled along at least some edges along said gap.

21. The system of any of the examples above, wherein different ones of said compartments have different sizes.

22. The system of any of the examples above, the first compartment is configured for a battery and the second compartment is configured for an optical sensor.

23. The system of Example 25, further comprising a third compartment an optical sensor.

24. The system of Example 26, further comprising a fourth compartment configured for electronics.

25. The system of Example 26, further comprising a fourth compartment configured for a microcontroller.

26. The system of any of the examples above, further comprising a battery in said first compartment and an optical sensor in said second compartment.

27. The system of Example 25, further comprising an optical sensor in said a third compartment.

28. The system of Example 26, further comprising electronics in said fourth compartment.

29. The system of Example 26, further comprising a microcontroller in a fourth compartment.

30. The system of any of the examples above, further comprising at least one light source configured to provide illumination to said body surface region.

31. The system of any of the examples above, further comprising said wearable medical article configured to be placed over a wound on a body surface of a patient.

32. The system of Example 34, wherein said module is embedded in said wearable medical article.

33. The system of any of the examples above, wherein the housing includes at least three compartments are arranged along the length of said housing with two gaps between the three compartments.

34. The system of any of the examples above, wherein the housing includes at least four compartments are arranged along the length of said housing.

35. The system of any of the examples above, wherein the housing includes at least four compartments are arranged along the length of said housing with three gaps between the four compartments.

36. The system of any of the examples above, configured to transmit to cloud based system that processed images or image data to detect properties of wound or wound healing.

37. The system of any of the examples above, further comprising a wireless network interface configured to transmit the image data.

38. The system of any of the examples above, further comprising a computing system comprising one or more computer processors and executable instructions, wherein the computing system is configured to:

receive the image data from the plurality of optical sensors;

receive contextual data associated with the wearer; and determine a current state of the body surface region based at least partly on the image data and the contextual data.

39. The system of example 38, wherein to determine the current state of the body surface region, the computing system is configured to evaluate the image data and contextual data using a machine learning model to generate a score representing the current state of the body surface region.

40. The system of example 38, wherein the image data comprises a plurality of overlapping sub-sections of the body surface region and wherein the computing system is configured to generate a combined image for analysis based on the plurality of overlapping sub-sections.

41. The method of any of the examples above, wherein module is embedded in a wearable medical article.

42. The method of any of the examples above, wherein module is embedded in a dressing, bandage, wrap or cast.

43. The method of any of the examples above, wherein the module is placed on a subject above a wound together with wearable medical article.

Part 10

1. A system comprising:

a module configured to be embedded in a wearable medical article placed over a wound on a body surface of a wearer of the wearable medical article, wherein the module comprises:

at least one optical sensor configured to generate image data of a body surface region of the wearer of the wearable medical article;

at least one light source configured to provide illumination to said body surface region; and at least one interior surface having a diffusely reflecting surface.

2. The system of any of the examples above, wherein said diffusely reflecting surface has a surface finish to provide such diffuse reflection.

3. The system of any of the examples above, wherein said diffusely reflecting surface a material having particle embedded therein 4. The system of any of the examples above, wherein said particles comprise titanium dioxide.

5. The system of any of the examples above, wherein said material comprises silicone.

6. The system of any of the examples above, wherein said diffusely reflecting surface comprises Teflon.

7. The system of any of the examples above, wherein said diffusely reflecting surface comprises Spectralon.

8. The system of any of the examples above, wherein said diffusely reflecting surface comprises spectralon.

9. The system of any of the examples above, wherein said diffusely reflecting surface comprises barium sulfate.

10. The system of any of the examples above, wherein said white pigmented silicone.

11. The system of any of the examples above, configured to transmit to cloud based system that processed images or image data to detect properties of wound or wound healing.

12. The system of any of the examples above, further comprising a wireless network interface configured to transmit the image data.

13. The system of any of the examples above, further comprising a computing system comprising one or more computer processors and executable instructions, wherein the computing system is configured to:

receive the image data from the plurality of optical sensors;

receive contextual data associated with the wearer; and determine a current state of the body surface region based at least partly on the image data and the contextual data.

14. The system of example 13, wherein to determine the current state of the body surface region, the computing system is configured to evaluate the image data and contextual data using a machine learning model to generate a score representing the current state of the body surface region.

15. The system of example 13, wherein the image data comprises a plurality of overlapping sub-sections of the body surface region and wherein the computing system is configured to generate a combined image for analysis based on the plurality of overlapping sub-sections.

16. The method of any of the examples above, wherein module is embedded in a wearable medical article.

17. The method of any of the examples above, wherein module is embedded in a dressing, bandage, wrap or cast.

18. The method of any of the examples above, wherein the module is placed on a subject above a wound together with wearable medical article.

Part 11

1. A system comprising:

a wearable medical article configured to be placed over a wound on a body surface of a patient; and a module configured to be embedded within the wearable medical article, wherein the module comprises:

a plurality of optical sensors configured to generate image data of a body surface region of a wearer of the wearable medical article; and a wireless network interface configured to transmit the image data.

2. The system of any of the examples above, further comprising a computing system comprising one or more computer processors and executable instructions, wherein the computing system is configured to:

receive the image data from the plurality of optical sensors;

receive contextual data associated with the wearer; and determine a current state of the body surface region based at least partly on the image data and the contextual data.

3. The system of example 2 wherein to determine the current state of the body surface region, the computing system is configured to evaluate the image data and contextual data using a machine learning model to generate a score representing the current state of the body surface region.

4. The system of example 2 wherein the image data comprises a plurality of overlapping sub-sections of the body surface region and wherein the computing system is configured to generate a combined image for analysis based on the plurality of overlapping sub-sections.

5. The system of example 1 wherein the module is configured to operate each of the plurality of optical sensors sequentially.

6. The system of example 5, wherein an interval between operation of each of the plurality of optical sensors comprises at least 3 seconds.

7. The system of example 1 wherein the plurality of optical sensors comprises an array of image sensors.

8. The system of example 7, wherein each of the image sensors in the array of image sensors are configured to image a sub-section of the body surface region.

9. The system of example 8, wherein one or more imaged sub-sections of the body surface region at least partially overlap.

10. The system of example 1, wherein the plurality of optical sensors are configured to capture the image data in a visible wavelength range.

11. The system of example 1, wherein at least one of the plurality of optical sensors comprise a image sensor and lens assembly.

12. The system of example 11, wherein the lens assembly comprises a fisheye lens.

13. The system of example 11, wherein the lens assembly comprises a field of view greater than 90 degrees.

14. The system of example 11 wherein the lens assembly comprises a field of view less than 200 degrees.

15. The system of example 1 wherein the module comprises a rigid-flex circuit board assembly comprising a plurality of rigid components and plurality of flexible components, wherein at least some of the plurality of flexible components are configured to couple at least some of the plurality of rigid components together.

16. The system of example 15 wherein the plurality of optical sensors are coupled to the rigid-flex circuit board assembly.

17. The system of example 16 wherein each of the plurality of optical sensors are coupled to a separate rigid component of the plurality of rigid components of the rigid-flex circuit board assembly.

18. The system of example 1, wherein each imaged sub-section of the body surface region is configured to be illuminated by one or more light sources associated with an individual optical sensor of the plurality of optical sensors.

19. The system of example 18, wherein the one or more light sources comprise a single light source adjacent to each optical sensor of the plurality of optical sensors, the plurality of optical sensors being arranged in an array.

20. The system of example 19, wherein the one or more light sources comprise a plurality of light sources surrounding each optical sensor of the plurality of optical sensors, the plurality of optical sensors being arranged in an array.

21. The system of example 19 wherein the module comprises a light shield configured to prevent light shunts between the one or more light sources.

22. The system of example 19 wherein the module comprises a transmissive diffuser configured to diffuse light towards an imaged sub-section of the body surface region from the one or more light sources.

23. The system of example 19 wherein the module comprises a polarizer configured to polarize light reflected towards at least one optical sensor of the plurality of optical sensors.

24. The system of example 3, wherein the computing system is further configured to train the machine learning model using training data comprising training sensor data and training contextual data, wherein the training data is associated with one or more body surface region classifications to be generated by the machine learning model.

25. The system of example 3, wherein the computing system is further configured to train the machine learning model using training data comprising training sensor data and training contextual data, wherein the training data is associated with one or more state scores to be generated by the machine learning model.

26. The system of example 3, wherein the computing system is further configured to generate output data based at least partly on the score, wherein the output data represents at least one of: a treatment instruction, a sensor instruction, or a body surface region classification.

27. The system of example 2, wherein the computing system is further configured to transmit data to at least one of: the module, or a computing device in communication with the module.

28. A system comprising:

a wearable medical article configured to be placed over a body surface region of a patient; and a module configured to be mounted to the wearable medical article, wherein the module comprises:

at least one outer portion comprising at least one external sidewall and at least one distal surface, the at least one external sidewall comprising a plurality of notches configured to allow the at least one outer portion to at least partially follow a contour of the body surface region of the patient;

a proximal portion comprising a first transparent area, the first transparent area configured to allow visible light to pass through the first transparent area towards the body surface region of the patient;

an array of optical sensors configured to image a sub-region of a body surface region of a patient, each optical sensor configured to operate in conjunction with one or more light sources;

a light shield configured to prevent light shunts between one or more light sources operating in conjunction with each optical sensor;

a diffuser configured to diffuse light from the one or more light sources towards the body surface region of the patient;

at least one polarizer configured to reduce glare from light reflected towards each optical sensor; and a wireless network interface configured to transmit data.

29. The system of example 28, further comprising a computing system comprising one or more computer processors and executable instructions, wherein the computing system is configured to:

receive image data from the array of optical sensors;

receive contextual data associated with the patient; and determine a current state of the body surface region of the patient based at least partly on at least one of the image data and contextual data.

30. The system of example 29, wherein to determine the current state of the body surface region, the computing system is further configured to evaluate the image data and contextual data using a machine learning model to generate a score representing the current state of the body surface region.

31. The system of example 30, wherein the computing system is further configured to train the machine learning model using training data comprising training sensor data and training contextual data, wherein the training data is associated with one or more body surface region classifications to be generated by the machine learning model.

32. The system of example 30, wherein the computing system is further configured to train the machine learning model using training data comprising training sensor data and training contextual data, wherein the training data is associated with one or more state scores to be generated by the machine learning model.

33. The system of example 30, wherein the computing system is further configured to generate output data based at least partly on the score, wherein the output data represents at least one of: a treatment instruction, a sensor instruction, or a body surface region classification.

34. The system of example 33, wherein the computing system is further configured to transmit the output data to at least one of: the module, or a computing device in communication with the module.

Terminology

Depending on the embodiment, certain acts, events, or functions of any of the processes or algorithms described herein can be performed in a different sequence, can be added, merged, or left out altogether (e.g., not all described operations, sequencing, or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, or combinations of electronic hardware and computer software. To clearly illustrate this interchangeability, various illustrative components, blocks, modules, and steps have been described above generally in terms of their functionality. Whether such functionality is implemented as hardware, or as software that runs on hardware, depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a computer processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A computer processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others.

Reference throughout this specification to "some embodiments" or "an embodiment" means that a particular feature, structure, element, act, or characteristic described in connection with the embodiment is included in at least one embodiment. Thus, appearances of the phrases "in some embodiments" or "in an embodiment" in various places throughout this specification are not necessarily all referring to the same embodiment and may refer to one or more of the same or different embodiments. Furthermore, the particular features, structures, elements, acts, or characteristics may be combined in any suitable manner (including differently than shown or described) in other embodiments. Further, in various embodiments, features, structures, elements, acts, or characteristics can be combined, merged, rearranged, reordered, or left out altogether. Thus, no single feature, structure, element, act, or characteristic or group of features, structures, elements, acts, or characteristics is necessary or required for each embodiment. All possible combinations and sub-combinations are intended to fall within the scope of this disclosure.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

The foregoing description sets forth various example embodiments and other illustrative, but non-limiting, embodiments of the inventions disclosed herein. The description provides details regarding combinations, modes, and uses of the disclosed inventions. Other variations, combinations, modifications, equivalents, modes, uses, implementations, and/or applications of the disclosed features and aspects of the embodiments are also within the scope of this disclosure, including those that become apparent to those of skill in the art upon reading this specification. Additionally, certain objects and advantages of the inventions are described herein. It is to be understood that not necessarily all such objects or advantages may be achieved in any particular embodiment. Thus, for example, those skilled in the art will recognize that the inventions may be embodied or carried out in a manner that achieves or optimizes one advantage or group of advantages as taught herein without necessarily achieving other objects or advantages as may be taught or suggested herein. Also, in any method or process disclosed herein, the acts or operations making up the method or process may be performed in any suitable sequence and are not necessarily limited to any particular disclosed sequence.

The following is claimed:

1. A system comprising:

a wearable medical article configured to be placed over or with respect to a body surface region of a patient; and a module configured to be mounted to, embedded in, or integrated with a wearable medical article, wherein the module comprises:

a flexible standoff comprising at least one external sidewall and at least one distal surface, said flexible standoff configured to allow the at least one distal surface to at least partially follow a contour of the body surface region of the patient;

a plurality of imaging sensors, individual ones of said imaging sensors comprising a two-dimensional optical detector array and a lens configured to form an image on said two-dimensional optical detector array to image a sub-region of said body surface region of said patient, said imaging sensors capturing images of said sub-regions of said body surface region at one or more visible, infrared, near infrared or ultra-violet wavelengths, said lens comprising a wide angle lens; and light sources configured to provide illumination to at least a portion of the body surface region of the patient, said light sources comprising six light sources surrounding a respective imaging sensor closest thereto, said six light sources comprising three pairs of light sources, each of said three pairs of light sources comprising first and second light sources on opposite sides of said imaging sensor closest to the light source, wherein said flexible standoff provides a distance between the plurality of imaging sensors and the body surface region of the patient and includes an opening therein for passage of light, said standoff being ring-shaped, the opening in the standoff being defined by one or more internal sidewalls of the standoff, the distance between the one or more internal sidewalls on opposing sides of the opening being wider than the distance between the internal sidewall and the external sidewall on one of said sides, the standoff comprising foam, wherein said imaging sensors have a working distance of from 0.5 to 3 centimeters, and wherein different imaging sensors are configured to image different, respective sub-sections of the body surface region and said imaged respective sub-sections of the body surface region partially overlap.

2. The system of claim 1, further comprising a light shield configured to prevent light shunts between a first light source for a first imaging sensor and a second light source for a second imaging sensor.

3. The system of claim 1, further comprising a computing system comprising one or more computer processors and executable instructions, wherein the computing system is configured to:

receive a plurality of images comprising images of a plurality of partially overlapping sub-sections of the body surface region from the plurality of imaging sensors; and generate a combined image based on the images of the plurality of partially overlapping sub-sections.

4. The system of claim 1, wherein the plurality of imaging sensors comprises one or more imaging sensors configured to be auto-focusing.

5. The system of claim 1, wherein said imaging sensor includes zoom-in functionality that increases magnification of the imaging sensor, and a user device can allow a user to program or control the operation of the system to provide said increased magnification.

6. The system of claim 1, wherein the lens comprises a fisheye lens.

7. The system of claim 1, wherein the lens comprises a field of view greater than 90 degrees.

8. The system of claim 7, wherein the lens comprises a field of view less than 200 degrees.

9. The system of claim 1, wherein the light sources comprise six light sources associated with each individual imaging sensor of the plurality of imaging sensors that are configured to illuminate a different, respective sub-section of the body surface region.

10. The system of claim 1, wherein the light sources comprise eight light sources surrounding a respective imaging sensor closest thereto, said eight light sources comprising four pairs of light sources, each pair of light sources comprising first and second light sources on opposite sides of said imaging sensor closest to said light source.

11. The system of claim 1, wherein said standoff is oblong in shape having a pair of opposing long sides and a pair of opposing short sides, the distance between the one or more internal sidewalls on opposing long sides of the opening being wider than the distance between the internal sidewall and the external sidewall on one of said long sides.

12. The system of claim 1, wherein said at least one external sidewall of said standoff comprises a plurality of notches and tabs therebetween that provide flexibility at the external sidewalls.

13. The system of claim 1, further comprising at least one polarizer configured to reduce glare from light reflected towards at least one imaging sensor.

14. The system of claim 1, further comprising at least one circular polarizer configured to reduce glare from light reflected towards at least one imaging sensor.

15. The system of claim 1, further comprising a diffuser, configured to diffuse light from at least two of said plurality of light sources towards the body surface region of the patient.

16. The system of claim 1, wherein the module is configured to capture images sequentially by activating each of the plurality of imaging sensors sequentially thereby reducing instantaneous power draw from a battery.

17. The system of claim 1, wherein the module is configured to capture images sequentially by operating each of the plurality of imaging sensors sequentially with an interval between operation of each of the plurality of imaging sensors comprising at least 3 seconds.

18. The system of claim 1, wherein said module does not comprise an imaging sensor that uses an optical fiber to collect light to form an image.

19. The system of claim 1, wherein said module comprises a rigid-flex circuit board assembly comprising a plurality of rigid components coupled together by flexible components, wherein individual imaging sensors of the plurality of imaging sensors are supported on separate rigid components of the plurality of rigid components of the rigid-flex circuit board assembly.

* * * * *